US006265349B1

United States Patent
Yamaguchi et al.

(10) Patent No.: US 6,265,349 B1
(45) Date of Patent: Jul. 24, 2001

(54) PYRIDONE DERIVATIVES AND HERBICIDES

(75) Inventors: Mikio Yamaguchi; Yoshihiro Ito; Atsushi Shibayama, all of Iwata-gun; Yoshihiro Yamaji, Ogasa-gun; Ryo Hanai, Ogasa-gun; Sota Uotsu, Ogasa-gun; Hideo Sadohara, Niiza, all of (JP)

(73) Assignees: Kumiai Chemical Industry Co., Ltd; Ihara Chemical Industry Co., Ltd., both of Tokyo (JP)

( * ) Notice: Subject to any disclaimer, the term of this patent is extended or adjusted under 35 U.S.C. 154(b) by 0 days.

(21) Appl. No.: 09/427,988

(22) Filed: Oct. 27, 1999

Related U.S. Application Data

(62) Division of application No. 09/117,456, filed as application No. PCT/JP97/00192 on Jan. 29, 1997, now Pat. No. 6,048,823.

(30) Foreign Application Priority Data

Feb. 2, 1996 (JP) ....................................................... 8-40744

(51) Int. Cl.[7] ........................... A01N 43/60; C07D 241/40
(52) U.S. Cl. .......................... 504/235; 504/224; 504/221; 504/252; 504/253; 544/354; 544/58.2; 544/105; 546/270.1; 546/271.7; 546/273.7; 546/277.4; 546/281.1; 546/284.1
(58) Field of Search ................................... 504/235, 224, 504/221, 252, 253; 544/58.2, 105, 354; 546/270.1, 271.7, 273.7, 277.4, 281.1, 284.1

(56) References Cited

U.S. PATENT DOCUMENTS

| 2,965,682 | 12/1960 | Horvath . |
| 4,714,492 | 12/1987 | Carlson . |
| 5,403,934 | 4/1995 | Batchelor et al. . |

FOREIGN PATENT DOCUMENTS

| 0 488 220 | 6/1992 | (EP) . |
| 0 588 137 | 3/1994 | (EP) . |
| 51-48671 | 4/1976 | (JP) . |
| 51-51520 | 7/1976 | (JP) . |
| 5-504961 | 7/1993 | (JP) . |
| WO 91/13873 | 9/1991 | (WO) . |

OTHER PUBLICATIONS

CA 131:44738, Yamaji et al, 1999.*
M. Kuzuya, et al., Chemical Abstracts, vol. 107, No. 21, p. 733, AN 107:198019g, "Substituent Effects on The Formation of Inclusion Complexes With Guest Molecules of 2–Pyridones and Their Photochemical Reactivity in the Solid State", Nov. 23, 1987, (English Abstract only).
H. Gotthardt, et al., Chemische Berichte, vol. 121, No. 5, pp. 951–960, "NEUE 1,4–Dipolare Cycloadditionen Von 6–Oxo–6H–1,3–Oxazin–3–IUM–4–Olaten Und Eines 6–Oxo–6H–1,3–Thiazin–3–IUM–4–Olats An Keten–Derivate Und Enamine", 1988.
M. Mazaki, et al., Chemical Abstracts, vol. 112, No. 5, p. 562, AN 112:35682g, "Preparation of 2–Oxopyran–6–Carboxylates as Insecticides", Jan. 29, 1990, (English Abstract only).
Chemical Abstracts, vol. 76, No. 23, Jun. 5, 1972, AN 14040g, XP 002153510, 1972.
Kuzutani, M., et al., "Substituent effect on capability to be included of 2–pyridones as guest molecules and on solid optical reactivity of their inclusion complexes, "*Journ. Of the Chem. Soc. Of Japan*, No. 12, pp. 1746–1753 (1986).
Overman, L., et al., "Preparation of Substituted 2–Pyridones by Thermal Rearrangement of Propargylic Pyrrolidine Pseudoureas," *J. Am. Chem. Soc.*, vol. 102, No. 2, pp. 747–754 (1980).
Ishibe, et al., "Photoisomerization of 4–Pyridones to 2–Pyridones," *J. Am. Chem. Soc.*, vol. 96, pp. 1152–1158 (1974).

* cited by examiner

*Primary Examiner*—Jane Fan
(74) *Attorney, Agent, or Firm*—Oblon, Spivak, McClelland, Maier & Neustadt, P.C.

(57) ABSTRACT

The present invention relates to pyridone derivatives and herbicidal compositions containing the pyridone derivatives as active ingredients.

7 Claims, No Drawings

PYRIDONE DERIVATIVES AND HERBICIDES

This is a division of Ser. No. 09/117456, filed Aug. 3, 1998, now U.S. Pat. No. 6,048,823 Apr. 11, 2000 which is a 371 of PCT/JP97/00192 filed Jan. 29, 1997 now WO 87/28127, Aug. 7, 1997.

TECHNICAL FIELD

The present invention relates to pyridone derivatives and herbicides containing them as active ingredients.

BACKGROUND ART

Heretofore, some 3-(substituted)phenyl-2-pyridone derivatives have been known. However, no more than a few compounds have been known with respect to 3-(substituted) phenyl-6-(substituted)alkyl-2-pyridone derivatives, which represent the characteristic of the compounds of the present invention. For example, the specification of JP-B-46-30190 discloses 3-(4-chlorophenyl)-6-methyl-2-pyridone. Further, U.S. Pat. No. 3,720,768 discloses 3-phenyl-6-ethyl-2-pyridone. However, either specification discloses nothing about herbicidal activities. On the other hand, some 3-(substituted)phenyl-4-pyridone derivatives have been known. However, no more than a few compound have been known with respect to 3-(substituted)phenyl-6-(substituted) alkyl-4-pyridone derivatives, which represent the characteristic of the compounds of the present invention. For example, Chemical Abstract vol. 76, No. 140407, discloses 3-phenyl-6-methyl-4-pyridone, but discloses nothing about the herbicidal activities. Further, the specification of JP-A-62-167708 discloses a 3-(substituted)phenyl-6-(substituted) alkyl-4-pyridone derivative having a carbamoyl group at the 5-position, and a herbicidal activity is also disclosed. However, it is different from the compounds of the present invention.

In recent years, a herbicide is strongly desired which has selective activities to kill only weeds without giving adverse effects to crop plants even when it is applied to the crop plants and weeds simultaneously. Further, it is desired to develop an agent whereby complete effects can be obtained at a low dose, in order to prevent the agent from remaining excessively in the environment.

To solve the above problems, the present inventors have synthesized many pyridone derivatives and conducted various studies on their usefulness. As a result, it has been found that certain pyridone derivatives have excellent herbicidal activities and selectivity to solve the above problems, and the present invention has been accomplished.

DISCLOSURE OF THE INVENTION

Namely, the present invention provides a pyridone derivative represented by the general formula:

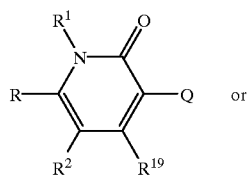

or

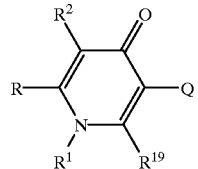

{wherein R is a $C_1$–$C_6$ alkyl group or a $C_1$–$C_6$ haloalkyl group, $R^1$ is a hydrogen atom, a $C_1$–$C_6$ alkyl group, a $C_1$–$C_6$ haloalkyl group, an acetyl group, a group of —N=$CR^{13}R^{14}$ or a group of —$NR^{23}R^{24}$ (provided that when $R^1$ is a hydrogen atom, R is a $C_1$–$C_6$ haloalkyl group), each of $R^{13}$ and $R^{14}$ which are independent of each other, is a hydrogen atom, a $C_1$–$C_6$ alkyl group, a group of —$NR^{23}R^{24}$ or a phenyl group (said group may be substituted by a halogen atom, a nitro group, a $C_1$–$C_6$ alkyl group, a $C_1$–$C_6$ haloalkyl group or a $C_1$–$C_6$ alkoxy group), each of $R^{23}$ and $R^{24}$ which are independent of each other, is a hydrogen atom, a $C_1$–$C_6$ alkyl group, a $C_1$–$C_6$ haloalkyl group, a $C_1$–$C_6$ alkylcarbonyl group, a $C_1$–$C_6$ alkoxycarbonyl group, a benzoyl group (said group may be substituted by a halogen atom, a nitro group, a $C_1$–$C_6$ alkyl group, a $C_1$–$C_6$ haloalkyl group or a $C_1$–$C_6$ alkoxy group), a phenoxycarbonyl group (said group may be substituted by a halogen atom, a nitro group, a $C_1$–$C_6$ alkyl group, a $C_1$–$C_6$ haloalkyl group or a $C_1$–$C_6$ alkoxy group), a formyl group or a $C_1$–$C_6$ alkylsulfonyl group, $R^2$ is a hydrogen atom, a $C_1$–$C_6$ alkyl group, a carboxyl group or a $C_1$–$C_6$ alkoxycarbonyl group, $R^{19}$ is a hydrogen atom, a halogen atom, a $C_1$–$C_6$ alkoxy group, a cyano group or a $C_1$–$C_6$ alkyl group, and Q represents a formula of

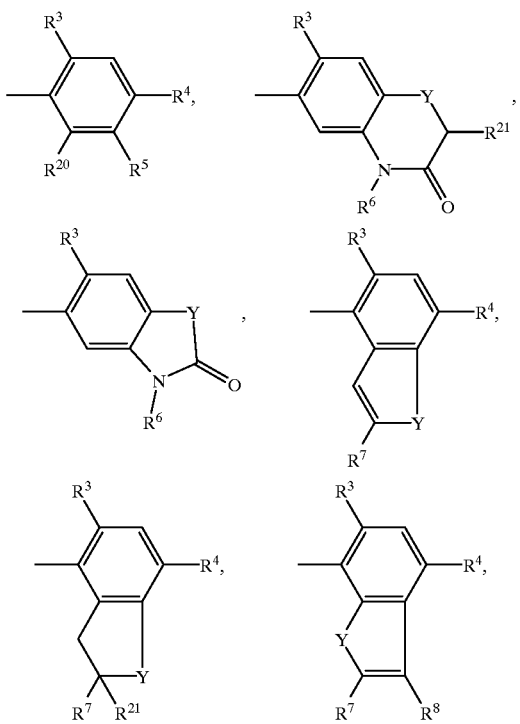

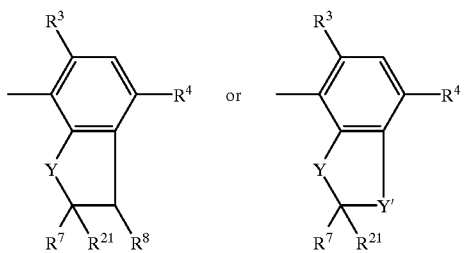

[wherein $R^3$ is a hydrogen atom or a halogen atom, $R^4$ is a hydrogen atom, a halogen atom, a nitro group, a $C_1$–$C_6$ alkoxycarbonyl $C_1$–$C_6$ alkoxy group, a $C_1$–$C_6$ alkoxycarbonyl $C_1$–$C_6$ alkylthio group, a $C_1$–$C_6$ alkoxycarbonyl $C_1$–$C_6$ alkylamino group, a benzyloxy group (said group may be substituted by a halogen atom, a nitro group, a $C_1$–$C_6$ alkyl group or a $C_1$–$C_6$ alkoxy group), a hydroxyl group, a thiol group, an amino group or a cyano group, $R^5$ is a hydrogen atom, a halogen atom, a $C_1$–$C_6$ alkyl group, a $C_2$–$C_6$ alkenyl group, a $C_1$–$C_6$ haloalkyl group, a hydroxyl group, a thiol group, an amino group, a nitro group, a chlorosulfonyl group, an acetylthio group, a cyano group, a cyano $C_1$–$C_6$ alkyl group, a formyl group, a hydroxymethyl group, a group of —$YR^9$, a group of —$CR^{21}$=$NOR^9$, a group of —$CO_2R^{10}$, a group of —$COSR^{10}$, a group of —$CONR^{10}R^{11}$, a group of —$SO_2NR^{10}R^{11}$, a group of —$NHCONHR^{11}$, a group of —$SOR^{12}$, a group of —$SO_2R^{12}$, an acyl group, a $C_1$–$C_6$ alkoxy $C_1$–$C_6$ alkyl group, a group of —$CO_2N$=$CR^{13}R^{14}$, a group of —CH(OH)$R^{21}$, a group of —$CH_2YR^9$, a hetero ring group or a group of —$CH_2CH(Cl)CO_2R^{10}$, Y is an oxygen atom, a sulfur atom or a group of —$NR^{21}$—, $R^{21}$ is a hydrogen atom, a $C_1$–$C_6$ alkyl group, a $C_3$–$C_6$ alkenyl group or a $C_3$–$C_6$ alkynyl group, $R^9$ is a $C_1$–$C_6$ alkyl group, a $C_3$–$C_6$ alkenyl group, a $C_3$–$C_6$ alkynyl group, a $C_3$–$C_8$ cycloalkyl group, a $C_1$–$C_6$ haloalkyl group, a hydroxy $C_1$–$C_6$ alkyl group, a $C_3$–$C_6$ haloalkenyl group, a $C_3$–$C_8$ cycloalkyl $C_1$–$C_6$ alkyl group, a $C_1$–$C_6$ alkoxy $C_1$–$C_6$ alkyl group, a $C_1$–$C_6$ alkoxycarbonyl group, a $C_1$–$C_6$ alkylsulfonyl group, a $C_1$–$C_6$ haloalkylsulfonyl group, a $C_1$–$C_6$ alkylthio $C_1$–$C_6$ alkyl group, a $C_1$–$C_6$ alkylsulfinyl $C_1$–$C_6$ alkyl group, a $C_1$–$C_6$ alkylsulfonyl $C_1$–$C_6$ alkyl group, a cyano $C_1$–$C_6$ alkyl group, a group of —CH($R^{15}$)COY$R^{16}$, a benzyl group (said group may be substituted by a halogen atom, a nitro group, a $C_1$–$C_6$ alkyl group, a $C_1$–$C_6$ haloalkyl group or a $C_1$–$C_6$ alkoxy group), a group of —$CH_2$ (3–6 membered hetero ring) (the hetero ring group of said group may be substituted by a halogen atom, a nitro group, an oxo group, a $C_1$–$C_6$ alkyl group, a $C_1$–$C_6$ haloalkyl group or a $C_1$–$C_6$ alkoxy group), a 3–6 membered hetero ring group (said group may be substituted by a halogen atom, a nitro group, an oxo group, a $C_1$–$C_6$ alkyl group, a $C_1$–$C_6$ haloalkyl group or a $C_1$–$C_6$ alkoxy group) or a phenyl group (said group may be substituted by a halogen atom, a nitro group, a $C_1$–$C_6$ alkyl group, a $C_1$–$C_6$ haloalkyl group or a $C_1$–$C_6$ alkoxy group), $R^{15}$ is a hydrogen atom, a $C_1$–$C_6$ alkyl group or a $C_3$–$C_8$ cycloalkyl group, $R^{16}$ is a hydrogen atom, a $C_1$–$C_6$ alkyl group, a $C_3$–$C_6$ alkenyl group, a $C_3$–$C_6$ alkynyl group, a $C_3$–$C_8$ cycloalkyl group, a $C_1$–$C_6$ haloalkyl group, a $C_3$–$C_6$ haloalkenyl group, a $C_3$–$C_6$ cycloalkyl $C_1$–$C_6$ alkyl group, a $C_1$–$C_6$ alkoxy $C_1$–$C_6$ alkyl group, a $C_1$–$C_6$ alkylthio $C_1$–$C_6$ alkyl group, a $C_1$–$C_6$ alkylsulfinyl $C_1$–$C_6$ alkyl group, a $C_1$–$C_6$ alkylsulfonyl $C_1$–$C_6$ alkyl group, a benzyl group (said group may be substituted by a halogen atom, a nitro group, a $C_1$–$C_6$ alkyl group, a $C_1$–$C_6$ haloalkyl group or a $C_1$–$C_6$ alkoxy group) or a phenyl group (said group may be substituted by a halogen atom, a nitro group, a $C_1$–$C_6$ alkyl group, a $C_1$–$C_6$ haloalkyl group, a $C_1$–$C_6$ alkoxycarbonyl $C_1$–$C_6$ alkyl group or a $C_1$–$C_6$ alkoxy group), $R^{10}$ is a hydrogen atom, a sodium atom, a $C_1$–$C_6$ alkyl group, a $C_3$–$C_6$ alkenyl group, a $C_3$–$C_6$ alkynyl group, a $C_3$–$C_8$ cycloalkyl group, a $C_1$–$C_6$ haloalkyl group, a $C_3$–$C_6$ haloalkenyl group, a $C_3$–$C_8$ cycloalkyl $C_1$–$C_6$ alkyl group, a $C_1$–$C_6$ alkoxy $C_1$–$C_6$ alkyl group, a $C_1$–$C_6$ alkylthio $C_1$–$C_6$ alkyl group, a $C_1$–$C_6$ alkylsulfinyl $C_1$–$C_6$ alkyl group, a $C_1$–$C_6$ alkylsulfonyl $C_1$–$C_6$ alkyl group, a $C_1$–$C_6$ alkoxycarbonyl $C_1$–$C_6$ alkyl group, a $C_3$–$C_6$ alkenyloxycarbonyl $C_1$–$C_6$ alkyl group, a $C_3$–$C_6$ alkynyloxycarbonyl $C_1$–$C_6$ alkyl group, a $C_3$–$C_8$ cycloalkyloxycarbonyl $C_1$–$C_6$ alkyl group, a $C_1$–$C_6$ alkoxy $C_1$–$C_6$ alkoxycarbonyl $C_1$–$C_6$ alkyl group, a halo $C_1$–$C_6$ alkoxycarbonyl $C_1$–$C_6$ alikyl group, a halo $C_3$–$C_6$ alkenyloxycarbonyl $C_1$–$C_6$ alkyl group, a benzyloxycarbonyl $C_1$–$C_6$ alkyl group (the benzyl group of said group may be substituted by a halogen atom, a nitro group, a $C_1$–$C_6$ alkyl group, a $C_1$–$C_6$ haloalkyl group or a $C_1$–$C_6$ alkoxy group), a $C_1$–$C_6$ alkylthiocarbonyl $C_1$–$C_6$ alkyl group, a $C_1$–$C_6$ alkylsulfinyl $C_1$–$C_6$ alkoxycarbonyl $C_1$–$C_6$ alkyl group, a $C_1$–$C_6$ alkylsulfonyl $C_1$–$C_6$ alkoxycarbonyl $C_1$–$C_6$ alkyl group, a $C_1$–$C_6$ monoalkylcarbamoyl $C_1$–$C_6$ alkyl group, a $C_1$–$C_6$ dialkylcarbamoyl $C_1$–$C_6$ alkyl group, a $C_1$–$C_6$ alkylthio $C_1$–$C_6$ alkoxycarbonyl $C_1$–$C_6$ alkyl group, a phenoxycarbonyl $C_1$–$C_6$ alkyl group (the phenyl group of said group may be substituted by a halogen atom, a nitro group, a $C_1$–$C_6$ alkyl group, a $C_1$–$C_6$ haloalkyl group or a $C_1$–$C_6$ alkoxy group), a $C_1$–$C_6$ alkoxycarbonyl $C_1$–$C_6$ alkoxycarbonyl $C_1$–$C_6$ alkyl group, a benzyl group (said group may be substituted by a halogen atom, a nitro group, a $C_1$–$C_6$ alkyl group, a $C_1$–$C_6$ haloalkyl group or a $C_1$–$C_6$ alkoxy group) or a phenyl group (said group may be substituted by a halogen atom, a nitrQ group, a $C_1$–$C_6$ alkyl group, a $C_1$–$C_6$ haloalkyl group or a $C_1$–$C_6$ alkoxy group), $R^{11}$ is a hydrogen atom, a $C_1$–$C_6$ alkyl group, a $C_3$–$C_6$ alkenyl group, a $C_3$–$C_6$ alkynyl group, a $C_3$–$C_8$ cycloalkyl group, a $C_1$–$C_6$ haloalkyl group, a $C_3$–$C_6$ haloalkenyl group, a $C_1$–$C_6$ alkylsulfonyl group, a $C_1$–$C_6$ alkylcarbonyl group, a $C_1$–$C_6$ alkoxycarbonyl group or a $C_3$–$C_8$ cycloalkyl $C_1$–$C_6$ alkyl group, $R^{12}$ is a hydrogen atom, a $C_1$–$C_6$ alkyl group, a $C_3$–$C_6$ alkenyl group, a $C_3$–$C_6$ alkynyl group, a $C_3$–$C_8$ cycloalkyl group, a $C_1$–$C_6$ haloalkyl group, a $C_3$–$C_6$ haloalkenyl group, a $C_1$–$C_6$ alkylcarbonyl group, a $C_1$–$C_6$ alkoxycarbonyl group or a $C_3$–$C_8$ cycloalkyl $C_1$–$C_6$ alkyl group, $R^6$ is a hydrogen atom, a $C_1$–$C_6$ alkyl group, a $C_3$–$C_6$ alkenyl group, a $C_3$–$C_6$ alkynyl group, a $C_1$–$C_6$ haloalkyl group, a $C_3$–$C_6$ haloalkenyl group, a $C_1$–$C_6$ alkoxy $C_1$–$C_6$ alkyl group, a $C_1$–$C_6$ alkoxycarbonyl group, a $C_1$–$C_6$ alkoxycarbonyl $C_1$–$C_6$ alkyl group, a cyano $C_1$–$C_6$ alkyl group, a benzyl group (said group may be substituted by a halogen atom, a nitro group, a $C_1$–$C_6$ alkyl group or a $C_1$–$C_6$ alkoxy group) or a group of —$CH_2$ (3–6 membered hetero ring), $R^7$ is a hydrogen atom, a halogen atom, a $C_1$–$C_6$ alkyl group, a $C_3$–$C_6$ cycloalkyl group, a $C_2$–$C_6$ alkenyl group, a $C_3$–$C_6$ alkynyl group, a $C_1$–$C_6$ haloalkyl group, a $C_1$–$C_6$ alkoxy $C_1$–$C_6$ alkyl group, a cyano group, a $C_1$–$C_6$ hydroxyalkyl group, a group of —$CO_2R^{10}$, a formyl group, an acyl group, a $C_1$–$C_6$ alkylthio $C_1$–$C_6$ alkyl group, a $C_1$–$C_6$ alkylsulfinyl $C_1$–$C_6$ alkyl group, a $C_1$–$C_6$ alkylsulfonyl $C_1$–$C_6$ alkyl group, a $C_1$–$C_6$ haloalkylthio $C_1$–$C_6$ alkyl group, a $C_1$–$C_6$ haloalkylsulfinyl $C_1$–$C_6$ alkyl group, a $C_1$–$C_6$ haloalkylsulfonyl $C_1$–$C_6$ alkyl group or a carboxyl group, $R^8$ is a hydrogen atom, a $C_1$–$C_6$ alkyl group, a $C_1$–$C_6$ haloalkyl group, an acyl group, a halogen atom or a nitro group, $R^{20}$ is a hydrogen atom, a halogen atom, a hydroxyl group, a $C_1$–$C_6$ alkoxy group, a $C_3$–$C_6$ alkenyloxy group, a $C_3$–$C_6$ alkynyloxy group, a $C_1$–$C_6$ haloalkoxy group, a $C_3$–$C_6$ haloalkenyloxy group or a group of —$NR^{11}R^{12}$, and Y' is an oxygen atom, a sulfur atom, a group of —$NR^{21}$— or a group of —CO—]}; and a herbicide containing it as an active ingredient.

In this specification, the halogen atom represents a fluorine atom, a chlorine atom, a bromine atom or an iodine atom.

The $C_1$–$C_6$ alkyl group represents a straight chain or branched chain alkyl group having from 1 to 6 carbon atoms. For example, a methyl group, an ethyl group, a n-propyl group, an isopropyl group, a n-butyl group, an isobutyl group, a sec-butyl group, a tert-butyl group, a n-pentyl group, an isopentyl group, a neopentyl group, a n-hexyl group, an isohexyl group or a 3,3-dimethylbutyl group may be mentioned.

The $C_1$–$C_6$ haloalkyl group represents a $C_1$–$C_6$ alkyl group substituted by halogen atoms. For example, a difluoromethyl group, a trifluoromethyl group or a pentafluoroethyl group may be mentioned.

The $C_2$–$C_6$ alkenyl group represents a straight chain or branched chain alkenyl group having from 2 to 6 carbon atoms. For example, a vinyl group, a propenyl group, an isopropenyl group, a butenyl group, a pentenyl group or a hexenyl group may be mentioned.

The $C_3$–$C_6$ haloalkenyl group represents a straight chain or branched chain alkenyl group having from 3 to 6 carbon atoms, substituted by a halogen atom. For example, a 2-chloro-2-propenyl group or a 3-chloro-2-propenyl group may be mentioned.

The $C_3$–$C_6$ alkynyl group represents a straight chain or nranched chain alkynyl group having from 3 to 6 carbon atoms. For example, a propynyl group, a butynyl group, a pentynyl group, a hexynyl group, a 3,3-dimethyl-1-butynyl group, a 4-methyl-1-pentynyl group or a 3-methyl-1-pentynyl group may be mentioned.

The $C_3$–$C_8$ cycloalkyl group represents a cycloalkyl group having from 3 to 8 carbon atoms. For example, a cyclopropyl group or a cyclohexyl group may be mentioned.

The 3–6 membered hetero ring group may, for example, be a pyrimidinyl group, a pyridyl group, a thienyl group, a thiazolyl group, a pyrazolyl group, an oxazolyl group, an isoxazolyl group, an oxoranyl group, a dioxoranyl group or an oxiranyl group.

Now, specific examples of the compounds of the present invention will be disclosed in Tables 1 to 33. However, the compounds of the present invention are not limited to such compounds. The compound numbers will be referred to in the subsequent description.

(In the Tables, * represents a triple bond, and the same applies hereinafter.)

TABLE 1

[I-1-1]

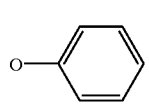

| Comp. Nos. | R | $R^1$ | $R^2$ | $R^3$ | $R^4$ | $R^5$ | m.p. (° C.) |
|---|---|---|---|---|---|---|---|
| 1-1 | $CF_3$ | $CH_3$ | H | H | Cl | H | 112–114 |
| 1-2 | $CF_3$ | $CH_3$ | H | F | Cl | H | 103–104 |
| 1-3 | $CF_3$ | $CH_3$ | H | Cl | Cl | H | 126–129 |
| 1-4 | $CF_3$ | $NH_2$ | H | F | Cl | H | |
| 1-5 | $CF_3$ | $NH_2$ | H | Cl | Cl | H | 98–100 |
| 1-6 | $CH_3$ | $CH_3$ | H | Cl | Cl | H | 124–126 |
| 1-7 | $CH_3$ | $NH_2$ | H | Cl | Cl | H | 149–150 |
| 1-8 | $CH_3$ | $CHF_2$ | H | Cl | Cl | H | 83–85 |
| 1-9 | $C_4H_9$-t | $CH_3$ | H | Cl | Cl | H | |
| 1-10 | $C_4H_9$-t | $NH_2$ | H | Cl | Cl | H | 108–110 |
| 1-11 | $CF_3$ | $CH_3$ | $CH_3$ | Cl | Cl | H | 121–122 |
| 1-12 | $CF_3$ | $CH_3$ | H | F | F | H | 123–124 |
| 1-13 | $CF_3$ | $CH_3$ | H | F | Cl | OH | 182–184 |
| 1-14 | $CF_3$ | $CH_3$ | H | F | Cl | $OC_3H_7$-i | 75–78 |
| 1-15 | $CF_3$ | $CH_3$ | H | F | Cl | $OCH_3$ | 147–148 |
| 1-16 | $CF_3$ | $CH_3$ | H | F | Cl | $OCH_2CH=CH_2$ | 79–80 |
| 1-17 | $CF_3$ | $CH_3$ | H | F | Cl | $OCH(CH_3)C*CH$ | 68–69 |
| 1-18 | $CF_3$ | $CH_3$ | H | F | Cl | $OCH_2C*CH$ | 108–110 |
| 1-19 | $CF_3$ | $CH_3$ | H | F | Cl | $OCH_2CO_2C_2H_5$ | 97–99 |
| 1-20 | $CF_3$ | $CH_3$ | H | F | Cl | $OCH_2CO_2C_5H_{11}$ | oil |
| 1-21 | $CF_3$ | $CH_3$ | H | F | Cl | $OCH(CH_3)CO_2C_2H_5$ | 53–54 |
| 1-22 | $CF_3$ | $CH_3$ | H | F | Cl | 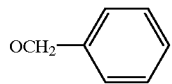 | oil |
| 1-23 | $CF_3$ | $CH_3$ | H | F | Cl |  | 100–101 |

TABLE 1-continued

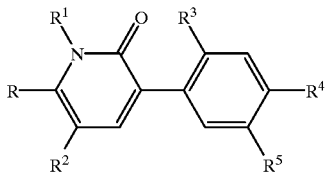

[I-1-1]

| Comp. Nos. | R | $R^1$ | $R^2$ | $R^3$ | $R^4$ | $R^5$ | m.p. (° C.) |
|---|---|---|---|---|---|---|---|
| 1-24 | $CF_3$ | $CH_3$ | H | F | Cl | $OCH_2OCH_3$ | 43–44 |
| 1-25 | $CF_3$ | $CH_3$ | H | F | Cl | $OCH_2CN$ | 135–137 |
| 1-26 | $CF_3$ | $CH_3$ | H | F | Cl | cyclopentyl-O- | 72–74 |
| 1-27 | $CF_3$ | $CH_3$ | H | F | Cl | pyrimidin-2-yl-O- | 179–180 |
| 1-28 | $CF_3$ | $CH_3$ | H | Cl | Cl | OH | 209–211 |

TABLE 2

| Comp. Nos. | R | $R^1$ | $R^2$ | $R^3$ | $R^4$ | $R^5$ | m.p. (° C.) |
|---|---|---|---|---|---|---|---|
| 1-29 | $CF_3$ | $CH_3$ | H | Cl | Cl | $OC_3H_7$-i | 88–89 |
| 1-30 | $CF_3$ | $CH_3$ | H | Cl | Cl | $OCH_2C^*CH$ | 127–129 |
| 1-31 | $CF_3$ | $CH_3$ | H | Cl | Cl | $OCH(CH_3)C^*CH$ | 121–122 |
| 1-32 | $CF_3$ | $CH_3$ | H | Cl | Cl | $OCH_2CH=CH_2$ | 122–124 |
| 1-33 | $CF_3$ | $CH_3$ | H | Cl | Cl | $OCH_2CO_2C_2H_5$ | 124–126 |
| 1-34 | $CF_3$ | $CH_3$ | H | Cl | Cl | $OCH_2CO_2C_5H_{11}$ | |
| 1-35 | $CF_3$ | $CH_3$ | H | Cl | Cl | $OCH(CH_3)CO_2C_2H_5$ | |
| 1-36 | $CF_3$ | $CH_3$ | H | Cl | Cl | phenyl-O- | oil |
| 1-37 | $CF_3$ | $CH_3$ | H | Cl | Cl | $OCH_2$-phenyl | 159–160 |
| 1-38 | $CF_3$ | $CH_3$ | H | Cl | Cl | $OCH_2OCH_3$ | 101–102 |
| 1-39 | $CF_3$ | $CH_3$ | H | Cl | Cl | $OCH_2CN$ | |
| 1-40 | $CF_3$ | $CH_3$ | H | Cl | Cl | cyclopentyl-O- | 97–98 |
| 1-41 | $CF_3$ | $CH_3$ | H | Cl | Cl | pyrimidin-2-yl-O- | oil |
| 1-42 | $CF_3$ | $CH_3$ | H | F | Cl | SH | 141–142 |
| 1-43 | $CF_3$ | $CH_3$ | H | F | Cl | $SC_3H_7$-i | 60–61 |
| 1-44 | $CF_3$ | $CH_3$ | H | F | Cl | $SCH_2C^*CH$ | 100–102 |
| 1-45 | $CF_3$ | $CH_3$ | H | F | Cl | $SCH_2CO_2C_2H_5$ | 76–77 |
| 1-46 | $CF_3$ | $CH_3$ | H | F | Cl | $SCH_2CO_2CH_3$ | 95–96 |

TABLE 2-continued

| Comp. Nos. | R | $R^1$ | $R^2$ | $R^3$ | $R^4$ | $R^5$ | m.p. (° C.) |
|---|---|---|---|---|---|---|---|
| 1-47 | $CF_3$ | $CH_3$ | H | F | Cl | $SCH_2CO_2$-cyclopentyl | 69–70 |
| 1-48 | $CF_3$ | $CH_3$ | H | F | Cl | $SCH(C_3H_7)CO_2C_2H_5$ | oil |
| 1-49 | $CF_3$ | $CH_3$ | H | F | Cl | $SCH_2CO_2C_2H_4OCH_3$ | 69–70 |
| 1-50 | $CF_3$ | $CH_3$ | H | Cl | Cl | SH | 161–163 |
| 1-51 | $CF_3$ | $CH_3$ | H | Cl | Cl | $SC_3H_7$-i | 72–73 |
| 1-52 | $CF_3$ | $CH_3$ | H | Cl | Cl | $SCH_2C^*CH$ | 120–122 |
| 1-53 | $CF_3$ | $CH_3$ | H | Cl | Cl | $SCH_2CO_2C_2H_5$ | 114–116 |
| 1-54 | $CF_3$ | $CH_3$ | H | Cl | Cl | $SCH_2CO_2CH_3$ | 105–106 |
| 1-55 | $CF_3$ | $CH_3$ | H | Cl | Cl | $SCH_2CO_2$-cyclopentyl | 100–102 |
| 1-56 | $CF_3$ | $CH_3$ | H | Cl | Cl | $SCH(C_3H_7)CO_2C_2H_5$ | oil |
| 1-57 | $CF_3$ | $CH_3$ | H | Cl | Cl | $SCH_2CO_2C_2H_4OCH_3$ | 67–68 |
| 1-58 | $CF_3$ | $CH_3$ | H | F | Cl | $NO_2$ | 139–140 |
| 1-59 | $CF_3$ | $CH_3$ | H | F | Cl | $NH_2$ | 155–157 |
| 1-60 | $CF_3$ | $CH_3$ | H | F | Cl | $NHSO_2CH_3$ | 113–114 |
| 1-61 | $CF_3$ | $CH_3$ | H | F | Cl | $NHSO_2C_2H_5$ | 155–156 |

TABLE 3

| Comp. Nos. | R | $R^1$ | $R^2$ | $R^3$ | $R^4$ | $R^5$ | m.p. (° C.) |
|---|---|---|---|---|---|---|---|
| 1-62 | $CF_3$ | $CH_3$ | H | F | Cl | $NHCH_2C^*CH$ | 115–116 |
| 1-63 | $CF_3$ | $CH_3$ | H | F | Cl | $NHCH_2CO_2C_2H_5$ | 109–110 |
| 1-64 | $CF_3$ | $CH_3$ | H | F | Cl | $NHCH(CH_3)CO_2C_2H_5$ | oil |
| 1-65 | $CF_3$ | $CH_3$ | H | F | Cl | $CO_2C_2H_5$ | 85–86 |
| 1-66 | $CF_3$ | $CH_3$ | H | F | Cl | $CO_2C_3H_7$-i | 90–92 |
| 1-67 | $CF_3$ | $CH_3$ | H | F | Cl | $COSC_2H_5$ | 70–72 |
| 1-68 | $CF_3$ | $CH_3$ | H | F | Cl | $CO_2N{=}C(CH_3)_2$ | oil |
| 1-69 | $CF_3$ | $CH_3$ | H | F | Cl | $COC_2H_5$ | 71–72 |
| 1-70 | $CF_3$ | $CH_3$ | H | F | Cl | $CH_2CH(Cl)CO_2CH_3$ | oil |
| 1-71 | $CF_3$ | $CH_3$ | H | F | Cl | $SO_2NHCH_3$ | 150–151 |
| 1-72 | $CF_3$ | $CH_3$ | H | F | Cl | $CH{=}NOCH_3$ | 106–107 |
| 1-73 | $CF_3$ | $CH_3$ | H | F | Cl | $SO_2CH_3$ | 144–145 |
| 1-74 | $CF_3$ | $CH_3$ | H | F | Cl | $OCHF_2$ | 84–85 |
| 1-75 | $CF_3$ | $CH_3$ | H | Cl | Cl | $NHSO_2CH_3$ | 181–182 |
| 1-76 | $CF_3$ | $CH_3$ | $CH_3$ | F | Cl | $OCH_2C^*CH$ | 107–108 |
| 1-77 | $CF_3$ | $CH_3$ | $CH_3$ | F | Cl | $OCH_2CH{=}CH_2$ | 95–96 |
| 1-78 | $CF_3$ | $CH_3$ | $CH_3$ | F | Cl | $OCH(CH_3)C^*CH$ | 77–78 |
| 1-79 | $CF_3$ | $CH_3$ | $CH_3$ | F | Cl | OH | 207–208 |
| 1-80 | $CF_3$ | $CH_3$ | $CH_3$ | F | Cl | $OC_3H_7$-i | 51–54 |
| 1-81 | $CF_3$ | $CH_3$ | H | F | Cl | CHO | 162–163 |
| 1-82 | $CF_3$ | $CH_3$ | H | F | Cl | $CH_2Br$ | 117–118 |
| 1-83 | $CF_3$ | $CH_3$ | H | F | Cl | $NHCONHC_3H_7$ | |
| 1-84 | $CF_3$ | $CH_3$ | H | F | Cl | $SO_2Cl$ | 77–78 |
| 1-85 | $CF_3$ | $CH_3$ | H | F | Cl | $SCOCH_3$ | 91–92 |
| 1-86 | $CF_3$ | $CH_3$ | H | F | $OCH_2CO_2CH_3$ | $NO_2$ | |
| 1-87 | $CF_3$ | $CH_3$ | H | F | Cl | $SCH_3$ | 147–150 |
| 1-88 | $CF_3$ | $CH_3$ | H | F | Cl | $SOCH_3$ | 147–148 |
| 1-89 | $CF_3$ | $CH_3$ | H | F | SH | $NH_2$ | |
| 1-90 | $CF_3$ | $CH_3$ | H | F | Cl | $CH_3$ | 115–116 |
| 1-91 | $CF_3$ | $CH_3$ | H | F | Cl | $SCH_2OCH_3$ | 100–102 |
| 1-92 | $CF_3$ | $NHCO_2CH_3$ | H | Cl | Cl | H | |
| 1-93 | $CF_3$ | $COCH_3$ | H | Cl | Cl | H | |
| 1-94 | $CF_3$ | H | H | F | F | H | 224–227 |

TABLE 4

| Comp. Nos. | R | R¹ | R² | R³ | R⁴ | R⁵ | m.p. (° C.) |
|---|---|---|---|---|---|---|---|
| 1-95 | $CF_3$ | H | H | Cl | Cl | H | 172–177 |
| 1-96 | $CF_3$ | H | H | F | Cl | H | |
| 1-97 | $CF_3$ | H | $CH_3$ | Cl | Cl | H | 201–202 |
| 1-98 | $CF_3$ | $CH_3$ | $CH_3$ | F | F | H | 95–96 |
| 1-99 | $CF_3$ | H | H | F | Cl | $OCH_2CO_2CH_3$ | 73–74 |
| 1-100 | $CF_3$ | $CH_3$ | H | F | F | $NO_2$ | 115–118 |
| 1-101 | $CF_3$ | $CH_3$ | H | F | SH | $NO_2$ | 141–142 |
| 1-102 | $CF_3$ | $CH_3$ | H | F | Cl | $OCH_2CO_2$-cyclopentyl | 65–66 |
| 1-103 | $CF_3$ | $CH_3$ | H | F | Cl | 2-oxy-4-chlorothiazole | 134–135 |
| 1-104 | $CF_3$ | $CH_3$ | H | F | Cl | $OCH_2CO_2C_3H_7$ | oil |
| 1-105 | $CF_3$ | $CH_3$ | H | F | Cl | $OCH_2CO_2H$ | 199–200 |
| 1-106 | $CF_3$ | $CH_3$ | H | H | Cl | $OCH_2C^*CH$ | 72–73 |
| 1-107 | $CF_3$ | $CH_3$ | H | H | Cl | $OCH_2CO_2C_2H_5$ | 108–109 |
| 1-108 | $CF_3$ | $CH_3$ | H | H | Cl | $OCH_3$ | 85–87 |
| 1-109 | $CF_3$ | $CH_3$ | H | H | Cl | OH | 165–166 |
| 1-110 | $CF_3$ | $CH_3$ | H | H | Cl | SH | 102–104 |
| 1-111 | $CF_3$ | $CH_3$ | H | H | Cl | $SC_3H_7$-i | oil |
| 1-112 | $CF_3$ | $CH_3$ | H | H | Cl | $SCH_2C^*CH$ | 93–94 |
| 1-113 | $CF_3$ | $CH_3$ | H | H | Cl | $SCH_2CO_2C_2H_5$ | 55–57 |
| 1-114 | $CF_3$ | $CH_3$ | H | H | Cl | $SCH_2CO_2CH_3$ | 83–85 |
| 1-115 | $CF_3$ | $CH_3$ | H | H | Cl | $SCH_2CO_2$-cyclopentyl | oil |
| 1-116 | $CF_3$ | $CH_3$ | H | H | Cl | $SCH(C_3H_7)CO_2C_2H_5$ | oil |
| 1-117 | $CF_3$ | $CH_3$ | H | H | Cl | $SCH_2CO_2C_2H_4OCH_3$ | 55–58 |
| 1-118 | $CF_3$ | $CH_3$ | H | H | | H | 108–109 |
| | | | | | | $OCH_2$-(4-chlorophenyl) | |
| 1-119 | $CF_3$ | $CH_3$ | H | F | Cl | CN | 180–181 |
| 1-120 | $CF_3$ | $CH_3$ | H | H | OH | H | 143–144 |
| 1-121 | $CF_3$ | $CH_3$ | H | F | Cl | $OCH(C_3H_7)CO_2C_2H_5$ | oil |
| 1-122 | $CF_3$ | $CH_3$ | H | F | Cl | $OCH(C_2H_5)C^*CH$ | 57–58 |
| 1-123 | $CF_3$ | $CH_3$ | H | Cl | Cl | $SCH_2CO_2C_5H_{11}$ | 63–64 |
| 1-124 | $CF_3$ | $CH_3$ | H | Cl | Cl | $SCH(CH_3)CO_2C_2H_5$ | 72–73 |

TABLE 5

| Comp. Nos. | R | R¹ | R² | R³ | R⁴ | R⁵ | m.p. (° C.) |
|---|---|---|---|---|---|---|---|
| 1-125 | $CF_3$ | $CH_3$ | H | Cl | Cl | $SCH(C_2H_5)CO_2C_2H_5$ | 65–67 |
| 1-126 | $CF_3$ | $CH_3$ | H | Cl | Cl | $SCH_2OCH_3$ | 59–61 |
| 1-127 | $CF_3$ | $CH_3$ | H | Cl | Cl | $SCH_2CO_2H$ | 209–211 |
| 1-128 | $CF_3$ | $CH_3$ | H | Cl | Cl | S-cyclopentyl | 108–109 |
| 1-129 | $CF_3$ | $CH_3$ | H | Cl | Cl | $SCH_2CO_2C_2H_4OC_3H_7$-i | 59–60 |

TABLE 5-continued

| Comp. Nos. | R | R¹ | R² | R³ | R⁴ | R⁵ | m.p. (° C.) |
|---|---|---|---|---|---|---|---|
| 1-130 | $CF_3$ | $CH_3$ | H | Cl | Cl | $SCH_2CO_2C_3H_7$ | 92–94 |
| 1-131 | $CF_3$ | $CH_3$ | H | Cl | Cl | 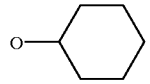 | 163–165 |
| 1-132 | $CF_3$ | $CH_3$ | H | Cl | Cl | 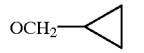 | 159–160 |
| 1-133 | $CF_3$ | $CH_3$ | H | F | Cl | 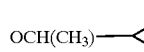 | 113–114 |
| 1-134 | $CF_3$ | $CH_3$ | H | F | Cl | $CO_2C_2H_4Br$ | 83–84 |
| 1-135 | $CF_3$ | $CH_3$ | H | F | Cl | $CH_2OH$ | 160–161 |
| 1-136 | $CF_3$ | $CH_3$ | H | F | Cl | Cl | 158–159 |
| 1-137 | $CF_3$ | $CH_3$ | H | $OC_3H_7$ | Cl | $CO_2C_2H_5$ | oil |
| 1-138 | $CF_3$ | $CH_3$ | H | F | Cl | Br | 146–148 |
| 1-139 | $CF_3$ | $CH_3$ | H | F | Cl | $CH_2CH(Cl)CO_2C_2H_5$ | oil |
| 1-140 | $CF_3$ | $CH_3$ | H | F | Cl | $N(CH_3)SO_2C_2H_5$ | oil |
| 1-141 | $CF_3$ | $CH_3$ | H | F | Cl | $CO_2H$ | 209–210 |
| 1-142 | $CF_3$ | $CH_3$ | H | F | Cl | $CO_2CH_2CO_2C_2H_5$ | oil |
| 1-143 | $CF_3$ | $CH_3$ | H | F | Cl | $CO_2CH(CH_3)CO_2C_2H_5$ | 53–55 |
| 1-144 | $CF_3$ | $CH_3$ | H | F | Cl | $CO_2Na$ | 288–290 |
| 1-145 | $CF_3$ | $CH_3$ | H | F | Cl | $CONH_2$ | 75–77 |
| 1-146 | $CF_3$ | $CH_3$ | H | F | H | $OCH_3$ | 104–105 |
| 1-147 | $CF_3$ | $CH_3$ | H | F | Cl | $CONHSO_2CH_3$ | 145–147 |
| 1-148 | $CF_3$ | $CH_3$ | H | F | Cl | $OCH_2CO_2C_4H_9$ | oil |
| 1-149 | $CF_3$ | $CH_3$ | H | F | Cl | $OCH_2CO_2C_6H_{13}$ | oil |
| 1-150 | $CF_3$ | $CH_3$ | H | F | Cl | $OC_2H_5$ | 107–109 |
| 1-151 | $CF_3$ | $CH_3$ | H | F | Cl | $OCH_2C(CH_3)=CH_2$ | 86–87 |
| 1-152 | $CF_3$ | $CH_3$ | H | F | Cl | $OCH_2CH=CHCH_3$ | 72–74 |
| 1-153 | $CF_3$ | $CH_3$ | H | F | Cl | $OCO_2CH_3$ | 116–118 |

TABLE 6

| Comp. Nos. | R | R¹ | R² | R³ | R⁴ | R⁵ | m.p. (° C.) |
|---|---|---|---|---|---|---|---|
| 1-154 | $CF_3$ | $CH_3$ | H | F | Cl | $OC_3H_7$ | 85–87 |
| 1-155 | $CF_3$ | $CH_3$ | H | F | Cl | $OCH_2CF_3$ | 82–84 |
| 1-156 | $CF_3$ | $CH_3$ | H | Cl | Cl | I | 145–147 |
| 1-157 | $CF_3$ | $CH_3$ | H | F | Cl | $CO_2CH_3$ | 98–99 |
| 1-158 | $CF_3$ | $CH_3$ | H | F | Cl | $CO_2C_3H_7$ | 63–64 |
| 1-159 | $CF_3$ | $CH_3$ | H | F | Cl | 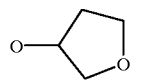 | oil |
| 1-160 | $CF_3$ | $CH_3$ | H | F | Cl | $OCH_2$-cyclopropyl | 56–57 |
| 1-161 | $CF_3$ | $CH_3$ | H | F | Cl | $OCH(CH_3)$-cyclopropyl | oil |
| 1-162 | $CF_3$ | $CH_3$ | H | F | Cl | (tetrahydrofuran-3-yl)O | 118–120 |
| 1-163 | $CF_3$ | $CH_3$ | H | F | Cl | $OC_2H_4OC_2H_5$ | 65–66 |
| 1-164 | $CF_3$ | $CH_3$ | H | F | Cl | CH=NOH | 225–227 |
| 1-165 | $CF_3$ | $CH_3$ | H | F | Cl | 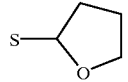 | 113–114 |
| 1-166 | $CF_3$ | $CH_3$ | H | F | Cl | $OC_4H_9$ | 60–61 |
| 1-167 | $CF_3$ | $CH_3$ | H | F | Cl | $OCH(CH_3)C_2H_5$ | oil |
| 1-168 | $CF_3$ | $CH_3$ | H | F | Cl | $OCH_2CH(CH_3)_2$ | 85–86 |
| 1-169 | $CF_3$ | $CH_3$ | H | F | Cl | $OC_2H_4OC_3H_7$-i | 61–63 |
| 1-170 | $CF_3$ | $CH_3$ | H | F | Cl | $OC_2H_4OCH_3$ | 106–108 |
| 1-171 | $CF_3$ | $CH_3$ | H | F | Cl | $OC_2H_4Cl$ | 85–86 |
| 1-172 | $CF_3$ | $CH_3$ | H | F | Cl | $OC_2H_4F$ | 92–93 |
| 1-173 | $CF_3$ | $CH_3$ | H | F | Cl | $OCH_2CHF_2$ | 79–80 |
| 1-174 | $CF_3$ | $CH_3$ | H | F | Cl | $OCH_2CH=C(CH_3)_2$ | oil |
| 1-175 | $CF_3$ | $CH_3$ | H | F | Cl | $OCH_2C*CCH_3$ | 77–78 |
| 1-176 | $CF_3$ | $CH_3$ | H | F | Cl | $OCH(CH_3)CN$ | oil |

TABLE 6-continued

| Comp. Nos. | R | R¹ | R² | R³ | R⁴ | R⁵ | m.p. (° C.) |
|---|---|---|---|---|---|---|---|
| 1-177 | CF₃ | CH₃ | H | F | Cl | 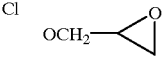 | 100–102 |
| 1-178 | CF₃ | NH₂ | H | F | Cl | OCH₂C*CH | 127–129 |
| 1-179 | CF₃ | NH₂ | H | F | Cl | OCH₃ | 187–188 |

TABLE 6-continued

| Comp. Nos. | R | R¹ | R² | R³ | R⁴ | R⁵ | m.p. (° C.) |
|---|---|---|---|---|---|---|---|
| 1-180 | CF₃ | CH₃ | H | F | Cl | 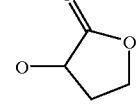 | 102–103 |
| 1-181 | CF₃ | CH₃ | H | F | Cl | OCH₂OC₂H₅ | oil |

TABLE 7

| Comp. Nos. | R | R¹ | R² | R³ | R⁴ | R⁵ | m.p. (° C.) |
|---|---|---|---|---|---|---|---|
| 1-182 | CF₃ | CH₃ | H | F | Cl | OCH(CH₃)CH=CH₂ | oil |
| 1-183 | CF₃ | CH₃ | H | F | Cl | 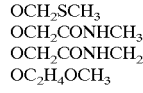 | 70–72 |
| 1-184 | CF₃ | CH₃ | H | F | Cl | (cyclopentyl-CO₂–) | 102–103 |
| 1-185 | CF₃ | CH₃ | H | H | Cl | Cl | 101–103 |
| 1-186 | CF₃ | CH₃ | H | Cl | Cl | Cl | 98–101 |
| 1-187 | CF₃ | CH₃ | H | F | Cl | CH=NOC₂H₅ | 63–65 |
| 1-188 | CF₃ | CH₃ | H | F | Cl | CH=NOC₃H₇ | 67–68 |
| 1-189 | CF₃ | CH₃ | H | F | Cl | CH=NOC₃H₇-i | 61–63 |
| 1-190 | CF₃ | CH₃ | H | F | Cl | COCH₃ | 89–90 |
| 1-191 | CF₃ | CH₃ | H | F | Cl | CH=NOCH₂CO₂C₂H₅ | 84–86 |
| 1-192 | CF₃ | CH₃ | H | F | Cl | C(CH₃)=NOCH₃ | 53–55 |
| 1-193 | CF₃ | CH₃ | H | F | Cl | CH(OH)C₃H₇ | 120–122 |
| 1-194 | CF₃ | CH₃ | H | F | Cl | COC₃H₇ | oil |
| 1-195 | CF₃ | CH₃ | H | F | Cl | CH(OH)CH(CH₃)₂ | oil |
| 1-196 | CF₃ | CH₃ | H | F | Cl | COC₃H₇-i | 58–59 |
| 1-197 | CF₃ | CH₃ | H | F | Cl | CH(OH)CH=CH₂ | 103–104 |
| 1-198 | CF₃ | CH₃ | H | F | Cl | COCH=CH₂ | oil |
| 1-199 | CF₃ | CH₃ | H | F | Cl | CH₂OCH₂C*CH | 99–101 |
| 1-200 | CF₃ | CH₃ | H | F | Cl | CH₂OCH₂OCH₃ | oil |
| 1-201 | CF₃ | CH₃ | H | F | Cl | (cyclopentyl-CH₂O–) | oil |
| 1-202 | CF₃ | CH₃ | H | F | Cl | CH(OH)C*CH | 88–90 |
| 1-203 | CF₃ | CH₃ | H | F | Cl | OCH₂C(Cl)=CH₂ | 94–96 |
| 1-204 | CF₃ | CH₃ | H | F | Cl | OC₃H₆F | 91–93 |
| 1-205 | CF₃ | CH₃ | H | Cl | Cl | OCH₃ | 164–165 |
| 1-206 | CF₃ | CH₃ | H | Cl | Cl | OCH₂OC₂H₅ | 68–69 |
| 1-207 | CF₃ | CH₃ | H | F | Cl | OCH₂OC₂H₄OCH₃ | oil |
| 1-208 | CF₃ | CH₃ | H | F | Cl | OCH₂SCH₃ | oil |
| 1-209 | CF₃ | CH₃ | H | F | Cl | OCH₂CONHCH₃ | 160–161 |
| 1-210 | CF₃ | CH₃ | H | F | Cl | OCH₂CONHCH₂C*CH | 149–150 |
| 1-211 | CF₃ | CH₃ | H | Cl | Cl | OC₂H₄OCH₃ | 132–134 |
| 1-212 | CF₃ | CH₃ | H | Cl | Cl | (tetrahydrofuran-2-yloxy) | 109–111 |

TABLE 8

| Comp. Nos. | R | R¹ | R² | R³ | R⁴ | R⁵ | m.p. (° C.) |
|---|---|---|---|---|---|---|---|
| 1-213 | $CF_3$ | $CH_3$ | H | Cl | Cl | $SCH_2OC_2H_5$ | oil |
| 1-214 | $CF_3$ | $CH_3$ | H | Cl | Cl | $SC_2H_4OCH_3$ | 76–78 |
| 1-215 | $CF_3$ | $CH_3$ | H | Cl | Cl | $SC_2H_4OC_2H_5$ | 49–51 |
| 1-216 | $CF_3$ | $CH_3$ | H | Cl | Cl | $SCH_2SCH_3$ | 111–112 |
| 1-217 | $CF_3$ | $CH_3$ | H | Cl | Cl | $SC_2H_4SCH_3$ | 92–93 |
| 1-218 | $CF_3$ | $CH_3$ | H | Cl | Cl | 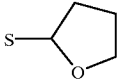 | 160–162 |
| 1-219 | $CF_3$ | $CH_3$ | H | Cl | Cl | $SCF_3$ | 73–75 |
| 1-220 | $CF_3$ | $CH_3$ | H | Cl | Cl | $SCH(C_2H_5)CH_2OCH_3$ | oil |
| 1-221 | $CF_3$ | $NHCH_3$ | H | F | Cl | $OCH_2C^*CH$ | |
| 1-222 | $CF_3$ | $NHC_2H_5$ | H | F | Cl | $OCH_2C^*CH$ | |
| 1-223 | $CF_3$ | $NHCHF_2$ | H | F | Cl | $OCH_2C^*CH$ | |
| 1-224 | $CF_3$ | $N(CH_3)_2$ | H | F | Cl | $OCH_2C^*CH$ | |
| 1-225 | $CF_3$ | $N=C(CH_3)_2$ | H | F | Cl | $OCH_2C^*CH$ | 117–118 |
| 1-226 | $CF_3$ | 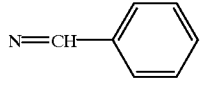 | H | F | Cl | $OCH_2C^*CH$ | 135–136 |
| 1-227 | $CF_3$ | $N=CHN(CH_3)_2$ | H | F | Cl | $OCH_2C^*CH$ | 119–120 |
| 1-228 | $CF_3$ | $N=CHC_3H_7$-i | H | F | Cl | $OCH_2C^*CH$ | 67–69 |
| 1-229 | $CF_3$ | NHCHO | H | F | Cl | $OCH_2C^*CH$ | |
| 1-230 | $CF_3$ | $NHCOCH_3$ | H | F | Cl | $OCH_2C^*CH$ | 165–167 |
| 1-231 | $CF_3$ | $NHSO_2CH_3$ | H | F | Cl | $OCH_2C^*CH$ | 162–164 |
| 1-232 | $CF_3$ | $N(COCH_3)_2$ | H | F | Cl | $OCH_2C^*CH$ | 179–181 |
| 1-233 | $CF_3$ | $N(SO_2CH_3)_2$ | H | F | Cl | $OCH_2C^*CH$ | |
| 1-234 | $CF_3$ | $NHCOC_3H_7$-i | H | F | Cl | $OCH_2C^*CH$ | |
| 1-235 | $CF_3$ | $NHCO_2C_2H_5$ | H | F | Cl | $OCH_2C^*CH$ | |
| 1-236 | $CF_3$ | $NHCO_2CH_3$ | H | F | Cl | $OCH_2C^*CH$ | 182–184 |
| 1-237 | $CF_3$ | $NHCO_2C_4H_9$-t | H | F | Cl | $OCH_2C^*CH$ | |
| 1-238 | $CF_3$ | $CH_3$ | H | Cl | Cl | $SCH(C_2H_5)CO_2CH_3$ | oil |
| 1-239 | $CF_3$ | $CH_3$ | H | Cl | Cl | $SCH(C_2H_5)CO_2C_3H_7$ | oil |
| 1-240 | $CF_3$ | $CH_3$ | H | Cl | Cl | $SCH(C_2H_5)CO_2C_3H_7$-i | oil |
| 1-241 | $CF_3$ | $CH_3$ | H | Cl | Cl | $SCH(C_3H_7)CO_2CH_3$ | oil |
| 1-242 | $CF_3$ | $CH_3$ | H | Cl | Cl | $SCH(C_3H_7)CO_2C_3H_7$ | oil |
| 1-243 | $CF_3$ | $CH_3$ | H | Cl | Cl | $SCH(C_3H_7)CO_2C_3H_7$-i | oil |
| 1-244 | $CF_3$ | $CH_3$ | H | Cl | F | $OCH_2CF_2CF_3$ | |

TABLE 9

| Comp. Nos. | R | R¹ | R² | R³ | R⁴ | R⁵ | m.p. (° C.) |
|---|---|---|---|---|---|---|---|
| 1-245 | $CF_3$ | $CH_3$ | H | Cl | F | $OCH_2CF_2CHF_2$ | 65–67 |
| 1-246 | $CF_3$ | $CH_3$ | H | Cl | F | $OCH_2C_3F_7$ | |
| 1-247 | $CF_3$ | $CH_3$ | H | Cl | F | $OCH(CH_3)CF_3$ | |
| 1-248 | $CF_3$ | $CH_3$ | H | Cl | F | $OCH(CF_3)_2$ | |
| 1-249 | $CF_3$ | $CH_3$ | H | Cl | F | $OCH(CH_3)C_3F_7$ | |
| 1-250 | $CF_3$ | $CH_3$ | H | Cl | F | $OC_2H_4CF_3$ | |
| 1-251 | $CF_3$ | $CH_3$ | H | F | F | $OCH_3$ | 141–142 |
| 1-252 | $CF_3$ | $CH_3$ | H | F | F | $OCH_2C^*CH$ | 121–122 |
| 1-253 | $CF_3$ | $CH_3$ | H | F | F | $OCH(CH_3)C^*CH$ | 68–69 |
| 1-254 | $CF_3$ | $CH_3$ | H | F | F | $OCH(C_2H_5)C^*CH$ | 78–79 |
| 1-255 | $CF_3$ | $CH_3$ | H | F | F | OH | 193–195 |
| 1-256 | $CF_3$ | $CH_3$ | H | Cl | Cl | $SO_2NHCH_3$ | 59–61 |
| 1-257 | $CF_3$ | $CH_3$ | H | H | Cl | $SO_2NHCH_3$ | 154–155 |
| 1-258 | $CF_3$ | $CH_3$ | H | Cl | Cl | 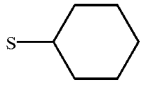 | 117–119 |
| 1-259 | $CF_3$ | $N(CO_2CH_3)_2$ | H | F | Cl | $OCH_2C^*CH$ | 146–148 |

TABLE 9-continued

| Comp. Nos. | R | $R^1$ | $R^2$ | $R^3$ | $R^4$ | $R^5$ | m.p. (° C.) |
|---|---|---|---|---|---|---|---|
| 1-260 | $CF_3$ | $CH_3$ | H | Cl | Cl | 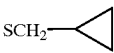 | 108–109 |
| 1-261 | $CF_3$ | $CH_3$ | H | Cl | Cl | 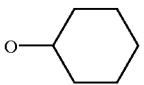 | 96–97 |
| 1-262 | $CF_3$ | $CH_3$ | H | Cl | Cl | $OCH_2C(CH_3)=CH_2$ | 124–126 |
| 1-263 | $CF_3$ | $CH_3$ | H | Cl | Cl | $OCH_2CH=CHCH_3$ | 93–95 |
| 1-264 | $CF_3$ | $CH_3$ | H | Cl | Cl | 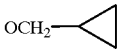 | 99–100 |
| 1-265 | $CF_3$ | $CH_3$ | H | Cl | Cl | 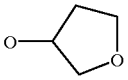 | 153–154 |
| 1-266 | $CF_3$ | $CH_3$ | H | Cl | Cl | $OC_2H_4OC_2H_5$ | 108–109 |
| 1-267 | $CF_3$ | $CH_3$ | H | Cl | Cl | $OC_2H_4OC_3H_7\text{-i}$ | 85–87 |
| 1-268 | $CF_3$ | $CH_3$ | H | Cl | Cl | $OCH_2CH=C(CH_3)_2$ | 117–118 |
| 1-269 | $CF_3$ | $CH_3$ | H | Cl | Cl | $OC_2H_5$ | 117–118 |
| 1-270 | $CF_3$ | $CH_3$ | H | Cl | Cl | $OC_3H_7$ | 77–78 |
| 1-271 | $CF_3$ | $CH_3$ | H | Cl | Cl | $OCH(C_2H_5)C*CH$ | 122–123 |
| 1-272 | $CF_3$ | $CH_3$ | H | F | CN | $OCH_2C*CH$ | |
| 1-273 | $CF_3$ | $CH_3$ | H | Cl | Cl | $SCH(C_2H_5)CH_2OC_2H_5$ | oil |
| 1-274 | $CF_3$ | $CH_3$ | H | Cl | Cl | $SCH(C_2H_5)CH_2OC_3H_7$ | |

TABLE 10

| Comp. Nos. | R | $R^1$ | $R^2$ | $R^3$ | $R^4$ | $R^5$ | m.p. (° C.) |
|---|---|---|---|---|---|---|---|
| 1-275 | $CF_3$ | $CH_3$ | H | Cl | Cl | $SCH(C_2H_5)CH_2OC_3H_7\text{-i}$ | |
| 1-276 | $CF_3$ | $CH_3$ | H | F | Cl | $CO_2C(CH_3)_2CO_2C_2H_5$ | 168–170 |
| 1-277 | $CF_3$ | $CH_3$ | H | Cl | Cl | $OC_2H_4CH_2F$ | |
| 1-278 | $CF_3$ | $CH_3$ | H | Cl | OH | $NO_2$ | |
| 1-279 | $CF_3$ | $CH_3$ | H | Cl | OH | $NH_2$ | |
| 1-280 | $CF_3$ | $CH_3$ | H | Cl | $OC_2H_4CO_2C_2H_5$ | $NO_2$ | |
| 1-281 | $CF_3$ | $CH_3$ | H | Cl | Cl | $SC_2H_4OC_3H_7\text{-i}$ | oil |
| 1-282 | $CF_3$ | $CH_3$ | H | Cl | Cl | $SCH(C_3H_7)CH_2OCH_3$ | |
| 1-283 | $CF_3$ | $CH_3$ | H | Cl | Cl | $SCH(C_3H_7)CH_2OC_2H_5$ | |
| 1-284 | $CF_3$ | $CH_3$ | H | Cl | Cl | $SCH(C_3H_7)CH_2OC_3H_7$ | |
| 1-285 | $CF_3$ | $CH_3$ | H | Cl | Cl | $SCH(C_3H_7)CH_2OC_3H_7\text{-i}$ | |
| 1-286 | $CF_3$ | $CH_3$ | H | Cl | Cl | $SCH(C_3H_7)CH_2OH$ | 131–132 |

TABLE 11

[I-1-1']

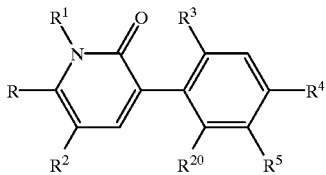

| Comp. Nos. | R | $R^1$ | $R^2$ | $R^3$ | $R^4$ | $R^5$ | $R^{20}$ | m.p. (° C.) |
|---|---|---|---|---|---|---|---|---|
| 1'-1 | $CF_3$ | $CH_3$ | H | F | Cl | H | $OCH_3$ | 113–114 |
| 1'-2 | $CF_3$ | $CH_3$ | H | F | Cl | H | OH | 174–175 |
| 1'-3 | $CF_3$ | $CH_3$ | H | F | Cl | H | $OCH_2CH=CH_2$ | 97–98 |
| 1'-4 | $CF_3$ | $CH_3$ | H | F | Cl | H | $OCH_2C*CH$ | 91–93 |
| 1'-5 | $CF_3$ | $CH_3$ | H | F | Cl | H | $OCH(CH_3)C*CH$ | 102–103 |
| 1'-6 | $CF_3$ | $CH_3$ | H | F | Cl | H | $OCH(C_2H_5)C*CH$ | 106–107 |

TABLE 12

[I-1-2]

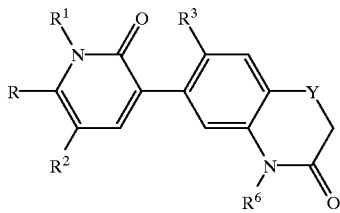

| Comp. Nos. | R | $R^1$ | $R^2$ | $R^3$ | Y | $R^6$ | m.p. (° C.) |
|---|---|---|---|---|---|---|---|
| 2-1 | $CF_3$ | $CH_3$ | H | F | O | $CH_2C*CH$ | 166–168 |
| 2-2 | $CF_3$ | $CH_3$ | $CH_3$ | F | O | $CH_2C*CH$ | 171–172 |
| 2-3 | $CF_3$ | $NH_2$ | H | F | O | $CH_2C*CH$ | |
| 2-4 | $CF_3$ | $CH_3$ | H | F | O | H | 216–218 |
| 2-5 | $CF_3$ | $CH_3$ | $CH_3$ | F | O | H | |
| 2-6 | $CF_3$ | $NH_2$ | H | F | O | H | |
| 2-7 | $CF_3$ | $CH_3$ | H | F | O | $CH_2CH=CH_2$ | 97–98 |
| 2-8 | $CF_3$ | $CH_3$ | $CH_3$ | F | O | $CH_2CH=CH_2$ | |
| 2-9 | $CF_3$ | $NH_2$ | H | F | O | $CH_2CH=CH_2$ | |
| 2-10 | $CF_3$ | $CH_3$ | H | F | O | $C_3H_7$ | 102–103 |
| 2-11 | $CF_3$ | $CH_3$ | H | F | O | $CH_2C(CH_3)=CH_2$ | 136–137 |
| 2-12 | $CF_3$ | $CH_3$ | H | F | O | $CH_2CH=CHCH_3$ | 107–108 |
| 2-13 | $CF_3$ | $CH_3$ | H | F | O | $CH_2C(Cl)=CH_2$ | 142–143 |
| 2-14 | $CF_3$ | $CH_3$ | H | F | O | $CH_2CH=CHCl$ | 124–126 |
| 2-15 | $CF_3$ | $CH_3$ | H | F | O | $C_2H_5$ | 158–159 |
| 2-16 | $CF_3$ | $CH_3$ | H | F | O | $CH_3$ | 211–212 |
| 2-17 | $CF_3$ | $CH_3$ | H | F | O | $CH_2CN$ | 195–197 |
| 2-18 | $CF_3$ | $CH_3$ | H | F | O | $CH_2CO_2C_2H_5$ | 127–128 |
| 2-19 | $CF_3$ | $CH_3$ | H | F | O | $CH_2OCH_3$ | 173–174 |
| 2-20 | $CF_3$ | $CH_3$ | H | F | O | $CH_2$—(epoxide) | 107–109 |
| 2-21 | $CF_3$ | $CH_3$ | H | F | S | $CH_2C*CH$ | 171–173 |
| 2-22 | $CF_3$ | $CH_3$ | H | F | S | H | 258–260 |
| 2-23 | $CF_3$ | $CH_3$ | H | F | NH | $CH_2C*CH$ | |
| 2-24 | $CF_3$ | $CH_3$ | H | F | NH | H | |
| 2-25 | $CF_3$ | $CH_3$ | H | Cl | O | $CH_2C*CH$ | 209–210 |
| 2-26 | $CF_3$ | $CH_3$ | H | Cl | O | $CH_2CH=CH_2$ | 184–186 |
| 2-27 | $CF_3$ | $CH_3$ | H | Cl | O | H | 235–236 |
| 2-28 | $CF_3$ | $CH_3$ | H | F | O | $CH(CH_3)C*CH$ | |

TABLE 13

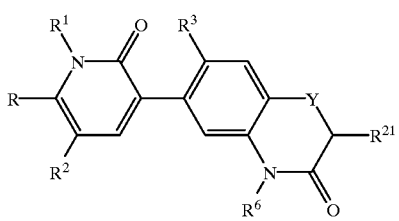

| Comp. Nos. | R | R¹ | R² | R³ | Y | R⁶ | m.p. (° C.) |
|---|---|---|---|---|---|---|---|
| 2-29 | $CF_3$ | $CH_3$ | H | H | O | $CH_2C*CH$ | 75–76 |
| 2-30 | $CF_3$ | $CH_3$ | H | H | O | H | 216–217 |
| 2-31 | $CF_3$ | $CH_3$ | H | H | O | $CH_2CH=CH_2$ | 100–101 |
| 2-32 | $CF_3$ | $CH_3$ | H | F | O | $CH_2$–phenyl | 145–146 |

TABLE 14

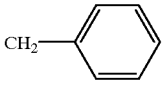

[I-1-2']

| Comp. Nos. | R | R¹ | R² | R³ | Y | R²¹ | R⁶ | m.p. (° C.) |
|---|---|---|---|---|---|---|---|---|
| 2'-1 | $CF_3$ | $CH_3$ | H | Cl | O | CH3 | $CH_2C*CH$ | 203–204 |
| 2'-2 | $CF_3$ | $CH_3$ | H | Cl | O | CH3 | H | |

TABLE 15

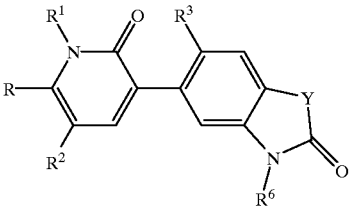

[I-1-3]

| Comp. Nos. | R | R¹ | R² | R³ | Y | R⁶ | m.p. (° C.) |
|---|---|---|---|---|---|---|---|
| 3-1 | $CF_3$ | $CH_3$ | H | F | S | $CH_2C*CH$ | 150–151 |
| 3-2 | $CF_3$ | $CH_3$ | H | F | S | H | |
| 3-3 | $CF_3$ | $CH_3$ | $CH_3$ | F | S | $CH_2C*CH$ | |
| 3-4 | $CF_3$ | $CH_3$ | $CH_3$ | F | S | H | |
| 3-5 | $CF_3$ | $CH_3$ | H | F | S | $CH_2CH=CH_2$ | 143–145 |
| 3-6 | $CF_3$ | $CH_3$ | H | F | S | $CH_3$ | 173–174 |
| 3-7 | $CF_3$ | $CH_3$ | H | F | S | $C_2H_5$ | 169–171 |
| 3-8 | $CF_3$ | $CH_3$ | H | F | S | $C_3H_7$ | |
| 3-9 | $CF_3$ | $CH_3$ | H | Cl | O | $CH_2C*CH$ | 187–189 |
| 3-10 | $CF_3$ | $CH_3$ | H | F | NH | $CH_2C*CH$ | |
| 3-11 | $CF_3$ | $CH_3$ | H | Cl | S | $CH_2C*CH$ | |
| 3-12 | $CF_3$ | $CH_3$ | H | Cl | S | $CH_2CH=CH_2$ | |
| 3-13 | $CF_3$ | $CH_3$ | H | Cl | S | $CH_3$ | |
| 3-14 | $CF_3$ | $CH_3$ | H | Cl | S | $C_2H_5$ | |
| 3-15 | $CF_3$ | $CH_3$ | H | Cl | S | $C_3H_7$ | |

TABLE 15-continued

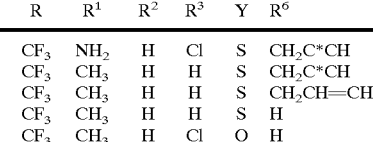

[I-1-3]

| Comp. Nos. | R | R¹ | R² | R³ | Y | R⁶ | m.p. (° C.) |
|---|---|---|---|---|---|---|---|
| 3-16 | $CF_3$ | $NH_2$ | H | Cl | S | $CH_2C*CH$ | |
| 3-17 | $CF_3$ | $CH_3$ | H | H | S | $CH_2C*CH$ | |
| 3-18 | $CF_3$ | $CH_3$ | H | H | S | $CH_2CH=CH_2$ | |
| 3-19 | $CF_3$ | $CH_3$ | H | H | S | H | |
| 3-20 | $CF_3$ | $CH_3$ | H | Cl | O | H | 263–265 |

TABLE 16

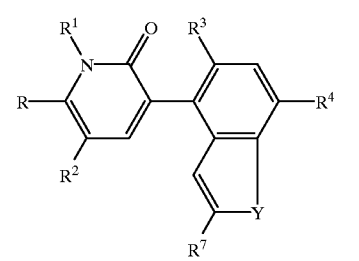

[I-1-4]

| Comp. Nos. | R | R¹ | R² | R³ | R⁴ | Y | R⁷ | m.p. (° C.) |
|---|---|---|---|---|---|---|---|---|
| 4-1 | $CF_3$ | $CH_3$ | H | F | Cl | O | $CH_3$ | 129–130 |
| 4-2 | $CF_3$ | $CH_3$ | H | F | Cl | O | $C_2H_5$ | 115–117 |
| 4-3 | $CF_3$ | $CH_3$ | H | F | Cl | O | $C_3H_7$ | 143–145 |
| 4-4 | $CF_3$ | $CH_3$ | H | F | Cl | O | $CH_2OCH_3$ | 136–137 |
| 4-5 | $CF_3$ | $CH_3$ | H | F | Cl | O | $CH_2OH$ | 145–147 |
| 4-6 | $CF_3$ | $CH_3$ | H | F | Cl | O | $CO_2C_2H_5$ | 118–120 |
| 4-7 | $CF_3$ | $CH_3$ | H | F | Cl | O | $CH_2Br$ | 142–144 |
| 4-8 | $CF_3$ | $CH_3$ | $CH_3$ | F | Cl | O | $CH_3$ | |
| 4-9 | $CF_3$ | $CH_3$ | $CH_3$ | F | Cl | O | $C_2H_5$ | |
| 4-10 | $CF_3$ | $CH_3$ | H | Cl | Cl | O | $CH_3$ | 134–135 |
| 4-11 | $CF_3$ | $CH_3$ | H | Cl | Cl | O | $C_2H_5$ | 78–80 |
| 4-12 | $CF_3$ | $CH_3$ | H | Cl | Cl | O | $C_3H_7$ | 143–144 |
| 4-13 | $CF_3$ | $CH_3$ | H | Cl | Cl | O | $CH_2OCH_3$ | 177–179 |
| 4-14 | $CF_3$ | $CH_3$ | H | Cl | Cl | O | $CH_2OH$ | 32–33 |
| 4-15 | $CF_3$ | $CH_3$ | H | Cl | Cl | O | $CO_2C_2H_5$ | |
| 4-16 | $CF_3$ | $CH_3$ | H | Cl | Cl | O | $CH_2Br$ | 149–151 |
| 4-17 | $CF_3$ | $CH_3$ | $CH_3$ | Cl | Cl | O | $CH_3$ | |
| 4-18 | $CF_3$ | $CH_3$ | $CH_3$ | Cl | Cl | O | $C_2H_5$ | |
| 4-19 | $CF_3$ | $CH_3$ | H | F | Cl | S | $CH_3$ | |
| 4-20 | $CF_3$ | $CH_3$ | H | F | Cl | S | $C_2H_5$ | |
| 4-21 | $CF_3$ | $CH_3$ | H | F | Cl | NH | $CH_3$ | |
| 4-22 | $CF_3$ | $CH_3$ | H | F | Cl | NH | $C_2H_5$ | |
| 4-23 | $CF_3$ | $NH_2$ | H | F | Cl | O | $C_2H_5$ | |
| 4-24 | $CF_3$ | $CH_3$ | H | H | Cl | O | $CH_3$ | 149–151 |
| 4-25 | $CF_3$ | $CH_3$ | H | H | Cl | O | $C_2H_5$ | |
| 4-26 | $CF_3$ | $CH_3$ | H | F | Cl | O | $CO_2H$ | 233–235 |
| 4-27 | $CF_3$ | $CH_3$ | H | F | Cl | O | $CHBr_2$ | 107–109 |

TABLE 17

| Comp. Nos. | R | $R^1$ | $R^2$ | $R^3$ | $R^4$ | Y | $R^7$ | m.p. (° C.) |
|---|---|---|---|---|---|---|---|---|
| 4-28 | $CF_3$ | $CH_3$ | H | F | Cl | 0 | H | 178–179 |
| 4-29 | $CF_3$ | $CH_3$ | H | Cl | Cl | 0 | $CHBr_2$ | 110–112 |
| 4-30 | $CF_3$ | $CH_3$ | M | Cl | Cl | 0 | $CH_2OC_2H_5$ | 155–157 |
| 4-31 | $CF_3$ | $CH_3$ | H | F | Cl | 0 | $CH_2OC_2H_5$ | 78–80 |
| 4-32 | $CF_3$ | $CH_3$ | H | F | Cl | 0 | $CH_2OC_3H_7$ | 62–63 |
| 4-33 | $CF_3$ | $CH_3$ | H | F | Cl | 0 | $CH_2OC_3H_7$-i | 83–84 |
| 4-34 | $CF_3$ | $CH_3$ | H | F | Cl | 0 | $CH(CH_3)Br$ | 141–143 |
| 4-35 | $CF_3$ | $CH_3$ | H | F | Cl | 0 | $CH(CH_3)OCH_3$ | 93–94 |
| 4-36 | $CF_3$ | $CH_3$ | H | F | Cl | 0 | $CH(CH_3)OC_2H_5$ | Unmeasurable |
| 4-37 | $CF_3$ | $CH_3$ | H | F | Cl | 0 | $CH(CH_3)OC_3H_7$ | oil |
| 4-38 | $CF_3$ | $CH_3$ | H | F | Cl | 0 | $CH(C_2H_5)Br$ | 110–111 |
| 4-39 | $CF_3$ | $CH_3$ | H | F | Cl | 0 | $CH(C_2H_5)OCH_3$ | oil |
| 4-40 | $CF_3$ | $CH_3$ | H | Cl | Cl | 0 | $CBr_3$ | 225–227 |
| 4-41 | $CF_3$ | $CH_3$ | H | Cl | Cl | 0 | $CO_2H$ | 278–280 |
| 4-42 | $CF_3$ | $CH_3$ | H | F | Cl | 0 | $CH(CH_3)SO_2CH_3$ | 104–106 |
| 4-43 | $CF_3$ | $CH_3$ | H | F | Cl | 0 | $CH_2SO_2CH_3$ | 158–160 |
| 4-44 | $CF_3$ | $CH_3$ | H | F | Cl | 0 | $CH_2SCH_3$ | 169–171 |
| 4-45 | $CF_3$ | $CH_3$ | H | F | Cl | 0 | $CH(CH_3)OH$ | Unmeasurable |
| 4-46 | $CF_3$ | $CH_3$ | H | F | Cl | 0 | CHO | oil |
| 4-47 | $CF_3$ | $CH_3$ | H | F | Cl | 0 | $CH_2SOCH_3$ | 131–133 |
| 4-48 | $CF_3$ | $CH_3$ | H | F | Cl | 0 | $CH(CH_3)SCH_3$ | 83–85 |
| 4-49 | $CF_3$ | $CH_3$ | H | F | Cl | 0 | $CH(C_2H_5)OC_2H_5$ | oil |
| 4-50 | $CF_3$ | $CH_3$ | H | Cl | Cl | 0 | $CH(CH_3)OH$ | 129–131 |
| 4-51 | $CF_3$ | $CH_3$ | H | Cl | Cl | 0 | $CH(CH_3)OCH_3$ | 152–153 |
| 4-52 | $CF_3$ | $CH_3$ | H | Cl | Cl | 0 | $CH(CH_3)OC_2H_5$ | 88–89 |
| 4-53 | $CF_3$ | $CH_3$ | H | Cl | Cl | 0 | $CH(C_2H_5)OCH_3$ | 109–110 |
| 4-54 | $CF_3$ | $CH_3$ | H | Cl | Cl | 0 | $CH(C_2H_5)OC_2H_5$ | 91–92 |
| 4-55 | $CF_3$ | $CH_3$ | H | Cl | Cl | 0 | $CH(C_2H_5)OH$ | 148–150 |
| 4-56 | $CF_3$ | $CH_3$ | H | F | Cl | 0 | $CH(C_2H_5)SCH_3$ | 88–90 |
| 4-57 | $CF_3$ | $CH_3$ | H | F | Cl | 0 | $CH(C_2H_5)SOCH_3$ | 125–127 |
| 4-58 | $CF_3$ | $CH_3$ | H | F | Cl | 0 | $CH(C_2H_5)SO_2CH_3$ | 146–148 |
| 4-59 | $CF_3$ | $CH_3$ | H | F | Cl | 0 | $CH(CH_3)SOCH_3$ | Unmeasurable |
| 4-60 | $CF_3$ | $CH_3$ | H | F | Cl | 0 | $CH(C_2H_5)OH$ | 103–105 |

TABLE 18

| Comp. Nos. | R | $R^1$ | $R^2$ | $R^3$ | $R^4$ | Y | $R^7$ | m.p. (° C.) |
|---|---|---|---|---|---|---|---|---|
| 4-61 | $CF_3$ | $CH_3$ | H | F | F | 0 | $CH_3$ | 187–188 |
| 4-62 | $CF_3$ | $CH_3$ | H | F | F | 0 | $C_2H_5$ | 120–121 |
| 4-63 | $CF_3$ | $CH_3$ | H | F | F | 0 | $CH_2Br$ | 132–134 |
| 4-64 | $CF_3$ | $CH_3$ | H | F | F | 0 | $CH_2OCH_3$ | 98–100 |
| 4-65 | $CF_3$ | $CH_3$ | H | F | F | 0 | $CH_2OC_2H_5$ | 88–89 |
| 4-66 | $CF_3$ | $CH_3$ | H | F | F | 0 | $CH_2SCH_3$ | |
| 4-67 | $CF_3$ | $CH_3$ | H | F | F | 0 | $CH_2SC_2H_5$ | |
| 4-68 | $CF_3$ | $CH_3$ | H | F | F | 0 | $CH_2SOCH_3$ | |
| 4-69 | $CF_3$ | $CH_3$ | H | F | F | 0 | $CH_2SOC_2H_5$ | |
| 4-70 | $CF_3$ | $CH_3$ | H | F | F | 0 | $CH_2SO_2CH_3$ | |
| 4-71 | $CF_3$ | $CH_3$ | H | F | F | 0 | $CH_2SO_2C_2H_5$ | |
| 4-72 | $CF_3$ | $CH_3$ | H | F | F | 0 | $CH(CH_3)Br$ | 131–133 |
| 4-73 | $CF_3$ | $CH_3$ | H | F | F | 0 | $CH(CH_3)OCH_3$ | 86–87 |
| 4-74 | $CF_3$ | $CH_3$ | H | F | F | 0 | $CH(CH_3)OC_2H_5$ | oil |
| 4-75 | $CF_3$ | $CH_3$ | H | F | F | 0 | $CH(CH_3)SCH_3$ | 109–110 |
| 4-76 | $CF_3$ | $CH_3$ | H | F | F | 0 | $CH(CH_3)SC_2H_5$ | 148–150 |
| 4-77 | $CF_3$ | $CH_3$ | H | F | F | 0 | $CH(CH_3)SOCH_3$ | 119–120 |
| 4-78 | $CF_3$ | $CH_3$ | H | F | F | 0 | $CH(CH_3)SOC_2H_5$ | Unmeasurable |
| 4-79 | $CF_3$ | $CH_3$ | H | F | F | 0 | $CH(CH_3)SO_2CH_3$ | 154–155 |
| 4-80 | $CF_3$ | $CH_3$ | H | F | F | 0 | $CH(CH_3)SO_2C_2H_5$ | oil |
| 4-81 | $CF_3$ | $CH_3$ | H | F | F | 0 | $CH(C_2H_5)OCH_3$ | 77–78 |
| 4-82 | $CF_3$ | $CH_3$ | H | F | F | 0 | $CH(C_2H_5)OC_2H_5$ | |
| 4-83 | $CF_3$ | $CH_3$ | H | F | F | 0 | $CH(C_2H_5)SCH_3$ | oil |
| 4-84 | $CF_3$ | $CH_3$ | H | F | F | 0 | $CH(C_2H_5)SC_2H_5$ | |
| 4-85 | $CF_3$ | $CH_3$ | H | F | F | 0 | $CH(C_2H_5)SOCH_3$ | oil |
| 4-86 | $CF_3$ | $CH_3$ | H | F | F | 0 | $CH(C_2H_5)SOC_2H_5$ | |
| 4-87 | $CF_3$ | $CH_3$ | H | F | F | 0 | $CH(C_2H_5)SO_2CH_3$ | 145–147 |
| 4-88 | $CF_3$ | $CH_3$ | H | F | F | 0 | $CH(C_2H_5)SO_2C_2H_5$ | |
| 4-89 | $CF_3$ | $CH_3$ | H | F | F | 0 | $CH(CH_3)OH$ | oil |
| 4-90 | $CF_3$ | $CH_3$ | H | F | F | 0 | $CH(C_2H_5)OH$ | |
| 4-91 | $CF_3$ | $CH_3$ | H | F | F | 0 | $C_3H_7$ | 100–101 |

TABLE 18-continued

| Comp. Nos. | R | R¹ | R² | R³ | R⁴ | Y | R⁷ | m.p. (° C.) |
|---|---|---|---|---|---|---|---|---|
| 4-92 | $CF_3$ | $CH_3$ | H | F | Cl | O | $CH(CH_3)SC_2H_5$ | 85–86 |
| 4-93 | $CF_3$ | $CH_3$ | H | F | Cl | O | $CH(CH_3)SOC_2H_5$ | Unmeasurable |

TABLE 19

| Comp. Nos. | R | R¹ | R² | R³ | R⁴ | Y | R⁷ | m.p. (° C.) |
|---|---|---|---|---|---|---|---|---|
| 4-94 | $CF_3$ | $CH_3$ | H | F | Cl | O | $CH(CH_3)SO_2C_2H_5$ | 140–141 |
| 4-95 | $CF_3$ | $CH_3$ | H | F | Cl | O | $CH(C_2H_5)SC_2H_5$ | Unmeasurable |
| 4-96 | $CF_3$ | $CH_3$ | H | F | Cl | O | $CH(C_2H_5)SOC_2H_5$ | oil |
| 4-97 | $CF_3$ | $CH_3$ | H | F | Cl | O | $CH(C_2H_5)SO_2C_2H_5$ | 118–120 |
| 4-98 | $CF_3$ | $CH_3$ | H | F | Cl | O | $CH_2SC_2H_5$ | 135–136 |
| 4-99 | $CF_3$ | $CH_3$ | H | F | Cl | O | $CH_2SOC_2H_5$ | 131–132 |
| 4-100 | $CF_3$ | $CH_3$ | H | F | Cl | O | $CH_2SO_2C_2H_5$ | 198–200 |
| 4-101 | $CF_3$ | $CH_3$ | H | F | Cl | O | $CH_2SCHF_2$ | |
| 4-102 | $CF_3$ | $CH_3$ | H | Cl | Cl | O | $CH_2SCH_3$ | 158–159 |
| 4-103 | $CF_3$ | $CH_3$ | H | Cl | Cl | O | $CH_2SOCH_3$ | 77–79 |
| 4-104 | $CF_3$ | $CH_3$ | H | Cl | Cl | O | $CH_2SO_2CH_3$ | 164–166 |
| 4-105 | $CF_3$ | $CH_3$ | H | Cl | Cl | O | $CH_2SC_2H_5$ | 108–109 |
| 4-106 | $CF_3$ | $CH_3$ | H | Cl | Cl | O | $CH_2SOC_2H_5$ | 155–156 |
| 4-107 | $CF_3$ | $CH_3$ | H | Cl | Cl | O | $CH_2SC_2C_2H_5$ | 106–108 |
| 4-108 | $CF_3$ | $CH_3$ | H | Cl | Cl | O | $CH(CH_3)SCH_3$ | 138–139 |
| 4-109 | $CF_3$ | $CH_3$ | H | Cl | Cl | O | $CH(CH_3)SOCH_3$ | 80–81 |
| 4-110 | $CF_3$ | $CH_3$ | H | Cl | Cl | O | $CH(CH_3)SO_2CH_3$ | 95–96 |
| 4-111 | $CF_3$ | $CH_3$ | H | Cl | Cl | O | $CH(CH_3)SC_2H_5$ | 99–100 |
| 4-112 | $CF_3$ | $CH_3$ | H | Cl | Cl | O | $CH(CH_3)SOC_2H_5$ | 68–69 |
| 4-113 | $CF_3$ | $CH_3$ | H | Cl | Cl | O | $CH(CH_3)SO_2C_2H_5$ | 81–82 |
| 4-114 | $CF_3$ | $CH_3$ | H | Cl | Cl | O | $CH(C_2H_5)SCH_3$ | 107–108 |
| 4-115 | $CF_3$ | $CH_3$ | H | Cl | Cl | O | $CH(C_2H_5)SOCH_3$ | 123–125 |
| 4-116 | $CF_3$ | $CH_3$ | H | Cl | Cl | O | $CH(C_2H_5)SO_2CH_3$ | 80–82 |
| 4-117 | $CF_3$ | $CH_3$ | H | Cl | Cl | O | $CH(C_2H_5)SC_2H_5$ | 87–88 |
| 4-118 | $CF_3$ | $CH_3$ | H | Cl | Cl | O | $CH(C_2H_5)SOC_2H_5$ | Unmeasurable |
| 4-119 | $CF_3$ | $CH_3$ | H | Cl | Cl | O | $CH(C_2H_5)SO_2C_2H_5$ | 49–51 |
| 4-120 | $CF_3$ | $CH_3$ | H | Cl | Cl | O | H | 145–146 |
| 4-121 | $CF_3$ | $CH_3$ | H | F | Cl | O | $CH(CH_3)SC_3H_7$ | oil |
| 4-122 | $CF_3$ | $CH_3$ | H | F | Cl | O | $CH(CH_3)SC_3H_7$-i | oil |
| 4-123 | $CF_3$ | $CH_3$ | H | F | F | O | $CH(C_2H_5)Br$ | 107–108 |
| 4-124 | $CF_3$ | $CH_3$ | H | F | F | O | $CH=CHCH_3$ | 159–160 |
| 4-125 | $CF_3$ | $CH_3$ | H | F | Cl | O | $C(CH_3)_2SO_2CH_3$ | |
| 4-126 | $CF_3$ | $CH_3$ | H | F | Cl | O | $CH_2SOCHF_2$ | |

TABLE 20

| Comp. Nos. | R | R¹ | R² | R³ | R⁴ | Y | R⁷ | m.p. (° C.) |
|---|---|---|---|---|---|---|---|---|
| 4-127 | $CF_3$ | $CH_3$ | H | F | Cl | O | $CH_2SO_2CHF_2$ | |
| 4-128 | $CF_3$ | $CH_3$ | H | F | Cl | O | $CH_2OC_4H_9$ | oil |
| 4-129 | $CF_3$ | $CH_3$ | H | F | Cl | O | $CH_2OC_4H_9$-s | oil |
| 4-130 | $CF_3$ | $CH_3$ | H | F | Cl | O | $CH_2OC_4H_9$-i | oil |
| 4-131 | $CF_3$ | $CH_3$ | H | F | Cl | O | $CH(CH_3)OC_4H_9$ | oil |
| 4-132 | $CF_3$ | $CH_3$ | H | F | Cl | O | $CH(CH_3)OC_4H_9$-s | oil |
| 4-133 | $CF_3$ | $CH_3$ | H | F | Cl | O | $CH(CH_3)OC_4H_9$-i | oil |
| 4-134 | $CF_3$ | $CH_3$ | H | F | Cl | O | $CH(CH_3)SOC_3H_7$ | Unmeasurable |
| 4-135 | $CF_3$ | $CH_3$ | H | F | Cl | O | $CH(CH_3)SO_2C_3H_7$ | 141–142 |
| 4-136 | $CF_3$ | $CH_3$ | H | F | Cl | O | $CH(CH_3)SOC_3H_7$-i | Unmeasurable |
| 4-137 | $CF_3$ | $CH_3$ | H | F | Cl | O | $CH(CH_3)SO_2C_3H_7$-i | 164–165 |
| 4-138 | $CF_3$ | $CH_3$ | H | F | Cl | O | $CH(C_2H_5)OC_3H_7$ | oil |
| 4-139 | $CF_3$ | $CH_3$ | H | F | Cl | O | $CH(C_2H_5)OC_3H_7$-i | oil |
| 4-140 | $CF_3$ | $CH_3$ | H | Cl | Cl | O | $CH_2OC_3H_7$ | 92–93 |
| 4-141 | $CF_3$ | $CH_3$ | H | Cl | Cl | O | $CH_2OC_3H_7$-i | 83–84 |
| 4-142 | $CF_3$ | $CH_3$ | H | Cl | Cl | O | $CH(CH_3)OC_3H_7$ | oil |
| 4-143 | $CF_3$ | $CH_3$ | H | Cl | Cl | O | $CH(CH_3)OC_3H_7$-i | 33–34 |
| 4-144 | $CF_3$ | $CH_3$ | H | Cl | Cl | O | $CH(C_2H_5)OC_3H_7$ | oil |

TABLE 20-continued

| Comp. Nos. | R | R¹ | R² | R³ | R⁴ | Y | R⁷ | m.p. (° C.) |
|---|---|---|---|---|---|---|---|---|
| 4-145 | CF₃ | CH₃ | H | Cl | Cl | O | CH(C₂H₅)OC₃H₇-i | oil |
| 4-146 | CF₃ | CH₃ | H | F | Cl | O | CH₂SC₃H₇ | |
| 4-147 | CF₃ | CH₃ | H | F | Cl | O | CH₂SOC₃H₇ | |
| 4-148 | CF₃ | CH₃ | H | F | Cl | O | CH₂SO₂C₃H₇ | |
| 4-149 | CF₃ | CH₃ | H | F | Cl | O | CH₂SC₃H₇-i | |
| 4-150 | CF₃ | CH₃ | H | F | Cl | O | CH₂SOC₃H₇-i | |
| 4-151 | CF₃ | CH₃ | H | F | Cl | O | CH₂SO₂C₃H₇-i | |
| 4-152 | CF₃ | CH₃ | H | F | Cl | O | CH(C₂H₅)SC₃H₇ | |
| 4-153 | CF₃ | CH₃ | H | F | Cl | O | CH(C₂H₅)SOC₃H₇ | |
| 4-154 | CF₃ | CH₃ | H | F | Cl | O | CH(C₂H₅)SO₂C₃H₇ | |
| 4-155 | CF₃ | CH₃ | H | F | Cl | O | CH(C₂H₅)SC₃H₇-i | |
| 4-156 | CF₃ | CH₃ | H | F | Cl | O | CH(C₂H₅)SOC₃H₇-i | |
| 4-157 | CF₃ | CH₃ | H | F | Cl | O | CH(C₂H₅)SO₂C₃H₇-i | |
| 4-158 | CF₃ | CH₃ | H | Cl | Cl | O | CH₂SC₃H₇ | |
| 4-159 | CF₃ | CH₃ | H | Cl | Cl | O | CH₂SOC₃H₇ | |

TABLE 21

| Comp. Nos. | R | R¹ | R² | R³ | R⁴ | Y | R⁷ | m.p. (° C.) |
|---|---|---|---|---|---|---|---|---|
| 4-160 | CF₃ | CH₃ | H | Cl | Cl | O | CH₂SO₂C₃H₇ | |
| 4-161 | CF₃ | CH₃ | H | Cl | Cl | O | CH₂SC₃H₇-i | |
| 4-162 | CF₃ | CH₃ | H | Cl | Cl | O | CH₂SOC₃H₇-i | |
| 4-163 | CF₃ | CH₃ | H | Cl | Cl | O | CH₂SO₂C₃H₇-i | |
| 4-164 | CF₃ | CH₃ | H | Cl | Cl | O | CH(CH₃)SC₃H₇ | |
| 4-165 | CF₃ | CH₃ | H | Cl | Cl | O | CH(CH₃)SOC₃H₇ | |
| 4-166 | CF₃ | CH₃ | H | Cl | Cl | O | CH(CH₃)SO₂C₃H₇ | |
| 4-167 | CF₃ | CH₃ | H | Cl | Cl | O | CH(CH₃)SC₃H₇-i | |
| 4-168 | CF₃ | CH₃ | H | Cl | Cl | O | CH(CH₃)SOC₃H₇-i | |
| 4-169 | CF₃ | CH₃ | H | Cl | Cl | O | CH(CH₃)SO₂C₃H₇-i | |
| 4-170 | CF₃ | CH₃ | H | Cl | Cl | O | CH(C₂H₅)SC₃H₇ | |
| 4-171 | CF₃ | CH₃ | H | Cl | Cl | O | CH(C₂H₅)SOC₃H₇ | |
| 4-172 | CF₃ | CH₃ | H | Cl | Cl | O | CH(C₂H₅)SO₂C₃H₇ | |
| 4-173 | CF₃ | CH₃ | H | Cl | Cl | O | CH(C₂H₅)SC₃H₇-i | |
| 4-174 | CF₃ | CH₃ | H | Cl | Cl | O | CH(C₂H₅)SOC₃H₇-i | |
| 4-175 | CF₃ | CH₃ | H | Cl | Cl | O | CH(C₂H₅)SO₂C₃H₇-i | |
| 4-176 | CF₃ | CH₃ | H | F | Cl | O | CH=CHCH₃ | |
| 4-177 | CF₃ | CH₃ | H | F | Cl | O | CH=CH₂ | |
| 4-178 | CF₃ | CH₃ | H | Cl | Cl | O | CH=CHCH₃ | |
| 4-179 | CF₃ | CH₃ | H | Cl | Cl | O | CH(C₂H₅)Br | 120–121 |
| 4-180 | CF₃ | CH₃ | H | Cl | Cl | O | CH(CH₃)Br | 110–112 |
| 4-181 | CF₃ | CH₃ | H | F | Cl | O | CH(CH₃)OC₃H₇-i | oil |
| 4-182 | CF₃ | CH₃ | H | F | Cl | O | CH(CH₃)OC₄H₉-t | 42–44 |
| 4-183 | CF₃ | CH₃ | H | F | Cl | O | CH(CH₃)OH | |

TABLE 22

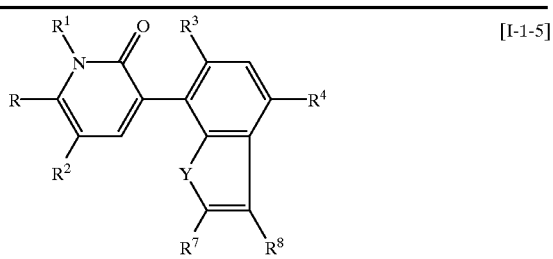

[I-1-5]

| Comp. Nos. | R | R¹ | R² | R³ | R⁴ | Y | R⁷ | R⁸ | m.p. (° C.) |
|---|---|---|---|---|---|---|---|---|---|
| 5-1 | CF₃ | CH₃ | H | F | Cl | O | CH₃ | H | 138–140 |
| 5-2 | CF₃ | CH₃ | H | F | Cl | O | C₂H₅ | H | 103–105 |

TABLE 22-continued

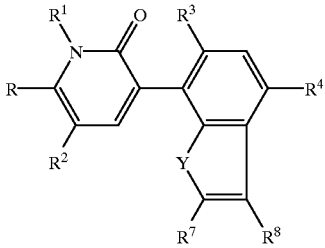

[I-1-5]

| Comp. Nos. | R | $R^1$ | $R^2$ | $R^3$ | $R^4$ | Y | $R^7$ | $R^8$ | m.p. (° C.) |
|---|---|---|---|---|---|---|---|---|---|
| 5-3 | $CF_3$ | $CH_3$ | H | F | Cl | O | $C_3H_7$ | H | 120–122 |
| 5-4 | $CF_3$ | $CH_3$ | H | F | Cl | O | $CH_2OH$ | H | |
| 5-5 | $CF_3$ | $CH_3$ | H | F | Cl | O | $CH_2OCH_3$ | H | |
| 5-6 | $CF_3$ | $CH_3$ | H | F | Cl | O | $CH_2SO_2CH_3$ | H | |
| 5-7 | $CF_3$ | $CH_3$ | H | F | Cl | O | $CH_2SO_2C_2H_5$ | H | |
| 5-8 | $CF_3$ | $CH_3$ | H | F | Cl | O | $CH_2SCH_3$ | H | |
| 5-9 | $CF_3$ | $CH_3$ | H | F | Cl | O | $CH_2SC_2H_5$ | H | |
| 5-10 | $CF_3$ | $CH_3$ | H | F | Cl | O | $COCH_3$ | H | |
| 5-11 | $CF_3$ | $CH_3$ | H | F | Cl | O | $CH(OH)CH_3$ | H | |
| 5-12 | $CF_3$ | $CH_3$ | H | F | Cl | O | H | H | |
| 5-13 | $CF_3$ | $CH_3$ | H | F | Cl | O | $CO_2C_2H_5$ | H | |
| 5-14 | $CF_3$ | $CH_3$ | H | F | Cl | O | $CO_2H$ | H | |
| 5-15 | $CF_3$ | $CH_3$ | H | F | Cl | O | $CH_3$ | $COCH_3$ | |
| 5-16 | $CF_3$ | $CH_3$ | H | F | Cl | S | $CH_3$ | H | |
| 5-17 | $CF_3$ | $CH_3$ | H | F | Cl | NH | $CH_3$ | H | |
| 5-18 | $CF_3$ | $CH_3$ | H | F | Cl | NH | $C_2H_5$ | H | |
| 5-19 | $CF_3$ | $CH_3$ | H | Cl | Cl | O | $CH_3$ | H | |
| 5-20 | $CF_3$ | $CH_3$ | H | Cl | Cl | O | $C_2H_5$ | H | |
| 5-21 | $CF_3$ | $CH_3$ | H | H | H | O | $CH_3$ | H | |
| 5-22 | $CF_3$ | $CH_3$ | H | H | H | O | $C_2H_5$ | H | |

TABLE 23

[I-2-1]

| Comp. Nos. | R | $R^1$ | $R^2$ | $R^3$ | $R^4$ | $R^5$ | m.p. (° C.) |
|---|---|---|---|---|---|---|---|
| 6-1 | $CF_3$ | $CH_3$ | H | H | Cl | H | 124–125 |
| 6-2 | $CF_3$ | $CH_3$ | H | F | Cl | H | 173–176 |
| 6-3 | $CF_3$ | $CH_3$ | H | Cl | Cl | H | 205–206 |
| 6-4 | $CF_3$ | $NH_2$ | H | Cl | Cl | H | |
| 6-5 | $CF_3$ | $CH_3$ | H | F | Cl | OH | 258–261 |
| 6-6 | $CF_3$ | $CH_3$ | H | F | Cl | $OCH_3$ | |
| 6-7 | $CF_3$ | $CH_3$ | H | F | Cl | $OC_3H_7$-i | 150–151 |
| 6-8 | $CF_3$ | $CH_3$ | H | F | Cl | $OCH_2CH=CH_2$ | 146–148 |
| 6-9 | $CF_3$ | $CH_3$ | H | F | Cl | $OCH_2C^*CH$ | 146–150 |
| 6-10 | $CF_3$ | $CH_3$ | H | F | Cl | $OCH(CH_3)C^*CH$ | 144–148 |
| 6-11 | $CF_3$ | $CH_3$ | H | F | Cl | $OCH_2CO_2C_2H_5$ | 128–129 |
| 6-12 | $CF_3$ | $CH_3$ | H | F | Cl | $OCH(CH_3)CO_2C_2H_5$ | |
| 6-13 | $CF_3$ | $CH_3$ | H | F | Cl | $OCH_2CON(C_2H_5)_2$ | |
| 6-14 | $CF_3$ | $CH_3$ | H | F | Cl | 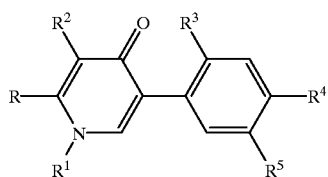 | 152–154 |

TABLE 23-continued

[I-2-1]

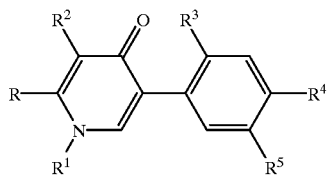

| Comp. Nos. | R | $R^1$ | $R^2$ | $R^3$ | $R^4$ | $R^5$ | m.p. (° C.) |
|---|---|---|---|---|---|---|---|
| 6-15 | $CF_3$ | $CH_3$ | H | F | Cl | $OCH_2$-Ph | |
| 6-16 | $CF_3$ | $CH_3$ | H | F | Cl | $OCHF_2$ | |
| 6-17 | $CF_3$ | $CH_3$ | H | F | Cl | $OCH_2OCH_3$ | |
| 6-18 | $CF_3$ | $CH_3$ | H | F | Cl | $OCH_2CN$ | |
| 6-19 | $CF_3$ | $CH_3$ | H | F | Cl | O-Ph | 159–161 |
| 6-20 | $CF_3$ | $CH_3$ | H | F | Cl | O-(2-pyrimidinyl) | |
| 6-21 | $CF_3$ | $CH_3$ | H | F | Cl | SH | |
| 6-22 | $CF_3$ | $CH_3$ | H | F | Cl | $SC_3H_7$-i | |
| 6-23 | $CF_3$ | $CH_3$ | H | F | Cl | $SCH_2C^*CH$ | |
| 6-24 | $CF_3$ | $CH_3$ | H | F | Cl | $SCH_2CO_2CH_3$ | |
| 6-25 | $CF_3$ | $CH_3$ | H | F | Cl | $SCH_2CO_2C_2H_5$ | |
| 6-26 | $CF_3$ | $CH_3$ | H | F | Cl | $SCH_2CO_2$-cyclopentyl | |
| 6-27 | $CF_3$ | $CH_3$ | H | F | Cl | $SCH(C_3H_7)CO_2C_2H_5$ | |
| 6-28 | $CF_3$ | $CH_3$ | H | F | Cl | $NHSO_2CH_3$ | 251–256 |

TABLE 24

| Comp. Nos. | R | $R^1$ | $R^2$ | $R^3$ | $R^4$ | $R^5$ | m.p. (° C.) |
|---|---|---|---|---|---|---|---|
| 6-29 | $CF_3$ | $CH_3$ | H | F | Cl | $NHSO_2C_2H_5$ | |
| 6-30 | $CF_3$ | $CH_3$ | H | F | Cl | $NHCH_2C^*CH$ | |
| 6-31 | $CF_3$ | $CH_3$ | H | F | Cl | $NHCH_2CO_2C_2H_5$ | |
| 6-32 | $CF_3$ | $CH_3$ | H | F | Cl | $NHCONHCH_3$ | |
| 6-33 | $CF_3$ | $CH_3$ | H | F | Cl | $CO_2C_2H_5$ | |
| 6-34 | $CF_3$ | $CH_3$ | H | F | Cl | $CO_2C_3H_7$-i | |
| 6-35 | $CF_3$ | $CH_3$ | H | F | Cl | $COSC_2H_5$ | |
| 6-36 | $CF_3$ | $CH_3$ | H | F | Cl | $CO_2N=C(CH_3)_2$ | |
| 6-37 | $CF_3$ | $CH_3$ | H | F | Cl | $CH_2CH(Cl)CO_2C_2H_5$ | |
| 6-38 | $CF_3$ | $CH_3$ | H | F | Cl | $SO_2NHCH_3$ | |
| 6-39 | $CF_3$ | $CH_3$ | H | F | Cl | $CH=NOCH_3$ | |
| 6-40 | $CF_3$ | $CH_3$ | H | F | Cl | $SO_2CH_3$ | |
| 6-41 | $CF_3$ | $CH_3$ | H | F | $OCH_2CO_2C_2H_5$ | $NO_2$ | |
| 6-42 | $CF_3$ | $CH_3$ | $CO_2C_2H_5$ | F | Cl | $OC_3H_7$-i | 170–172 |
| 6-43 | $CF_3$ | $CH_3$ | $CO_2H$ | F | Cl | $OC_3H_7$-i | |
| 6-44 | $CF_3$ | $CH_3$ | H | F | F | $NO_2$ | |
| 6-45 | $CF_3$ | $CH_3$ | H | F | Cl | $SCH_3$ | |
| 6-46 | $CF_3$ | $CH_3$ | H | F | Cl | $SOCH_3$ | |
| 6-47 | $CF_3$ | $CH_3$ | H | F | Cl | $CH_3$ | |
| 6-48 | $CF_3$ | $CH_3$ | H | F | Cl | $CH_2Br$ | |

TABLE 24-continued

| Comp. Nos. | R | $R^1$ | $R^2$ | $R^3$ | $R^4$ | $R^5$ | m.p. (° C.) |
|---|---|---|---|---|---|---|---|
| 6-49 | $CF_3$ | $CH_3$ | H | F | Cl | CHO | |
| 6-50 | $CF_3$ | $CH_3$ | H | F | Cl | $NO_2$ | |
| 6-51 | $CF_3$ | $CH_3$ | H | F | Cl | $NH_2$ | |
| 6-52 | $CF_3$ | $CH_3$ | H | F | SH | $NH_2$ | |
| 6-53 | $CF_3$ | H | $CO_2C_2H_5$ | H | Cl | H | 130–131 |
| 6-54 | $CF_3$ | H | $CO_2C_2H_5$ | F | Cl | H | 153–154 |
| 6-55 | $CF_3$ | H | $CO_2C_2H_5$ | Cl | Cl | H | |
| 6-56 | $CF_3$ | H | $CO_2C_2H_5$ | F | F | H | |
| 6-57 | $CF_3$ | H | $CO_2C_2H_5$ | F | Cl | $OC_3H_7$-i | 118–119 |
| 6-58 | $CF_3$ | $CH_3$ | $CO_2C_2H_5$ | F | Cl | H | 146–147 |
| 6-59 | $CF_3$ | $CH_3$ | $CO_2C_2H_5$ | F | Cl | $NHSO_2CH_3$ | 247–251 |
| 6-60 | $CF_3$ | $CH_3$ | $CO_2C_2H_5$ | F | Cl | $NH_2$ | 143–145 |
| 6-61 | $CF_3$ | $CH_3$ | $CO_2C_2H_5$ | H | Cl | H | 152–153 |

TABLE 25

| Comp. Nos. | R | $R^1$ | $R^2$ | $R^3$ | $R^4$ | $R^5$ | m.p. (° C.) |
|---|---|---|---|---|---|---|---|
| 6-62 | $CF_3$ | $CH_3$ | $CO_2C_2H_5$ | H | Cl | $NO_2$ | 171–172 |
| 6-63 | $CF_3$ | $CH_3$ | $CO_2C_2H_5$ | H | Cl | $NH_2$ | 175–176 |
| 6-64 | $CF_3$ | $CH_3$ | H | H | Cl | $OCH_2C^*CH$ | |

TABLE 26

[I-2-2]

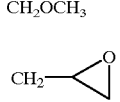

| Comp. Nos. | R | $R^1$ | $R^2$ | $R^3$ | Y | $R^6$ | m.p. (° C.) |
|---|---|---|---|---|---|---|---|
| 7-1 | $CF_3$ | $CH_3$ | H | F | O | $CH_2C^*CH$ | 169–170 |
| 7-2 | $CF_3$ | $NH_2$ | H | F | O | $CH_2C^*CH$ | |
| 7-3 | $CF_3$ | $CH_3$ | H | F | O | H | |
| 7-4 | $CF_3$ | $CH_3$ | H | F | O | $CH_3$ | |
| 7-5 | $CF_3$ | $CH_3$ | H | F | O | $C_2H_5$ | |
| 7-6 | $CF_3$ | $CH_3$ | H | F | O | $C_3H_7$ | |
| 7-7 | $CF_3$ | $CH_3$ | H | F | O | $CH(CH_3)C^*CH$ | |
| 7-8 | $CF_3$ | $CH_3$ | H | F | O | $CH_2CH=CH_2$ | |
| 7-9 | $CF_3$ | $CH_3$ | H | F | O | $CH_2C(CH_3)=CH_2$ | |
| 7-10 | $CF_3$ | $CH_3$ | H | F | O | $CH_2CH=CHCH_3$ | |
| 7-11 | $CF_3$ | $CH_3$ | H | F | O | $CH_2C(Cl)=CH_2$ | |
| 7-12 | $CF_3$ | $CH_3$ | H | F | O | $CH_2CH=CHCl$ | |
| 7-13 | $CF_3$ | $CH_3$ | H | F | O | $CH_2CN$ | |
| 7-14 | $CF_3$ | $CH_3$ | H | F | O | $CH_2CO_2C_2H_5$ | |
| 7-15 | $CF_3$ | $CH_3$ | H | F | O | $CH_2OCH_3$ | |
| 7-16 | $CF_3$ | $CH_3$ | H | F | O | 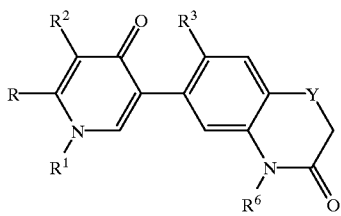 | |
| 7-17 | $CF_3$ | $CH_3$ | H | F | S | $CH_2C^*CH$ | |
| 7-18 | $CF_3$ | $CH_3$ | H | F | S | H | |
| 7-19 | $CF_3$ | $CH_3$ | H | F | NH | $CH_2C^*CH$ | |
| 7-20 | $CF_3$ | $CH_3$ | H | F | NH | H | |
| 7-21 | $CF_3$ | $CH_3$ | H | Cl | O | $CH_2C^*CH$ | |
| 7-22 | $CF_3$ | $CH_3$ | H | Cl | O | $CH_2CH=CH_2$ | |
| 7-23 | $CF_3$ | $CH_3$ | H | Cl | O | H | |

TABLE 26-continued

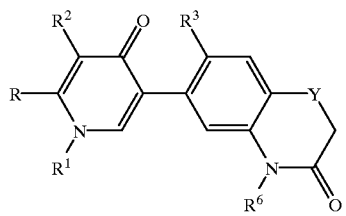

[I-2-2]

| Comp. Nos. | R | R¹ | R² | R³ | Y | R⁶ | m.p. (° C.) |
|---|---|---|---|---|---|---|---|
| 7-24 | $CF_3$ | $CH_3$ | H | H | O | $CH_2C^*CH$ | |
| 7-25 | $CF_3$ | $CH_3$ | H | H | O | $CH_2CH=CH_2$ | |
| 7-26 | $CF_3$ | $CH_3$ | H | H | O | H | |

TABLE 27

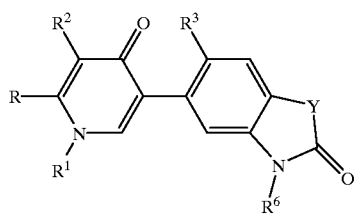

[I-2-3]

| Comp. Nos. | R | R¹ | R² | R³ | Y | R⁶ | m.p. (° C.) |
|---|---|---|---|---|---|---|---|
| 8-1  | $CF_3$ | $CH_3$ | H | F  | S  | $CH_2C^*CH$ | |
| 8-2  | $CF_3$ | $CH_3$ | H | F  | S  | H | |
| 8-3  | $CF_3$ | $CH_3$ | H | F  | S  | $CH_2CH=CH_2$ | |
| 8-4  | $CF_3$ | $CH_3$ | H | F  | S  | $CH_3$ | |
| 8-5  | $CF_3$ | $CH_3$ | H | F  | 3  | $C_2H_5$ | |
| 8-6  | $CF_3$ | $CH_3$ | H | F  | S  | $C_3H_7$ | |
| 8-7  | $CF_3$ | $CH_3$ | H | F  | S  | $CH_2CN$ | |
| 8-8  | $CF_3$ | $CH_3$ | H | F  | S  | $CH_2OCH_3$ | |
| 8-9  | $CF_3$ | $NH_2$ | H | F  | S  | $CH_2C^*CH$ | |
| 8-10 | $CF_3$ | $CH_3$ | H | F  | O  | $CH_2C^*CH$ | |
| 8-11 | $CF_3$ | $CH_3$ | H | F  | NH | $CH_2C^*CH$ | |
| 8-12 | $CF_3$ | $CH_3$ | H | Cl | S  | $CH_2C^*CH$ | |
| 8-13 | $CF_3$ | $CH_3$ | H | Cl | S  | H | |
| 8-14 | $CF_3$ | $CH_3$ | H | Cl | S  | $CH_2CH=CH_2$ | |
| 8-15 | $CF_3$ | $CH_3$ | H | Cl | S  | $CH_3$ | |
| 8-16 | $CF_3$ | $CH_3$ | H | Cl | S  | $C_2H_5$ | |
| 8-17 | $CF_3$ | $CH_3$ | H | Cl | S  | $C_3H_7$ | |
| 8-18 | $CF_3$ | $NH_2$ | H | Cl | S  | $CH_2C^*CH$ | |
| 8-19 | $CF_3$ | $CH_3$ | H | H  | S  | $CH_2C^*CH$ | |
| 8-20 | $CF_3$ | $CH_3$ | H | H  | S  | H | |
| 8-21 | $CF_3$ | $CH_3$ | H | H  | S  | $CH_2CH=CH_2$ | |

TABLE 28

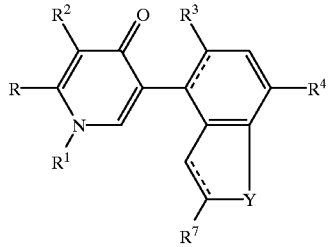

[I-2-4]

| Comp. Nos. | R | R¹ | R² | R³ | R⁴ | Y | R⁷ | m.p. (° C.) |
|---|---|---|---|---|---|---|---|---|
| 9-1  | $CF_3$ | $CH_3$ | H | F  | Cl | O  | $CH_3$ | 208–211 |
| 9-2  | $CF_3$ | $CH_3$ | H | F  | Cl | O  | $C_2H_5$ | 210–213 |
| 9-3  | $CF_3$ | $CH_3$ | H | F  | Cl | O  | $C_3H_7$ | |
| 9-4  | $CF_3$ | $CH_3$ | H | F  | Cl | O  | $CH_2OCH_3$ | |
| 9-5  | $CF_3$ | $CH_3$ | H | F  | Cl | O  | $CH_2OH$ | |
| 9-6  | $CF_3$ | $CH_3$ | H | F  | Cl | O  | $CO_2C_2H_5$ | |
| 9-7  | $CF_3$ | $CH_3$ | H | F  | Cl | O  | $CH_2Br$ | |
| 9-8  | $CF_3$ | $CH_3$ | H | Cl | Cl | O  | $CH_3$ | |
| 9-9  | $CF_3$ | $CH_3$ | H | Cl | Cl | O  | $C_2H_5$ | |
| 9-10 | $CF_3$ | $CH_3$ | H | Cl | Cl | O  | $C_3H_7$ | |
| 9-11 | $CF_3$ | $CH_3$ | H | Cl | Cl | O  | $CH_2OCH_3$ | |
| 9-12 | $CF_3$ | $CH_3$ | H | Cl | Cl | O  | $CH_2OH$ | |
| 9-13 | $CF_3$ | $CH_3$ | H | Cl | Cl | O  | $CO_2C_2H_5$ | |
| 9-14 | $CF_3$ | $CH_3$ | H | Cl | Cl | O  | $CH_2Br$ | |
| 9-15 | $CF_3$ | $CH_3$ | H | F  | Cl | S  | $CH_3$ | |
| 9-16 | $CF_3$ | $CH_3$ | H | F  | Cl | S  | $C_2H_5$ | |
| 9-17 | $CF_3$ | $CH_3$ | H | F  | Cl | NH | $CH_3$ | |
| 9-18 | $CF_3$ | $CH_3$ | H | F  | Cl | NH | $C_2H_5$ | |
| 9-19 | $CF_3$ | $NH_2$ | H | F  | Cl | O  | $CH_3$ | |
| 9-20 | $CF_3$ | $NH_2$ | H | F  | Cl | O  | $C_2H_5$ | |
| 9-21 | $CF_3$ | $CH_3$ | H | H  | Cl | O  | $CH_3$ | |
| 9-22 | $CF_3$ | $CH_3$ | H | H  | Cl | O  | $C_2H_5$ | |

TABLE 29

[I-2-5]

| Comp. Nos. | R | $R^1$ | $R^2$ | $R^3$ | $R^4$ | Y | $R^7$ | $R^8$ | m.p. (° C.) |
|---|---|---|---|---|---|---|---|---|---|
| 10-1 | $CF_3$ | $CH_3$ | H | F | Cl | O | $CH_3$ | H | |
| 10-2 | $CF_3$ | $CH_3$ | H | F | Cl | O | $C_2H_5$ | H | |
| 10-3 | $CF_3$ | $CH_3$ | H | F | Cl | O | $C_3H_7$ | H | |
| 10-4 | $CF_3$ | $CH_3$ | H | F | Cl | O | $CH_2OH$ | H | |
| 10-5 | $CF_3$ | $CH_3$ | H | F | Cl | O | $CH_2OCH_3$ | H | |
| 10-6 | $CF_3$ | $CH_3$ | H | F | Cl | O | $CH_2SO_2CH_3$ | H | |
| 10-7 | $CF_3$ | $CH_3$ | H | F | Cl | O | $CH_2SO_2C_2H_5$ | H | |
| 10-8 | $CF_3$ | $CH_3$ | H | F | Cl | O | $CH_2SCH_3$ | H | |
| 10-9 | $CF_3$ | $CH_3$ | H | F | Cl | O | $CH_2SC_2H_5$ | H | |
| 10-10 | $CF_3$ | $CH_3$ | H | F | Cl | O | $COCH_3$ | H | |
| 10-11 | $CF_3$ | $CH_3$ | H | F | Cl | O | $CH(OH)CH_3$ | H | |
| 10-12 | $CF_3$ | $CH_3$ | H | F | Cl | O | H | H | |
| 10-13 | $CF_3$ | $CH_3$ | H | F | Cl | O | $CO_2C_2H_5$ | H | |
| 10-14 | $CF_3$ | $CH_3$ | H | F | Cl | O | $CO_2H$ | H | |
| 10-15 | $CF_3$ | $CH_3$ | H | F | Cl | O | $CH_3$ | $COCH_3$ | |
| 10-16 | $CF_3$ | $CH_3$ | H | F | Cl | S | $CH_3$ | H | |
| 10-17 | $CF_3$ | $CH_3$ | H | F | Cl | NH | $CH_3$ | H | |
| 10-18 | $CF_3$ | $CH_3$ | H | F | Cl | NH | $C_2H_5$ | H | |
| 10-19 | $CF_3$ | $CH_3$ | H | H | Cl | O | $CH_3$ | H | |
| 10-20 | $CF_3$ | $CH_3$ | H | H | Cl | O | $C_2H_5$ | H | |
| 10-21 | $CF_3$ | $CH_3$ | H | Cl | Cl | O | $CH_3$ | H | |
| 10-22 | $CF_3$ | $CH_3$ | H | Cl | Cl | O | $C_2H_5$ | H | |

TABLE 30

[I-1'-1]

| Comp. Nos. | R | $R^1$ | $R^2$ | $R^{19}$ | $R^3$ | $R^4$ | $R^5$ | m.p. (° C.) |
|---|---|---|---|---|---|---|---|---|
| 11-1 | $CF_3$ | $CH_3$ | H | Cl | H | Cl | H | 48–50 |
| 11-2 | $CF_3$ | $CH_3$ | H | F | H | Cl | H | 120–122 |
| 11-3 | $CF_3$ | $CH_3$ | H | Cl | H | Cl | $NHSO_2CH_3$ | 161–163 |
| 11-4 | $CF_3$ | $CH_3$ | H | Cl | F | Cl | $OCH_2C^*CH$ | 119–121 |
| 11-5 | $CF_3$ | $CH_3$ | H | F | F | Cl | $OCH_2C^*CH$ | 100–102 |
| 11-6 | $CF_3$ | $CH_3$ | H | CN | F | Cl | $OCH_2C^*CH$ | oil |
| 11-7 | $CF_3$ | $CH_3$ | H | Cl | H | Cl | $NO_2$ | |
| 11-8 | $CF_3$ | $CH_3$ | H | Cl | H | Cl | $NH_2$ | |

TABLE 31

[I-1'-2]

| Comp. Nos. | R | $R^1$ | $R^2$ | $R^{19}$ | $R^3$ | Y | $R^6$ | m.p. (° C.) |
|---|---|---|---|---|---|---|---|---|
| 12-1 | $CF_3$ | $CH_3$ | H | Cl | H | O | $CH_2C^*CH$ | 204–206 |

TABLE 32
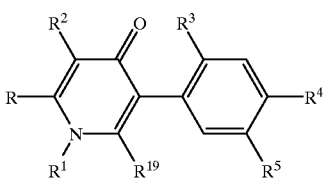
| Comp. Nos. | R | $R^1$ | $R^2$ | $R^{19}$ | $R^3$ | $R^4$ | $R^5$ | m.p. (° C.) |
|---|---|---|---|---|---|---|---|---|
| 13-1 | $CF_3$ | $CH_3$ | H | Cl | H | Cl | H | 88–90 |
TABLE 33
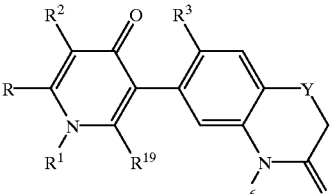
| Comp. Nos. | R | $R^1$ | $R^2$ | $R^{19}$ | $R^3$ | Y | $R^6$ | m.p. (° C.) |
|---|---|---|---|---|---|---|---|---|
| 14-1 | $CF_3$ | $CH_3$ | H | Cl | H | O | $CH_2C^*CH$ | 144–146 |
The compounds of the present invention can be produced, for example, in accordance with the following processes. However, the method for their production is not limited to such processes.
Process 1
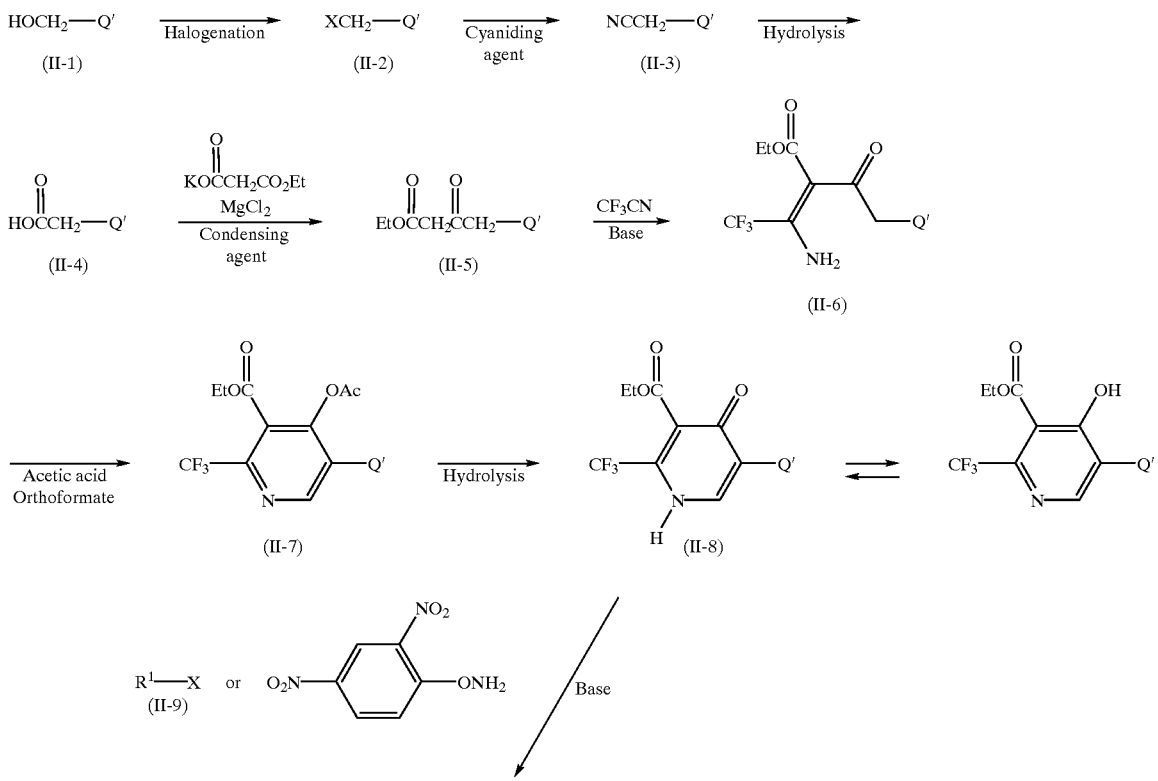

-continued

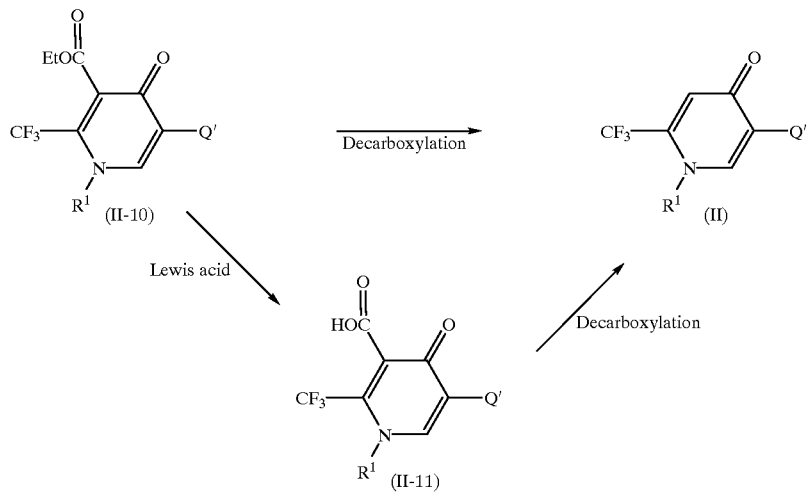

{In the formulae, $R^1$ is as defined above, X is a halogen atom, Et is an ethyl group, Ac is an acetyl group, and Q' represents a formula of

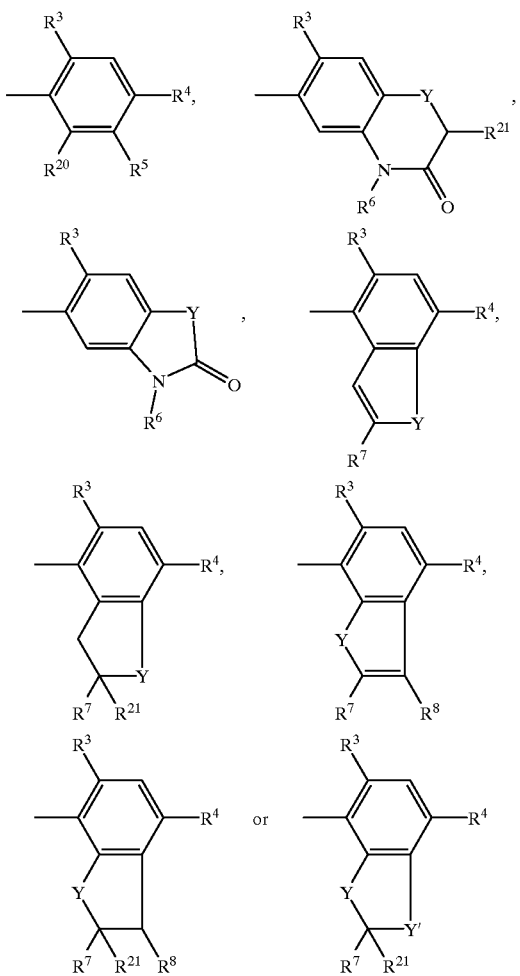

[wherein each of $R^3$, $R^{20}$, $R^{21}$ and Y is as defined above, $R^{4'}$ is a hydrogen atom, a halogen atom or a nitro group, $R^{5'}$ is a hydrogen atom, a halogen atom, a $C_1$–$C_6$ alkyl group, a $C_2$–$C_6$ alkenyl group, a $C_1$–$C_6$ haloalkyl group, a nitro group, a group of —$YR^{9'}$, a group of —$SOR^{9'}$, a group of —$SO_2R^{9'}$ or a $C_1$–$C_6$ alkoxy $C_1$–$C_6$ alkyl group, $R^{6'}$ is a $C_1$–$C_6$ alkyl group, a $C_3$–$C_6$ alkenyl group, a $C_3$–$C_6$ alkynyl group, a $C_1$–$C_6$ haloalkyl group, a $C_3$–$C_6$ haloalkenyl group, an oxiranemethyl group or a $C_1$–$C_6$ alkoxy $C_1$–$C_6$ alkyl group, $R^{7'}$ is a hydrogen atom, a $C_1$–$C_6$ alkyl group, a $C_3$–$C_6$ cycloalkyl group, a $C_3$–$C_6$ alkenyl group, a $C_3$–$C_6$ alkynyl group, a $C_1$–$C_6$ haloalkyl group, a $C_1$–$C_6$ alkoxy $C_1$–$C_6$ alkyl group, a halogen atom or a hydroxyl group, $R^{8'}$ is a hydrogen atom, a halogen atom, a $C_1$–$C_6$ alkyl group, a $C_1$–$C_6$ haloalkyl group or a nitro group, $R^{9'}$ is a $C_1$–$C_6$ alkyl group, a $C_3$–$C_6$ alkenyl group, a $C_3$–$C_6$ alkynyl group, a $C_1$–$C_6$ haloalkyl group, a $C_3$–$C_6$ haloalkenyl group, a $C_1$–$C_6$ alkoxy $C_1$–$C_6$ alkyl group, a $C_3$–$C_6$ cycloalkyl group, a $C_3$–$C_6$ cycloalkyl $C_1$–$C_6$ alkyl group, a $C_1$–$C_6$ alkylsulfonyl $C_1$–$C_6$ alkyl group, a $C_1$–$C_6$ alkylsulfinyl $C_1$–$C_6$ alkyl group, a $C_1$–$C_6$ alkylthio $C_1$–$C_6$ alkyl group, a benzyloxy group (said group may be substituted by a halogen atom, a nitro group, a $C_1$–$C_6$ alkyl group, a $C_1$–$C_6$ haloalkyl group, $C_1$–$C_6$ alkoxy group, or the like) or a 5–6 membered hetero ring group (said group may be substituted by a halogen atom, a nitro group, a $C_1$–$C_6$ alkyl group, a $C_1$–$C_6$ haloalkyl group, a $C_1$–$C_6$ alkoxy group, or the like)]}.

By halogenating a compound represented by the general formula (II-1), a compound represented by the general formula (II-2) can be produced. As a halogenating agent, phosphorus tribromide, thionyl bromide, thionyl chloride, hydrogen chloride or hydrogen bromide may, for example, be used. As a solvent, an ether such as diethyl ether, tetrahydrofuran (THF) or dioxane, or a hydrocarbon such as n-hexane, benzene or toluene, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the obtained compound of the general formula (II-2) and a cyaniding agent are reacted to obtain a compound of the general formula (II-3). As the cyaniding agent, sodium cyanide or potassium cyanide may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, an alcohol such as methanol or ethanol, or an aprotic polar solvent such as acetonitrile, N,N-dimethylformamide (DMF) or N,N-dimethylacetamide (DMAC), may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the obtained compound of the general formula (II-3) is hydrolyzed in the presence of a base or an acid to obtain a compound of the general formula (II-4). As the base, an inorganic base such as sodium hydroxide or potassium hydroxide, may, for example, be used. As a solvent, an alcohol such as methanol or ethanol, or a protic polar solvent such as water, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, in the presence of a condensing agent and magnesium chloride, the compound of the general formula (II-4) and potassium salt of monoethyl malonate are reacted to obtain a compound of the general formula (II-5). As the condensing agent, 1,1'-carbonyldiimidazole (CDI), 2-chloro-1-methylpyridinium iodide, 1-(3-dimethylaminopropyl)-3-ethylcarbodiimide hydrochloride, 1,3-dicyclohexylcarbodiimide, diphenylphosphorylazide or triphenylphosphine may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the general formula (II-5) and trifluoroacetonitrile are reacted in the presence of a base to obtain a compound Df the general formula (II-6). As the base, an organic amine such as triethylamine, 1,8-diazabicyclo[5.4.0]-7-undecene (DBU), pyridine, picoline or quinoline, or an inorganic base such as sodium methoxide, potassium tert-butoxide, sodium hydroxide, potassium hydroxide, sodium carbonate, potassium carbonate, sodium acetate, potassium acetate, sodium hydrogencarbonate or potassium hydrogencarbonate, may, for example, be used. As a solvent, an alcohol such as methanol or ethanol, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, Ior an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires. Then, the compound of the general formula (II-6) and an orthoformate are reacted in the presence of acetic anhydride to produce a compound of the general formula (II-7). As the orthoformate, methyl orthoformate or ethyl orthoformate may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aprotic polar solvent such as acetonitrile, DMF or DMAC, a carboxylic acid such as acetic acid, or acetic anhydride, may, for example, be used. The above reaction is carried out within a range of from room temperature to the boiling point of the solvent and is usually completed with from 1 to 24 hours. The object compound can be isolated from the reaction solution by a conventional method. Further, it is purified by recrystallization or column chromatography, as the case requires.

Then, the compound of the general formula (II-7) is hydrolyzed to obtain a compound of the present invention represented by the general formula (II-8). As a base, an inorganic base such as sodium hydroxide or potassium hydroxide, may, for example, be used. As an acid, sulfuric acid or hydrochloric acid may, for example, be used. As a solvent, an alcohol such as methanol or ethanol, or a protic polar solvent such as water, or an ether such as dioxane or THF, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires. Further, this compound has keto-enol tautomers.

Then, the compound of the present invention represented by the general formula (II-8) and a compound represented by the general formula (II-9) are reacted in the presence of a base to obtain a compound of the present invention represented by the general formula (II-10). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Then, the obtained compound of the present invention represented by the general formula (II-10) and a Lewis acid are reacted, and then water is added thereto to obtain a compound of the present invention represented by the general formula (II-11), followed by decarboxylation in the presence of a copper catalyst, to obtain a compound of the present invention represented by the general formula (II). As the Lewis acid, boron tribromide or aluminum trichloride may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, an aprotic polar solvent such as acetonitrile, DMF or DMAC, or an alcohol such as methanol or ethanol, may, for example, be used. Further, for the decarboxylation, a high boiling point solvent such as quinoline may be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Further, as another method, the compound of the present invention represented by the general formula (II-10) is decarboxylated in the presence of dimethylsulfoxide, water and sodium chloride, to obtain a compound of the present invention represented by the general formula (II). The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

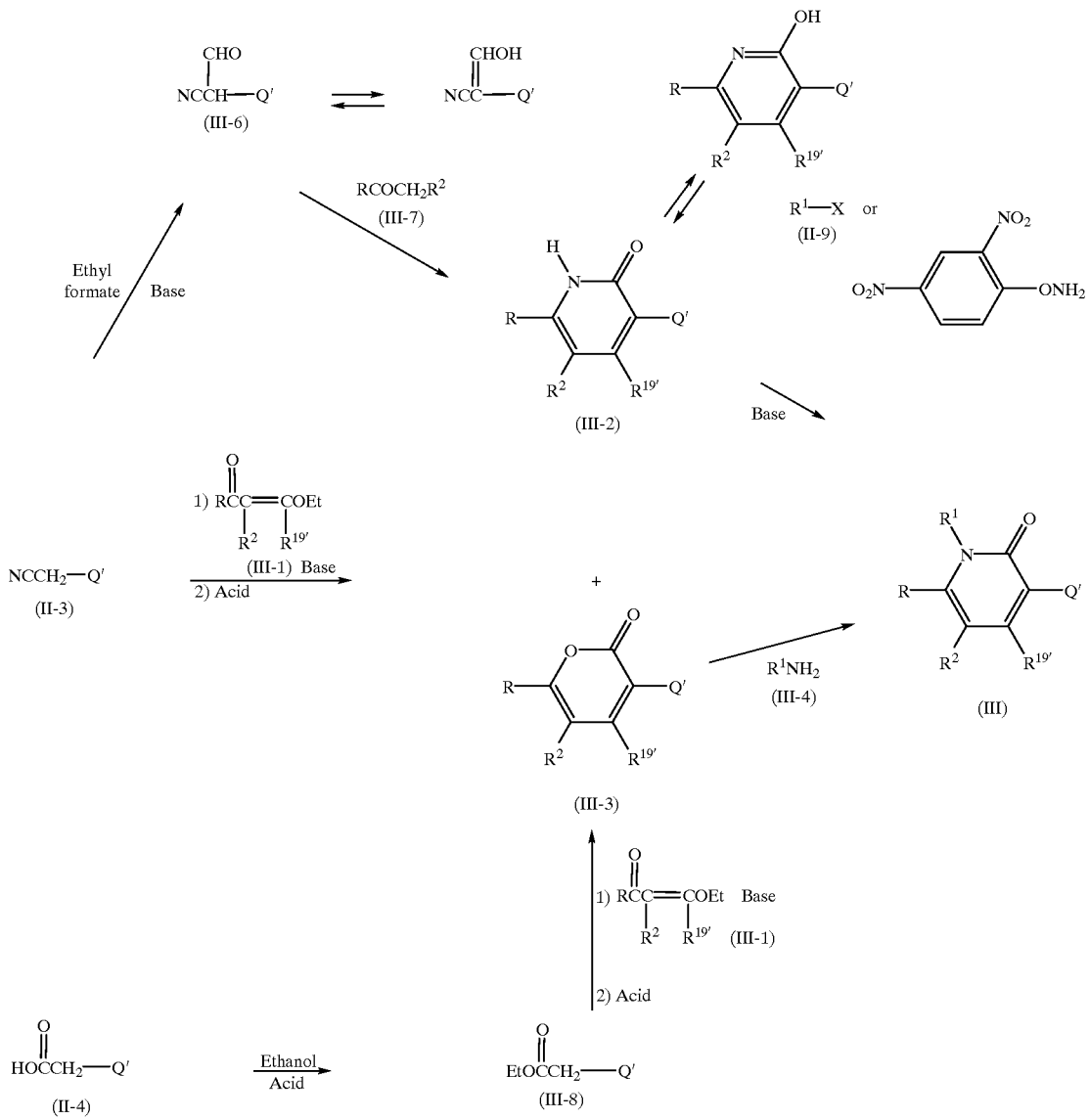

Process 2

(In the formulae, $Q'$, $R$, $R^1$, $R^2$ and $X$ are as defined above, and $R^{19'}$ is a hydrogen atom or a $C_1$–$C_6$ alkyl group.) A compound represented by the general formula (II-3) and a compound represented by the general formula (III-1) are reacted in the presence of a base, followed by treatment with an acid to obtain a mixture comprising a compound of the present invention represented by the general formula (III-2) and a compound represented by the general formula (III-3). As the base, an organic amine such as triethylamine, DBU, pyridine, picoline or quinoline, or an inorganic base such as sodium methoxide, potassium tert-butoxide, sodium hydroxide, potassium hydroxide, sodium carbonate, potassium carbonate, sodium acetate, potassium acetate, sodium hydrogencarbonate or potassium hydrogencarbonate, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. As the acid, hydrochloric acid or sulfuric acid may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires. Further, the compound of the present invention represented by the general formula (III-2) has keto-enol tautomers.

Then, the obtained compound of the present invention represented by the general formula (III-2) and a compound represented by the general formula (II-9) or 2,4-dinitrophenoxyamine, are reacted in the presence of a base in some cases by using a phase transfer catalyst to obtain a compound of the present invention represented by the general formula (III). As the base, an organic amine such as triethylamine, DBU, pyridine, picoline or quinoline, or an inorganic base such as sodium, sodium hydride, sodium methoxide, potassium tert-butoxide, sodium hydroxide, potassium hydroxide, sodium carbonate, potassium carbonate, sodium acetate, potassium acetate, sodium hydrogencarbonate or potassium hydrogencarbonate, may, for example, be used. As the phase transfer catalyst, tetra-n-butylammonium bromide or benzyl triethylammonium chloride may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, a carboxylic acid such as acetic acid, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Further, as another method, the compound represented by the general formula (III-3) and a compound represented by the general formula (III-4) may be reacted to produce the compound of the present invention represented by the general formula (III). As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, a carboxylic acid such as acetic acid, an alcohol such as methanol or ethanol, or an aprotic polar solvent such as acetonitrile, DMF or DMAC, may, for example, be used. The above reaction is carried out within a range of from −10° C. to the boiling point of the solvent under anhydrous condition and is usually completed within from 1 to 24 hours. In some cases, the intermediate amide derivative may be isolated and ring-closed in the presence of an acid catalyst such as p-toluene sulfonic acid. The object compound can be isolated from the reaction solution by a conventional method. Further, it is purified by recrystallization or column chromatography, as the case requires.

Further, the compound of the present invention represented by the general formula (III-2) can be produced also by reacting the compound represented by the general formula (III-6) and a compound represented by the general formula (III-7), as another method. As a solvent, an acid such as acetic acid or polyphosphoric acid, a halogenated hydrocarbon such as dichloromethane, chloroform or carbon tetrachloride, an ether such as diethyl ether, THF or dioxane, a hydrocarbon such as n-hexane, benzene or toluene, or an aprotic polar solvent such as acetonitrile, DMF or DMAC, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Further, the compound represented by the general formula (III-6) can be produced by reacting the compound of the general formula (II-3) and ethyl formate in the presence of a base. As the base, an organic amine such as triethylamine, DBU, pyridine, picoline or quinoline, or an inorganic base such as sodium, sodium hydride, sodium methoxide, sodium ethoxide, potassium tertbutoxide, sodium hydroxide, potassium hydroxide, sodium carbonate, potassium carbonate, sodium acetate, potassium acetate, sodium hydrogencarbonate or potassium hydrogencarbonate, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, an alcohol such as methanol or ethanol, or an aprotic polar solvent such as acetonitrile, DMF or DMAC, may, for example, be used. The above reaction is carried out within a range of from room temperature to the boiling point of the solvent and is completed within a range of from 1 to 24 hours. In some cases, the salt may be isolated, and then acidified with e.g. acetic acid and then withdrawn. The object compound can be isolated from the reaction solution by a conventional method. Further, it is purified by recrystallization or column chromatography, as the case requires.

Further, the compound represented by the general formula (III-3) can be produced by reacting the compound represented by the general formula (III-8) and a compound represented by the general formula (III-1) in the presence of a base, followed by treatment with an acid, as another method. As the base, an organic amine such as lithium diisopropylamide (LDA), triethylamine, DBU, pyridine, picoline or quinoline, or an inorganic base such as sodium methoxide, potassium tert-butoxide, sodium hydroxide, potassium hydroxide, sodium carbonate, potassium carbonate, sodium acetate, potassium acetate, sodium hydrogencarbonate or potassium hydrogencarbonate, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, or an aprotic polar solvent such as acetonitrile, DMF or DMAC, may, for example, be used. As an acid, hydrochloric acid or sulfuric acid may be used. The above reaction is carried out within a range of from −70° C. to the boiling point of the solvent and is usually completed within from 1 to 24 hours. The object compound can be isolated from the reaction solution by a conventional method. Further, it is purified by recrystallization or column chromatography, as the case requires.

Further, the compound represented by the general formula (III-8) can be produced by reacting the compound represented by the general formula (II-4) with ethanol in the presence of an acid. As a solvent, ethanol may be used. As the acid, hydrochloric acid or sulfuric acid may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires Process 3

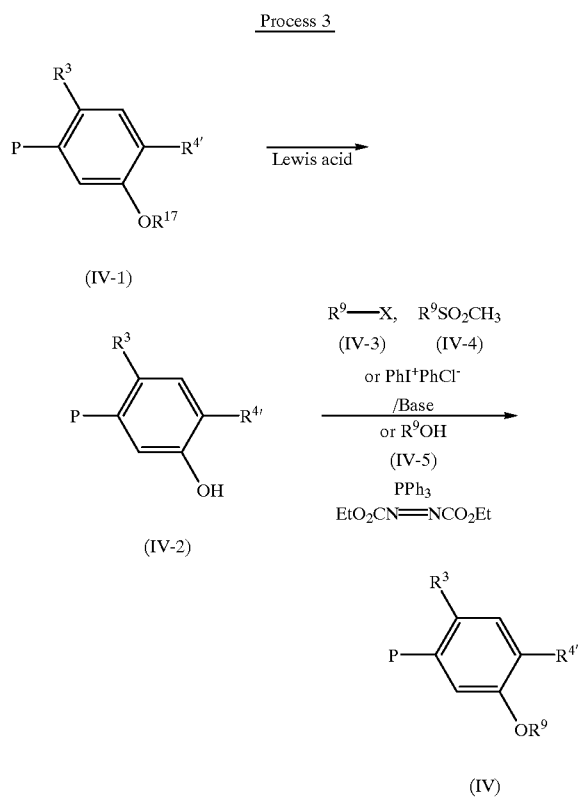

[In the formulae, each of $R^3$, $R^{4'}$ and $R^9$ is as defined above, $R^{17}$ is a $C_1$–$C_6$ alkyl group, and P represents a formula of

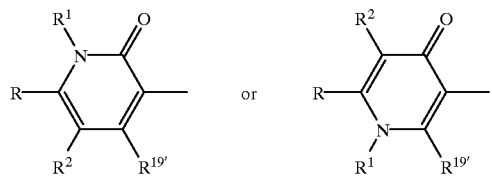

(wherein each of R, $R^1$, $R^2$ and $R^{19'}$ is as defined above.)]

A compound of the present invention represented by the general formula (IV-1) and a Lewis acid are reacted to obtain a compound of the present invention represented by the general formula (IV-2). As the Lewis acid, boron tribromide or aluminum trichloride may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, a carboxylic acid such as acetic acid, or an aprotic polar solvent such as acetonitrile, DMF or DMAC, may, for example, be used. The above reaction is carried out within a range of from $-10°$ C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (IV-2) and a compound represented by the general formula (IV-3), a compound represented by the general formula (IV-4) or diphenyliodonium chloride (when $R^9$ is a phenyl group), are reacted in the presence of a base, or it and a compound represented by the general formula (IV-5) are reacted in the presence of diethyl azodicarboxylate and triphenylphosphine, to obtain a compound of the present invention represented by the general formula (IV). As the base, an organic amine such as triethylamine, DBU, pyridine, picoline or quinoline, or an inorganic base such as sodium methoxide, potassium tert-butoxide, sodium hydroxide, potassium hydroxide, sodium carbonate, potassium carbonate, sodium acetate, potassium acetate, sodium hydrogencarbonate or potassium hydrogencarbonate, may, for example, be used. As a solvent, ahalogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, a carboxylic acid such as acetic acid, or an aprotic polar solvent such as acetonitrile, DMF or DMAC, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Process 4

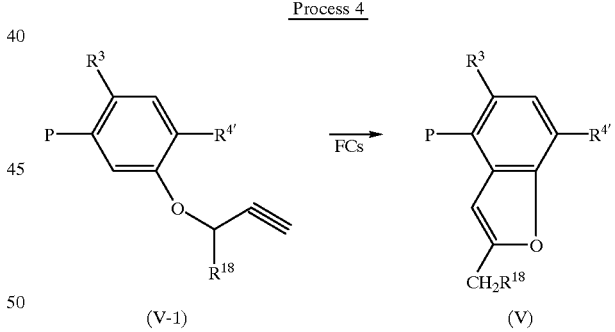

(In the formulae, each of P, $R^3$ and $R^{4'}$ is as defined above, and $R^{18}$ is a $C_1$–$C_5$ alkyl group or a hydrogen atom.)

A compound of the present invention represented by the general formula (V-1) is subjected to a ring-closure reaction in the presence of cesium fluoride to obtain a compound of the present invention represented by the general formula (V). As a solvent, an N,N-dialkylaniline such as N,N-diethylaniline or N,N-dimethylaniline, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Process 5

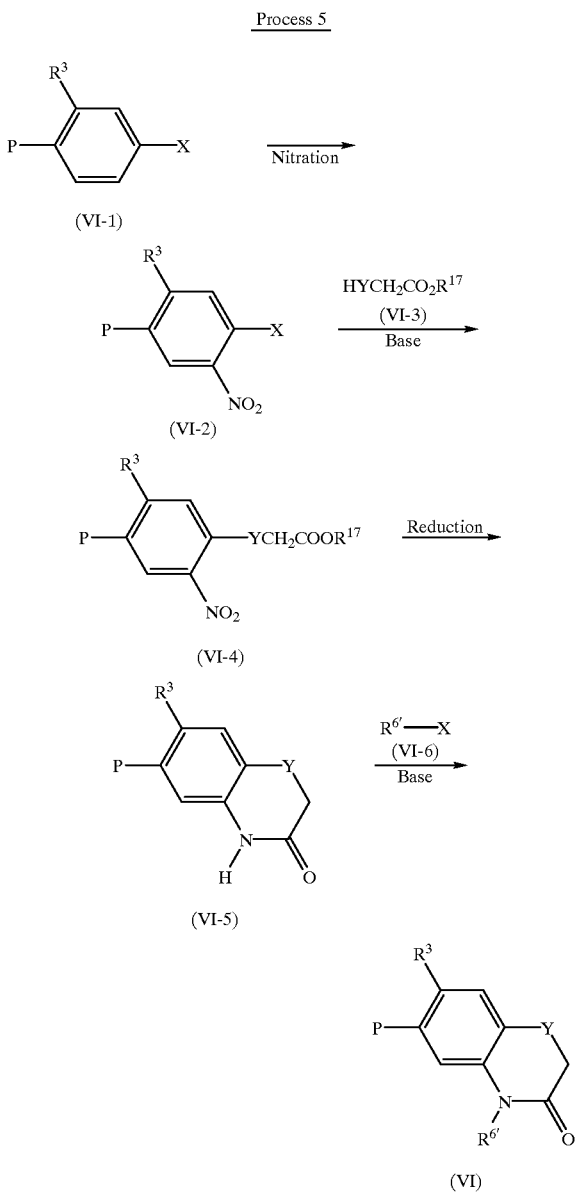

(In the formulae, each of P, $R^3$, $R^{6'}$, $R^{17}$, X and Y is as defined above.)

A compound of the present invention represented by the general formula (VI-1) is subjected to nitration to obtain a compound of the present invention represented by the general formula (VI-2) As the nitration agent, nitric acid or fuming nitric acid, or a mixed acid of nitric acid or fuming nitric acid with sulfuric acid, may, for example, be used. The above reaction is carried out within range of from −10° C. to the boiling point of the solvent and is usually completed within from 1 to 24 hours. The object compound can be isolated from the reaction solution by a conventional method. Further, it is purified by recrystallization for column chromatography, as the case requires.

Then, the compound of the present invention represented by the general formula (VI-2) and a compound represented by the general formula (VI-3) are reacted in the presence of a base to obtain a compound of the present invention represented by the general formula (VI-4). As the base, an inorganic base such as sodium, sodium hydride, sodium hydroxide, potassium hydroxide, sodium carbonate, potassium carbonate, sodium hydrogencarbonate or potassium hydrogencarbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, a carboxylic acid such as acetic acid, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (VI-4) is reduced to obtain a compound of the present invention represented by the general formula (VI-5). As the reducing agent, iron or tin/hydrochloric acid, may, for example, be used. As a solvent, a carboxylic acid such as acetic acid, a hydrocarbon such as benzene or toluene, an alcohol such as methanol or ethanol, or water, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (VI-5) and a compound represented by the general formula (VI-6) are reacted in the presence of a base to obtain a compound of the present invention represented by the general formula (VI). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Process 6

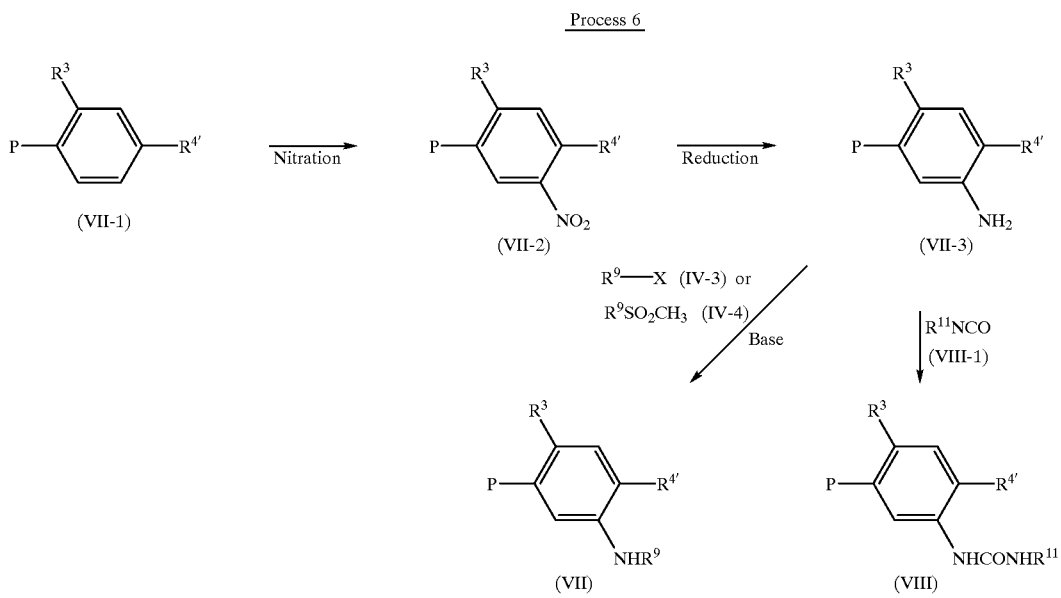

(In the formulae, each of P, $R^3$, $R^{4'}$, $R^9$, $R^{11}$ and X is as defined above.)

A compound of the present invention represented by the general formula (VII-1) is subjected to nitration to obtain a compound of the present invention represented by the general formula (VII-2). As the nitration agent, nitric acid or fuming nitric acid, or a mixed acid of nitric acid or fuming acid with sulfuric acid, may, for example, be used. The above reaction is carried out within a range of from –10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (VII-2) is reduced to obtain a compound of the present invention represented by the general formula (VII-3). As the reducing agent, iron or tin/hydrochloric acid, may, for example, be used. As a solvent, a carboxylic acid such as acetic acid, a hydrocarbon such as benzene or toluene, an alcohol such as methanol or ethanol, or water, may for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (VII-3) and a compound represented by the general formula (IV-3) or (IV-4) are reacted in the presence of a base to obtain a compound of the present invention represented by the general formula (VII). As the base, an inorganic base such as sodium, sodium hydride, sodium hydroxide, potassium hydroxide, sodium carbonate, potassium carbonate, sodium hydrogencarbonate or potassium hydrogencarbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from room temperature to the boiling point of the solvent and is usually completed within from 1 to 24 hours. In the case of the reaction with the compound represented by the general formula (IV-4), the formed bis product is hydrolyzed by an aqueous sodium hydroxide solution in ethanol. The object compound can be isolated from the reaction solution by a conventional method. Further, it is purified by recrystallization or column chromatography, as the case requires.

Further, a compound of the present invention represented by the general formula (VII-3) and a compound represented by the general formula (VIII-1) are reacted to obtain a compound of the present invention represented by the general formula (VIII). As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Process 7

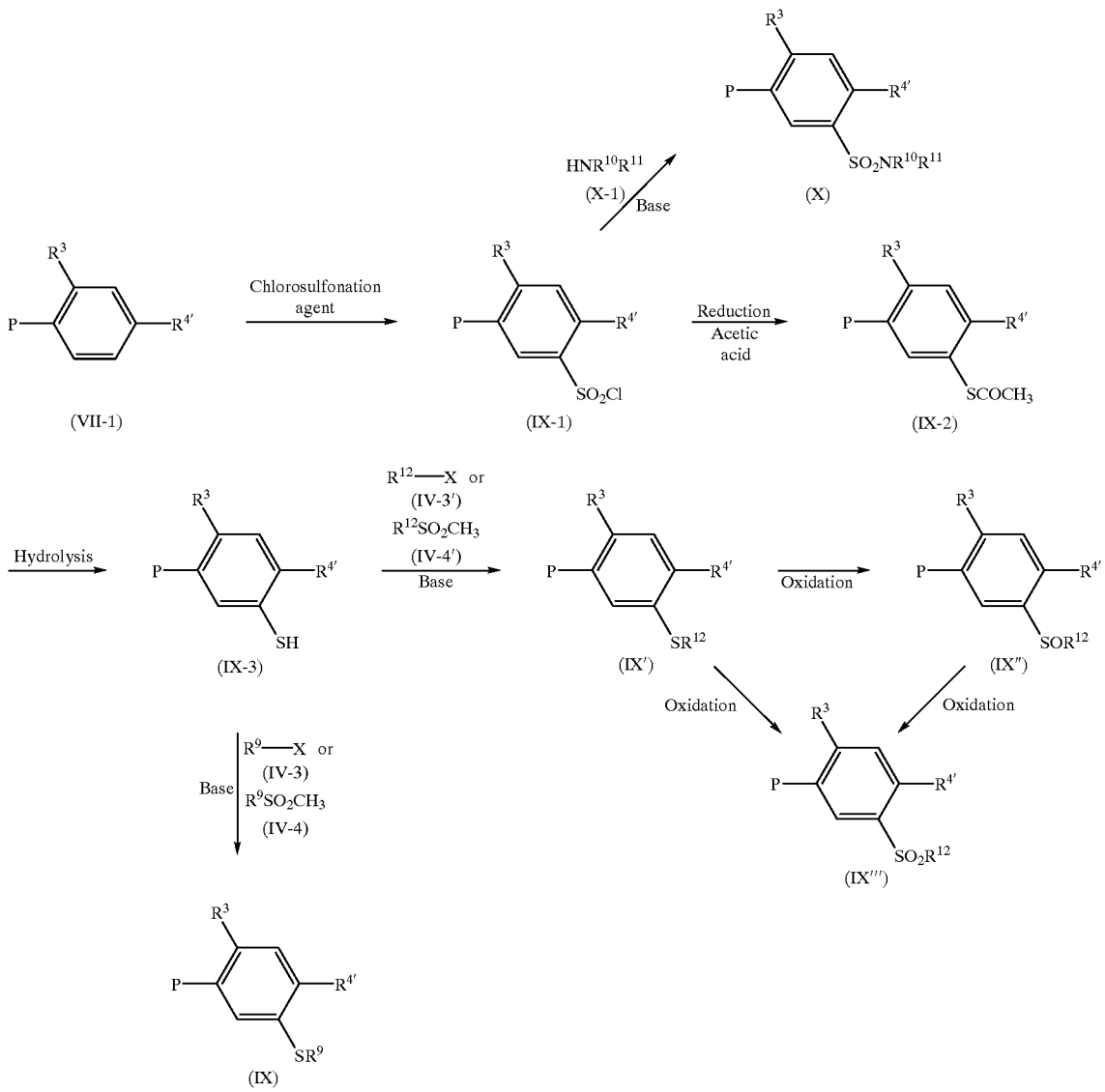

(In the formulae, each of P, $R^3$, $R^{4'}$, $R^9$, $R^{10}$, $R^{11}$, $R^{12}$ and X is as defined above.)

A comnpound of the present invention represented by the general formula (VII-1) and a chlorosulfonation agent are reacted to obtain a compound of the present invention represented by the general formula (IX-1). As the chlorosulfonation agent, chlorosulfonic acid or a mixed solution comprising sulfuric anhydride, sulfuric acid and carbon tetrachloride, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (IX-1) is reduced to obtain a compound of the present invention represented by the general formula (IX-2). As the reducing agent, a mixture of red phosphorus and iodine, or zinc, may, for example, be used.

As a solvent, acetic acid may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (IX-2) is subjected to alkali hydrolysis to obtain a compound of the present invention represented by the general formula (IX-3). As base, sodium hydroxide or potassium hydroxide, may, or example, be used. As a solvent, methanol, ethanol, water or a mixture thereof, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (IX-3) and a compound represented by the general formula (IV-3) or a compound represented by the general formula (IV-4) are reacted in the presence of a base to obtain a compound of the present invention represented by the general formula (IX). As the base, an inorganic base such as sodium, sodium hydride, sodium hydroxide, potassium hydroxide, sodium carbonate, potassium carbonate, sodium hydrogencarbonate or potassium hydrogencarbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

In the same manner as above, the compound of the present invention represented by the general formula (IX-3y) and a compound represented by the general formula (IV-3') or a compound represented by the general formula (IV-4') are reacted in the presence of a base, to obtain a compound of the present invention represented by the general formula (IX'). As the base, an inorganic base such as sodium, sodium hydride, sodium hydroxide, potassium hydroxide, sodium carbonate, potassium carbonate, sodium hydrogencarbonate or potassium hydrogencarbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within 1 to 24 hours. The object compound can be isolated from the reaction solution by a conventional method. Further, it is purified by recrystallization or column chromatography, as the case requires.

Then, the compound of the present invention represented by the general formula (IX') is oxidized to obtain a compound of the present invention represented by the general formula (IX″) or a compound of the present invention represented by the general formula (IX′″). As the oxidizing agent, hydrogen peroxide, m-chloroperbenzoic acid, sodium hypochlorite or potassium peroxymonosulfate (tradename: Oxone), may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, an aprotic polar solvent such as acetonitrile, DMF or DMAC, or a protic polar solvent such as methanol, ethanol or water, may, for example, be used. The above reaction is carried out within a range of from room temperature to the boiling point of the solvent and is usually completed within from 1 to 24 hours. The object compound can be isolated from the reaction solution by a conventional method.

Further, it is purified by recrystallization or column chromatography, as the case requires.

Further, a compound represented by the general formula (IX-1) and a compound represented by tne general formula (X-1) are reacted in the presence of a base to obtain a compound of the present invention represented by the general formula (X). As the base, an inorganic base such as sodium, sodium hydride, sodium hydroxide, potassium hydroxide, sodium carbonate, potassium carbonate, sodium hydrogencarbonate or potassium hydrogencarbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

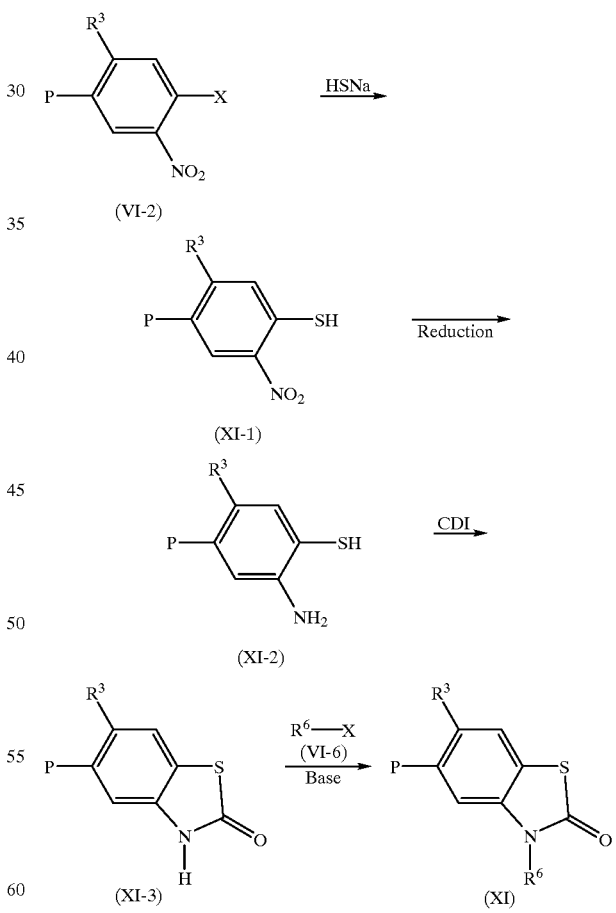

(In the formulae, each of P, $R^3$, $R^6$ and X is as defined above.)

A compound of the present invention represented by the general formula (VI-2) and sodium hydrogensulfide are reacted to obtain a compound of the present invention represented by the general formula (XI-1). As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, an acid such as acetic acid, or an aprotic polar solvent such as acetonitrile, DMF or DMAC, may, for example, be used. The above reaction is carried out within a range of from $-10°$ C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XI-1) is reduced to obtain a compound of the present invention represented by the general formula (XI-2). As the reducing agent, iron or tin/hydrochloric acid, may, for example, be used. As a solvent, a carboxylic acid such as acetic acid, a hydrocarbon such as benzene or toluene, an alcohol such as methanol or ethanol, or water, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XI-2) and CDI are reacted to obtain a compound of the present invention represented by the general formula (XI-3). As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from $-10°$ C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XI-3) and a compound represented by the general formula (VI-6) are reacted in the presence of a base to obtain a compound of the present invention represented by the general formula (XI). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene., an aliphatic ketone such as acetone or methyl ethyl ketone, or an aprotic polar solvent such as acetonitrile, DMF or DMAC, may, for example, be used. The above reaction is carried out within a range of from $-10°$ C. to the boiling point of the solvent and is usually completed within from 1 to 24 hours. The object compound can be isolated from the reaction solution by a conventional method. Further, it is purified by recrystallization or column chromatography, as the case requires.

Process 9

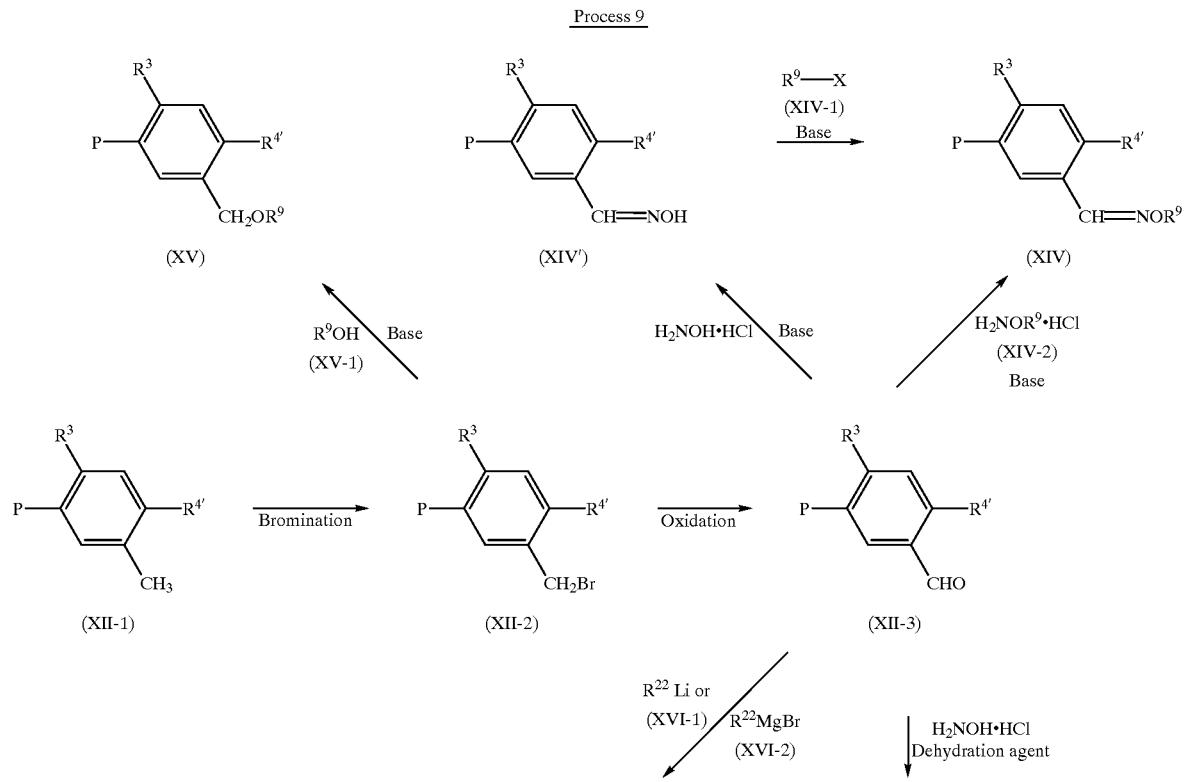

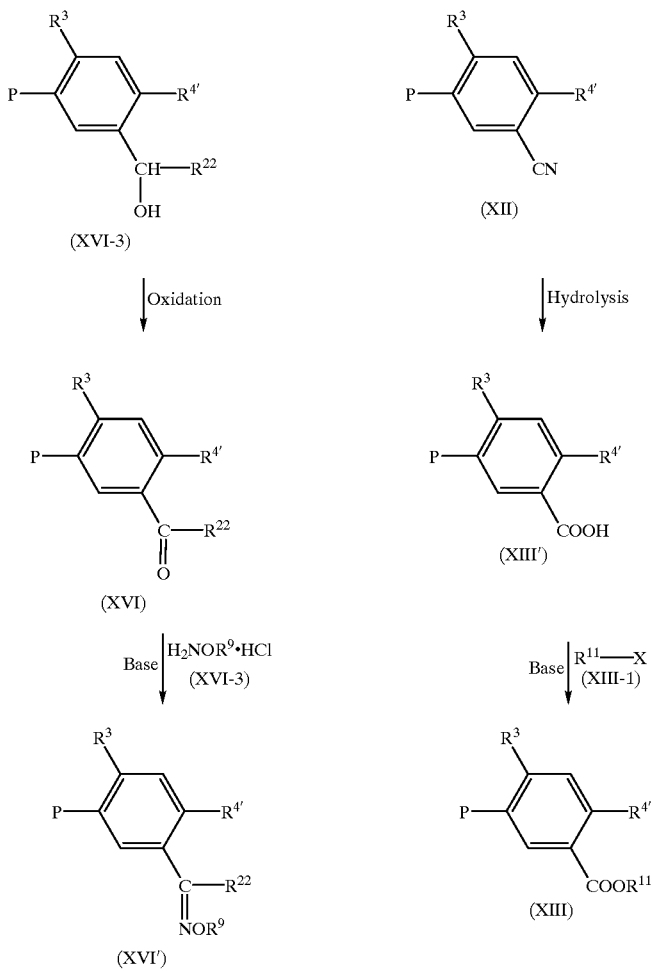

(In the formulae, each of P, $R^3$, $R^{4'}$, $R^9$, $R^{11}$ and X is as defined above, $R^{22}$ is a $C_1$–$C_6$ alkyl group, a $C_2$–$C_6$ alkenyl group or a $C_3$–$C_6$ alkynyl group.)

A compound of the present invention represented by the general formula (XII-1) is brominated to obtain a compound of the present invention represented by the general formula (XII-2). As the bromination agent, N-bromosuccinimide (NBS) may, for example, be used. As a catalyst, 2,2′-azobisisobutyronitrile is used, and as a solvent, a halogenated hydrocarbon such as carbon tetrachloride, may, for example, be used. The above reaction is carried out within a range of from room temperature to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XII-2) is oxidized to obtain a compound of the present invention represented by the general formula (XII-3). As the oxidizing agent, one prepared from sodium methoxide and 2-nitropropane, may, for example, be used. As a solvent, an alcohol such as methanol or ethanol may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires .

Then, the compound of the present invention represented by the general formula (XII-3) is treated with hydroxylamine hydrochloride and a dehydration agent to obtain a compound of the present invention represented by the general formula (XII). As the dehydration agent, magnesium sulfate, sodium sulfate or p-toluenesulfonic acid may, for example, be used. Further, they may be used as mixed in some cases. As a solvent, a hydrocarbon such as n-hexane, benzene, toluene or xylene, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XII) is hydrolyzed to obtain a compound of the present invention represented by the general formula (XIII′). As an acid, sulfuric acid or hydrochloric acid may, for example, be used. As a solvent, an alcohol such as methanol or ethanol, or a protonic polar solvent such as water, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XIII') and a compound represented by the general formula (XIII-1) are reacted in the presence of a base to obtain a compound of the present invention represented by the general formula (XIII). As the base, an inorganic base such as sodium, sodium hydride, sodium hydroxide, potassium hydroxide, sodium carbonate or potassium carbonate, may, for example, be used. As a solvent, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XII-3) and hydroxyamine hydrochloride are reacted in the presence of a base to obtain a compound of the present invention represented by the general formula (XIV'). As a base, an inorganic base such as sodium, sodium hydride, sodium hydroxide, potassium hydroxide, sodium acetate, potassium acetate, sodium carbonate or potassium carbonate, may, for example, be used. As a solvent, a hydrocarbon such as benzene or toluene, or an alcohol such as methanol or ethanol, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XIV') and a compound represented by the general formula (XIV-1) are reacted in the presence of a base to obtain a compound of the present invention represented by the general formula (XIV). As the base, an inorganic base such as sodium, sodium hydride, sodium hydroxide, potassium hydroxide, sodium carbonate or potassium carbonate, may, for example, be used. As a solvent, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, imay, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Further, as another method, a compound of the present invention represented by the general formula (XII-3) and a compound represented by the general formula (XIV-2) are reacted in the presence of a base to obtain a compound of the present invention represented by the general formula (XIV). As the base, an inorganic base such as sodium, sodium hydride, sodium hydroxide, potassium hydroxide, sodium acetate, potassium acetate, sodium carbonate or potassium carbonate, may, for example, be used. As a solvent, a hydrocarbon such as benzene or toluene, or an alcohol such as methanol or ethanol, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XII-2)) and a compound represented by the general formula (XV-1) are reacted in the presence of a base to obtain a compound of the present invention represented by the general formula (XV). As the base, an inorganic base such as sodium, sodium hydride, sodium hydroxide, potassium hydroxide, potassium hydroxide, sodium carbonate or potassium carbonate, may, for example, be used. As a solvent, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XII-3) and a compound represented by the general formula (XVI-1) or (XVI-2) are reacted to obtain a compound of the present invention represented by the general formula (XVI-3). As a solvent, an ether such as diethyl ether, THF or dioxane, or a hydrocarbon such as n-hexane, benzene or toluene, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XVI-3) is reacted with dimethylsulfoxide (DMSO) and oxalyl chloride and then oxidized by an addition of a base, to obtain a compound of the present invention represented by the general formula (XVI). As the base, an organic amine such as triethylamine, DBU, pyridine, picoline or quinoline, may, for example, be used. As a solvent, a halogenated hydrocarbon such as dichloromethane, chloroform or carbon tetrachloride, may, for example, be used. The above reaction is carried out within a range of from −80° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XVI) and a compound of represented by the general formula (XVI-3) are reacted in the presence of a base to obtain a compound of the present invention represented by the general formula (XVI'). As the base, an inorganic base such as sodium, sodium hydride, sodium hydroxide, potassium hydroxide, sodium acetate, potassium acetate, sodium carbonate or potassium carbonate, may, for example, be used. As a solvent, a hydrocarbon such as benzene or toluene, or an alcohol such as methanol or ethanol, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Process 10

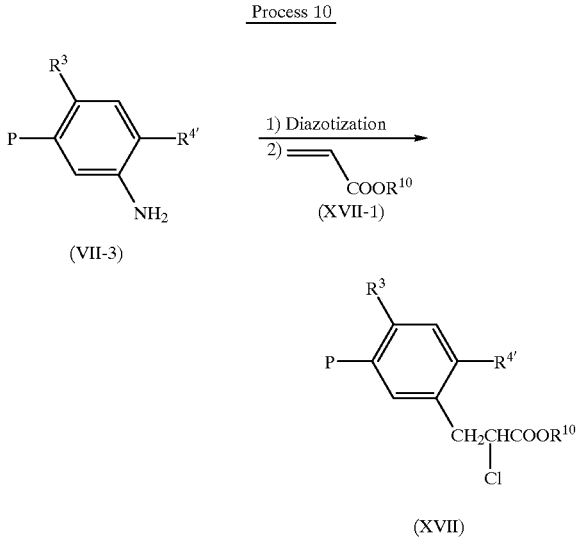

(In the formulae, each of P, $R^3$, $R^{4'}$ and $R^{10}$ is as defined above.)

A compound of the present invention represented by the general formula (VII-3) is reacted with tert-butyl nitrite and copper (II) chloride for diazotization and then reacted with a compound represented by the general formula (XVII-1) to obtain a compound of the present invention represented by the general formula (XVII). As a solvent, a halogenated hydrocarbon such as dichloromethane, chloroform or carbon tetrachloride, an ether such as diethyl ether, THF or dioxane, a hydrocarbon such as n-hexane, benzene or toluene, or an aprotic polar solvent such as acetonitrile, DMF or DMAC, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Process 11

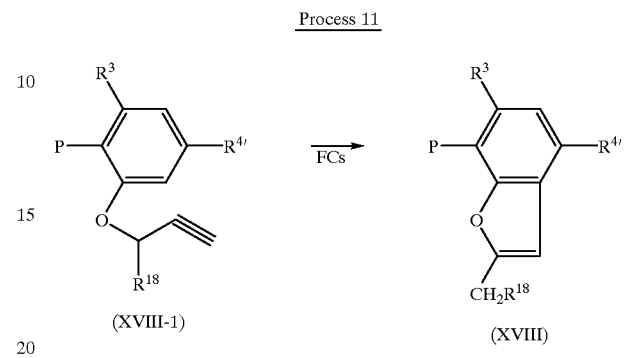

(In the formulae, each of P, $R^3$, $R^{4'}$ and $R^{18}$ is as defined above.)

A compound of the present invention represented by the general formula (XVIII-1) is subjected to a ring-closure reaction in the presence of cesium fluoride to obtain a compound of the present invention represented by the general formal (XVIII). As a solvent, an N,N-dialkylaniline such as N,N-diethylaniline or N,N-dimethylaniline, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Process 12

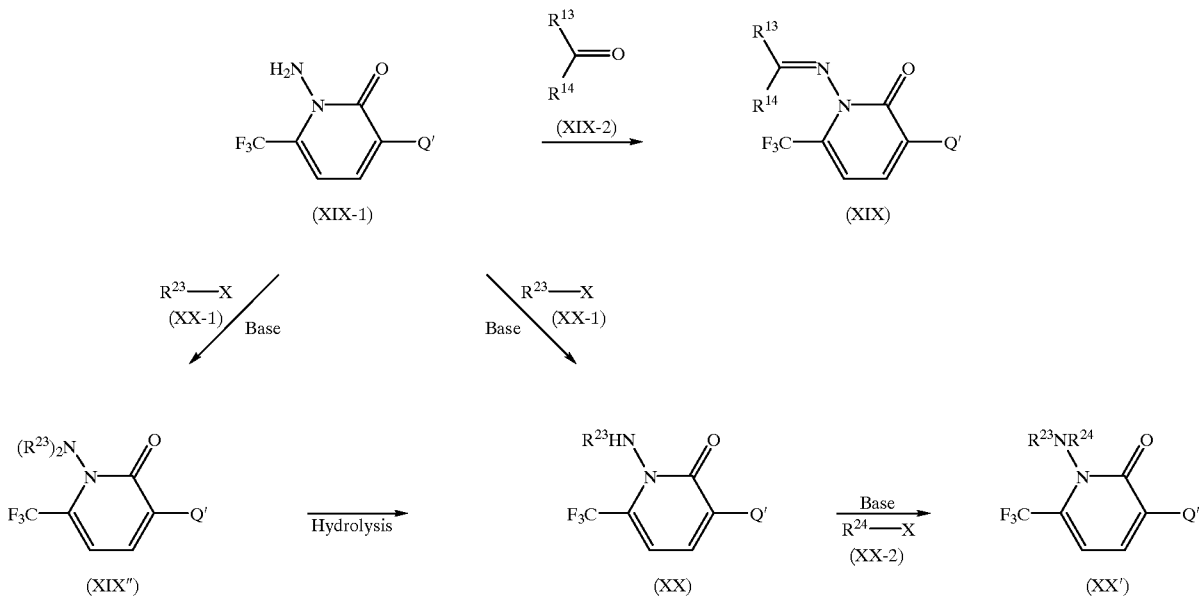

(In the formulae, each of Q', $R^{13}$, $R^{14}$, $R^{23}$ and $R^{24}$ is as defined above.)

A compound of the present invention represented by the general formula (XIX-1) is reacted with a compound represented by the general formula (XIX-2) in some cases by means of a Lewis acid to obtain a compound of the present invention represented by the general formula (XIX) As the Lewis acid, p-toluene sulfonic acid or titanium tetrachloride may be used. As a solvent, a halogenated hydrocarbon such as dichloromethane, chloroform or carbon tetrachloride, an ether such as diethyl ether, THF or dioxane, a hydrocarbon such as n-hexane, benzene or toluene, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XIX-1) and a compound represented by the general formula (XX-1) are reacted in some cases in the presence of a base to obtain a compound of the present invention represented by the general formula (XX) or a compound of the present invention represented by the general formula (XIX"). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XX) and a compound represented by the general formula (XX-2) are reacted in some cases in the presence of a base to obtain a compound of the present invention represented by the general formula (XX'). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

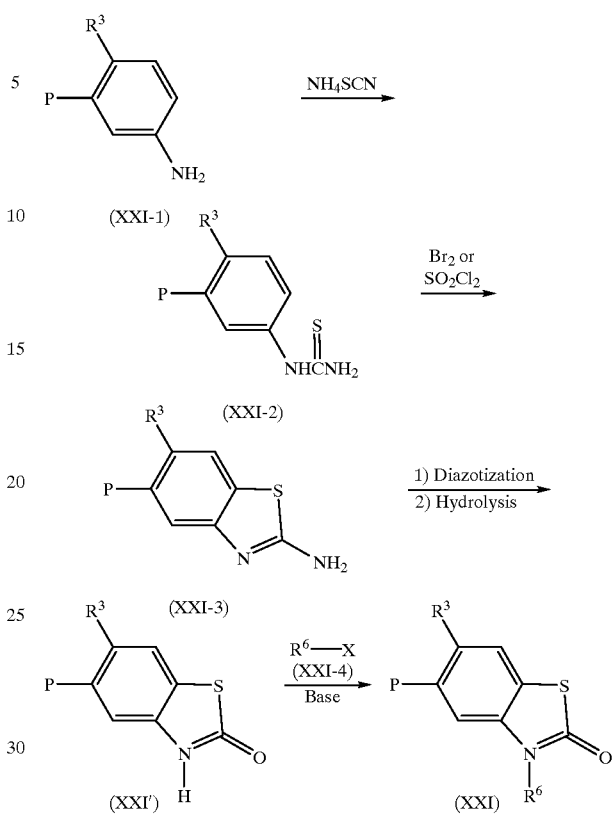

Process 13

(In the formulae, each of P, $R^3$, $R^6$ and X is as defined above.)

A compound of the present invention represented by the general formula (XXI-1) is reacted with ammonium thiocyanate to produce the compound of the present invention represented by the general formula (XXI-2). As a solvent, a hydrocarbon such as benzene or toluene, an acid such as acetic acid, or an alcohol such as methanol or ethanol, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XXI-2) is reacted with bromine or sulfuryl chloride to obtain a compound of the present invention represented by the general formula (XXI-3). As a solvent, a halogenated hydrocarbon such as dichloromethane, chloroform or carbon tetrachloride, an ether such as diethyl ether, THF or dioxane, a hydrocarbon such as n-hexane, benzene or toluene, an acid such as acetic acid, an aliphatic ketone such as acetone or methyl ethyl ketone, or an aprotic polar solvent such as acetonitrile, DMF and DMAC, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XXI-3) is diazotized and then hydrolyzed in some cases by means of a catalyst such as copper (II) nitrate or copper (I) oxide, to obtain a compound of the present invention represented by the general formula (XXI). As the diazotization agent, sodium nitrite may, for example, be used, and as a solvent, acetic acid, hydrochloric acid, sulfuric acid, water or a mixture thereof, may, for example, be used. The above reaction is carried out within a range of from −10° C. to the boiling point of the solvent and is usually completer within from 1 to 24 hours. The object compound can be isolated from the reaction solution by a conventional method. Further, it is purified by recrystallization or column chromatography, as the case requires.

Then, the compound of the present invention represented by the general formula (XXI') and a compound represented by the general formula (XXI-4) are reacted in the presence of a base to obtain a compound of the present invention represented by the general formula (XXI) As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

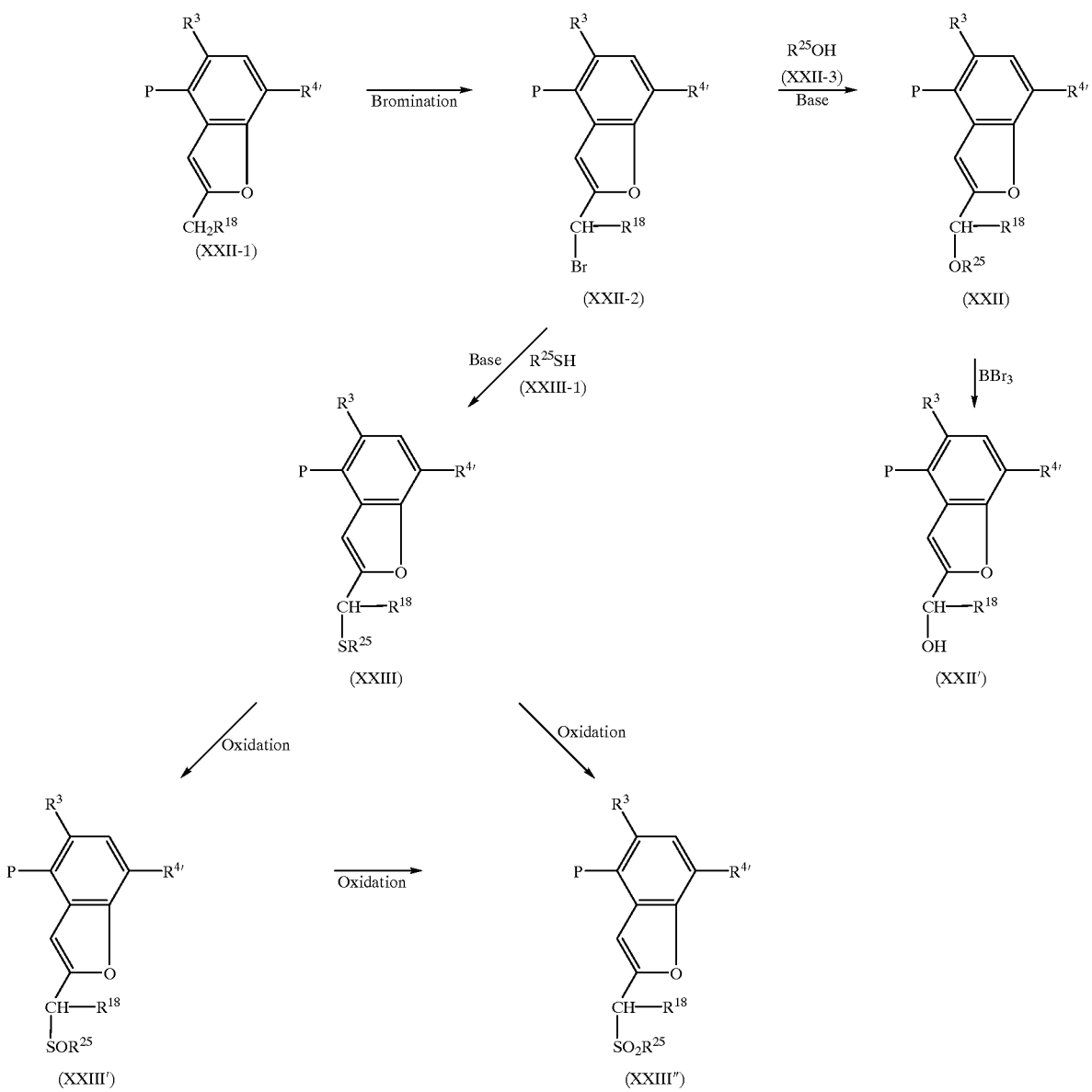

(In the formulae, each of P, $R^3$, $R^{4'}$ and $R^{18}$ is as defined above, and $R^{25}$ is a hydrogen atom or an alkyl group.)

A compound of the present invention represented by the general formula (XXII-1) is brominated to obtain a compound of the present invention represented by the general formula (XXII-2). As the bromination agent, NBS may, for example, be used. As a catalyst, 2,2'-azobisisobutyronitrile may, for example, be used. As a solvent, a halogenated hydrocarbon such as carbon tetrachloride may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XXII-2) and a compound represented by the general formula (XXII-3) a re reacted in the presence of a base to obtain a compound of the present invention represented by the general formula (XXII). As the base, an inorganic base such as sodium, sodium hydride, sodium hydroxide, potassium hydroxide, sodium carbonate or potassium carbonate, may, for example, be used. As a solvent, an ether such as diethyl ether, THF or dioxane, a hydrocarbon such as n-hexane, benzene or toluene, an aliphatic ketone such as acetone or methyl ethyl ketone, an aprotic polar solvent such as acetonitrile, DMF or DMAC, or an excess amount of the compound represented by the general formula (XXII-3) may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XXII) is reacted with boron tribromide to obtain a compound of the present invention represented by the general formula (XXII') As the solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −70° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XXII-2) and a compound represented by the general formula (XXIII-1) are reacted in the presence of a base to obtain a compound of the present invention represented by the general formula (XXIII). As the base, an inorganic base such as sodium, sodium hydride, sodium hydroxide, potassium hydroxide, sodium carbonate or potassium carbonate, may, for example, be used. As a solvent, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XXIII) is oxidized to obtain a compound of the present invention represented by the general formula (XXIII') or a compound of the present invention represented by the general formula (XXIII"). As the oxidizing agent, hydrogen peroxide, m-chloroperbenzoic acid, sodium hypochlorite or potassium peroxymonosulfate (tradename: Oxone), may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, an aprotic polar solvent such as acetonitrile, DMF or DMAC, or a protic polar solvent such as methanol, ethanol or water, may, for example, be used. The above reaction is carried out within a range of from room temperature to the boiling point of the solvent and is usually completed within from 1 to 24 hours. The object compound can be isolated from the reaction solution by a conventional method. Further, it is purified by recrystallization or column chromatography, as the case requires.

Process 15

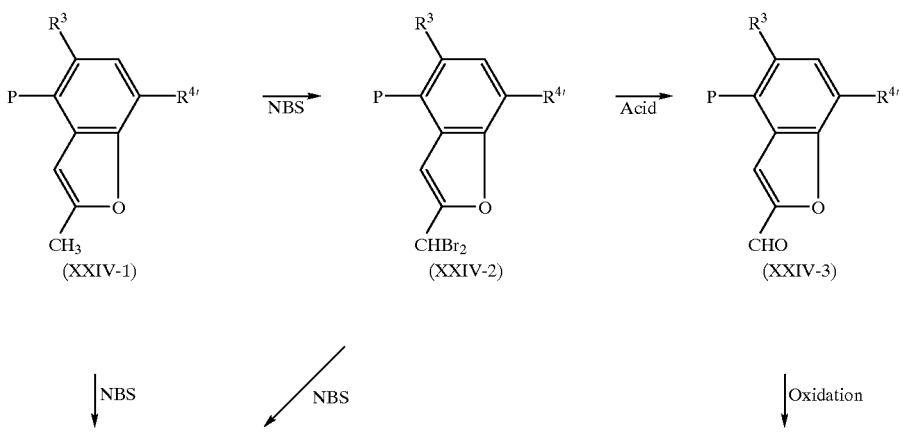

-continued

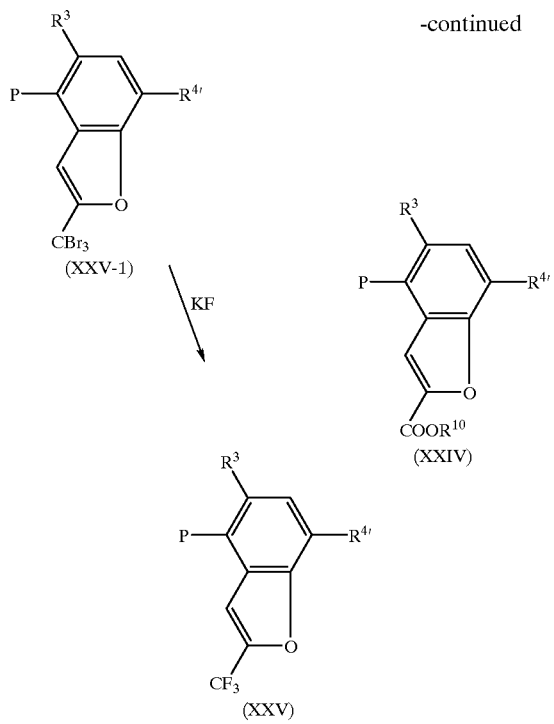

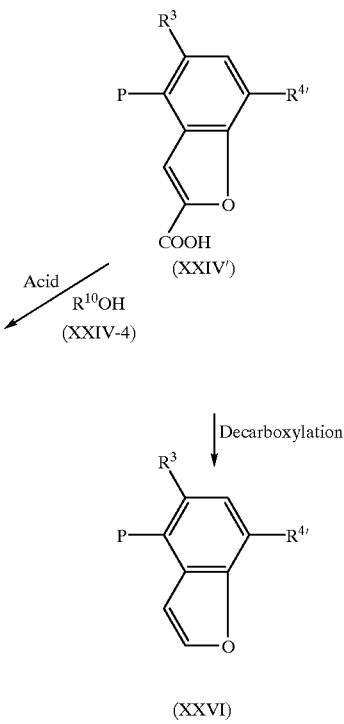

(In the formulae, each of P, $R^3$, $R^{4'}$ and $R^{10}$ is as defined above.)

A compound of the present invention represented by the general formula (XXIV-1) is brominated to obtain a compound of the present invention represented by the general formula (XXIV-2) or a compound of the present invention represented by the general formula (XXV-1). As the bromination agent, NBS may, for example, be used. As a catalyst, 2,2'-azobisisobutyronitrile may, for example, be used. As a solvent, a halogenated hydrocarbon such as carbon tetrachloride may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

The compound of the present invention represented by the general formula (XXIV-2) is subjected to acid treatment to obtain a compound of the present invention represented by the general formula (XXIV-3). As the acid, sulfuric acid or hydrochloric acid may be used. The above reaction is carried out within a range of from −10° C. to the boiling point of the solvent in some cases in the presence of a nitrogen stream and is usually completed within from 1 to 24 hours. The object compound can be isolated from the reaction solution by a conventional method. Further, it is purified by recrystallization or column chromatography, as the case requires.

The compound of the present invention represented by the general formula (XXIV-3) is oxidized to obtain a compound of the present invention represented by the general formula (XXIV'). As the oxidizing agent, a Jones reagent ($CrO_3$—$H_2SO_4$) may be used. As a solvent, a ketone such as acetone may, for example, be used. The above reaction is carried out within a range of from −20° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

The compound of the present invention represented by the general formula (XXIV') and a compound represented by the general formula (XXIV-4) are reacted in the presence of a catalyst to obtain a compound of the present invention represented by the general formula (XXIV). As the catalyst, sulfuric acid or p-toluene sulfonic acid may, for example, be used. Further, as a solvent, a compound represented by the general formula (XXIV-4) may be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

The compound of the present invention represented by the general formula (XXIV') is decarboxylated in some cases by means of a catalyst such as copper, to obtain a compound of the present invention represented by the general formula (XXVI). As a solvent, a basic solvent such as quinoline, may, for example, be used, or the reaction can be carried out in the absence of a solvent. The above reaction is carried out within a range of from 100° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

The compound of the present invention represented by the general formula (XXV-1) is reacted with a fluorination agent to obtain a compound of the present invention represented by the general formula (XXV). As the fluorination agent, potassium fluoride may, for example, be used. As a solvent, an aprotic polar solvent such as acetonitrile, DMF or DMAC, may, for example, be used. The above reaction is carried out within a range of from −10° C. to the boiling point of the solvent in some cases in a nitrogen stream and

Process 16

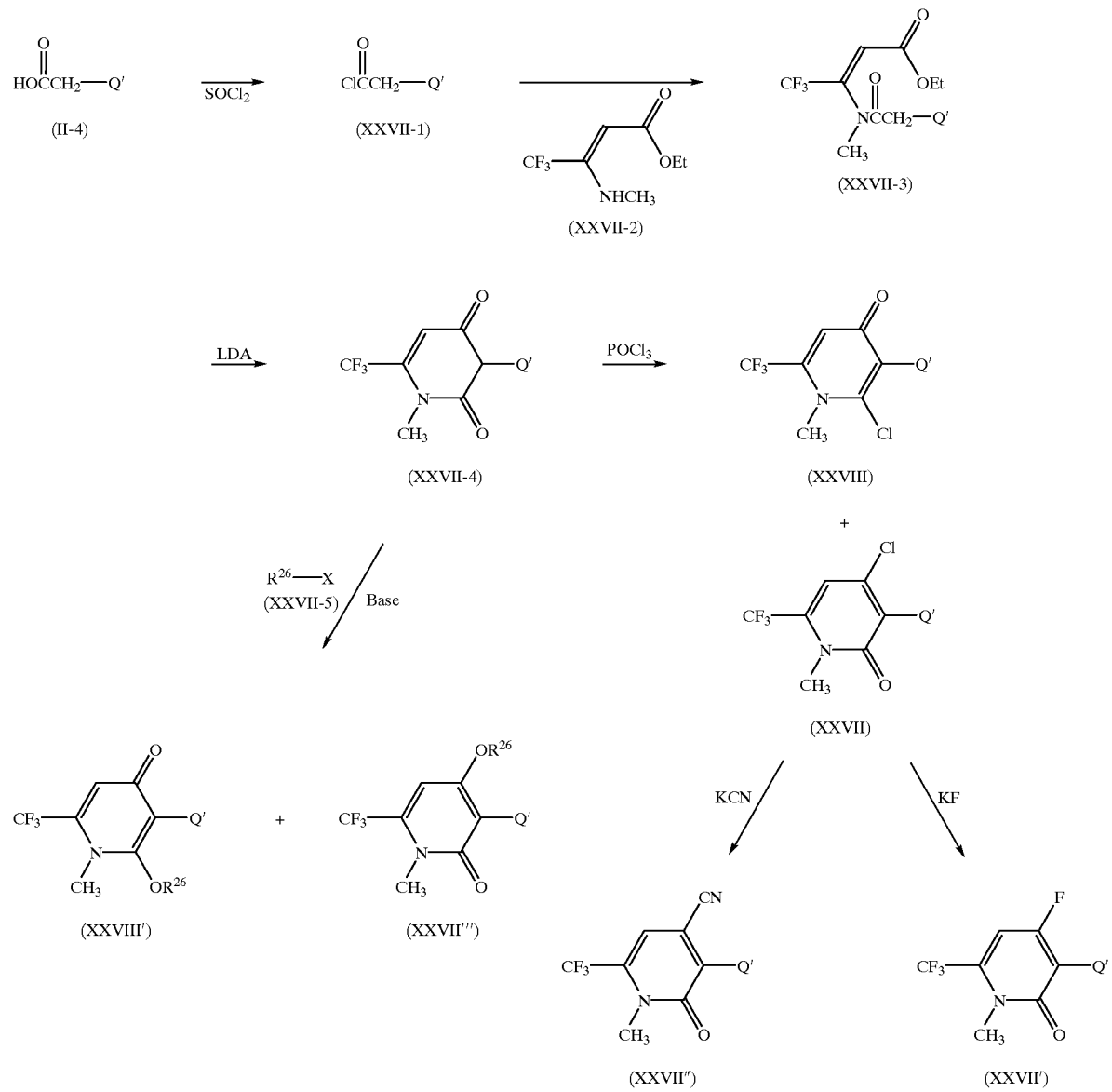

(In the formulae, Q' is as defined above, and $R^{26}$ is a $C_1$–$C_6$ alkyl group.)

A compound of the present invention represented by the general formula (II-4) is reacted with thionyl chloride to obtain a compound of the present invention represented by the general formula (XXVII-1). As a solvent, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. Further, thionyl chloride may be used also as a solvent. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound represented by the general formula (XXVII-1) and a compound represented by the general formula (XXVII-2) are reacted in some cases in the presence of a base to obtain a compound represented by the general formula (XXVII-3). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform. or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound represented by the general formula (XXVII-3) is reacted with LDA to obtain a compound represented by the general formula (XXVII-4). As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used The above reaction is carried out within a range of from −80° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound represented by the general formula (XXVII-4) is reacted with phosphorus oxychloride to obtain a compound of the present invention represented by the general formula (XXVII) and a compound of the present invention represented by the general formula (XXVIII). As a solvent, diethylaniline, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, may, for example, be used. Further, phosphorus oxychloride may be used as a solvent. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization, column chromatography or liquid column chromatography, as the case requires.

Then, the compound represented by the general formula (XXVII) is reacted with potassium fluoride to obtain a compound of the present invention represented by the general formula (XXVII'). As a solvent, an ether such as diethyl ether, THF or dioxaie, a hydrocarbon such as n-hexane, benzene or toluene, or an aprotic polar solvent such as acetonitrile, DMF or DMAC, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound represented by the general formula (XXVII) is reacted with potassium cyanide to obtain a compound of the present invention represented by the general formula (XXVI''). As a solvent, an ether such as diethyl ether, THF or dioxane, a hydrocarbon such as n-hexane, benzene or toluene, or an aprotic polar solvent such as acetonitrile, DMF, DMAC or DMSO, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XXVII-4) and a compound represented by the general formula (XXVII-5) are reacted in the presence of a base to obtain a compound of the present invention represented by the general formula (XXVIII') and a compound of the present invention represented by the general formula (XXVII'''). As the base, an inorganic base such as sodium, sodium hydride, sodium hydroxide, potassium hydroxide, sodium carbonate or potassium carbonate, may, for example, be used. As a solvent, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF, DMAC or DMSO, may, for example, be used. The above reaction is carried out within a range of from −10° C. to the boiling point of the solvent in some cases in a nitrogen stream and is usually completed within from 1 to 48 hours. The object compound can be isolated from the reaction solution by a conventional method. Further, it is purified by recrystallization, column chromatography or liquid column chromatography, as the case requires.

Process 17

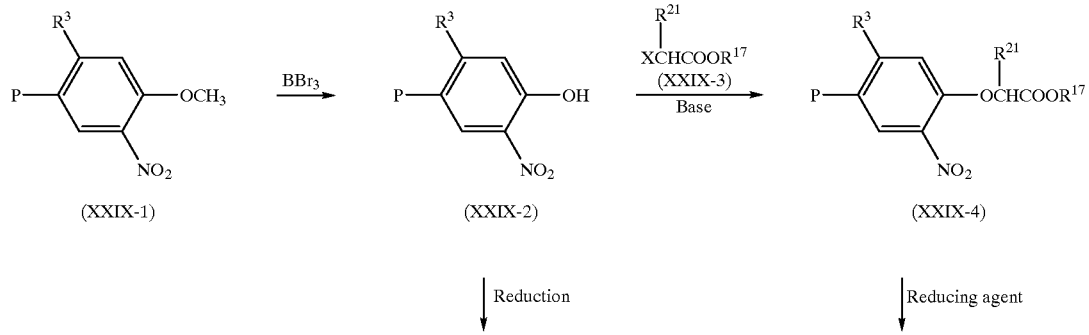

-continued

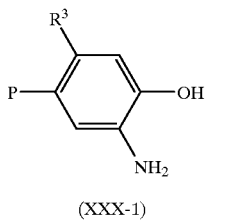

(XXX-1)

↓ CDI

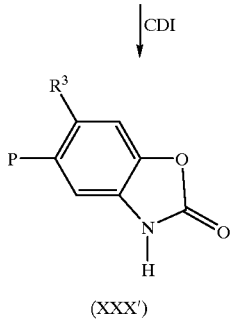

(XXX')

R⁶—X   Base
(XXX-2)

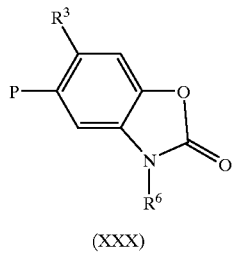

(XXX)

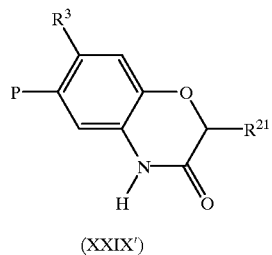

(XXIX')

R⁶—X
(XXIX-5)  Base

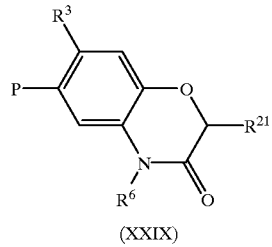

(XXIX)

(In the formulae, each of P, R³, R⁶, R¹⁷, R²¹ and X is as defined above.)

A compound of the present invention represented by the general formula (XXIX-1) is reacted with boron tribromide to obtain a compound of the present invention represented by the general formula (XXIX-2). As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −70° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

Then, the compound of the present invention represented by the general formula (XXIX-2) and a compound represented by the general formula (XXIX-3) are reacted in the presence of a base to obtain a compound of the present invention represented by the general formula (XXIX-4). As the base, an inorganic base such as sodium, sodium hydride, sodium hydroxide, potassium hydroxide, sodium carbonate or potassium carbonate, an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XXIX-4) is reacted with a reducing agent to obtain a compound of the present invention represented by the general formula (XXIX'). As the reducing agent, iron powder or tin, may, for example, be used, and in some cases, hydrochloric acid is used. As a solvent, a hydrocarbon such as benzene or toluene, an ester such as ethyl acetate or methyl acetate, an acid such as acetic acid, an alcohol such as methanol or ethanol or water, may, for example, be used. Further, in some cases, these solvents may be used as mixed. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XXIX') and a compound represented by the general formula (XXIX-5)) are reacted in the presence of a base to obtain a compound of the present invention represented by the general formula (XXIX). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XXIX-2) is reacted with a reducing agent to obtain a compound of the present invention represented by the general formula (XXX-1). As the reducing agent, iron powder or tin, may, for example, be used, and in some cases, hydrochloric acid may be used. As a solvent, a hydrocarbon such as benzene or toluene, an ester such as ethyl acetate or methyl acetate, an acid such as acetic acid, an alcohol such as methanol or ethanol, or water, may, for example, be used. Further, in some cases, these solvents may be mixed for use. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XXX-1) is reacted with CDI to obtain a compound of the present invention represented by the general formula (XXX'). As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, an alcohol such as methanol or ethanol, or an aprotic polar solvent such as acetonitrile, DMF or DMAC, may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Then, the compound of the present invention represented by the general formula (XXX') and a compound represented by the general formula (XXX-2) are reacted in the presence of a base to obtain a compound of the present invention represented by the general formula (XXX). As the base, an inorganic base such as sodium, sodium hydride, sodium hydroxide, potassium hydroxide, sodium carbonate or potassium carbonate, or an organic amine such as triethylamine, DBU, pyridine, picoline or quinoline, may, for example, be used. As a solvent, a halogenated hydrocarbon such as dichloromethane, chloroform or carbon tetrachloride, an ether such as diethyl ether, THF or dioxane, a hydrocarbon such as n-hexane, benzene or toluene, an aliphatic ketone such as acetone or methyl ethyl ketone, or an aprotic polar solvent such as acetonitrile, DMF, DMAC may, for example, be used. The above reaction is carried out within a range of from −10° C. to the boiling point of the solvent and is usually completed within from 1 to 24 hours. The object compound can be isolated from the reaction solution by a conventional method. Further, it is purified by recrystallization or column chromatography, as the case requires.

Process 18

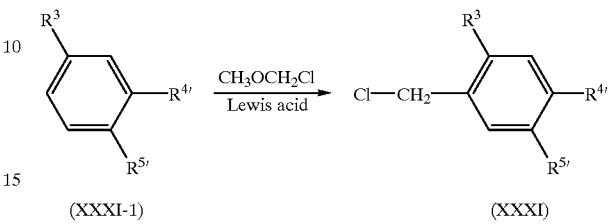

(XXXI-1) (XXXI)

(In the formulae, each of $R^3$ and $R^{4'}$ is as defined above, and $R^{5'}$ is a $C_1$–$C_6$ alkoxy group, a $C_3$–$C_6$ alkynyloxy group, a $C_3$–$C_6$ alkenyloxy group or a $C_1$–$C_6$ alkyl group.)

A compound represented by the general formula (XXXI-1) and methoxymethyl chloride are reacted in the presence of a Lewis acid to obtain a compound of the present invention represented by the general formula (XXXI). As the Lewis acid, titanium tetrachloride or aluminum chloride may, for example, be used. As a solvent, a halogenated hydrocarbon such as dichloromethane, chloroform or carbon tetrachloride, or an ether such as diethyl ether, THF or dioxane, may, for example, be used. The above reaction is carried out within a range of from −10° C. to the boiling point of the solvent in some cases in a nitrogen stream and is usually completed within from 1 to 24 hours. The object compound can be isolated from the reaction solution by a conventional method. Further, it is purified by recrystallization or column chromatography, as the case requires.

BEST MODE FOR CARRYING OUT THE INVENTION

Now, the processes for producing the compounds of the present invention, the formulation methods and the applications will be described in detail with reference to Examples. However, the present invention is by no means restricted to specific Examples. Firstly, specific processes for producing the compounds of the present invention will be described.

PREPARATION EXAMPLE 1

Preparation of 5-(4-chloro-2-fluoro-5-isopropoxyphenyl)-3-ethoxycarbonyl-2-trifluoromethyl-4(1H)-pyridone (Compound No. 6-57)

Preparation of 4-chloro-2-fluoro-5-isopropoxybenzyl bromide (Intermediate No. 15-1)

124 g (0.56 mol) of 4-chloro-2-fluoro-5-isopropoxybenzyl alcohol was dissolved in 900 ml of diethyl ether, and 55 g (0.20 mol) of phosphorus tribromide was dropwise added thereto under cooling with ice. After stirring at room temperature for 3 hours, the reaction solution was poured into ice water and extracted with diethyl ether. The extract was washed with water and an aqueous sodium hydrogencarbonate solution, and then, the organic layer was dried over anhydrous magnesium sulfate. Diethyl ether was distilled off under reduced pressure to obtain 143 g (yield: 89%) of the desired product.

Preparation of 4-chloro-2-flluoro-5-isopropoxyphenyl acetonitrile (Intermediate No. 15-2)

26 g (0.53 mol) of sodium cyanide was dissolved in 700 ml of DMF, and 143 g (0.50 mol) of 4-chloro-2-fluoro-5-isopropoxybenzyl bromide was dropwise added thereto at room temperature. After stirring at room temperature for 8 hours, the reaction solution was poured into water and extracted with ethyl acetate. After washing with water, the organic layer was dried over anhydrous magnesium sulfate. Ethyl acetate was distilled off under reduced pressure to obtain 107 g (yield: 92%) of the desired product.

Preparation of 4-chloro-2-fluoro-5-isopropoxyphenyl acetic acid (Intermediate No. 15-3)

107 g (0.47 mol) of 4-chloro-2-fluoro-5-isopropoxyphenyl acetonitrile was dissolved in 400 ml of ethanol, and 100 g (1.78 mol) of potassium hydroxide was added thereto, followed by refluxing for 1 hour. Ethanol was distilled off under reduced pressure, and then, the obtained residue was poured into water, washed with diethyl ether, then acidified with citric acid and extracted with ethyl acetate. After washing with water, the organic layer was dried over anhydrous magnesium sulfate. Ethyl acetate was distilled off under reduced pressure, and then, the obtained crude crystals were washed with diisopropyl ether to obtain 70 g (yield: 61%) of the desired product. Melting point: 75–76° C. $^1$H-NMR (300 MHz, CDCl$_3$) δ value: 1.35(6H,d), 3.66(2H,s), 4.45(1H,m), 6.84(1H,d), 7.16(1H,d)ppm.

Preparation of ethyl 4-chloro-2-fluoro-5-isopropoxyphenyl acetoacetate (Intermediate No. 15-4)

47 g (0.19 mol) of 4-chloro-2-fluoro-5-isopropoxyphenyl acetic acid was dissolved in 300 ml of THF, and 134 g (0.21 mol) of CDI was added thereto, followed by stirring at room temperature for 3 hours. To this reaction solution, 50 g (0.29 mol) of potassium monoethyl malonate and 28 g (0.29 mol) of anhydrous magnesium chloride were added, followed by stirring at 60° C. for 3 hours. THF was distilled off under reduced pressure, and then the obtained residue was poured into water, and acidified to pH1 with 1N hydrochloric acid and then extracted with ethyl acetate. After washing with water and an aqueous sodium hydrogencarbonate solution, the organic layer was dried over anhydrous magnesium sulfate. Ethyl acetate was distilled off under reduced pressure, and then, the obtained crude crystals were washed with n-hexane to obtain 35 g (yield: 58%) of the desired product. Melting point: 57–58° C. $^1$H-NMR (300 MHz, CDCl$_3$) δ value: 1.28(3H,t), 1.35(6H,d), 3.51(2H,s), 3.82 (2H,s), 4.19(2H,t), 4.47(1H,m), 6.77(1H,d), 7.12(1H,d)ppm.

Preparation of 4-amino-1-(4-chloro-2-fluoro-5-isopropoxyphenyl)-3-ethoxycarbonyl-5,5,5-trifluoro-3-penten-2-one (Intermediate No. 15-7)

To 400 ml of ethanol, 35 g (0.11 mol) of ethyl 4-chloro-2-fluoro-5-isopropoxyphenyl acetoacetate and 11 g (0.13 mol) of sodium acetate, were added, and stirred for 6 hours under heating and refluxing while blowing trifluoroacetonitrile [generated by heating and refluxing 84 g (0.68 mol) of trifluoroacetamide and 96 g (0.68 mol) of diphosphorus pentoxide in toluene]. Ethanol was distilled off under reduced pressure, and then, the obtained residue was poured into water and extracted with ethyl acetate. After washing with water, the organic layer was dried over anhydrous magnesium sulfate. Ethyl acetate was distilled off under reduced pressure, and then, the obtained crude crystals were washed with diisopropyl ether and n-hexane to obtain 22 g (yield: 48%) of the desired product. Melting point: 58–59° C. $^1$H-NMR (300 MHz, CDCl$_3$) δ value: 1.28(6H,d), 1.35 (3H,t), 3.51(2H,s), 3.83(2H,s), 4.20(2H,q), 6.77(1H,d), 7.13 (1H,d)ppm.

Preparation of ethyl 4-acetoxy-5-(4-chloro-2-fluoro-5-isopropoxyphenyl)-2-trifluoromethyl nicotinate (Intermediate No. 16-4)

22 g (53 mmol) of 4-amino-1-(4-chloro-2-fluoro-5-isopropoxyphenyl)-3-ethoxycarbonyl-5,5,5,-trifluoro-3-penten-2-one and 15 g (101 mmol) of ethyl orthoformate were dissolved in 100 ml of acetic anhydride, followed by stirring for 8 hours under heating and refluxing. Acetic anhydride was distilled off under reduced pressure, and then, the obtained residue was poured into hot water, stirred for 1 hour and then extracted with ethyl acetate. After washing with water and an aqueous sodium hydrogencarbonate solution, the organic layer was dried over anhydrous magnesium sulfate. Ethyl acetate was distilled off under reduced pressure to obtain 23 g (yield: 92%) of the desired product.

Preparation of 5-(4-chloro-2-fluoro-5-isopropoxyphenyl)-3-ethoxycarbonyl-2-trifluoromethyl-4(1H)-pyridone (Compound No. 6-57)

23 g (50 mmol) of ethyl 4-acetoxy-5-(4-chloro-2-fluoro-5-isopropoxyphenyl)-2-trifluoromethyl nicotinate was dissolved in 30 ml of ethanol, and 6 g (107 mmol) of potassium hydroxide and 15 ml of water were added, followed by stirring at 60° C. for 1 hour. Ethanol was distilled off under reduced pressure, and then, the obtained residue was poured into water, acidified with citric acid and then extracted with ethyl acetate. After washing with water, the organic layer was dried over anhydrous magnesium sulfate. Ethyl acetate was distilled off under reduced pressure to obtain 20 g (yield: 95%) of the desired product. Melting point: 118–119° C. $^1$H-NMR (300 MHz, CDCl$_3$) δ value: 1.38(6H,d), 1.46 (3H,t), 4.54(2H,q), 6.98(1H,d), 7.26(1H,d), 8.54(1H,s), 11.66(1H,s)ppm.

PREPARATION EXAMPLE 2

Preparation of 5-(4-chloro-2-fluoro-5-isopropoxyphenyl)-3-ethoxycarbonyl-1-methyl-2-trifluoromethyl-4(1H)-pyridone (Compound No. 6-42)

20 g (47 mol) of 5-(4-chloro-2-fluoro-5-isopropoxyphenyl)-3-ethoxycarbonyl-2-trifluoromethyl-4 (1H)-pyridone was dissolved in 150 ml of DMF, and 2.1 g (53 mmol) of 60% sodium hydride was added thereto under cooling with ice, followed by stirring at room temperature for 15 minutes. Then, 14 g (99 mmol) of methyl iodide was added thereto. After stirring at room temperature for 8 hours, the reaction solution was poured into water and extracted with ethyl acetate. After washing with water, the organic layer was dried over anhydrous magnesium sulfate. Ethyl acetate was distilled off under reduced pressure, and then, the obtained residue was purified by silica gel column chromatography to obtain 6 g (yield: 28%) of the desired product. Melting point: 170–172° C. $^1$H-NMR (400 MHz, CDCl$_3$) δ value: 1.40(9H,m), 3.85(3H,s), 4.40(2H,q), 4.51 (1H,m), 7.17(1H,d), 7.40(1H,d), 7.63(1H,s)ppm.

PREPARATION EXAMPLE 3

Preparation of 5-(4-chloro-2-fluoro-5-isopropoxyphenyl)-1-methyl-2-trifluoromethyl-4(1H)-pyridone (Compound No. 6-7)

0.7 g (1.6 mmol) of 5-(4-chloro-2-fluoro-5-isopropoxyphenyl)-3-ethoxycarbonyl-1-methyl-2-trifluoromethyl-4(1H)-pyridone, 0.15 g (2.5 mmol) of sodium chloride and 0.1 ml of water were added to 5 ml of dimethylsulfoxide, followed by stirring at 190° C. for 3 hours. After cooling, this reaction solution was poured into water and extracted with ethyl acetate. After washing with water, the organic layer was dried over anhydrous magnesium sulfate. Ethyl acetate was distilled off under reduced pressure, and then, the obtained residue was purified by silica gel column chromatography to obtain 0.10 g (yield: 17%) of the desired product. Melting point: 150–151° C.

PREPARATION EXAMPLE 4

Preparation of 5-(2,4-dichlorophenyl)-1-methyl-2-trifluoromethyl-4(1H)-pyridone (Compound No. 6-3)

4.1 g (10.4 mmol) of 5-(2,4-dichlorophenyl)-3-ethoxycarbonyl-1-methyl-2-trifluoromethyl-4(1H)-pyridone was dissolved in 100 ml of dichloromethane, and 10 ml of a dichloromethane solution of 3N boron tribromide was dropwise added thereto under cooling to −60° C. After stirring at room temperature for 3 hours, the reaction solution was poured into ice water, and precipitated crystals were collected by filtration and washed with water. They were dried under reduced pressure to obtain crude crystals. To 50 ml of quinoline, the crude crystals and 0.04 g (0.6 mmol) of copper were added, followed by stirring at 170° C. for 1 hour. This reaction solution was poured into water, and precipitated crude crystals were collected by filtration. The crude crystals were dissolved in a small amount of DMF, and insoluble matters were filtered off. Then, the filtrate was poured into water, and precipitated crystals were collected by filtration. The crystals were washed with water and then dried to obtain 0.9 g (yield: 26%) of the desired product. Melting point: 205–206° C.

PREPARATION EXAMPLE 5

Preparation of 3-(2,4-difluorophenyl)-1-methyl-6-trifluoromethyl-2(1H)-pyridone (Compound No. 1-12)

Preparation of 3-(2,4-difluorophenyl)-6-trifluoromethyl-2H-pyran-2-one (Intermediate No. 17-1)

7.7 g (69 mmol) of potassium tert-butoxide was dissolved in 200 ml of THF, and 10 g (65 mmol) of 2,4-difluorophenyl acetonitrile was dropwise added thereto under cooling with ice. Ten minutes later, 13.5 g (69 immol) of (E)-4-ethoxy-1,1,1-trifluoro-3-buten-2-one was dropwise added thereto, followed by stirring at room temperature for 4 hours. THF was distilled off under reduced pressure. Then, the obtained residue was poured into water, acidified to pH 1 with 1N hydrochloric acid and then extracted with ethyl acetate. After washing with water and an aqueous sodium hydrogencarbonate solution, the organic layer was dried over anhydrous magnesium sulfate. And then, the ethyl acetate was distilled off under reduced pressure. To the obtained residue, 150 ml of concentrated hydrochloric acid was added, followed by stirring for 4 hours under heating and refluxing. This reaction solution was poured into ice water and extracted with ethyl acetate, followed by washing with water. The organic layer was dried over anhydrous magnesium sulfate, and then, ethyl acetate was distilled off under reduced pressure. The obtained residue was purified by silica gel column chromatography to obtain 13.8 g (yield: 76%) of the desired product. Melting point: 98–100° C. $^1$H-NMR (400 MHz, CDCl$_3$) δ value: 6.78(1H,d), 6.95(2H,m), 7.52 (1H,d), 7.56(1H,q)ppm.

Preparation of 3-(2,4-difluorophenyl)-1-methyl-6-trifluoromethyl-2(1H)pyridone (Compound No. 1-12)

13.8 g (50 mmol) of 3-(2,4-difluorophenyl)-6-trifluoromethyl-2H-pyran-2-one was dissolved in 150 ml of ethanol, and 5.5 g (70 mmol) of a 40% methylamine methanol solution was added, followed by stirring for 6 hours under heating and refluxing. The reaction solution was poured into ice water and extracted with ethyl acetate. After washing with 1N hydrochloric acid and water, the organic layer was dried over anhydrous. magnesium sulfate. Ethyl acetate was distilled off under reduced pressure, and then, the obtained residue was purified by silica gel column chromatography to obtain 3.8 g (yield: 26%) of the desired product. Melting point: 123–124° C. $^1$H-NMR (400 MHz, CDCl$_3$) δ value: 3.70(3H,s), 6.75(1H,d), 6.90(2H,m), 7.43 (1H,d), 7.58(1H,m)ppm.

PREPARATION EXAMPLE 6

Preparation of 3-(4-chloro-2-fluorophenyl)-1-methyl-6-trifluoromethyl-2(1H)-pyridone (Compound No. 1-2)

Preparation of ethyl 4-chloro-2-fluorophenyl acetate 18 g (96 mmol) of 4-chloro-2-fluorophenyl acetic acid and 2.3 g of sulfuric acid were added to 300 ml of ethanol, followed by refluxing for 4 hours. After cooling, ethanol was distilled off, and ethyl acetate was added. The mixture was washed with water and a saturated sodium hydrogencarbonate aqueous solution. The organic layer was dried over anhydrous magnesium sulfate and then, the solvent was distilled off. Crude crystals were washed with n-hexane to obtain 19 g (88 mmol) of the desired product. Melting point: 53–54° C.

Preparation of 3-(4-chloro-2-fluorophenyl)-6-trifluoromethyl-2H-pyran-2-one (Intermediate No. 17-4)

19 g (88 mmol) of ethyl 4-chloro-2-fluorophenyl acetate dissolved in 40 ml of THF, was dropwise added to a LDA-THF solution [prepared from 83 ml (133 mmol) of 1.6N-n-butyl lithium, 15.2 g (150 mmol) of diisopropylamine and 200 ml of THF] under cooling to −65 to −60° C., followed by stirring for 1 hour. Then, 30 g (180 mmol) of 4-ethoxy-1,1,1-trifluoro-3-buten-2-one was dropwise added thereto. Then, cooling was stopped followed by stirring at room temperature for 1 hour. After distilling off most THF, 1N hydrochloric acid was added, followed by extraction with ethyl acetate and washing with water. The solvent was distilled of f, and then, 300 ml of concentrated hydrochloric acid was added, followed by refluxing for 4 hours. After cooling, water was added, followed by extraction with ethyl acetate and washing with water and a saturated sodium hydrogencarbonate aqueous solution. The organic layer was dried over anhydrous magnesium sulfate, and then, the solvent was distilled off. The obtained residue was purified by silica gel column chromatography to obtain 16 g (55 nmol) of the desired product. Melting point: 107–108° C.

Preparation of 3-(4-chloro-2-fluorophenyl)-1-methyl-6-trifluoromethyl-2(1H)-pyridone (Compound No. 1-2)

9.3 g (32 mmol) of 3-(4-chloro-2-fluorophenyl)-6-trifluoromethyl-2H-pyran-2-one was added to 160 ml of methanol, and 3.8 g (48 mmol) of a 40% methylamine/methanol solution was dropwise added under cooling with ice, followed by stirring for 2 hours under cooling with ice. This reaction solution was acidified by an addition of a 10% citric acid aqueous solution and then extracted with ethyl acetate, followed by washing with water. The organic layer was dried over anhydrous magnesium sulfate, and then, the solvent was distilled off. The obtained residue was dissolved in 160 ml of toluene, and 0.4 g (2.1 mmol) of p-toluenesulfonic acid was added thereto, followed by refluxing for 4 hours. After cooling, the reaction solution was washed with water. Then, the organic layer was dried over anhydrous magnesium sulfate, and then, the solvent was distilled off. The obtained residue was purified by silica gel column chromatography to obtain 5.7 g (19 mmol) of the desired product. Melting point: 103–104° C.

PREPARATION EXAMPLE 7

Preparation of 3-(2,4-dichlorophenyl)-1-difluoromethyl-6-methyl-2(1H)-pyridone (Compound No. 1-8)

Preparation of α-(2,4-dichlorophenyl)-α-hydroxymethylene acetonitrile 0.6 g of metal sodium was added to dry ethanol to obtain an ethanol solution of sodium ethoxide. Then, a mixed liquid comprising 37.2 g of 2,4-dichlorophenyl acetonitrile and 22.2 g of ethyl formate, was added thereto under heating to 70° C. After the addition, the mixture was further heated and refluxed for 2 hours and then, left to stand for 1 day. The reaction solution was cooled to 0° C. and then subjected to filtration. After washing with diethyl ether, the sodium salt collected by filtration was added to 130 ml of distilled water, and 9 ml of acetic acid was dropwise added thereto under cooling at 0° C. After the dropwise addition, the mixture was stirred at room temperature for about 30 minutes. Then, the formed precipitate was collected by filtration and washed with water. It was dried to obtain 31.7 g (yield: 74%) of the desired product. Melting point: 162–163° C.

Preparation of 3-(2,4-dichlorophenyl)-6-methyl-2(1H)-pyridone

α-(2,4-dichlorophenyl)-α-hydroxymethylene acetonitrile and 8.8 g of acetone were thoroughly mixed with 110 g of polyphosphoric acid, and the mixture was heated to about 130° C. At this temperature, an exothermic reaction started. The temperature was maintained from 130 to 140° C. for 30 minutes, while heating as the case required. The cooled mixture was poured into ice water, and this suspension was stirred for 18 hours. This crude product was stirred with ethyl acetate and an excess amount of a dilute aqueous potassium hydroxide solution to make it alkaline. The formed precipitate was collected by filtration and washed sequentially with water, ethyl acetate and diethyl ether to obtain 8.0 g (yield: 45%) of the desired product. Melting point: 266–268° C.

Preparation of 3-(2,4-dichlorophenyl)-1-difluoromethyl-6-methyl-2(1H)-pyridone (Compound No. 1-8)

4.0 g of 3-(2,4-dichlorophenyl)-6-methyl-2(1H)-pyridone, 0.8 g of tetrabutylammonium bromide and 2.6 g of potassium hydroxide were dissolved in 100 ml of THF, and chlorodifluoromethane was blown therein under cooling to 0° C. After completion of the blowing, stirring was continued further at room temperature for 1 hour to complete the reaction. Then, the solvent was distilled off under reduced pressure, and the residue was extracted with ethyl acetate and washed with water. Then, the organic layer was dried over anhydrous magnesium sulfate. The solvent was distilled off, and the obtained crude product was purified by silica gel column chromatography to obtain 0.70 (yield: 14%) of the desired product. Melting point: 83–85° C.

PREPARATION EXAMPLE 8

Preparation of 1-amino-3-(2,4-dichlorophenyl)-6-trifluoromethyl-2(1H)-pyridone (Compound No. 1-5)

10 ml of DMF was added to 0.10 g of 60% sodium hydride, and 0.72 g of 3-(2,4-dichlorophenyl)-6-trifluoromethyl-2(1H)-pyridone was added thereto under cooling with ice, followed by stirring further at room temperature for 30 minutes. Then, 0.47 g of 2,4-dinitrophenoxyamine was added thereto at room temperature. Then, the mixture was stirred at 50° C. for 1 hour to complete the reaction. After completion of the reaction, the reaction solution was washed with water and extracted with ethyl acetate. The organic layer was dried over anhydrous magnesium sulfate, and then, the solvent was distilled off to obtain a crude product. This crude product was purified by silica gel column chromatography to obtain 0.50 g (yield: 68%) of the desired product. Melting point: 98–100° C.

PREPARATION EXAMPLE 9

Preparation of 3-(4-chloro-2-fluoro-5-hydroxyphenyl)-1,5-dimethyl-6-trifluoromethyl-2(1H)-pyridone (Compound No. 1-79)

1.3 g (10.4 mmol) of 3-(4-chloro-2-fluoro-5-isopropoxyphenyl)-1,5-dimethyl-6-trifluoromethyl-2(1H))-pyridone was dissolved in 20 ml of dichloromethane, and 6.6 ml of a 3N boron tribromide dichloromethane solution was dropwise added thereto under cooling to −60° C. After stirring at room temperature for 3 hours, this reaction solution was poured into water and extracted with ethyl acetate. The extract was washed with water and dried over anhydrous magnesium sulfate. The organic layer was distilled off under reduced pressure, and then, the obtained residue was purified by silica gel column chromatography to obtain 0.8 g (yield: 69%) of the desired product. Melting point: 207–208° C.

PREPARATION EXAMPLE 10

Preparation of 3-(4-chloro-2-fluoro-5-propargyloxyphenyl)-1,5-dimethyl-6-trifluoromethyl-2(1H)-pyridone (Compound No. 1-76)

To 10 ml of DMF, 0.20 g (0.6 mmol) of 3-(4-chloro-2-fluoro-5-hydroxyphenyl)-1,5-dimethyl-6-trifluoromethyl-2(1H)-pyridone, 0.1 g (0.7 mmol) of potassium carbonate and 0.1 g (0.8 mmol) of propargyl bromide were added, followed by stirring at 60° C. for 2 hours. This reaction solution was poured into water and extracted with ethyl acetate. After washing with water, the organic layer was dried over anhydrous magnesium sulfate. Ethyl acetate was distilled off under reduced pressure, and then, the obtained residue was purified by silica gel column chromatography to obtain 0.12 g of the desired product (yield: 53%). Melting point: 107–108° C.

PREPARATION EXAMPLE 11

Preparation of 5-(4-chloro-2-fluoro-5-phenoxyphenyl)-1-methyl-2-trifluoromethyl-4(1H)-pyridone (Compound No. 6-19)

To 10 ml of methanol, 0.30 g (0.93 mmol) of 5-(4-chloro-2-fluoro-5-hydroxyphenyl)-1-methyl-2-trifluoromethyl-4(1H)-pyridone, 0.5 g (1.6 mmol) of diphenyliodonium chloride and 0.06 g (1.1 mmol) of sodium methoxide were added, and the mixture was stirred at room temperature for 12 hours. This reaction solution was poured into water and extracted with ethyl acetate. After washing with water, the organic layer was dried over anhydrous magnesium sulfate. Ethyl acetate was distilled off under reduced pressure. Then, the obtained residue was purified by silica gel column chromatography to obtain 0.17 g (yield: 46%) of the desired product. Melting point: 159–161° C.

PREPARATION EXAMPLE 12

Preparation of 5-(4-chloro-2-fluoro-5-cyclopentyloxyphenyl)-1-methyl-2-trifluoromethyl-4(1H)-pyridone (Compound No. 6-14)

To 3 ml of THF, 0.30 g (0.93 mmol) of 5-(4-chloro-2-fluoro-5-hydroxyphenyl)-1-methyl-2-trifluoromethyl-4(1H)-pyridone, 0.37 g (1.4 mmol) of triphenylphosphine and 0.12 g (1.4 mmol) of cyclopentanol were added, and 0.2 g (1.1 mmol) of diethyl azodicarboxylate was dropwise added thereto under cooling with ice. The mixture was stirred at room temperature for 2 hours. Then, this reaction solution was poured into water and extracted with ethyl acetate. After washing with water, the organic layer was dried over anhydrous magnesium sulfate. Ethyl acetate was distilled off under reduced pressure, and then, the obtained residue was purified by silica gel column chromatography to obtain 0.30 g (yield: 83%) of the desired product. Melting point: 152–154° C.

PREPARATION EXAMPLE 13

Preparation of 5-(7-chloro-5-fluoro-2-methylbenzofuran-4-yl)-1-methyl-2-trifluoromethyl-4(1H)-pyridone (Compound No. 9-1)

To 50 ml of N,N-diethylaniline, 0.64 g (1.8 mmol) of 5-(4-chloro-2-fluoro-5-propargyloxyphenyl)-1-methyl-2-trifluoromethyl-4(1H)-pyridone and 0.56 g (3.7 mmol) of cesium fluoride were added, and the mixture was stirred at from 180 to 200° C. for 2.5 hours This reaction solution was poured into water and extracted with ethyl acetate. After washing with concentrated hydrochloric acid, water and an aqueous sodium hydrogencarbonate solution, the organic layer was dried over anhydrous magnesium sulfate. Ethyl acetate was distilled off under reduced pressure, and then, the obtained residue was purified by silica gel column chromatography to obtain 0.50 g (yield: 75%) of the desired product. Melting point: 208–211° C. $^1$H-NMR (400 MHz, CDCl$_3$) δ value: 2.46(3H,s), 3.80(3H,s), 6.31(1H,s), 7.01 (1H,s), 7.07(1H,d), 7.57(1H,d)ppm.

PREPARATION EXAMPLE 14

Preparation of 3-(2,4-difluoro-5-nitrophenyl)-1-methyl-6-trifluoromethyl-2(1H)-pyridone (Compound No. 1-100)

3.7 g (13 mmol) of 3-(2,4-difluorophenyl)-1-methyl-6-trifluoromethyl-2(1H)-pyridone was dissolved in 20 ml of sulfuric acid, and 0.9 g (14 mmol) of fuming nitric acid was dropwise added thereto under cooling with ice, followed by stirring for 30 minutes under cooling with ice. The reaction solution was poured into ice water and extracted with ethyl acetate. The organic layer was washed with an aqueous sodium hydrogencarbonate solution and water and then, dried over anhydrous magnesium sulfate. Ethyl acetate was distilled off under reduced pressure, and then, the obtained residue was purified by silica gel column chromatography to obtain 4.2 g (yield: 98%) of the desired product. Melting point: 115–118° C. $^1$H-NMR (400 MHz, CDCl$_3$) δ value: 3.71(3H,s), 6.81(1H,d), 7.13(1H,t), 7.57(1H,d), 8.43(1H,m) ppm.

PREPARATION EXAMPLE 15

Preparation of 3-(2-fluoro-4-methoxycarbonylmethoxy-5-nitrophenyl)-1-methyl-6-trifluoromethyl-2(1H)-pyridone (Compound No. 1-86)

To 20 ml of THF, 0.24 g (60 mmol) of 60% sodium hydride was suspended under cooling with ice, and 0.32 g (6.6 mmol) of methyl glycolate, was added thereto, followed by stirring for 15 minutes. To this mixture, 2 g (6.0 mmol) of 3-(2,4-difluoro-5-nitrophenyl)-1-methyl-6-trifluormethyl-2(1H)-pyridone was added, followed by stirring at room temperature for 3 hours. The product was poured into water and extracted with ethyl acetate. After washing with water, the organic layer was dried over anhydrous magnesium sulfate. After distilling off ethyl acetate under reduced pressure, the obtained residue was purified by silica gel column chromatography to obtain 1.57 g (yield: 65%) of the desired product. $^1$H-NMR (400 MHz, CDCl$_3$) δ value: 3.70(3H,s), 3.84(3H,s), 4.81(2H,s), 6.76(1H,d), 6.78 (1H,d), 7.53(1H,d), 8.26(1H,d)ppm.

PREPRATION EXAMPLE 16

Preparation of 3-(7-fluoro-2,3-dihydro-1,4-benzoxazin-3-on-6-yl)-1-methyl-6-trifluoromethyl-2 (1H)-pyridone (Compound No. 2-4)

1.5 g (3.7 mmol) of 3-(2-fluoro-4-methoxycarbonylmethoxy-5-nitrophenyl)-1-methyl-6-trifluoromethyl-2-(1H)-pyridone was dissolved in 50 ml of acetic acid, and 0.64 g (11.5 mmol) of iron powder was added under heating and refluxing, followed by stirring for 1 hour. The reaction solution was subjected to filtration, and the filtrate was distilled off under reduced pressure. The obtained residue was poured into water and extracted with ethyl acetate. After washing with water, the organic layer was dried over anhydrous magnesium sulfate. Ethyl acetate was distilled off under reduced pressure, and then, the obtained residue was purified by silica gel column chromatography to obtain 0.95 g (yield: 80%) of the desired product. Melting point: 216–218° C. $^1$H-NMR (400 MHz, CDCl$_3$) δ value: 3.69(3H,s), 4.60(2H,s), 6.78(1H,d), 6.80 (1H,d), 7.18(1H,d), 7.53(1H,d), 8.47(1H,s)ppm.

PREPARATION EXAMPLE 17

Preparation of 3-[7-fluoro-2,3-dihydro-4-(2-propynyl)-1,4-benzoxazin-3-on-6-yl]-1-methyl-6-trifluoromethyl-2(1H)-pyridone (Compound No. 2-1)

0.3 g (0.87 mmol) of 3-(7-fluoro-2,3-dihydro-1,4-benzoxazin-3-on-6-yl)-1-methyl-6-trifluoromethyl-2(1H)- pyridone was dissolved in 1 ml of DMF, and 0.04 g (1 mmol) of 60% sodium hydride was added under cooling with ice, followed by stirring at room temperature for 15 minutes. Then, 0.12 g (1 mmol) of propargyl bromide was added thereto. The mixture was stirred at room temperature for 3 hours, then poured into water and extracted with ethyl acetate. After washing with water, the organic layer was dried over anhydrous magnesium sulfate. Ethyl acetate was distilled off under reduced pressure, and then, the obtained residue was purified by silica gel column chromatography to obtain 0.24 g (yield: 72%) of the desired product. Melting point: 166–168° C. $^1$H-NMR (400 MHz, CDCl$_3$) δ value: 2.24(1H,t), 3.68(3H,s), 4.63(2H,s), 4.68(2H,d), 6.76(1H,d), 6.83(1H,d), 7.40(1H,d), 7.51(1H,d)ppm.

PREPARATION EXAMPLE 18

Preparation of 3-(4-chloro-2-fluoro-5-nitrophenyl)-1-methyl-6-trifluoromethyl-2(1H)-pyridone (Compound No. 1-58)

1.0 g (3.3 mmol) of 3-(4-chloro-2-fluorophenyl)-1-methyl-6-trifluoromethyl-2(1H)-pyridone was dissolved in 10 ml of concentrated sulfuric acid, and 0.25 g (4.0 mmol) of fuming nitric acid was dropwise added thereto under cooling with ice, followed by stirring for 1 hour. This reaction solution was poured into.ice water and extracted with ethyl acetate. After washing with water and a saturated sodium hydrogencarbonate aqueous solution, the organic layer was dried over anhydrous magnesium sulfate. Ethyl acetate was distilled off under reduced pressure, and then, the obtained residue was purified by silica gel column chromatography to obtain 1.1 g (yield: 96%) of the desired product. Melting point: 139–140° C.

PREPARATION EXAMPLE 19

Preparation of 3-(5-amino-4-chloro-2-fluorophenyl)-1-methyl-6-trifluoromethyl-2(1H)-pyridone (Compound No. 1-59)

1.0 g (2.8 mmol) of 3-(4-chloro-2-fluoro-5-nitrophenyl)-1-methyl-6-trifluoromethyl-2(1H)-pyridone and 1.3 g (11 mmol) of tin were suspended in 30 ml of ethanol, and 5 ml of concentrated hydrochloric acid was added at room temperature, followed by stirring for 1 hour. After completion of the reaction, the reaction solution was poured into water and neutralized. Insoluble substances were filtered off, and the filtrate was extracted with ethyl acetate. After washing with water and a saturated sodium hydrogencarbonate aqueous solution, the organic layer was dried over anhydrous magnesium sulfate. Ethyl acetate was distilled off under reduced pressure. Then, the obtained crude crystals were washed with diisopropyl ether to obtain 0.90 g (yield: 98%) of the desired product. Melting point: 155–157° C.

PREPARATION EXAMPLE 20

Preparation of 3-(4-chloro-2-fluoro-5-methylsulfonylaminophenyl)-1-methyl-6-trifluoromethyl-2(1H)-pyridone (Compound No. 1-60)

0.9 g (2.8 mmol) of 3-(5-amino-4-chloro-2-fluorophenyl)-1-methyl-6-trifluoromethyl-2(1H)-pyridone and 0.6 g (5.9 mmol) of triethylamine were dissolved in 20 ml of dichloromethane, and 0.7 g (6.1 mmol) of methylsulfonyl chloride was dropwise added thereto under cooling with ice. The mixture was stirred at room temperature for 2 hours and then diluted with an aqueous ammonium chloride solution. The mixture was extracted with ethyl acetate. After washing with water and a saturated sodium chloride aqueous solution, the organic layer was dried over anhydrous magnesium sulfate. Ethyl acetate was distilled off under reduced pressure. Then, the obtained crude crystals of the bissulfone compound were dissolved in 25 ml of ethanol, and 10 ml (5.0 mmol) of a 0.5N sodium hydroxide aqueous solution was added at room temperature, followed by stirring for 1 hour. The mixture was poured into water, acidified with citric acid and extracted with ethyl acetate After washing with water, the organic layer was dried over anhydrous magnesium sulfate Ethyl acetate was distilled off under reduced pressure. Then, the obtained crude crystals were washed with n-hexane to obtain 0.80 g (yield: 72%) of the desired product. Melting point: 113–114° C.

PREPARATION EXAMPLE 21

Preparation of 3-(4-chloro-5-chlorosulfonyl-2-fluorophenyl)-1-methyl-6-trifluoromethyl-2(1H)-pyridone (Compound No. 1-84)

2.9 g (9.5 mmol) of 3-(4-chloro-2-fluorophenyl)-1-methyl-6-trifluoromethyl-2(1H)-pyridone was dissolved in 70 g of chlorosulfonic acid, followed by heating and stirring at 100° C. for 5 hours. After cooling, the mixture was gradually dropwise added to ice water, followed by extraction with ethyl acetate. After washing with water and a saturated sodium hydrogencarbonate aqueous solution, the organic layer was dried over anhydrous magnesium sulfate. Ethyl acetate was distilled off under reduced pressure. Then, the obtained crude crystals were washed with n-hexane to obtain 3.3 g (yield: 86%) of the desired product. Melting point: 77–78° C.

PREPARATION EXAMPLE 22

Preparation of 3-(5-acetylthio-4-chloro-2-fluorophenyl)-1-methyl-6-trifluoromethyl-2(1H)-pyridone (Compound No. 1-85)

To 50 ml of acetic acid, 3.1 g (7.7 mmol) of 3-(4-chloro-5-chlorosulfonyl-2-fluorophenyl)-1-methyl-6-trifluoromethyl-2(1H)-pyridone, 1.2 g (38 mmol) of red phosphorus and 0.12 g (0.47 mmol) of iodine were added, followed by heating and refluxing for 1 hour. After cooling, insoluble substances were filtered off, and majority of acetic acid was distilled off. Then, the obtained residue was poured into water and extracted with ethyl acetate. After washing with water and a saturated sodium hydrogencarbonate aqueous solution, the organic layer was washed with anhydrous magnesium sulfate. Ethyl acetate was distilled off under reduced pressure. Then, the obtained residue was purified by silica gel column chromatography to obtain 2.8 g (yield: 98%) of the desired product. Melting point: 91–92° C.

PREPARATION EXAMPLE 23

Preparation of 3-(4-chloro-2-fluoro-5-mercaptophenyl)-1-methyl-6-trifluoromethyl-2(1H)-pyridone (Compound No. 1-42)

2.8 g (7.7 mmol) of 3-(5-acetylthio-4-chloro-2-fluorophenyl)-1-methyl-6-trifluoromethyl-2(1H)-pyridone was dissolved in 30 ml of methanol, 8.5 ml (8.5 mmol) of a 1N sodium hydroxide aqueous solution was dropwise added thereto under cooling with ice After stirring at room temperature for 1 hour, the mixture was poured into water and acidified with citric acid and extracted with ethyl acetate. After washing with water and a saturated sodium chloride aqueous solution, the organic layer was dried over anhydrous magnesium sulfate. Ethyl acetate was distilled off under reduced pressure. Then, the obtained crude crystals were washed with n-hexane to obtain 2.4 g (yield: 93%) of the desired product. Melting point: 141–142° C.

PREPARATION EXAMPLE 24

Preparation of 3-(4-chloro-2-fluoro-5-methylthiophenyl)-1-methyl-6-trifluoromethyl-2(1H)-pyridone (Compound No. 1-87)

To 20 ml of acetone, 0.8 g (2.4 mmol) of 3-(4-chloro-2-fluoro-5-mercaptophenyl)-1-methyl-6-trifluoromethyl-2(1H)-pyridone, 0.5 g (3.5 mmol) of methyl iodide and 0.5 g (3.6 mmol) of potassium carbonate were suspended, followed by stirring for 1 hour under heating and refluxing. After cooling, the insoluble substances were filtered off. Then, the solvent was distilled off, and the obtained residue was purified by silica gel cclumn chromatography to obtain 0.7 g (yield: 84%) of the desired product. Melting point: 147–150° C.

PREPARATION EXAMPLE 25

Preparation of 3-(4-chloro-2-fluoro-5-methylsulfinylphenyl)-1-methyl-6-trifluoromethyl-2(1H)-pyridone (Compound No. 1-88)

0.30 g (0.85 mmol) of 3-(4-chloro-2-fluoro-5-methylthiophenyl)-1-methyl-6-trifluoromethyl-2(1H)-pyridone was dissolved in 10 ml of chloroform, and 0.20 g (0.93 mmol) of 80% m-chloroperbenzoic acid was added under cooling with ice, followed by stirring for 2 hours. After completion of the reaction, the product was washed with a saturated sodium sulfite aqueous solution and a saturated sodium hydrogencarbonate aqueous solution. The organic layer was dried over anhydrous magnesium sulfate. The solvent was distilled off under reduced pressure. Then, the obtained crude crystals were washed with n-hexane to obtain 0.24 g (yield: 76%) of the desired product. Melting point: 147–148° C.

PREPARATION EXAMPLE 26

Preparation of 3-(4-chloro-2-fluoro-5-methylsulfonylphenyl)-1-methyl-6-trifluoromethyl-2(1H)-pyridone (Compound No. 1-73)

0.30 g (0.85 mmol) of 3-(4-chloro-2-fluoro-5-methylthiophenyl)-1-methyl-6-trifluoromethyl-2(1H)-pyridone was dissolved in 10 ml of chloroform, and 0.40 g (1.86 mmol) of 80% m-chloroperbhnzoic acid was added under cooling with ice, followed by stirring for 2 hours. After completion of the reaction, the product was washed with a saturated sodium sulfite aqueous solution and a saturated sodium hydrogencarbonate aqueous solution. The organic layer was dried over anhydrous magnesium sulfate. The solvent was distilled off under reduced pressure. Then, the obtained crude crystals were washed with n-hexane to obtain 0.25 g (yield: 73%) of the desired product. Melting point: 144–145° C.

PREPARATION EXAMPLE 27

Preparation of 3-(4-chloro-2-fluoro-5-methylsulfamoylphenyl)-1-methyl-6-trifluoromethyl-2(1H)-pyridone (Compound No. 1-71)

To 25 ml of chloroform, 0.6 g (1.5 mmol) of 3-(4-chloro-5-chlorosulfonyl-2-fluorophenyl)-1-methyl-6-trifluoromethyl-2(1H)-pyridone and 1.8 g (26.7 mmol) of methylamine hydrochloride were added, and 6.0 g (59.4 mmol) of triethylamine was dropwise added thereto under cooling with ice, followed by stirring at room temperature for 2 hours. This reaction solution was poured into water and extracted with chloroform. After washing with water and a 10% citric acid aqueous solution, the organic layer was dried over anhydrous magnesium sulfate. The solvent was distilled off under reduced pressure. Then, the obtained residue was purified by silica gel column chromatography to obtain 0.4 g (yield:67) of the desired product. Melting point: 150–151° C.

PREPARATION EXAMPLE 28

Preparation of 3-(4-chloro-2-fluoro-5-bromomethylphenyl)-1-methyl-6-trifluoromethyl-2(1H)-pyridone (Compound No. 1-82)

2.63 g (8.23 mmol) of 3-(4-chloro-2-fluoro-5-methylphenyl)-1-methyl-6-trifluoromethyl-2(1H)-pyridone and 1.46 g (8.23 mmol) of NBS were dissolved in 100 ml of carbon tetrachloride. Then, 0.27 g (1.67 mmol) of 2,2'-azobisisobutyronitrile was slowly added thereto with stirring under heating and refluxing. Then, the mixture was further reacted for 5 hours. After cooling, the insoluble substances were filtered off, and the organic layer was washed with water and dried over magnesium sulfate. The solvent was distilled off under reduced pressure. Then, the obtained residue was purified by silica gel column chromatography to obtain 2.67 g (yield: 81%) of the desired product. Melting point: 117–118° C.

PREPARATION EXAMPLE 29

Preparation of 5-[1-methyl-6-trifluoromethyl-2(1H)-pyridon-3-yl]-2-chloro-4-fluorobenzaldehyde (Compound No. 1-81)

0.15 g (2.78 mmol) of sodium methoxide was dissolved in 5 ml of ethanol, and 0.27 g (2.98 mmol) of 2-nitropropane was dropwise added thereto, followed by stirring at room temperature for 1 hour. Then, 1.02 g (2.56 mmol) of 3-(4-chloro-2-fluoro-5-bromomethylphenyl)-1-methyl-6-trifluoromethyl-2(1H)-pyridone was added thereto, and the mixture was stirred overnight. The reaction mixture was poured into ice water, extracted with ethyl ether and dried over magnesium sulfate. The solvent was distilled off under reduced pressure. Then, the obtained residue was purified by silica gel column chromatography to obtain 0.68 g (yield: 77%) of the desired product. Melting point: 162–163° C.

PREPARATION EXAMPLE 30

Preparation of 3-(4-chloro-5-cyano-2-fluorophenyl)-1-methyl-6-trifluoromethyl-2(1H)-pyridone (Compound No. 1-119)

0.50 g (1.50 mmol) of 5-[1-methyl-6-trifluoromethyl-2(1H)-pyridon-3-yl]-2-chloro-4-fluorobenzaldehyde, 0.12 g (1.66 nmol) of hydroxylamine hydrochloride, 0.67 g of magnesium sulfate and 0.10 g of p-toluenesulfonic.acid were heated and refluxed in 5 ml of xylene. After completion of the reaction, the reaction mixture was poured into water and extracted with ethyl acetate. The extract was washed with water and an aqueous sodium hydrogencarbonate solution. The solvent was distilled off under reduced pressure. Then, the crude product was washed with isopropyl ether to obtain 0.49 g (yield: 99%) of the desired product. Melting point: 180–181° C.

PREPARATION EXAMPLE 31

Preparation of 5-(1-methyl-6-trifluoromethyl-2(1H)-pyridon-3-yl)-2-chloro-4-fluorobenzoic acid (Compound No. 1-141)

0.50 g (1.51 mmol) of 3-(4-chloro-5-cyano-2-fluorophenyl)-1-methyl-6-trifluoromethyl-2(1H)-pyridone was stirred in 5 ml of 70% sulfuric acid at 70° C. for 1 hour. After cooling, the mixture was poured into ice water, extracted with chloroform and dried over magnesium sulfate. The solvent was distilled off under reduced pressure to obtain 0.51 g (yield: 96%) of the desired product. Melting point: 209–210° C.

PREPARATION EXAMPLE 32

Preparation of isopropyl 5-(1-methyl-6-trifluoromethyl-2(1H)-pyridon-3-yl)-2-chloro-4-fluorobenzoate (Compound No. 1-66)

0.20 g (0.57 mmol) of 5-(1-methyl-6-trifluoromethyl-2(1H)-pyridon-3-yl)-2-chloro-4-fluorobenzoic acid and 0.16 g (1.14 mimol) of potassium carbonate were suspended in 5 ml of DMF, and 0.15 g (0.86 mmol) of isopropyl iodide was dropwise added thereto at room temperature, followed by stirring for 1 day. The reaction mixture was poured into water and extracted with ethyl ether. The organic layer was washed with water and dried over magnesium sulfate. The solvent was distilled off under reduced pressure. Then, the obtained residue was purified by silica gel column chromatography to obtain 0.22 g (yield: 100%) of the desired product. Melting point: 90–92° C.

PREPARATION EXAMPLE 33

Preparation of 3-(4-chloro-2-fluoro-5-propargyloxymethylphenyl)-1-methyl-6-trifluoromethyl-2(1H)-pyridone (Compound No. 1-199)

0.04 g (1.10 mmol) of sodium hydride was suspended in 5 ml of DMF, and 0.06 g (1.10 mmol) of propargyl alcohol was dropwise added thereto at room temperature, followed by stirring for 30 minutes. Then, 0.40 g (1.00 mmol) of 3-(4-chloro-2-fluoro-5-bromomethylphenyl)-1-methyl-6-trifluoromethyl-2(1H)-pyridone was dissolved in 5 ml of DMF, and dropwise added thereto, followed by stirring for 2 hours. The reaction mixture was poured into water and extracted with ethyl ether. The extract was dried over magnesium sulfate. Then, the solvent was distilled off under reduced pressure. Then, the obtained residue was purified by silica gel column chromatography to obtain 0.34 g (yield: 91%) of the desired product. Melting point: 99–101C.

PREPARATION EXAMPLE 34

Preparation of 3-[4-chloro-2-fluoro-5-(1-hydroxybutyl)phenyl]-1-methyl-6-trifluoromethyl-2(1H)-pyridone (Compound No. 1-193)

In a nitrogen atmosphere, 1.00 g (3.00 mmol) of 5-(1-methyl-6-trifluoromethyl-2(1H)-pyridon-3-yl)-2-chloro-4-fluorobenzaldehyde was dissolved in 20 ml of THF, followed by stirring, and 3.0 ml (6.00 mmol) of a 2.0M magnesium-n-propyl bromide THF solution was dropwise added at 0° C. After completion of the dropwise addition, the mixture was gradually heated to room temperature and left to stand overnight. After completion of the reaction, the mixture was treated with an aqueous ammonium chloride solution and then extracted with ethyl ether. The organic layer was washed with water. It was dried over magnesium sulfate, and then, the solvent was distilled off under reduced pressure. Then, the obtained residue was purified by silica gel column chromatography to obtain 0.43 g (yield: 38%) of the desired product. Melting point: 120–122° C.

PREPARATION EXAMPLE 35

Preparation of 3-[4-chloro-2-fluoro-5-(1-oxobutyl)phenyl]-1-methyl-6-trifluoromethyl-2(1H)-pyridone (Compound No. 1-194)

0.21 g (1.64 mmol) of oxalyl chloride was dissolved in 10 ml of dichloromethane and cooled to −65° C. In a nitrogen atmosphere, 0.17 g (2.18 mmol) of dimethylsulfoxide was slowly dropwise added thereto, followed by stirring for 15 minutes. Then, 0.31 g (0.82 mmol) of 3-[4-chloro-2-fluoro-5-(1-hydroxybutyl)phenyl]-1-methyl-6-trifluoromethyl-2(1H)-pyridone was dissolved in 10 ml of dichloromethane and dropwise added thereto, followed by stirring for 1 hour. Further, 0.42 g (4.1 mmol) of triethylamine was dropwise added thereto, followed by heating to room temperature. An aqueous ammonium chloride solution was added thereto, followed by extraction with ethyl acetate. The organic layer was washed with water and then dried over magnesium sulfate. The solvent was distilled off under reduced pressure. Then, the obtained residue was purified by silica gel column chromatography to obtain 0.29 g (yield: 94%) of the desired product. $^1$H-NMR (300 MHz, CDCl$_3$) σ value: 0.99(3H,t), 1.74(2H,sext), 2.94(2H,t), 3.70(3H,s), 6.78(1H,d), 7.25(1H, d), 7.53(1H,d), 7.75(1H,d)ppm.

PREPARATION EXAMPLE 36

Preparation of 5-(1-methyl-6-trifluoromethyl-2(1H)-pyridon-3-yl)-2-chloro-4-fluorobenzaldehydeoxime-O-methyl ether (Compound No. 1-72)

0.40 g (1.2 mmol) of 5-(1-methyl-6-trifluoromethyl-2(1H)-pyridon-3-yl)-2-chloro-4-fluorobenzaldehyde, 0.15 g (1.8 mmol) of methoxyamine hydrochloride and 0.13 g (1.2 mmol) of sodium carbonate were heated and refluxed for 1 hour in 10 ml of ethanol. After cooling, the solvent was distilled off under reduced pressure, followed by extraction with ethyl acetate. The organic layer was washed with water and dried over magnesium sulfate, and the solvent was distilled off under reduced pressure. Then, obtained crude crystals were washed with isopropyl ether to obtain 0.26 g (yield: 60%) of the desired product. Melting point: 106–107° C.

PREPARATION EXAMPLE 37

Preparation of ethyl 2-chloro-3-[2-chloro-4-fluoro-5-(1-methyl-6-trifluoromethyl-2(1H)pyridon-3-yl)] phenyl propionate (Compound No. 1-139)

0.48 g (4.68 mmol) of tert-butyl nitrite, 0.50 g (3.74 mmol) of copper (II) chloride and 6.5 g (65 mmol) of ethyl acrylate were stirred in 15 ml of acetonitrile, and a suspension of 1.00 g (3.11 mmol) of 3-(5-amino-4-chloro-2-fluorophenyl)-1-methyl-6-trifluoromethyl-2(1H)-pyridone in 30 ml of acetonitrile, was dropwise added thereto under cooling with ice. The mixture was left to stand overnight. The reaction was terminated with dilute hydrochloric acid and then extracted with ethyl ether. The organic layer was washed with water and dried over magnesium sulfate. The solvent was distilled off under reduced pressure. Then, the obtained residue was purified by silica gel column chromatography to obtain 0.56 g (yield: 41%) of the desired product. $^1$H-NMR (300 MHz, CDCl$_3$) σ value: 1.27(3H,t), 3.27(1H,dd), 3.51(1H,dd), 3.69(3H,s), 4.23(2H,m), 4.57 (1H,dd), 6.76(1H,d), 7.22(1H,d), 7.48(1H,d), 7.50(1H,d) ppm.

PREPARATION EXAMPLE 38

Preparation of 3-(4-chloro-6-fluoro-2-methylbenzofuran-7-yl)-1-methyl-6-trifluoromethyl-2(1H)-pyridone (Compound No. 5-1)

2.78 g (7.73 mmol) of 3-[4-chloro-2-fluoro-6-propargyloxyphenyl]-1-methyl-6-trifluoromethyl-2(1H)-pyridone and 2.35 g (15.46 mmol) of cesium fluoride was heated to 180° C. in 50 ml of N,N-diethylaniline and reacted for 1 hour. The solvent was distilled off under reduced pressure, followed by extraction with ethyl acetate. The organic layer was washed with dilute hydrochloric acid and dried over magnesium sulfate. Then, the solvent was distilled off under reduced pressure. Then, the obtained residue was purified by silica gel column chromatography to obtain 0.58 g (yield: 21%) of the desired product. Melting point: 138–140° C.

PROCESS 39

Preparation of 3-[2-fluoro-4-chloro-5-(2-propionyloxy)phenyl]-1-benzylideneamino-6-trifluoromethyl-2(1H))-pyridone (Compound No. 1-226)

To 10 ml of toluene, 0.28 g (0.78 mmol) of 3-[2-fluoro-4-chloro-5-(2-propynyloxy)phenyl]-1-amino-6-trifluoromethyl-2(1H)-pyridone, 0.1 g (0.95 mmol) of benzaldehyde and one drop of a 1N titanium tetrachloride/dichloromethane solution, were added, followed by stirring at room temperature for 8 hours. After completion of the reaction, the reaction solution was poured into water and extracted with ethyl acetate. The extract was washed with water and a saturated sodium hydrogencarbonate aqueous solution and then dried over anhydrous magnesium sulfate. Ethyl acetate was distilled off under reduced pressure. The obtained residue was purified by silica gel column chromatography to obtain 0.24 g (yield: 69%) of the desired product. Melting point: 135–136° C. $^1$H-NMR (400 MHz, CDCl$_3$) δ value: 2.52(1H,t), 4.75(2H,d), 6.83(1H,d), 7.24 (1H,d), 7.35(1H,d), 7.50(2H,m), 7.91(2H,d), 9.81(1H,s) ppm.

PROCESS 40

Preparation of 3-(6-fluoro-benzothiazolin-2-on-5-yl)-1-methyl-6-trifluoromethyl-2-(1H)-pyridone (Compound No. 3-2)

To 40 ml of acetic acid, 10.3 g (36 mmol) of 3-(5-amino-2-fluorophenyl)-1-methyl-6-trifluoromethyl-2(1H)-pyridone was dissolved, and 6.8 g (89 mmol) of ammonium thiocyanate was added thereto, followed by stirring at room temperature for 2 hours. To this reaction solution, an acetic acid solution of 6.6 g (41 mmol) of bromine was added under cooling with ice, followed by stirring further at room temperature for 8 hours. After completion of the reaction, the reaction solution was poured into water and made alkaline by an addition of aqueous ammonia. Precipitated crystals were collected by filtration, and obtained crude crystals were washed with ethyl acetate to obtain 8.0 g of a mixture of 2-aminobenzothiazole. This mixture was dissolved in 15 ml of sulfuric acid and 15 ml of acetic acid, and 15 ml of an aqueous solution containing 1.7 g (26 mmol) of sodium nitrite, was added under cooling with ice, followed by stirring for 1.5 hours. 200 ml of an aqueous solution containing 33 g (0.14 mol) of copper (II) nitrate trihydrate, was added at a temperature of not higher than 15° C., followed by stirring for 30 minutes. Then, 3.6 g (25 mmol) of copper (I) oxide was added, followed by stirring for further 30 minutes. After completion of the reaction, the reaction solution was extracted with ethyl acetate. The organic layer was washed with water and dried over anhydrous magnesium sulfate. The organic layer was distilled off under reduced pressure, and the obtained residue was purified by silica gel column chromatography to obtain 0.9 g (yield: 7.2%) of the desired product. $^1$H-NMR (300 MHz, CDCl$_3$+DMSO-d$_6$) δ value: 3.66(3H,d), 6.68(1H,s), 6.73 (1H,d), 6.89(1H,s), 7.37(1H,d)ppm.

PREPARATION EXAMPLE 41

Preparation of 3-[6-fluoro-3-(2-propynyl) benzothiazolin-2-on-5-yl]-1-methyl-6-trifluoromethyl-2(1H)-pyridone (Compound No. 3-1)

To 10 ml of DMF, 0.4 g (1.2 mmol) of 3-(6-fluoro-benzothiazolin-2-on-5-yl)-1-methyl-6-trifluoromethyl-2 (1H)-pyridone, 0.18 g (1.3 mmol) of potassium carbonate and 0.15 g (1.3 mmol) of propargyl bromide were added, followed by heating and stirring at 70° C. for 2 hours. After completion of the reaction, the reaction solution was poured into water and extracted with ethyl acetate. The organic layer was washed with water and dried over anhydrous magnesium sulfate. The organic layer was distilled off under reduced pressure, and the obtained residue was purified by silica gel column chromatography to obtain 0.32 g (yield: 72%) of the desired product. Melting point: 150–151° C. $^1$H-NMR (300 MHz, CDCl$_3$) δ value: 2.30(1H,t), 3.73(3H, s), 4.73(2H,d), 6.80(1H,d), 7.27(1H,d), 7.45(1H,d), 7.56 (1H,d)ppm.

PREPARATION EXAMPLE 42

Preparation of 3-(2-bromomethyl-7-chloro-5-fluorobenzofuran-4-yl)-1-methyl-6-trifluoromethyl-2-(1H)-pyridone (Compound No. 4-7)

0.98 g (2.72 mmol) of 3-(7-chloro-5-fluoro-2-methylbenzofuran-4-yl)-1-methyl-6-trifluoromethyl-2-(1H)-pyridone was dissolved in 25 ml of carbon tetrachloride, and 0.51 g (2.86 mmol) of NBS and 0.04 g (0.27 mmol) of 2,2'-azobisisobutyronitrile were added thereto, followed by refluxing for 2 hours. Succinic acid imide was removed by filtration. Then, carbon tetrachloride was distilled off under reduced pressure, and the obtained residue was poured into water and extracted with ethyl acetate. After washing with water, the organic layer was dried over anhydrous magnesium sulfate. Ethyl acetate was distilled off under reduced pressure, and the obtained crude crystals were washed with n-hexane to obtain 0.94 g (yield: 79%) of the desired product. Melting point: 142–144° C. $^1$H-NMR (300 MHz, CDCl$_3$) δ value: 3.73(3H,s), 4.56(2H, s), 6.66(1H,s), 6.80(1H,d), 7.20(1H,d), 7.55(1H,d)ppm.

PREPARATION EXAMPLE 43

Preparation of 3-(7-chloro-5-fluoro-2-methoxymethylbenzofuran-4-yl)-1-methyl-6-trifluoromethyl-2-(1H)-pyridone (Compound No. 4-4)

0.38 g (0.87 mmol) of 3-(2-bromomethyl-7-chloro-5-fluorobenzofuran-4-yl)-1-methyl-6-trifluoromethyl-2-

(1H))-pyridone was dissolved in 10 ml of methanol, and 0.04 g (1.04 mmol) of sodium hydroxide was added, followed by heating and refluxing for 1 hour. Methanol was distilled off under reduced pressure. Then, the obtained residue was poured into water and extracted with ethyl acetate. After washing with water, the organic layer was dried over anhydrous magnesium sulfate. Ethyl acetate was distilled off under reduced pressure. Then, the obtained crude crystals were washed with n-hexane to obtain 0.31 g (yield: 92%) of the desired product. Melting point: 136–137° C. $^1$H-NMR (300 MHz, CDCl$_3$) δ value: 3.44(3H, s), 3.73(3H,s), 4.56(2H,s), 6.59(1H,s), 6.80(1H,d), 7.17(1H, d), 7.54(1H,d)ppm.

PREPAPRATION EXAMPLE 44

Preparation of 3-(7-chloro-5-fluoro-2-hydroxymethylbenzofuran-4-yl)-1-methyl- 6-trifluoromethyl-2-(1H)-pyridone (Compound No. 4-5)

0.20 g (0.51 mmol) of 3-(7-chloro-5-fluoro-2-methoxymethylbenzofuran-4-yl)-1-methyl-6-trifluoromethyl-2-(1H)-pyridone was dissolved in 10 ml of dichloromethane, and 1.54 ml (1.54 mmol) of a 1.0M boron tribromide dichloromethane solution was added thereto at ±65° C. The mixture was stirred at −65° C. for 1 hour and then poured into water, followed by stirring at room temperature for 30 minutes. Then, it was extracted with dichloromethane. After washing with water, the organic layer was dried over anhydrous magnesium sulfate. Dichloromethane was distilled off under reduced pressure. Then, the obtained crude crystals were washed with n-hexane to obtain 0.19 g (yield: 99%) of the desired product. Melting point: 145–147° C. $^1$H-NMR (300 MHz, CDCl$_3$) δ value: 3.73(3H, s), 4.55(2H,s), 6.66(1H,s), 6.80(1H,d), 7.20(1H,d), 7.55(1H, d)ppm.

PREPARATION EXAMPLE 45

Preparation of 3-(7-chloro-5-fluoro-2-methylthiomethylbenzofuran-4-yl)-1-methyl-6-trifluoromethyl-2-(1H)-pyridone (Compound No. 4-44)

0.31 g (0.71 mmol) of 3-(2-bromomethyl-7-chloro-5-fluorobenzofuran-4-yl)-1-methyl-6-trifluoromethyl-2-(1H)-pyridone was dissolved in 20 ml of THF, and 0.014 g (0.85 mmol) of a methanethiol 30% methanol solution and 0.12 g (0.85 mmol) of potassium carbonate were added thereto, followed by stirring at room temperature for 8 hours. THF was distilled off under reduced pressure. Then, the obtained residue was poured into water and extracted with ethyl acetate. After washing with water, the organic layer was dried over anhydrous magnesium sulfate. Ethyl acetate was distilled off under reduced pressure. Then, the obtained crude crystals were washed with n-hexane to obtain 0.28 g (yield: 98%) of the desired product. $^1$H-NMR (300 MHz, CDCl$_3$) δ value: 2.17(3H,s), 3.73(3H,s), 3.79(2H,s), 6.47 (1H,s), 6.80(1H,d), 7.14(1H,d), 7.54(1H,d)ppm.

PREPARATION EXAMPLE 46

Preparation of 3-[7-chloro-5-fluoro-2-(1-methylsulfinylpropyl)benzofuran-4-yl]-1-methyl-6-trifluoromethyl-2-(1H)-pyridone (Compound No. 4-57)

0.20 g (0.461 mmol) of 3-[7-chloro-5-fluoro-2-(methylthiopropyl)benzofuran-4-yl]-1-methyl-6-trifluoromethyl-2-(1H)-pyridone obtained in the same manner as in Preparation Example 45, was dissolved in 15 ml of methanol, and 5 ml of water and 0.23 g (0.369 mmol) of Oxone were added thereto, followed by stirring at room temperature for 2 hours. Insoluble substances were removed by filtration. Then, methanol was distilled off under reduced pressure, and the obtained residue was poured into water and extracted with ethyl acetate. After washing with water, the organic layer was dried over anhydrous magnesium sulfate. Ethyl acetate was distilled off under reduced pressure. Then, the obtained residue was purified by silica gel column chromatography to obtain 0.11 g (yield: 52%) of the desired product. Melting point: 125–127° C.

PREPARATION EXAMPLE 47

Preparation of 3-[7-chloro-5-fluoro-2-(1-methylsulfonylpropyl)benzofuran-4-yl]-1-methyl-6-trifluoromethyl-2-(1H)-pyridone (Compound No. 4-58)

0.20 g (0.461 mmol) of 3-[7-chloro-5-fluoro-2-(1-methylthiopropyl)benzofuran-4-yl]-1-methyl-6-trifluoromethyl-2-(1H)-pyridone was dissolved in 15 ml of methanol, and 5 ml of water and 0.57 g (0.922 mmol) of Oxone were added thereto, followed by stirring at room temperature for 2 hours. Insoluble substances were removed by filtration. Then, methanol was distilled off under reduced pressure, and the obtained residue was poured into water and extracted with ethyl acetate. After washing with water, the organic layer was dried over anhydrous magnesium sulfate. Ethyl acetate was distilled off under reduced pressure. Then, the obtained residue was purified by silica gel column chromatography to obtain 0.18 g (yield: 85%) of the desired product. Melting point: 146–148° C.

PREPARATION EXAMPLE 48

Preparation of 3-(7-chloro-2-dibromomethyl-5-fluorobenzofuran-4-yl)-1-methyl-6-trifluoromethyl-2-(1H)-pyridone (Compound No. 4-27)

1.50 g (4.17 mmol) of 3-(7-chloro-5-fluoro-2-methylbenzofuran-4-yl)-1-methyl-6-trifluoromethyl-2-(1H)-pyridone was dissolved in 30 ml of carbon tetrachloride, and 2.97 g (16.68 mmol) of NBS and 0.21 g (1.25 mmol) of 2,2'-azobisisobutyronitrile were added thereto, followed by heating and refluxing for 10 hours. Succinic acid imide was removed by filtration, and then, carbon tetrachloride was distilled off under reduced pressure. Then, the obtained residue was poured into water and extracted with ethyl acetate. After washing with water, the organic layer was dried over anhydrous magnesium sulfate. Ethyl acetate was distilled off under reduced pressure. Then, the obtained residue was purified by silica gel column chromatography to obtain 0.97 g (yield: 45%) of the desired product. Melting point: 107–109° C. $^1$H-NMR (300 MHz, CDCl$_3$) δ value: 3.74(3H,s), 6.65(1H,s), 6.81(1H,d), 6.82 (1H,s), 7.26(1H,d), 7.55(1H,d)ppm.

PREPARATAION EXAMPLE 49

Preparation of 3-(5,7-dichloro-2-tribromomethylbenzofuran-4-yl)-1-methyl-6-trifluoromethyl-2-(1H)-pyridone (Compound No.4-40)

1.92 g (5.10 mmol) of 3-(5,7-dichloro-2-methylbenzofuran-4-yl)-1-methyl-6-trifluoromethyl-2-

(1H)-pyridone was dissolved in 70 ml of carbon tetrachloride, and 3.81 g (21.42 mmol) of NBS and 0.33 g (2.00 mmol) of 2,2'-azobisisobutyronitrile were added thereto, followed by refluxing for 15 hours. Succinic acid imide was removed by filtration and then, carbon tetrachloride was distilled off under reduced pressure. Then, the obtained residue was poured into water and extracted with ethyl acetate. After washing with water, the organic layer was dried over anhydrous magnesium sulfate. Ethyl acetate was distilled off under reduced pressure. Then, the obtained residue was purified by silica gel column chromatography to obtain 0.19 g (yield: 6%) of the desired product. Melting point: 225–227° C. $^1$H-NMR (300 MHz, CDCl$_3$) δ value: 3.75(3H,s), 6.84(1H,d), 6.93(1H,s), 7.50(1H,d), 7.57(1H,s) ppm.

PREPARATION EXAMPLE 50

Preparation of 3-(7-chloro-5-fluoro-2-formylbenzofuran-4-yl)-1-methyl-6-trifluoromethyl-2-(1H)-pyridone (Compound No. 4-46).

0.29 g (0.56 mmol) of 3-(7-chloro-2-dibromomethyl-5-fluorobenzofuran-4-yl)-1-methyl-6-trifluoromethyl-2-(1H)-pyridone was added to 15 ml of sulfuric acid, followed by stirring at 50° C. for 1 hour. Then, the mixture was poured into water and extracted with diethyl ether. After washing with water, the organic layer was dried over anhydrous magnesium sulfate. Ethyl acetate was distilled off under reduced pressure. Then, the obtained crude crystals were washed with n-hexane to obtain 0.20 g (yield: 96%) of the desired product. $^1$H-NMR (300 MHz, CDCl$_3$) δ value: 3.75(3H,s), 6.84(1H,d), 7.42(1H,d), 7.46(1H,s), 7.61(1H,d), 9.90(1H,s)ppm.

PREPRATION EXAMPLE 51

Preparation of 3-(2-carboxy-7-chloro-5-fluorobenzofuran-4-yl)-1-methyl-6-trifluoromethyl-2-(1H)-pyridone (Compound No. 4-26)

0.37 g (0.99 mmol) of 3-(7-chloro-5-fluoro-2-formylbenzofuran-4-yl)-1-methyl-6-trifluoromethyl-2-(1H)-pyridone was dissolved in 20 ml of acetone, and a Jones reagent (CrO$_3$—H$_2$SO$_4$) was added thereto at −20° C. After stirring at −20° C. for 2 hours, the mixture was poured into water and extracted with ethyl acetate. An aqueous sodium hydroxide solution was added to make the extract alkaline, and the aqueous layer was washed with ethyl acetate and acidified by an addition of hydrochloric acid and then extracted with ethyl acetate. After washing with water, the organic layer was dried over anhydrous magnesium sulfate. Ethyl acetate was distilled off under reduced pressure. Then, the obtained crude crystals were washed with diisopropyl ether to obtain 0.29 g (yield: 75%) of the desired products Melting point: 233–235° C. $^1$H-NMR (300 MHz, CDCl$_3$) δ value: 3.79(3H,s), 6.87(1H,d), 7.38(1H,d), 7.47 (1H,s), 7.61(1H,d)ppm.

PREPARATION EXAMPLE 52

Preparation of 3-(7-chloro-2-ethoxycarbonyl-5-fluorobenzofuran-4-yl)-1-methyl-6-trifluoromethyl-2(1H)-pyridone (Compound No. 4-6)

0.08 g (0.21 mmol) of 3-(2-carboxy-7-chloro-5-fluorobenzofuran-4-yl)-1-methyl-6-trifluoromethyl-2-(1H)-pyridone was dissolved in 10 ml of ethanol, and 4.0 mg (0.04 mmol) of sulfuric acid was added thereto, followed by refluxing for 2 hours. Ethanol was distilled off under reduced pressure. Then, the obtained residue was poured into water and extracted with diethyl ether. After washing with water, the organic layer was dried over anhydrous magnesium sulfate. Diethyl ether was distilled off under reduced pressure. Then, the obtained crude crystals were washed with n-hexane to obtain 0.09 g (yield: 99%) of the desired product. Melting point: 118–120° C. $^1$H-NMR (300 MHz, CDCl$_3$) δ value: 1.41(3H,t), 3.75(3H,s), 4.43(2H,q), 6.82 (1H,d), 7.34(1H,d), 7.38(1H,s), 7.57(1H,d)ppm.

PREPARATION EXAMPLE 53

Preparation of 3-(7-chloro-5-fluorobenzofuran-4-yl)-1-methyl-6-trifluoromethyl-2-(1H)-pyridone (Compound No. 4-28)

0.29 g (0.74 mmol) of 3-(2-carboxy-7-chloro-5-fluorobenzofuran-4-yl)-1-methyl-6-trifluoromethyl-2-(1H)-pyridone was dissolved in 15 ml of quinoline, and 0.05 g (0.75 mmol) of copper powder was added thereto, followed by stirring at 210° C. for 15 minutes. Then, copper was removed by filtration, and the filtrate was poured into water and acidified by an addition of hydrochloric acid, and then extracted with ethyl acetate. After washing with water, the organic layer was dried over anhydrous magnesium sulfate. Ethyl acetate was distilled off under reduced pressure. Then, the obtained residue was purified by silica gel column chromatography to obtain 0.18 g (yield: 70%) of the desired product. Melting point: 178–179° C. $^1$H-NMR (300 MHz, CDCl$_3$) δ value: 3.74(3H,s), 6.66(1H,d), 6.81(1H,d), 7.20 (1H,d), 7.56(1H,d), 7.72(1H,d)ppm.

PREPARATION EXAMPLE 54

Preparation of 3-(4-chlorophenyl)-4-chloro-1-methyl-6-trifluoromethyl-2(1H)-pyridone (Compound No. 11-1), 3-(4-chlorophenyl)-2-chloro-1-methyl-6-trifluoromethyl-4(1H)-pyridone (Compound No. 13-1)

Preparation of 3-(4-chlorophenyl)-2,4-dioxo-1-methyl-6-trifluoromethyl-1,2,3,4-tetrahydropyridine To 200 ml of toluene, 6.7 g (35 mmol) of 4-chlorophenylacetyl chloride and 14.0 g (71 mmol) of ethyl 3-methylamino-4,4,4-trifluorocrotonate were added, followed by stirring for 8 hours under heating and refluxing. After completion of the reaction, the reaction solution was washed with water and a saturated sodium chloride aqueous solution and dried over anhydrous magnesium sulfate. Toluene was distilled off under reduced pressure, and the obtained residue was purified by silica gel column chromatography. This crotonic acid ester was dissolved in 20 ml of THF and dropwise added to a LDA-THF solution [prepared from 54 ml (86 mmol) of a 1.6N-n-butyllithium-hexane solution, 11.3 g (112 mmol) of diisopropylamine and 200 ml of THF] under cooling to −65 to −60° C., followed by stirring at room temperature for 2 hours. After completion of the reaction, excess THF was distilled off, and a 10% citric acid aqueous solution was added thereto. Precipitated crude crystals were washed with ethyl acetate to obtain 3.6 g (yield: 34%) of the desired product. $^1$H-NMR (300 MHz, DMSO-d$_6$) δ value: 3.39(3H,s), 5.82(1H,s), 7.14(2H,d), 7.40(2H,d)ppm.

Preparation of 3-(4-chlorophenyl)-4-chloro-1-methyl-6-trifluoromethyl-2(1H)-pyridone (Compound No. 11-1), 3-(4-chlorophenyl)-2-chloro-1-methyl-6-trifluoromethyl-4(1H)-pyridone (Compound No. 13-1)

3.3 g (10.9 mmol) of 3-(4-chlorophenyl)-2,4-dioxo-1-methyl-6-trifluoromethyl-1,2,3,4-tetrahydropyridine was added to 8.3 g (42.3 mmol) of phosphorus oxychloride and 30 ml of diethylaniline, followed by stirring at from 100 to 120° C. for 4 hours. The reaction solution was distilled off under reduced pressure, and ethyl acetate was added to the obtained residue, followed by washing with water and a saturated sodium hydrogencarbonate aqueous solution. The organic layer was dried over anhydrous magnesium sulfate. The organic layer was distilled off under reduced pressure, and the obtained residue was separated and purified by high performance liquid chromatography to obtain 1.3 g (yield: 37%) of the desired 2-pyridone compound (Compound No. 11-1) and 1.0 g (yield: 29%) of the 4-pyridone compound (Compound No. 13-1), respectively.

2-pyridone compound (Compound No. 11-1) Melting point: 48–50° C. $^1$H-NMR (300 MHz, CDCl$_3$) δ value: 3.74(3H,s), 6.62(1H,s), 7.17(2H,d), 7.39(2H,d)ppm.

4-pyridone compound (Compound No. 13-1) Melting point: 88–90° C. $^1$H-NMR (300 MHz, CDCl$_3$) δ value: 3.77(3H,s), 6.96(1H,s), 7.15(2H,d), 7.41(2H,d)ppm.

PREPARTION EXAMPLE 55

Preparation of 3-(4-chloro-3-nitrophenyl)-4-chloro-1-methyl-6-trifluoromethyl-2(1H)-pyridone (Compound No. 11-7)

0.2 g (0.62 mmol) of 3-(4-chlorophenyl)-4-chloro-1-methyl-6-trifluoromethyl-2(1H)-pyridone was dissolved in 2 ml of concentrated sulfuric acid, and 0.04 g (0.64 mmol) of fuming nitric acid was added thereto under cooling with ice, followed by stirring for 1 hour. After completion of the reaction, the reaction solution was poured into ice water and extracted with ethyl acetate. The organic layer was washed with water and a saturated sodium hydrogencarbonate aqueous solution and dried over anhydrous magnesium sulfate. The organic layer was distilled off under reduced pressure, and the obtained crude crystals were washed with isopropyl ether to obtain 0.21 g (yield: 91%) of the desired product. $^1$H-NMR (300 MHz, CDCl$_3$) δ value: 3.74(3H,s), 6.66(1H,s), 7.40(1H,dd), 7.61(1H,d), 7.59(1H,s), 7.82(1H,d)ppm.

PREPARATION EXAMPLE 56

Preparation of 3-(3-amino-4-chlorophenyl)-4-chloro-1-methyl-6-trifluoromethyl-2(1H)-pyridone (Compound No. 11-8)

0.5 g (1.37 mmol) of 3-(4-chloro-3-nitrophenyl)-4-chloro-1-methyl-6-trifluoromethyl-2(1H)-pyridone was dissolved in 20 ml of ethanol, and 0.8 g (6.78 mmol) of tin was added thereto with stirring at room temperature, followed by stirring for 1 hour. After completion of the reaction, excess ethanol was distilled off under reduced pressure, and ethyl acetate and a saturated sodium hydrogencarbonate aqueous solution were added. The precipitate was collected by filtration and washed with water and a 10% citric acid aqueous solution. The organic layer was dried over anhydrous magnesium sulfate. The organic layer was distilled off under reduced pressure, and the obtained crude crystals were washed with isopropyl ether to obtain 0.40 g (yield: 87%) of the desired product. $^1$H-NMR (300 MHz, CDCl$_3$) δ value: 3.74(3H,s), 4.06(2H,s), 6.54(1H,dd), 6.59(1H,s), 6.62(1H,d), 7.27(1H,d)ppm.

PREPARATION EXAMPLE 57

Preparation of 3-(4-chloro-3-methylsulfonylaminophenyl)-4-chloro-1-methyl-6-trifluoromethyl-2(1H)-pyridone (Compound No. 11-3)

To 20 ml of dichloromethane, 0.4 g (1.19 mmol) of 3-(3-amino-4-chlorophenyl)-4-chloro-1-methyl-6-trifluoromethyl-2(1H)-pyridone and 0.3 g (2.62 mmol) of methylsulfonyl chloride were dissolved, and 0.3 g (2.96 mmol) of triethylamine was added thereto under cooling with ice, followed by stirring at room temperature for 1 hour. After completion of the reaction, the reaction solution was poured into water and extracted with dichloromethane. The organic layer was washed with water and a 10% citric acid aqueous solution and dried over anhydrous magnesium sulfate. The organic layer was distilled off under reduced pressure, and the obtained crude crystals were dissolved in a mixed solvent comprising 15 ml of ethanol and 5 ml of DMF, and 3 ml of an aqueous sodium hydroxide solution [0.05 g (1.25 mmol) of sodium hydroxide] was added, followed by stirring at room temperature for 1 hour. After completion of the reaction, the reaction solution was poured into water and weakly acidified with citric acid and then extracted with ethyl acetate. The organic layer was washed with water and dried over anhydrous magnesium sulfate. The organic layer was distilled off under reduced pressure, and the obtained residue was purified by silica gel column chromatography to obtain 0.47 g (yield: 95%) of the desired product. Melting point: 161–163° C. $^1$H-NMR (400 MHz, CDCl$_3$) δ value: 3.02(3H,s), 3.75(3H,s), 6.60(1H,s), 6.92(1H,s), 7.06(1H,dd), 7.26(1H,s), 7.47(1H,d), 7.59(1H,d) ppm.

PREPARATION EXAMPLE 58

Preparation of 3-(4-chlorophenyl)-4-fluoro-1-methyl-6-trifluoromethyl-2(1H)-pyridone (Compound No. 11-2)

To 10 ml of dimethylsulfoxide, 0.33 g (1.09 mmol) of 3-(4-chlorophenyl)-4-chloro-1-methyl-6-trifluoromethyl-2(1H)-pyridone and 0.05 g (0.86 mmol) of potassium fluoride were dissolved, followed by heating and stirring at 120° C. for 2 hours. After completion of the at reaction, the reaction solution was poured into ice water and extracted with ethyl acetate. The organic layer was washed with water and a saturated sodium chloride aqueous solution and dried over anhydrous magnesium sulfate. The organic layer was distilled off under reduced pressure, and the obtained residue was purified by silica gel column chromatography to obtain 0.12 g (yield: 38%) of the desired product. Melting point: 120–122° C. $^1$H-NMR (300 MHz, CDCl$_3$) δ value: 3.42(3H, d), 6.20(1H,d), 7.16(2H,d), 7.40(2H,d)ppm.

PREPARATION EXAMPLE 59

Preparation of 3-[2-fluoro-4-chloro-5-(2-propionyloxy)phenyl]-4-cyano-1-methyl-6-trifluoromethyl-2(1H)-pyridone (Compound No. 11-6)

To 10 ml of dimethylsulfoxide, 0.30 g (0.76 mmol) of 3-[2-fluoro-4-chloro-5-(2-propynyloxy)phenyl]-4-chloro-1-methyl-6-trifluoromethyl-2(1H)-pyridone and 0.06 g (0.92 mmol) of potassium cyanide were dissolved, followed by heating and stirring at 120° C. for 2 days. After completion of the reaction, the reaction solution was poured into ice water and extracted with ethyl acetate. The organic layer was washed with water and a saturated sodium chloride aqueous solution and dried over anhydrous magnesium sulfate. The organic layer was distilled off under reduced pressure, and the obtained residue was purified by silica gel column chromatography to obtain 0.09 g (yield: 29%) of the desired product. Refractive index: 1.5684 $^1$H-NMR (400 MHz, CDCl$_3$) δ value: 2.50(1H,t), 3.78(3H,s), 4.71(2H,m), 6.90 (1H,d), 7.20(1H,s), 7.25(1H,d)ppm.

PROCESS 60

Preparation of 3-(2-chloro-4-hydroxy-5-nitrophenyl)-1-methyl-6-trifluoromethyl-2(1H)-pyridone (Compound No. 1-278)

10.3 g (28.6 mmol) of 3-(2-chloro-4-methoxy-5-nitrophenyl)-1-methyl-6-trifluoromethyl-$^2$(1H)-pyridone was dissolved in 150 ml of dichloromethane, and 30 ml (90 mmol) of a 3N boron tribromide/dichloromethane solution was dropwise added thereto under cooling in a dry ice-acetone bath. The temperature was raised to room temperature, followed by stirring for 2 hours. Then, the mixture was poured into ice water and extracted with dichloromethane. The organic layer was washed with water and a saturated sodium hydrogencarbonate aqueous solution and then dried over anhydrous magnesium sulfate. The organic layer was distilled off under reduced pressure to obtain 8.0 g (yield: 80%) of the desired product.

PREPARATION EXAMPLE 61

Preparation of 3-(5-amino-2-chloro-4-hydroxyphenyl)-1-methyl-6-trifluoromethyl-2(1H)-pyridone (Compound No. 1-279)

8.0 g (23 mmol) of 3-(2-chloro-4-hydroxy-5-nitrophenyl)-1-methyl-6-trifluoromethyl-2(1H)-pyridone and 8.2 g (69 mmol) of tin were added to 100 ml of ethanol, and 5 ml of concentrated hydrochloric acid was added thereto under stirring at room temperature, followed by stirring for 1 hour. After completion of the reaction, excess ethanol was distilled off, and the residue was neutralized with a saturated sodium hydrogencarbonate aqueous solution and then extracted with ethyl acetate. The organic layer was washed with water and dried over anhydrous magnesium sulfate. The organic layer was distilled off under reduced pressure to obtain 6.5 g (yield: 90%) of the desired product. $^1$H-NMR (300 MHz, CDCl$_3$) δ value: 3.74(3H,s), 6.83(1H,d), 7.23(1H,d), 7.30(1H,d), 7.57(1H,d)ppm.

PREPARATION EXAMPLE 62

Preparation of 3-(6-chlorobenzoxazolin-2-on-5-yl)-1-methyl-6-trifluoromethyl-2(1H)-pyridone (Compound No. 3-20)

0.6 g (1.9 mmol) of 3-(5-amino-2-chloro-4-hydroxyphenyl)-1-methyl-6-trifluoromethyl-2(1H)-pyridone and 0.35 g (2.2 mmol) of CDI were dissolved in 5 ml of THF, followed by stirring for 1 hour under heating and refluxing. After completion of the reaction, the reaction solution was poured into water and extracted with ethyl acetate. The organic layer was washed with water and dried over anhydrous magnesium sulfate. The organic layer was distilled off under reduced pressure, and the obtained residue was purified by silica gel column chromatography to obtain 0.41 g (yield: 63%) of the desired product. Melting point: 263–265° C. $^1$H-NMR (400 MHz, CDCl$_3$) δ value: 3.78(3H, s), 6.84(1H,s), 6.85(1H,d), 7.28(1H,s), 7.46(1H,d)ppm.

PREPARATION EXAMPLE 63

Preparation of 3-[6-chloro-3-(2-propynyl)-benzoxazolin-2-on-5-yl]-1-methyl-6-trifluoromethyl-2(1H)-pyridone (Compound No. 3-9)

0.20 g (0.58 mmol) of 3-(6-chlorobenzoxazolin-2-on-5-yl)-1-methyl-6-trifluoromethyl-2(1H)-pyridone was dissolved in 10 ml of DMF, and 0.026 g (0.65 mmol) of 60% sodium hydride was added thereto at room temperature, followed by stirring for 0.5 hour. Further, 0.09 g (0.76 mmol) of propargyl bromide was added thereto, followed by stirring at room temperature for 2 hours. After completion of the reaction, the reaction solution was poured into water and extracted with ethyl acetate. The organic layer was washed with water and dried over anhydrous magnesium sulfate. The organic layer was distilled off under reduced pressure, and the obtained residue was purified by silica gel column chromatography to obtain 0.17 g (yield: 78%) of the desired product. Melting point: 187–189° C. H-NMR (400 MHz, CDCl$_3$) δ value: 2.38(1H,t), 3.72(3H,s,), 4.60(2H,d), 6.80 (1H,d), 7.18(1H,s), 7.37(1H,s), 7.43(1H,d)ppm.

PREPARATION EXAMPLE 64

Preparation of 3-[2-chloro-4-(1-ethoxycarbonylethoxy)-5-nitrophenyl]-1-methyl-6-trifluoromethyl-2(1H)-pyridone (Compound No. 1-280)

To 10 ml of DMF, 0.8 g (2.2 mmol) of 3-(2-chloro-4-hydroxy-5-nitrophenyl)-1-methyl-6-trifluoromethyl-2(1H)-pyridone, 0.42 g (3.0 mmol) of potassium carbonate and 0.56 g (3.3 nmol) of ethyl 2-bromopropionate were added, followed by heating and stirring at 60° C. for 2 hours. After completion of the reaction, the reaction solution was poured into water and extracted with ethyl acetate. The organic layer was washed with water and dried over anhydrous magnesium sulfate. The organic layer was distilled off under reduced pressure, and the obtained residue was purified by silica gel column chromatography to obtain 0.90 g (yield: 94%) of the desired product.

PREPARATION EXAMPLE 65

Preparation of 3-(7-chloro-2,3-dihydro-2-methyl-1,4-benzoxazin-3-on-6-yl)-6-trifluoromethyl-1-methyl-2(1H)-pyridone (Compound No. 2'-2)

To 10 ml of ethanol, 0.90 g (2.0 mmol) of 3-[2-chloro-4-(1-ethoxycarbonylethoxy)-5-nitrophenyl]-1-methyl-6-trifluoromethyl-2(1H)-pyridone and 1 g (8.5 mmol) of tin were added, and 2 ml of concentrated hydrochloric acid was added thereto with stirring at room temperature, followed by stirring for 1 hour. After completion of the reaction, excess ethanol was distilled off under reduced pressure, and the residue was neutralized with a saturated sodium hydrogencarbonate aqueous solution and then extracted with ethyl acetate. The organic layer was washed with water and dried over anhydrous magnesium sulfate. The organic layer was distilled off under reduced pressure to obtain 0.7 g (yield: 91%) of the desired product. $^1$H-NMR (300 MHz, CDCl$_3$) δ value: 1.63(3H,d), 3.70(3H,d), 4.67(1H,q), 6.77(1H,d), 6.83 (1H,s), 7.08(1H,s), 7.35(1H,d,J=7.80)ppm.

PREPARATION EXAMPLE 66

Preparation of 3-[7-chloro-2,3-dihyro-2-methyl-4-(2-propynyl)-1,4-benzoxazin-3-on-6-yl]-6-trifluoromethyl-1-methyl-2(1H)-pyridone (Compound No. 2'-1)

0.40 g (1.1 mmol) of 3-(7-chloro-2,3-dihydro- 3-methyl-1,4-benzoxazin-3-on-6-yl)-6-trifluoromethyl-1-methyl-2 (1H)-pyridone was dissolved in 10 ml of DMF, and 0.05 g (1.2 mmol) of 60% sodium hydride was added thereto at room temperature, followed by stirring for 0.5 hour. Further, 0.2 g (1.7 mmol) of propargyl bromide was added thereto, followed by stirring at room temperature for 2 hours. After completion of the reaction, the reaction solution was poured into water and extracted with ethyl acetate. The organic layer was washed with water and dried over anhydrous magnesium sulfate. The organic layer was distilled off under reduced pressure, and the obtained residue was purified by silica gel column chromatography to obtain 0.34 g (yield: 77%) of the desired product. Melting point: 203–204° C. $^1$H-NMR (300 MHz, CDCl$_3$) δ value: 1.60(3H,d), 2.24(1H, t), 3.71(3H,d), 4.66(3H,m), 6.78(1H,d), 7.13(2H,d), 7.46 (1H,d)ppm.

PREPARATION EXAMPLE 67

Preparation of 4-chloro-2-fluoro-5-methoxybenzyl chloride (Intermediate No. 15-15)

17.6 g (0.11 mol) of 2-chloro-4-fluoroanisole was dissolved in a dichloromethane solution of 1N titanium tetrachloride, and 88.3 g (1.10 mol) of methoxymethyl chloride was dropwise added thereto at room temperature, followed by stirring at room temperature for 5 hours. After completion of the reaction, the reaction solution was poured into water, followed by stirring at room temperature for 2 hours, and then the aqueous phase was removed. The organic layer was dried over anhydrous magnesium sulfate, and the solvent was distilled off. Then, the obtained residue was purified by silica gel column chromatography to obtain 15.5 g (yield: 68%) of the desired product. $^1$H-NMR (300 MHz, CDCl$_3$) δ value: 3.89(3H,s), 5.00(2H,s), 6.97(1H,d), 7.18(1H,d)ppm.

Now, with respect to some of the compounds of the present invention, $^1$H-NMR data will be shown below.

TABLE 34

| Comp. Nos. | NMR (ppm) | MHz Solvent |
|---|---|---|
| 1-20 | 0.88 (3H, t) 1.30 (4H, m) 1.65 (2H, m) 3.69 (3H, s) 4.19 (2H, t) 4.70 (2H, s) 6.76 (1H, d) 7.20 (1H, d) 7.23 (1H, d) 7.51 (1H, d) | 300 CDCl$_3$ |
| 1-22 | 3.69 (3H, s) 6.73 (1H, d) 6.95~7.36 (7H, m) 7.47 (1H, d) | 300 CDCl$_3$ |
| 1-36 | 3.66 (3H, s) 6.71 (1H, d) 6.95 (1H, s) 6.99~7.38 (6H, m) 7.58 (1H, s) | 300 CDCl$_3$ |
| 1-41 | 3.70 (3H, s) 6.77 (1H, d) 7.08 (1H, d) 7.32 (1H, s) 7.49 (1H, d) 7.61 (1H, s) 8.57 (2H, d) | 300 CDCl$_3$ |
| 1-48 | 0.95 (3H, t) 1.15 (3H, t) 1.3~1.6 (2H, m) 1.7~2.0 (2H, m) 3.70 (3H, s) 3.73 (1H, dd) 4.10 (2H, q) 6.75 (1H, d) 7.27 (1H, d) 7.46 (1H, d) 7.73 (1H, d) | 300 CDCl$_3$ |
| 1-56 | 0.95 (3H, t) 1.16 (3H, t) 1.45 (2H, m) 1.87 (2H, m) 3.69 (3H, s) 3.76 (1H, t) 4.10 (2H, q) 6.76 (1H, d) 7.38 (1H, d) 7.48 (1H, s) 7.54 (1H, s) | 300 CDCl$_3$ |
| 1-64 | 1.26 (3H, t) 1.52 (3H, d) 3.69 (3H, s) 4.14 (1H, dq) 4.21 (2H, q) 4.70 (1H, d) 6.74 (1H, d) 6.77 (1H, d) 7.14 (1H, d) 7.46 (1H, d) | 400 CDCl$_3$ |
| 1-68 | 2.11 (3H, s) 2.13 (3H, s) 3.71 (3H, d) 6.79 (1H, d) 7.30 (1H, d) 7.53 (1H, d) 8.70 (1H, d) | 400 CDCl$_3$ |
| 1-70 | 3.27 (1H, dd) 3.52 (1H, dd) 3.70 (3H, d) 3.79 (3H, s) 4.58 (1H, dd) 6.76 (1H, d) 7.22 (1H, d) 7.48 (1H, d) 7.49 (1H, d) | 400 CDCl$_3$ |
| 1-104 | 0.92 (3H, t) 1.68 (2H, tq) 3.69 (3H, s) 4.16 (2H, t) 4.71 (2H, s) 6.76 (1H, d) 7.20 (1H, d) 7.23 (1H, d) 7.51 (1H, d) | 300 CDCl$_3$ |

TABLE 35

| Comp. Nos. | NMR (ppm) | MHz Solvent |
|---|---|---|
| 1-111 | 1.37 (6H, d) 3.54 (1H, m) 3.70 (3H, s) 7.27 (1H, d) 7.42 (1H, d) 7.45 (1H, d) 7.49 (1H, d) 7.77 (1H, s) | 300 CDCl$_3$ |
| 1-115 | 1.48~1.83 (8H, m) 3.70 (3H, s) 5.16 (1H, qi) 6.76 (1H, d) 7.42 (1H, d) 7.51 (1H, d) 7.54 (1H, d) 7.76 (1H, s) | 300 CDCl$_3$ |
| 1-116 | 0.96 (3H, t) 1.14 (3H, t) 1.48 (2H, m) 1.88 (2H, m) 3.70 (3H, s) 3.84 (1H, t) 4.10 (2H, q) 6.76 (1H, d) 7.45 (1H, d) 7.49 (1H, d) 7.64 (1H, d) 7.80 (1H, s) | 300 CDCl$_3$ |
| 1-117 | 3.33 (1H, s) 3.57 (2H, tt) 3.69 (3H, s) 3.77 (2H, s) 4.28 (2H, tt) 6.77 (1H, d) 7.43 (1H, d) 7.54 (1H, d) 7.56 (1H, d) 7.76 (1H, s) | 300 CDCl$_3$ |
| 1-120 | 1.06 (3H, t) 1.64 (1H, m) 1.86 (1H, m) 3.26 (1H, m) 3.34 (3H, s) 3.49 (2H, m) 3.69 (3H, s) 6.75 (1H, d) 7.41 (2H, t) 7.52 (1H, s) | 300 CDCl$_3$ |
| 1-121 | 0.99 (3H, t) 1.25 (3H, t) 1.65 (2H, m) 1.99 (2H, m) 3.69 (3H, s) 4.22 (2H, q) 4.62 (1H, t) 6.74 (1H, d) 7.09 (1H, d) 7.21 (1H, d) 7.47 (1H, d) | 300 CDCl$_3$ |
| 1-137 | 0.95 (3H, t) 1.37 (3H, t) 1.74 (2H, sext) 3.67 (3H, d) 3.98 (2H, t) 4.35 (2H, q) 6.73 (1H, d) 7.00 (1H, s) 7.44 (1H, d) 7.69 (1H, s) | 400 CDCl$_3$ |
| 1-139 | 1.27 (3H, t) 3.27 (1H, dd) 3.51 (1H, dd) 3.69 (3H, s) 4.23 (2H, m) 4.57 (1H, dd) 6.76 (1H, d) 7.22 (1H, d) 7.48 (1H, d) 7.50 (1H, d) | 400 CDCl$_3$ |
| 1-140 | 1.45 (3H, t) 3.18 (2H, q) 3.31 (3H, s) 3.70 (3H, s) 6.78 (1H, d) 7.29 (1H, d) 7.54 (1H, d) 7.75 (1H, d) | 400 CDCl$_3$ |
| 1-142 | 1.30 (3H, t) 3.70 (3H, s) 4.26 (2H, q) 4.84 (2H, s) 6.78 (1H, d) 7.31 (1H, d) 7.53 (1H, d) 8.24 (1H, d) | 400 CDCl$_3$ |

TABLE 36

| Comp. Nos. | NMR (ppm) | MHz Solvent |
|---|---|---|
| 1-148 | 0.90 (3H, t) 1.35 (2H, m) 1.63 (2H, m) 3.69 (3H, s) 4.21 (2H, t) 4.70 (2H, s) 6.76 (1H, d) 7.20 (1H, d) 7.25 (1H, d) 7.51 (1H, d) | 300 CDCl$_3$ |
| 1-149 | 0.87 (3H, t) 1.20~1.40 (6H, m) 1.64 (2H, m) 3.69 (3H, s) 4.19 (2H, t) 4.70 (2H, s) 6.76 (1H, d) 7.20 (1H, d) 7.23 (1H, d) 7.51 (1H, d) | 300 CDCl$_3$ |
| 1-159 | 1.24~2.00 (10H, m) 3.70 (3H, s) 4.24 (1H, qi) 6.76 (1H, d) 7.19 (1H, d) 7.19 (1H, d) 7.51 (1H, d) | 300 CDCl$_3$ |
| 1-161 | 0.25 (1H, m) 0.36 (1H, m) 0.56 (2H, m) 1.14 (1H, m) 1.41 (3H, d) 3.70 (3H, s) 3.77 (1H, dq) 6.76 (1H, d) 7.19 (1H, d) 7.23 (1H, d) 7.51 (1H, d) | 300 CDCl$_3$ |
| 1-167 | 1.00 (3H, t) 1.33 (3H, d) 1.73 (2H, m) 3.70 (3H, s) 4.29 (1H, dt) 6.76 (1H, d) 7.20 (1H, d) 7.20 (1H, d) 7.52 (1H, d) | 300 CDCl$_3$ |
| 1-174 | 1.73 (3H, s) 1.80 (3H, s) 3.70 (3H, s) 4.57 (2H, s) 5.51 (1H, t) 6.76 (1H, d) 7.18 (1H, d) 7.20 (1H, d) 7.51 (1H, d) | 300 CDCl$_3$ |
| 1-176 | 1.84 (3H, d) 3.71 (3H, s) 4.89 (1H, q) 6.78 (1H, d) 7.26 (1H, d) 7.46 (1H, d) 7.55 (1H, d) | 300 CDCl$_3$ |
| 1-181 | 1.23 (3H, t) 3.70 (3H, s) 3.79 (2H, q) 5.28 (2H, s) 6.76 (1H, d) 7.21 (1H, d) 7.38 (1H, d) 7.49 (1H, d) | 300 CDCl$_3$ |
| 1-182 | 1.48 (3H, d) 3.69 (3H, s) 4.77 (1H, dq) 5.21 (1H, d) 5.25 (1H, d) 5.93 (1H, m) 6.75 (1H, d) 7.19 (1H, d) 7.20 (1H, d) 7.50 (1H, d) | 300 CDCl$_3$ |
| 1-194 | 0.99 (3H, t) 1.74 (2H, sext) 2.94 (2H, t) 3.70 (3H, s) 6.78 (1H, d) 7.25 (1H, d) 7.53 (1H, d) 7.75 (1H, d) | 400 CDCl$_3$ |

TABLE 37

| Comp. Nos. | NMR (ppm) | MHz Solvent |
|---|---|---|
| 1-195 | 0.96 (3H, d) 0.97 (3H, d) 1.65 (1H, bs) 2.03 (1H, d) 3.69 (3H, d) 4.88 (1H, d) 6.76 (1H, d) 7.16 (1H, d) 7.49 (1H, d) 7.68 (1H, d) | 400 CDCl$_3$ |
| 1-198 | 3.70 (3H, d) 6.08 (1H, dd) 6.26 (1H, dd) 6.78 (1H, d) 6.79 (1H, dd) 7.27 (1H, d) 7.53 (1H, d) 7.69 (1H, d) | 400 CDCl$_3$ |

TABLE 37-continued

| Comp. Nos. | NMR (ppm) | MHz Solvent |
|---|---|---|
| 1-200 | 3.42 (3H, s) 3.70 (3H, d) 4.67 (2H, s) 4.75 (2H, s) 6.76 (1H, d) 7.21 (1H, d) 7.49 (1H, d) 7.67 (1H, d) | 400 CDCl$_3$ |
| 1-201 | 1.53~1.56 (2H, in) 1.71~1.79 (6H, m) 3.70 (3H, d) 4.02~4.06 (1H, m) 4.52 (2H, s) 6.75 (1H, d) 7.18 (1H, d) 7.46 (1H, d) 7.60 (1H, d) | 400 CDCl$_3$ |
| 1-207 | 3.37 (3H, s) 3.57 (2H, t) 3.69 (3H, s) 3.89 (2H, t) 5.32 (2H, s) 6.75 (1H, d) 7.20 (1H, d) 7.39 (1H, d) 7.48 (1H, d) | 300 CDCl$_3$ |
| 1-208 | 2.29 (3H, s) 3.70 (3H, s) 5.22 (2H, s) 6.77 (1H, d) 7.23 (1H, d) 7.29 (1H, d) 7.53 (1H, d) | 300 CDCl$_3$ |
| 1-213 | 1.20 (3H, t) 3.68 (2H, q) 3.70 (3H, s) 5.04 (2H, s) 6.76 (1H, d) 7.40 (1H, d) 7.50 (1H, s) 7.58 (1H, d) | 300 CDCl$_3$ |
| 1-238 | 1.05 (3H, t) 1.85 (2H, m) 3.68 (3H, s) 3.69 (3H, d) 6.76 (1H, d) 7.39 (1H, d) 7.49 (1H, d) 7.55 (1H, s) | 300 CDCl$_3$ |
| 1-239 | 0.86 (3H, t) 1.05 (3H, t) 1.56 (2H, m) 1.91 (2H, m) 3.69 (3H, d) 3.71 (1H, m) 4.02 (2H, t) 6.75 (1H, s) 7.38 (1H, d) 7.49 (1H, d) 7.53 (1H, d) | 300 CDCl$_3$ |
| 1-240 | 1.05 (3H, t) 1.12 (3H, d) 1.18 (3H, d) 1.89 (2H, m) 3.68 (1H, m) 3.69 (3H, d) 4.97 (1H, m) 6.75 (1H, d) 7.38 (1H, d) 7.49 (1H, s) 7.53 (1H, s) | 300 CDCl$_3$ |

TABLE 38

| Comp. Nos. | NMR (ppm) | MHz Solvent |
|---|---|---|
| 1-241 | 0.84 (3H, t) 1.45 (2H, m) 1.88 (2H, m) 3.65 (3H, s) 3.70 (3H, d) 3.80 (1H, t) 6.75 (1H, d) 7.38 (1H, d) 7.49 (1H, s) 7.53 (1H, s) | 400 CDCl$_3$ |
| 1-242 | 0.85 (3H, t) 0.95 (3H, t) 1.50 (2H, m) 1.58 (2H, m) 1.90 (2H, m) 3.75 (3H, d) 3.80 (1H, t) 3.99 (2H, t) 6.75 (1H, d) 7.38 (1H, d) 7.49 (1H, s) 7.53 (1H, s) | 400 CDCl$_3$ |
| 1-243 | 0.95 (3H, t) 1.10 (3H, d) 1.17 (3H, d) 1.45 (2H, m) 1.90 (2H, m) 3.69 (3H, d) 3.75 (1H, dd) 4.95 (1H, m) 6.75 (1H, d) 7.38 (1H, d) 7.48 (1H, d) 7.53 (1H, s) | 300 CDCl$_3$ |
| 1-273 | 1.06 (3H, t) 1.15 (3H, t) 1.60 (1H, m) 1.88 (1H, m) 3.28 (1H, m) 3.52 (4H, m) 3.69 (3H, s) 63.75 (1H, d) 7.40 (1H, d) 7 42 (1H, s) 7.50 (1H, s) | 300 CDCl$_3$ |
| 1-278 | 1.13 (6H, d) 3.10 (2H, t) 3.50~3.60 (3H, m) 3.69 (3H, d) 6.76 (1H, d) 7.31 (1H, s) 7.40 (1H, d) 7.48 (1H, s) | 300 CDCl$_3$ |
| 2-5 | 2.35 (3H, q) 3.69 (3H, q) 4.61 (2H, s) 6.80 (1H, d) 7.16 (1H, d) 7.36 (1H, s) | 300 CDCl$_3$ |
| 4-36 | 1.21 (3H, t) 1.58 (3H, d) 3.54 (2H, q) 3.73 (3H, s) 4.59 (1H, q) 6.50 (1H, s) 6.80 (1H, d) 7.14 (1H, d) 7.53 (1H, d) | 300 CDCl$_3$ |
| 4-37 | 0.91 (3H, t) 1.57 (3H, d) 1.53~1.64 (2H, m) 3.39~3.48 (2H, m) 3.73 (3H, s) 4.58 (1H, q) 6.49 (1H, s) 6.80 (1H, d) 7.14 (1H, d) 7.53 (1H, d) | 300 CDCl$_3$ |
| 4-39 | 0.94 (3H, t) 1.94 (2H, dq) 3.36 (3H, s) 3.74 (3H, s) 4.24 (1H, t) 6.52 (1H, s) 6.80 (1H, d) 7.15 (1H, d) 7.54 (1H, d) | 300 CDCl$_3$ |

TABLE 39

| Comp. Nos. | NMR (ppm) | MHz Solvent |
|---|---|---|
| 4-45 | 1.61 (3H, d) 3.73 (3H, s) 4.99 (1H, q) 6.49 (1H, s) 6.81 (1H, d) 7.14 (1H, d) 7.54 (1H, d) | 300 CDCl$_3$ |
| 4-49 | 0.97 (3H, t) 1.21 (3H, t) 1.92 (2H, m) 3.42~3.73 (2H, m) 3.73 (3H, s) 4.33 (1H, t) 6.50 (1H, s) 6.79 (1H, d) 7.14 (1H, d) 7.53 (1H, d) | 300 CDCl$_3$ |
| 4-59 | 1.77 (3H, d) 2.43, 2.55 (3H, s) 3.73 (3H, s) 4.07, 4.08 (1H, q) 6.63, 6.67 (1H, s) 6.81 (1H, d) 7.19 (1H, d) 7.55 (1H, d) | 300 CDCl$_3$ |
| 4-65 | 1.23 (3H, t) 3.60 (2H, q) 3.69 (3H, s) 4.57 (2H, s) 6.57 (1H, s) 6.74 (1H, d) 6.91 (1H, d) 7.53 (1H, d) | 400 CDCl$_3$ |
| 4-78 | 1.35 (3H, t) 1.76 (3H, dd) 2.62 (2H, m) 3.73 (3H, s) 4.68 (1H, q) 6.60 (1H, d) 6.80 (1H, d) 6.94 (1H, t) 7.53 (1H, d) | 300 CDCl$_3$ |

TABLE 39-continued

| Comp. Nos. | NMR (ppm) | MHz Solvent |
|---|---|---|
| 4-80 | 1.40 (3H, t) 1.85 (3H, m) 3.01 (2H, q) 3.73 (3H, s) 4.45 (1H, q) 6.77 (1H, d) 6.81 (1H, d) 6.97 (1H, t) 7.54 (1H, d) | 300 CDCl$_3$ |
| 4-82 | 0.96 (3H, t) 1.20 (3H, t) 1.92 (2H, q) 3.52 (2H, m) 3.73 (3H, d) 4.31 (1H, t) 6.51 (1H, d) 6.79 (1H, d) 6.89 (1H, t) 7.52 (1H, d) | 300 CDCl$_3$ |
| 4-83 | 1.03 (3H, t) 2.01 (2H, m) 2.04 (3H, s) 3.73 (3H, d) 3.74 (1H, t) 6.42 (1H, d) 6.79 (1H, d) 6.88 (1H, t) 7.52 (1H, d) | 360 CDCl$_3$ |
| 4-85 | 1.09 (3H, t) 2.07 (1H, m) 2.26 (1H, m) 2.46 (3H, s) 3.76 (3H, s) 3.89 (1H, dd) 6.65 (1H, d) 6.81 (1H, d) 6.95 (1H, d) 7.55 (1H, d) | 300 CDCl$_3$ |

TABLE 40

| Comp. Nos. | NMR (ppm) | MHz Solvent |
|---|---|---|
| 4-87 | 1.06 (3H, t) 2.23 (1H, m) 2.47 (1H, m) 2.86 (3H, s) 3.73 (3H, s) 4.19 (1H, dd) 6.80 (1H, d) 6.82 (1H, d) 6.98 (1H, t) 7.54 (1H, d) | 300 CDCl$_3$ |
| 4-89 | 1.62 (3H, d) 1.75 (1H, bs) 3.73 (3H, d) 4.99 (1H, q) 6.50 (1H, d) 6.80 (1H, d) 6.90 (1H, t) 7.52 (1H, d) | 300 CDCl$_3$ |
| 4-93 | 1.37 (3H, t) 1.77 (3H, d) 2.60, 2.73 (2H, m) 3.73 (3H, s) 4.09 (1H, q) 6.60 (1H, s) 6.80 (1H, d) 7.19 (1H, d) 7.54 (1H, d) | 300 CDCl$_3$ |
| 4-95 | 1.05 (3H, t) 1.22 (3H, t) 2.01 (2H, m) 2.52 (2H, q) 3.73 (3H, s) 3.86 (1H, t) 0.44 (1H, s) 6.80 (1H, d) 7.12 (1H, d) 7.53 (1H, d) | 300 CDCl$_3$ |
| 4-96 | 1.08 (3H, t) 1.34 (3H, t) 2.04~2.72 (4H, m) 3.73 (3H, s) 3.89 (1H, t) 6.61 (1H, s) 6.81 (1H, d) 7.19 (1H, d) 1.49 (1H, t) 1.32 (3H, t) 2.04~2.72 (4H, m) 3.73 (3H, s) 3.90 (1H, t) 6.67 (1H, s) 6.79 (1H, d) 7.17 (1H, d) 7.55 (1H, d) | 300 CDCl$_3$ |
| 4-118 | 1.04~1.17 (3H, m) 1.24~1.37 (3H, m) 2.03~2.69 (4H, m) 3.73 (3H, s) 3.82~3.95 (1H, m) 6.49, 6.50, 6.55, 6.58 (1H, s) 6.81 (1H, d) 7.44~7.53 (1H, m) 7.55 (1H, d) | 300 CDCl$_3$ |
| 4-121 | 0.97 (3H, t) 1.60 (2H, m) 1.67 (3H, d) 2.54 (2H, m) 3.73 (3H, s) 4.09 (1H, q) 6.42 (1H, s) 6.80 (1H, d) 7.12 (1H, d) 7.52 (1H, d) | 300 CDCl$_3$ |
| 4-122 | 1.22 (3H, d) 1.33 (3H, d) 1.66 (3H, d) 2.99 (1H, m) 3.73 (3H, s) 4.16 (1H, q) 6.43 (1H, s) 6.80 (1H, d) 7.12 (1H, d) 7.52 (1H, d) | 300 CDCl$_3$ |
| 4-128 | 0.91 (3H, t) 1.38 (2H, m) 1.57 (2H, m) 3.55 (2H, t) 3.73 (3H, s) 4.59 (2H, s) 6.57 (1H, s) 6.79 (1H, d) 7.11 (1H, d) 7.53 (1H, d) | 300 CDCl$_3$ |

TABLE 41

| Comp. Nos. | NMR (ppm) | MHz Solvent |
|---|---|---|
| 4-129 | 0.91 (3H, t) 1.19 (3H, d) 1.49 (2H, m) 3.52 (1H, q) 3.73 (3H, s) 4.61 (2H, dd) 6.56 (1H, s) 6.79 (1H, d) 7.14 (1H, d) 7.53 (1H, d) | 300 CDCl$_3$ |
| 4-130 | 0.91 (6H, d) 1.87 (1H, m) 3.30 (2H, d) 3.73 (3H, s) 4.59 (2H, s) 6.57 (1H, s) 6.79 (1H, d) 7.15 (1H, d) 7.53 (1H, d) | 300 CDCl$_3$ |
| 4-131 | 0.90 (3H, t) 1.37 (2H, sext) 1.51~1.61 (2H, m) 1.57 (3H, d) 3.41~3.53 (2H, m) 3.73 (3H, s) 4.57 (1H, q) 6.50 (1H, s) 6.80 (1H, d) 7.14 (1H, d) 7.53 (1H, d) | 300 CDCl$_3$ |
| 4-132 | 0.85, 0.92 (3H, t) 1.11, 1.17 (3H, d) 1.37~1.57 (5H, m) 3.44~3.55 (1H, m) 3.73 (3H, s) 4.63~4.72 (1H, m) 6.49 (1H, s) 6.80 (1H, d) 7.13 (1H, d) 7.53 (1H, d) | 300 CDCl$_3$ |
| 4-133 | 0.89 (3H, d) 0.90 (3H, d) 1.57 (3H, d) 1.85 (1H, m) 3.18~3.30 (2H, m) 3.73 (3H, s) 4.56 (1H, q) 6.49 (1H, s) 6.80 (1H, d) 7.14 (1H, d) 7.53 (1H, d) | 300 CDCl$_3$ |

TABLE 41-continued

| Comp. Nos. | NMR (ppm) | MHz Solvent |
|---|---|---|
| 4-134 | 1.06 (3H, t) 1.77 (3H, d) 1.81 (2H, m) 2.65 (2H, m) 3.73 (3H, s) 4.11 (1H, q) 6.62 (1H, s) 6.81 (1H, d) 7.18 (1H, d) 7.55 (1H, d) 0.88 (3H, t) 1.60 (3H, d) 1.80 (2H, m) 2.50 (2H, m) 3.73 (3H, s) 4.11 (1H, q) 6.66 (1H, s) 6.81 (1H, d) 7.18 (1H, d) 7.55 (1H, d) | 300 CDCl$_3$ |
| 4-136 | 1.30 (3H, d) 1.35 (3H, d) 1.76 (3H, d) 2.73 (1H, m) 3.73 (3H, s) 4.11 (1H, q) 6.58 (1H, s) 6.81 (1H, d) 7.18 (1H, d) 7.54 (1H, d) 1.25 (3H, d) 1.34 (3H, d) 1.76 (3H, d) 2.53 (1H, m) 3.73 (3H, s) 4.11 (1H, q) 6.66 (1H, s) 6.81 (1H, d) 7.17 (1H, d) 7.54 (1H, d) | 300 CDCl$_3$ |

TABLE 42

| Comp. Nos. | NMR (ppm) | MHz Solvent |
|---|---|---|
| 4-138 | 0.92 (3H, t) 0.98 (3H, t) 1.60 (2H, sext) 1.93 (2H, qi) 3.36 (1H, dt) 3.49 (1H, dt) 3.73 (3H, s) 4.32 (1H, t) 6.50 (1H, s) 6.80 (1H, d) 7.13 (1H, d) 7.53 (1H, d) | 300 CDCl$_3$ |
| 4-139 | 0.98 (3H, t) 1.14 (3H, d) 1.19 (3H, d) 1.83~1.94 (2H, m) 3.65~3.73 (1H, m) 3.73 (3H, s) 4.43 (1H, t) 6.50 (1H, s) 6.79 (1H, d) 7.12 (1H, d) 7.53 (1H, d) | 300 CDCl$_3$ |
| 4-142 | 0.90, 0.91 (3H, t) 1.55~1.62 (5H, m) 3.35~3.51 (2H, m) 3.73 (3H, s) 4.53~4.60 (1H, m) 6.39 (1H, s) 6.81 (1H, d) 7.40 (1H, s) 7.46, 7.48 (1H, d) | 300 CDCl$_3$ |
| 4-181 | 1.18 (6H, d) 1.56 (3H, d) 3.73 (3H, s) 3.73 (1H, m) 4.70 (1H, q) 6.49 (1H, s) 7.12 (1H, d) 7.13 (1H, d) 7.54 (1H, d) | 300 CDCl$_3$ |
| 6-55 | 1.44 (3H, t) 4.51 (2H, q) 7.27 (1H, d) 7.37 (1H, dd) 7.56 (1H, d) 8.45 (1H, s) 11.6 (1H, s) | 400 CDCl$_3$ |
| 6-56 | 1.41 (3H, t) 4.48 (2H, q) 6.97 (2H, m) 7.40 (1H, m) 8.52 (1H, s) 11.6 (1H, s) | 400 |

Now, typical examples of the intermediate compounds represented by the above general formulas (II-2), (II-3), (II-4), (II-5), (II-6), (II-7), (III-3) and (III-8) will be disclosed in Tables 43 to 46. These intermediate compounds are novel compounds not disclosed in literatures.

TABLE 43

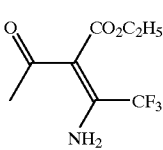

| Intermediate No. | Z | R$^3$ | R$^{4'}$ | R$^{5'}$ | m.p. (° C.) or NMR |
|---|---|---|---|---|---|
| 15-1 | Br | F | Cl | OC$_3$H$_7$-i | |
| 15-2 | CN | F | Cl | OC$_3$H$_7$-i | |
| 15-3 | CO$_2$H | F | Cl | OC$_3$H$_7$-i | 75–76 |
| 15-4 | COCH$_2$CO$_2$C$_2$H$_5$ | F | Cl | OC$_3$H$_7$-i | 57–58 |
| 15-5 | COCH$_2$CO$_2$C$_2$H$_5$ | Cl | Cl | H | 45–47 |
| 15-6 | 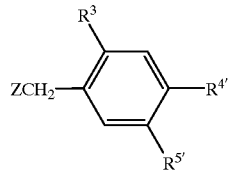 | H | Cl | H | |

TABLE 43-continued

| Intermediate No. | Z | R$^3$ | R$^{4'}$ | R$^{5'}$ | m.p. (° C.) or NMR |
|---|---|---|---|---|---|
| 15-7 | (structure with CO$_2$C$_2$H$_5$, CF$_3$, NH$_2$) | F | Cl | OC$_3$H$_7$-i | 58–59 |
| 15-8 | COCH$_2$CO$_2$C$_2$H$_5$ | F | Cl | H | NMR |
| 15-9 | COCH$_2$CO$_2$C$_2$H$_5$ | F | F | H | NMR |
| 15-10 | (structure with CO$_2$C$_2$H$_5$, CF$_3$, NH$_2$) | Cl | Cl | H | |
| 15-11 | (structure with CO$_2$C$_2$H$_5$, CF$_3$, NH$_2$) | F | Cl | H | 79–80 |
| 15-12 | (structure with CO$_2$C$_2$H$_5$, CF$_3$, NH$_2$) | Cl | F | H | |
| 15-13 | CO$_2$C$_2$H$_5$ | F | Cl | OC$_3$H$_7$-i | |
| 15-14 | CO$_2$C$_2$H$_5$ | F | Cl | OCH$_3$ | 73–75 |
| 15-15 | Cl | F | Cl | OCH$_3$ | NMR |
| 15-16 | Cl | Cl | Cl | OCH$_3$ | NMR |
| 15-17 | CN | Cl | Cl | OCH$_3$ | NMR |
| 15-18 | COOH | Cl | Cl | OCH$_3$ | 121–123 |
| 15-19 | CO$_2$C$_2$H$_5$ | Cl | Cl | OCH$_3$ | 63–64 |
| 15-20 | Cl | F | F | OCH$_3$ | NMR |
| 15-21 | CN | F | F | OCH$_3$ | NMR |
| 15-22 | COOH | F | F | OCH$_3$ | NMR |
| 15-23 | CO$_2$C$_2$H$_5$ | F | F | OCH$_3$ | |

With respect to some of compounds shown in Table 43, $^1$H-NMR data will be given below.

TABLE 44

| Comp. Nos. | NMR (ppm) | MHz Solvent |
|---|---|---|
| 15-8 | 1.26 (3H, t) 3.50 (2H, s) 3.83 (2H, s) 4.19 (2H, q) 7.10 (3H, m) | 300 CDCl$_3$ |
| 15-9 | 1.27 (3H, t) 3.51 (2H, s) 3.85 (2H, s) 4.19 (2H, s) 4.19 (2H, q) 6.84 (2H, m) 7.16 (1H, m) | 300 CDCl$_3$ |
| 15-15 | 3.89 (3H, s) 5.00 (2H, s) 6.97 (1H, d) 7.18 (1H, d) | 300 CDCl$_3$ |
| 15-16 | 3.92 (3H, s) 4.65 (2H, s) 7.01 (1H, d) 7.40 (1H, s) | 300 CDCl$_3$ |

TABLE 44-continued

| Comp. Nos. | NMR (ppm) | MHz Solvent |
|---|---|---|
| 15-17 | 3.82 (2H, s) 3.94 (3H, s) 7.06 (1H, s) 7.43 (1H, s) | 300 CDCl$_3$ |
| 15-18 | 3.79 (2H, s) 3.89 (3H, s) 6.85 (1H, s) 7.41 (1H, s) | 300 CDCl$_3$ |
| 15-20 | 3.89 (3H, s) 4.59 (2H, s) 6.76 (1H, dd) 6.99 (1H, dd) | 300 CDCl$_3$ |
| 15-21 | 3.73 (2H, s) 3.90 (3H, s) 6.91 (1H, t) 6.99 (1H, t) | 300 CDCl$_3$ |
| 15-22 | 3.66 (2H, d) 3.87 (3H, s) 6.87 (2H, m) | 300 CDCl$_3$ |

TABLE 45

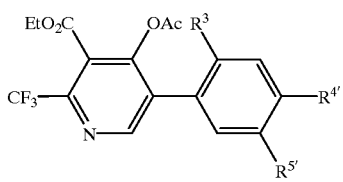

| Intermediate No. | $R^3$ | $R^{4'}$ | $R^{5'}$ | m.p. (° C.) or NMR |
|---|---|---|---|---|
| 16-1 | H | Cl | H | 92–94 |
| 16-2 | F | Cl | H | |
| 16-3 | Cl | Cl | H | |
| 16-4 | F | Cl | OC$_3$H$_7$-i | |

TABLE 46

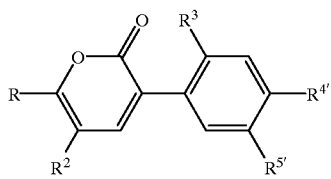

| Intermediate No. | R | $R^2$ | $R^3$ | $R^{4'}$ | $R^{5'}$ | m.p. (° C.) or NMR |
|---|---|---|---|---|---|---|
| 17-1 | CF$_3$ | H | F | F | H | 98–100 |
| 17-2 | CF$_3$ | CH$_3$ | Cl | Cl | H | 147–149 |
| 17-3 | CF$_3$ | H | F | Cl | OCH$_3$ | 121–122 |
| 17-4 | CF$_3$ | H | F | Cl | H | 107–108 |
| 17-5 | CF$_3$ | H | Cl | Cl | H | |
| 17-6 | CF$_3$ | H | Cl | Cl | OCH$_3$ | 132–134 |

The herbicide of the present invention comprises a pyridone derivative of the formula (I-1) or (I-2) as an active ingredient. For the compound of the present invention to be used as a herbicide, the compound of the present invention may be used by itself. However, it may be used in the form of a formulation such as a dust, a wettable powder, an emulsifiable concentrate, a microgranule or a granule by blending it with a carrier which is commonly used for formulations, a surfactant, a dispersant or an adjuvant.

The carrier to be used for such formulations, may, for example, be a solid carrier such as talc, bentonite, clay, kaolin, diatomaceous earth, fine silica, vermiculite, calcium carbonate, slaked lime, silica sand, ammonium sulfate or urea, or a liquid carrier such as isopropyl alcohol, xylene, cyclohexane or methylnaphthalene.

As the surfactant and dispersant, a metal salt of alkylbenzenesulfonic acid, a metal salt of dinaphthylmethane disulfonic acid, a salt of alcohol sulfuric acid ester, an alkylaryl sulfonate, a lignin sulfonate, a polyoxyethylene glycol ether, a polyoxyethylene alkylaryl ether or a polyoxyethylene sorbitol monoalkylate may, for example, be mentioned. The adjuvant may, for example, be carboxymethyl cellulose, polyethylene glycol or gum arabic. In practical use, the herbicide may be diluted to a suitable concentration before application, or may be directly applied.

The herbicide of the present invention may be used for application to foliage, soil or water surface. The blending proportion of the active ingredient is suitably selected as the case requires. However, in a case of a dust or a granule, the proportion of the active ingredient is selected suitably within a range of from 0.01 to 10% by weight, preferably from 0.05 to 5% by weight. In a case of an emulsifiable concentrate or a wettable powder, the proportion is selected suitably within a range of from 1 to 50% by weight, preferably from 5 to 30% by weight.

The dose of the herbicide of the present invention varies depending upon the type of the compound, the weeds to be controlled, the germination tendency, the environmental conditions and the type of the formulation to be used. However, in the case of a dust or a granule which is used by itself, the dose of the active ingredient is selected suitably within a range of from 0.1 g to 5 kg, preferably from 1 g to 1 kg, per 10 ares. In a case of an emulsifiable concentrate or a wettable powder which is used in a liquid state, the dose of the active ingredient is selected suitably within a range of from 1 to 50,000 ppm, preferably from 10 to 10,000 ppm.

Further, the compound of the present invention may be used in combination with an insecticide, a fungicide, other herbicide, a plant growth controlling agent, a fertilizer or the like, as the case requires.

Now, the formulation method will be described with reference to typical Formulation Examples. The compounds, types of the additives and blending ratios are not limited to such specific Examples and may be changed within wide ranges. In the following description, "parts" means "parts by weight".

FORMULATION EXAMPLE 1 (Wettable powder)

To 10 parts of Compound (2-1), 0.5 part of polyoxyethyleneoctylphenyl ether, 0.5 part of sodium β-naphthalene sulfonate-formalin condensate, 20 parts of diatomaceous earth and 69 parts of clay were mixed and pulverized to obtain a wettable powder.

FORMULATION EXAMPLE 2 (Wettable powder)

To 10 parts of Compound (1-14), 0.5 part of polyoxyethyleneoctylphenyl ether, 0.5 part of sodium β-naphthalene sulfonate-formalin condensate, 20 parts of diatomaceous earth, 5 parts of fine silica and 64 parts of clay were mixed and pulverized to obtain a wettable powder.

FORMULATION EXAMPLE 3 (Wettable powder)

To 10 parts of Compound (6-19), 0.5 part of polyoxyethyleneoctylphenyl ether, 0.5 part of sodium β-naphthalene sulfonate-formalin condensate, 20 parts of diatomaceous earth, 5 parts of fine silica and 64 parts of calcium carbonate, were mixed and pulverized to obtain a wettable powder.

FORMULATION EXAMPLE 4 (Emulsifiable concentrate)

To 30 parts of Compound (2-7), 60 parts of a mixture comprising equal amounts of xylene and isophorone and 10 parts of a mixture comprising a polyoxyethylene sorbitol alkylate surfactant, a polyoxyethylenealkylaryl polymer and an alkylaryl sulfonate, were added, and the mixture was thoroughly stirred to obtain an emulsifiable concentrate.

FORMULATION EXAMPLE 5 (Granule)

10 Parts of Compound (6-9), 80 parts of a bulking agent comprising a 1:3 mixture of talc and bentonite, 5 parts of fine silica, 5 parts of a mixture comprising a polyoxyethylene sorbitol alkylate surfactant, a polyoxyethylenealkylaryl polymer and an alkylaryl sulfonate and 10 parts of water were mixed and thoroughly kneaded to obtain a paste, which was extruded from sieve apertures with a diameter of 0.7 mm. The extruded product was dried and then cut into a length of from 0.5 to 1 mm to obtain granules.

Now, the effects of the compounds of the present invention will be described with reference to Test Examples. Further, as a comparative agent, the following compound was used.

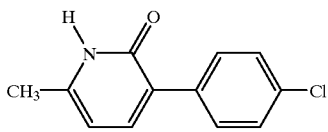

Compound disclosed in the specification of JP-B-46-30190

TEST EXAMPLE 1 (Test on herbicidal effects by paddy field soil treatment)

In a plastic pot (surface area: 100 cm$^2$) filled with paddy field soil, barnyardgrass (Ec), monochoria (Mo) and bulrush (Sc) were sown after puddling and leveling, and flooded to a water depth of 3 cm. Next day, a wettable powder prepared in accordance with Formulation Example 1 was diluted with water and applied dropwise to the water surface. The dose was 100 g of the active ingredient per 10 ares. The plants were then cultured in a green house, and the evaluation of the herbicidal effects was conducted on the 21st day after the application in accordance with the standards as identified in Table 47. The results are shown in Tables 48–55.

TABLE 47

| Index No. | Herbicidal effects (growth-controlling degree) or phytotoxicity |
|---|---|
| 5 | Herbicidal effect or phytotoxicity: at least 90% |
| 4 | Herbicidal effect or phytotoxicity: at least 70% and less than 90% |
| 3 | Herbicidal effect or phytotoxicity: at least 50% and less than 70% |
| 2 | Herbicidal effect or phytotoxicity: at least 30% and less than 50% |
| 1 | Herbicidal effect or phytotoxicity: at least 10% and less than 30% |
| 0 | Herbicidal effect or phytotoxicity: 0 to less than 10% |

TABLE 48

| Compound Nos. | Herbicidal effects | | |
|---|---|---|---|
| | Ec | Mo | Sc |
| 1-1 | 5 | 5 | 5 |
| 1-2 | 5 | 5 | 5 |
| 1-3 | 5 | 5 | 5 |
| 1-5 | 5 | 5 | 5 |
| 1-11 | 5 | 5 | 5 |
| 1-12 | 5 | 5 | 5 |
| 1-13 | 5 | 5 | 5 |
| 1-14 | 5 | 5 | 5 |
| 1-15 | 5 | 5 | 5 |
| 1-16 | 5 | 5 | 5 |
| 1-17 | 5 | 5 | 5 |
| 1-18 | 5 | 5 | 5 |
| 1-19 | 5 | 5 | 5 |
| 1-20 | 5 | 5 | 5 |
| 1-21 | 5 | 5 | 5 |
| 1-22 | 5 | 5 | 5 |
| 1-23 | 5 | 5 | 5 |
| 1-24 | 5 | 5 | 5 |
| 1-25 | 5 | 5 | 5 |
| 1-26 | 5 | 5 | 5 |
| 1-27 | 5 | 5 | 5 |
| 1-29 | 5 | 5 | 5 |
| 1-30 | 5 | 5 | 5 |
| 1-32 | 5 | 5 | 5 |
| 1-33 | 5 | 5 | 5 |
| 1-36 | 5 | 5 | 5 |
| 1-38 | 5 | 5 | 5 |
| 1-40 | 5 | 5 | 5 |
| 1-41 | 5 | 5 | 5 |

TABLE 49

| Compound Nos. | Herbicidal effects | | |
|---|---|---|---|
| | Ec | Mo | Sc |
| 1-43 | 5 | 5 | 5 |
| 1-44 | 5 | 5 | 5 |
| 1-45 | 5 | 5 | 5 |
| 1-46 | 5 | 5 | 5 |
| 1-47 | 5 | 5 | 5 |
| 1-48 | 5 | 5 | 5 |
| 1-49 | 5 | 5 | 5 |
| 1-51 | 5 | 5 | 5 |
| 1-53 | 5 | 5 | 5 |
| 1-54 | 5 | 5 | 5 |
| 1-58 | 5 | 5 | 5 |
| 1-60 | 5 | 5 | 5 |
| 1-61 | 5 | 5 | 5 |
| 1-62 | 5 | 5 | 5 |
| 1-64 | 5 | 5 | 5 |
| 1-65 | 5 | 5 | 5 |
| 1-66 | 5 | 5 | 5 |
| 1-67 | 5 | 5 | 5 |
| 1-68 | 5 | 5 | 5 |
| 1-69 | 5 | 5 | 5 |
| 1-70 | 5 | 5 | 5 |
| 1-71 | 5 | 5 | 5 |
| 1-72 | 5 | 5 | 5 |
| 1-73 | 5 | 5 | 5 |
| 1-75 | 5 | 5 | 5 |
| 1-76 | 5 | 5 | 5 |
| 1-77 | 5 | 5 | 5 |
| 1-78 | 5 | 5 | 5 |
| 1-80 | 5 | 5 | 5 |

TABLE 50

| Compound No. | Herbicidal effects | | |
|---|---|---|---|
| | Ec | Mo | Sc |
| 1-81 | 5 | 5 | 5 |
| 1-82 | 5 | 5 | 5 |
| 1-87 | 5 | 5 | 5 |
| 1-88 | 5 | 5 | 5 |
| 1-90 | 5 | 5 | 5 |
| 1-91 | 5 | 5 | 5 |
| 1-97 | 5 | 5 | 5 |
| 1-99 | 5 | 5 | 5 |
| 1-102 | 5 | 5 | 5 |
| 1-103 | 5 | 5 | 5 |
| 1-104 | 5 | 5 | 5 |
| 1-105 | 5 | 5 | 5 |
| 1-106 | 5 | 5 | 5 |
| 1-107 | 5 | 5 | 5 |
| 1-108 | 5 | 5 | 5 |
| 1-112 | 5 | 5 | 5 |
| 1-115 | 5 | 5 | 5 |
| 1-119 | 5 | 5 | 5 |
| 1-121 | 5 | 5 | 5 |
| 1-122 | 5 | 5 | 5 |
| 1-123 | 5 | 5 | 5 |
| 1-124 | 5 | 5 | 5 |
| 1-126 | 5 | 5 | 5 |
| 1-127 | 5 | 5 | 5 |
| 1-128 | 5 | 5 | 4 |
| 1-130 | 5 | 5 | 5 |
| 1-131 | 5 | 5 | 5 |
| 1-133 | 5 | 5 | 5 |
| 1-134 | 5 | 5 | 5 |

TABLE 51

| Compound No. | Herbicidal effects | | |
|---|---|---|---|
| | Ec | Mo | Sc |
| 1-135 | 5 | 5 | 5 |
| 1-136 | 5 | 5 | 5 |
| 1-138 | 5 | 5 | 5 |
| 1-139 | 5 | 5 | 5 |
| 1-140 | 5 | 5 | 5 |
| 1-141 | 5 | 5 | 5 |
| 1-142 | 5 | 5 | 5 |
| 1-143 | 5 | 5 | 5 |
| 1-144 | 5 | 5 | 5 |
| 1-145 | 5 | 5 | 5 |
| 1-147 | 5 | 5 | 5 |
| 1-149 | 5 | 5 | 5 |
| 1-150 | 5 | 5 | 5 |
| 1-151 | 5 | 5 | 5 |
| 1-152 | 5 | 5 | 5 |
| 1-153 | 5 | 5 | 5 |
| 1-154 | 5 | 5 | 5 |
| 1-155 | 5 | 5 | 5 |
| 1-157 | 5 | 5 | 5 |
| 1-158 | 5 | 5 | 5 |
| 1-159 | 5 | 5 | 5 |
| 1-160 | 5 | 5 | 5 |
| 1-161 | 5 | 5 | 5 |
| 1-162 | 5 | 5 | 5 |
| 1-163 | 5 | 5 | 5 |
| 1-164 | 5 | 5 | 5 |
| 1-165 | 5 | 5 | 5 |
| 1-166 | 5 | 5 | 5 |
| 1-167 | 5 | 5 | 5 |

TABLE 52

| Compound No. | Herbicidal effects | | |
|---|---|---|---|
| | Ec | Mo | Sc |
| 1-168 | 5 | 5 | 5 |
| 1-169 | 5 | 5 | 5 |
| 1-170 | 5 | 5 | 5 |
| 1-171 | 5 | 5 | 5 |
| 1-172 | 5 | 5 | 5 |
| 1-173 | 5 | 5 | 5 |
| 1-174 | 5 | 5 | 5 |
| 1-175 | 5 | 5 | 5 |
| 1-176 | 5 | 5 | 5 |
| 1-177 | 5 | 5 | 5 |
| 1-178 | 5 | 5 | 5 |
| 1-179 | 5 | 5 | 5 |
| 1-180 | 5 | 5 | 5 |
| 1-181 | 5 | 5 | 5 |
| 1-182 | 5 | 5 | 5 |
| 1-183 | 5 | 5 | 5 |
| 1-184 | 5 | 5 | 5 |
| 1-186 | 5 | 5 | 4 |
| 1-187 | 5 | 5 | 5 |
| 1-188 | 5 | 5 | 5 |
| 1-189 | 5 | 5 | 5 |
| 1-190 | 5 | 5 | 5 |
| 1-191 | 5 | 5 | 5 |
| 1-192 | 5 | 5 | 5 |
| 1-193 | 5 | 5 | 5 |
| 1-194 | 5 | 5 | 5 |
| 1-195 | 5 | 5 | 5 |
| 1-196 | 5 | 5 | 5 |
| 1-197 | 5 | 5 | 5 |

TABLE 53

| Compound No. | Herbicidal effects | | |
|---|---|---|---|
| | Ec | Mo | Sc |
| 1-198 | 5 | 5 | 5 |
| 1-199 | 5 | 5 | 5 |
| 1-200 | 5 | 5 | 5 |
| 1-201 | 5 | 5 | 5 |
| 1-202 | 5 | 5 | 5 |
| 1-203 | 5 | 5 | 5 |
| 1-204 | 5 | 5 | 5 |
| 1-205 | 5 | 5 | 5 |
| 1-206 | 5 | 5 | 5 |
| 1-207 | 5 | 5 | 5 |
| 1-208 | 5 | 5 | 5 |
| 1-209 | 5 | 5 | 5 |
| 1-210 | 5 | 5 | 5 |
| 1-211 | 5 | 5 | 5 |
| 1-212 | 5 | 5 | 4 |
| 1-256 | 5 | 5 | 5 |
| 1-257 | 5 | 5 | 5 |
| 1'-1 | 5 | 5 | 5 |
| 1'-3 | 5 | 5 | 4 |
| 1'-4 | 5 | 5 | 5 |
| 1'-5 | 5 | 5 | 5 |
| 1'-6 | 5 | 5 | 5 |
| 2-1 | 5 | 5 | 5 |
| 2-2 | 5 | 5 | 5 |
| 2-4 | 5 | 5 | 5 |
| 2-7 | 5 | 5 | 5 |
| 2-11 | 5 | 5 | 5 |
| 2-12 | 5 | 5 | 5 |
| 2-13 | 5 | 5 | 5 |

TABLE 54

| Compound No. | Herbicidal effects | | |
|---|---|---|---|
| | Ec | Mo | Sc |
| 2-15 | 5 | 5 | 5 |
| 2-16 | 5 | 5 | 5 |
| 2-17 | 5 | 5 | 5 |
| 2-18 | 5 | 5 | 5 |
| 2-19 | 5 | 5 | 5 |
| 2-20 | 5 | 5 | 5 |
| 2-21 | 5 | 5 | 5 |
| 2-25 | 5 | 5 | 5 |
| 2-26 | 5 | 5 | 5 |
| 2-27 | 5 | 5 | 5 |
| 2-29 | 5 | 5 | 5 |
| 2-30 | 5 | 5 | 5 |
| 2-31 | 5 | 5 | 5 |
| 2-32 | 5 | 5 | 5 |
| 2'-1 | 5 | 5 | 5 |
| 3-1 | 5 | 5 | 5 |
| 3-5 | 5 | 5 | 5 |
| 3-6 | 5 | 5 | 5 |
| 3-7 | 5 | 5 | 5 |
| 3-9 | 5 | 5 | 5 |
| 4-2 | 5 | 5 | 5 |
| 4-1 | 5 | 5 | 5 |
| 4-3 | 5 | 5 | 5 |
| 4-4 | 5 | 5 | 5 |
| 4-5 | 5 | 5 | 5 |
| 4-6 | 5 | 5 | 5 |
| 4-7 | 5 | 5 | 5 |
| 4-10 | 5 | 5 | 5 |
| 4-13 | 5 | 5 | 5 |

TABLE 55

| Compound No. | Herbicidal effects | | |
|---|---|---|---|
| | Ec | Mo | Sc |
| 4-16 | 5 | 5 | 5 |
| 4-24 | 5 | 5 | 5 |
| 4-26 | 5 | 5 | 5 |
| 4-27 | 5 | 5 | 5 |
| 4-28 | 5 | 5 | 5 |
| 4-29 | 5 | 5 | 5 |
| 4-30 | 5 | 5 | 5 |
| 4-31 | 5 | 5 | 5 |
| 4-32 | 5 | 5 | 5 |
| 4-33 | 5 | 5 | 5 |
| 4-34 | 5 | 5 | 5 |
| 5-1 | 5 | 5 | 5 |
| 5-2 | 5 | 5 | 5 |
| 5-3 | 5 | 5 | 5 |
| 6-1 | 5 | 5 | 5 |
| 6-7 | 5 | 5 | 5 |
| 6-8 | 5 | 5 | 5 |
| 6-9 | 5 | 5 | 5 |
| 6-10 | 5 | 5 | 5 |
| 6-14 | 5 | 5 | 5 |
| 6-19 | 5 | 5 | 5 |
| 7-1 | 5 | 5 | 5 |
| 9-1 | 5 | 5 | 5 |
| 9-2 | 5 | 5 | 5 |
| 11-6 | 5 | 5 | 5 |

TEST EXAMPLE 2 (Test on herbicidal effects by upland field soil treatment)

In a plastic pot (surface area: 120 cm$^2$) filled with sand, barnyardgrass (Ec), *Digitaria ciliaris* (Di), pale smartweed (Po), slender amaranth (Am), common lambsquarters (Ch) and rice flatsedge (Ci) were sown and covered with soil. A wettable powder prepared in accordance with Formulation Example 1 was diluted with water and applied uniformly to the soil surface by a small-sized sprayer in an amount of 100 lit./10 ares so as to apply 100 g of the active ingredient per 10 ares. The plants were then cultured in a green house, and the evaluation of the herbicidal effects was conducted on the 21st day after the application in accordance with the standards as identified in Table 47. The results are shown in Tables 56–62.

TABLE 56

| Compound No. | Herbicidal effects | | | | | |
|---|---|---|---|---|---|---|
| | Ec | Di | Po | Am | Ch | Ci |
| 1-1 | 5 | 5 | 5 | 5 | 5 | 5 |
| 1-2 | 5 | 5 | 5 | 5 | 5 | 5 |
| 1-3 | 5 | 5 | 5 | 5 | 5 | 5 |
| 1-5 | 5 | 5 | 5 | 5 | 5 | 5 |
| 1-11 | 5 | 5 | 5 | 5 | 5 | 5 |
| 1-14 | 5 | 5 | 5 | 5 | 5 | 5 |
| 1-15 | 5 | 5 | 5 | 5 | 5 | 5 |
| 1-16 | 5 | 5 | 5 | 5 | 5 | 5 |
| 1-17 | 5 | 5 | 5 | 5 | 5 | 5 |
| 1-18 | 5 | 5 | 5 | 5 | 5 | 5 |
| 1-20 | 5 | 5 | 5 | 5 | 5 | 5 |
| 1-21 | 5 | 5 | 5 | 5 | 5 | 5 |
| 1-24 | 5 | 5 | 5 | 5 | 5 | 5 |
| 1-25 | 5 | 5 | 5 | 5 | 5 | 5 |
| 1-26 | 5 | 5 | 5 | 5 | 5 | 5 |
| 1-27 | 5 | 5 | 5 | 5 | 5 | 5 |
| 1-29 | 5 | 5 | 5 | 5 | 5 | 5 |
| 1-30 | 5 | 5 | 5 | 5 | 5 | 5 |
| 1-32 | 5 | 5 | 5 | 5 | 5 | 5 |
| 1-38 | 5 | 5 | 5 | 5 | 5 | 5 |
| 1-41 | 5 | 5 | 5 | 5 | 5 | 5 |
| 1-43 | 5 | 5 | 5 | 5 | 5 | 5 |
| 1-44 | 5 | 5 | 5 | 5 | 5 | 5 |
| 1-51 | 4 | 5 | 5 | 5 | 5 | 5 |
| 1-52 | 5 | 5 | 5 | 5 | 5 | 5 |
| 1-60 | 5 | 5 | 5 | 5 | 5 | 5 |
| 1-61 | 5 | 5 | 5 | 5 | 5 | 5 |
| 1-62 | 5 | 5 | 5 | 5 | 5 | 5 |
| 1-64 | 5 | 5 | 5 | 5 | 5 | 5 |

TABLE 57

| Compound No. | Herbicidal effects | | | | | |
|---|---|---|---|---|---|---|
| | Ec | Di | Po | Am | Ch | Ci |
| 1-65 | 5 | 5 | 5 | 5 | 5 | 5 |
| 1-66 | 5 | 5 | 5 | 5 | 5 | 5 |
| 1-67 | 5 | 5 | 5 | 5 | 5 | 5 |
| 1-69 | 5 | 5 | 5 | 5 | 5 | 5 |
| 1-71 | 5 | 5 | 5 | 5 | 5 | 5 |
| 1-72 | 5 | 5 | 5 | 5 | 5 | 5 |
| 1-73 | 4 | 5 | 5 | 5 | 5 | 5 |
| 1-76 | 5 | 5 | 5 | 5 | 5 | 5 |
| 1-77 | 5 | 5 | 5 | 5 | 5 | 5 |
| 1-78 | 5 | 5 | 5 | 5 | 5 | 5 |
| 1-80 | 5 | 5 | 5 | 5 | 5 | 5 |
| 1-81 | 5 | 5 | 5 | 5 | 5 | 5 |
| 1-82 | 4 | 5 | 5 | 5 | 5 | 5 |
| 1-87 | 5 | 5 | 5 | 5 | 5 | 5 |
| 1-88 | 4 | 5 | 5 | 5 | 5 | 5 |
| 1-90 | 5 | 5 | 5 | 5 | 5 | 5 |
| 1-91 | 5 | 5 | 5 | 5 | 5 | 5 |
| 1-99 | 5 | 5 | 5 | 5 | 5 | 5 |
| 1-102 | 5 | 5 | 4 | 5 | 5 | 5 |
| 1-103 | 4 | 5 | 5 | 5 | 5 | 5 |
| 1-104 | 5 | 5 | 5 | 5 | 5 | 5 |
| 1-105 | 5 | 5 | 5 | 5 | 5 | 5 |
| 1-106 | 5 | 5 | 5 | 5 | 5 | 5 |
| 1-108 | 5 | 5 | 5 | 5 | 5 | 5 |
| 1-112 | 5 | 5 | 5 | 5 | 5 | 5 |
| 1-119 | 5 | 5 | 5 | 5 | 5 | 5 |

TABLE 57-continued

| Compound No. | Herbicidal effects | | | | | |
|---|---|---|---|---|---|---|
| | Ec | Di | Po | Am | Ch | Ci |
| 1-121 | 5 | 5 | 5 | 5 | 5 | 5 |
| 1-122 | 5 | 5 | 5 | 5 | 5 | 5 |
| 1-126 | 5 | 5 | 5 | 5 | 5 | 5 |

TABLE 58

| Compound No. | Herbicidal effects | | | | | |
|---|---|---|---|---|---|---|
| | Ec | Di | Po | Am | Ch | Ci |
| 1-131 | 5 | 5 | 5 | 5 | 5 | 5 |
| 1-133 | 5 | 5 | 5 | 5 | 5 | 5 |
| 1-134 | 5 | 5 | 5 | 5 | 5 | 5 |
| 1-135 | 5 | 5 | 5 | 5 | 5 | 5 |
| 1-136 | 5 | 5 | 5 | 5 | 5 | 5 |
| 1-138 | 5 | 5 | 5 | 5 | 5 | 5 |
| 1-140 | 5 | 5 | 5 | 5 | 5 | 5 |
| 1-141 | 4 | 5 | 5 | 5 | 5 | 5 |
| 1-143 | 5 | 5 | 5 | 5 | 5 | 5 |
| 1-144 | 5 | 5 | 5 | 5 | 5 | 5 |
| 1-148 | 5 | 5 | 5 | 5 | 5 | 5 |
| 1-149 | 5 | 5 | 5 | 5 | 5 | 5 |
| 1-150 | 5 | 5 | 5 | 5 | 5 | 5 |
| 1-151 | 5 | 5 | 5 | 5 | 5 | 5 |
| 1-152 | 5 | 5 | 5 | 5 | 5 | 5 |
| 1-154 | 5 | 5 | 5 | 5 | 5 | 5 |
| 1-155 | 5 | 5 | 5 | 5 | 5 | 5 |
| 1-157 | 5 | 5 | 5 | 5 | 5 | 5 |
| 1-158 | 5 | 5 | 5 | 5 | 5 | 5 |
| 1-159 | 5 | 5 | 5 | 5 | 5 | 5 |
| 1-160 | 5 | 5 | 5 | 5 | 5 | 5 |
| 1-161 | 5 | 5 | 5 | 5 | 5 | 5 |
| 1-162 | 5 | 5 | 5 | 5 | 5 | 5 |
| 1-163 | 5 | 5 | 5 | 5 | 5 | 5 |
| 1-164 | 5 | 5 | 5 | 5 | 5 | 5 |
| 1-165 | 5 | 5 | 5 | 5 | 5 | 5 |
| 1-166 | 5 | 5 | 5 | 5 | 5 | 5 |
| 1-167 | 5 | 5 | 5 | 5 | 5 | 5 |
| 1-168 | 5 | 5 | 5 | 5 | 5 | 5 |

TABLE 59

| Compound No. | Herbicidal effects | | | | | |
|---|---|---|---|---|---|---|
| | Ec | Di | Po | Am | Ch | Ci |
| 1-169 | 5 | 5 | 5 | 5 | 5 | 5 |
| 1-170 | 5 | 5 | 5 | 5 | 5 | 5 |
| 1-171 | 5 | 5 | 5 | 5 | 5 | 5 |
| 1-172 | 5 | 5 | 5 | 5 | 5 | 5 |
| 1-173 | 5 | 5 | 5 | 5 | 5 | 5 |
| 1-174 | 5 | 5 | 5 | 5 | 5 | 5 |
| 1-175 | 5 | 5 | 5 | 5 | 5 | 5 |
| 1-176 | 5 | 5 | 5 | 5 | 5 | 5 |
| 1-178 | 5 | 5 | 5 | 5 | 5 | 5 |
| 1-179 | 5 | 5 | 5 | 5 | 5 | 5 |
| 1-181 | 5 | 5 | 5 | 5 | 5 | 5 |
| 1-182 | 5 | 5 | 5 | 5 | 5 | 5 |
| 1-184 | 5 | 5 | 5 | 5 | 5 | 5 |
| 1-185 | 5 | 5 | 4 | 5 | 5 | 5 |
| 1-186 | 5 | 5 | 5 | 5 | 5 | 5 |
| 1-187 | 5 | 5 | 5 | 5 | 5 | 5 |
| 1-188 | 5 | 5 | 5 | 5 | 5 | 5 |
| 1-189 | 5 | 5 | 5 | 5 | 5 | 5 |
| 1-190 | 5 | 5 | 5 | 5 | 5 | 5 |
| 1-191 | 5 | 5 | 5 | 5 | 5 | 5 |
| 1-192 | 5 | 5 | 5 | 5 | 5 | 5 |
| 1-193 | 5 | 5 | 5 | 5 | 5 | 5 |
| 1-194 | 5 | 5 | 5 | 5 | 5 | 5 |
| 1-195 | 5 | 5 | 5 | 5 | 5 | 5 |

TABLE 59-continued

| Compound No. | Herbicidal effects | | | | | |
|---|---|---|---|---|---|---|
| | Ec | Di | Po | Am | Ch | Ci |
| 1-196 | 5 | 5 | 5 | 5 | 5 | 5 |
| 1-197 | 5 | 5 | 5 | 5 | 5 | 5 |
| 1-199 | 5 | 5 | 5 | 5 | 5 | 5 |
| 1-200 | 5 | 5 | 5 | 5 | 5 | 5 |
| 1-201 | 5 | 5 | 5 | 5 | 5 | 5 |

TABLE 60

| Compound No. | Herbicidal effects | | | | | |
|---|---|---|---|---|---|---|
| | Ec | Di | Po | Am | Ch | Ci |
| 1-202 | 5 | 5 | 5 | 5 | 5 | 5 |
| 1-203 | 5 | 5 | 5 | 5 | 5 | 5 |
| 1-204 | 5 | 5 | 5 | 5 | 5 | 5 |
| 1-205 | 5 | 5 | 5 | 5 | 5 | 5 |
| 1-206 | 5 | 5 | 5 | 5 | 5 | 5 |
| 1-207 | 5 | 5 | 5 | 5 | 5 | 5 |
| 1-208 | 5 | 5 | 5 | 5 | 5 | 5 |
| 1-209 | 4 | 4 | 5 | 5 | 5 | 5 |
| 1-210 | 5 | 4 | 5 | 5 | 5 | 5 |
| 1-211 | 5 | 5 | 5 | 5 | 5 | 5 |
| 1-256 | 5 | 5 | 5 | 5 | 5 | 5 |
| 1-257 | 5 | 5 | 5 | 5 | 5 | 5 |
| 1'-1 | 5 | 5 | 5 | 5 | 5 | 5 |
| 1'-3 | 5 | 5 | 5 | 5 | 5 | 5 |
| 1'-4 | 5 | 5 | 5 | 5 | 5 | 5 |
| 1'-5 | 5 | 5 | 5 | 5 | 5 | 5 |
| 1'-6 | 5 | 5 | 5 | 5 | 5 | 5 |
| 2-1 | 5 | 5 | 5 | 5 | 5 | 5 |
| 2-2 | 5 | 5 | 5 | 5 | 5 | 5 |
| 2-4 | 5 | 5 | 5 | 5 | 5 | 5 |
| 2-7 | 5 | 5 | 5 | 5 | 5 | 5 |
| 2-10 | 5 | 5 | 5 | 5 | 5 | 5 |
| 2-11 | 5 | 5 | 5 | 5 | 5 | 5 |
| 2-12 | 5 | 5 | 5 | 5 | 5 | 5 |
| 2-13 | 5 | 5 | 5 | 5 | 5 | 5 |
| 2-14 | 5 | 5 | 5 | 5 | 5 | 5 |
| 2-15 | 5 | 5 | 5 | 5 | 5 | 5 |
| 2-16 | 5 | 5 | 5 | 5 | 5 | 5 |
| 2-17 | 5 | 5 | 5 | 5 | 5 | 5 |

TABLE 61

| Compound No. | Herbicidal effects | | | | | |
|---|---|---|---|---|---|---|
| | Ec | Di | Po | Am | Ch | Ci |
| 2-19 | 5 | 5 | 5 | 5 | 5 | 5 |
| 2-21 | 5 | 5 | 5 | 5 | 5 | 5 |
| 2-25 | 5 | 5 | 5 | 5 | 5 | 5 |
| 2-26 | 5 | 5 | 5 | 5 | 5 | 5 |
| 2-27 | 5 | 5 | 5 | 5 | 5 | 5 |
| 2-29 | 5 | 5 | 5 | 5 | 5 | 5 |
| 2-31 | 5 | 5 | 5 | 5 | 5 | 5 |
| 2-32 | 5 | 5 | 5 | 5 | 5 | 5 |
| 2'-1 | 5 | 5 | 5 | 5 | 5 | 5 |
| 3-1 | 5 | 5 | 5 | 5 | 5 | 5 |
| 3-5 | 5 | 5 | 5 | 5 | 5 | 5 |
| 3-6 | 5 | 5 | 5 | 5 | 5 | 5 |
| 3-7 | 5 | 5 | 5 | 5 | 5 | 5 |
| 3-9 | 5 | 5 | 5 | 5 | 5 | 5 |
| 4-1 | 5 | 5 | 5 | 5 | 5 | 5 |
| 4-2 | 5 | 5 | 5 | 5 | 5 | 5 |
| 4-3 | 5 | 5 | 5 | 5 | 5 | 5 |
| 4-4 | 5 | 5 | 5 | 5 | 5 | 5 |
| 4-5 | 5 | 5 | 5 | 5 | 5 | 5 |
| 4-7 | 5 | 5 | 5 | 5 | 5 | 5 |
| 4-10 | 5 | 5 | 5 | 5 | 5 | 5 |
| 4-13 | 5 | 5 | 5 | 5 | 5 | 5 |

TABLE 61-continued

| Compound No. | Herbicidal effects | | | | | |
|---|---|---|---|---|---|---|
| | Ec | Di | Po | Am | Ch | Ci |
| 4-16 | 5 | 5 | 5 | 5 | 5 | 5 |
| 4-24 | 4 | 5 | 5 | 5 | 5 | 5 |
| 4-26 | 5 | 5 | 5 | 5 | 5 | 5 |
| 4-27 | 4 | 5 | 5 | 5 | 5 | 5 |
| 4-28 | 4 | 5 | 5 | 5 | 5 | 5 |
| 4-29 | 5 | 5 | 5 | 5 | 5 | 5 |
| 4-30 | 5 | 5 | 5 | 5 | 5 | 5 |

TABLE 62

| Compound No. | Herbicidal effects | | | | | |
|---|---|---|---|---|---|---|
| | Ec | Di | Po | Am | Ch | Ci |
| 4-31 | 5 | 5 | 5 | 5 | 5 | 5 |
| 4-32 | 5 | 5 | 5 | 5 | 5 | 5 |
| 4-33 | 5 | 5 | 5 | 5 | 5 | 5 |
| 4-34 | 5 | 5 | 5 | 5 | 5 | 5 |
| 4-35 | 5 | 5 | 5 | 5 | 5 | 5 |
| 4-36 | 5 | 5 | 5 | 5 | 5 | 5 |
| 4-37 | 5 | 5 | 5 | 5 | 5 | 5 |
| 5-1 | 5 | 5 | 5 | 5 | 5 | 5 |
| 5-2 | 5 | 5 | 5 | 5 | 5 | 5 |
| 5-3 | 5 | 5 | 5 | 5 | 5 | 5 |
| 6-2 | 4 | 5 | 5 | 5 | 5 | 5 |
| 6-7 | 5 | 5 | 5 | 5 | 5 | 5 |
| 6-8 | 5 | 5 | 5 | 5 | 5 | 5 |
| 6-9 | 5 | 5 | 5 | 5 | 5 | 5 |
| 6-10 | 5 | 5 | 5 | 5 | 5 | 5 |
| 6-14 | 5 | 5 | 5 | 5 | 5 | 5 |
| 6-19 | 5 | 5 | 5 | 5 | 5 | 5 |
| 7-1 | 5 | 5 | 5 | 5 | 5 | 5 |
| 9-1 | 5 | 5 | 5 | 5 | 5 | 5 |
| 9-2 | 5 | 5 | 5 | 5 | 5 | 5 |
| 11-6 | 5 | 5 | 5 | 5 | 5 | 5 |
| Comparative agent | 0 | 0 | 0 | 0 | 0 | 0 |

TEST EXAMPLE 3 (Test on herbicidal effects by upland field foliage treatment)

In a plastic pot (surface area: 120 cm$^2$) filled with sand, barnyardgrass (Ec), *Digitaria ciliaris* (Di), pale smartweed (Po), slender amaranth (Am), common lambsquarters (Ch) and rice flatsedge (Ci) were sown and covered with soil and were cultured in a green house for 2 weeks. A wettable powder prepared in accordance with Formulation Example 1 was diluted with water and applied onto the entire foliages of the plants from above by a small-sized sprayer in an amount of 100 lit./10 ares so as to apply 100 g of the active ingredient per 10 ares. The plants were then cultured in the green house, and the evaluation of the herbicidal effects was conducted on the 14th day after the treatment in accordance with the standards as identified in Table 47. The results are shown in Tables 63–69. Symbol—represents "not tested".

TABLE 63

| Compound No. | Herbicidal effects | | | | | |
|---|---|---|---|---|---|---|
| | Ec | Di | Po | Am | Ch | Ci |
| 1-2 | 5 | 5 | 5 | 5 | 5 | 5 |
| 1-3 | 5 | 5 | 5 | 5 | 5 | 5 |
| 1-5 | 5 | 5 | 5 | 5 | 5 | 5 |
| 1-11 | 5 | 5 | 5 | 5 | 5 | 5 |

TABLE 63-continued

| Compound No. | Herbicidal effects | | | | | |
|---|---|---|---|---|---|---|
| | Ec | Di | Po | Am | Ch | Ci |
| 1-13 | 5 | 5 | 5 | 5 | 5 | 5 |
| 1-14 | 5 | 5 | 5 | 5 | 5 | 5 |
| 1-15 | 5 | 5 | 5 | 5 | 5 | 5 |
| 1-16 | 5 | 5 | 5 | 5 | 5 | 5 |
| 1-17 | 5 | 5 | 5 | 5 | 5 | 5 |
| 1-18 | 5 | 5 | 5 | 5 | 5 | 5 |
| 1-19 | 5 | 5 | 5 | 5 | 5 | 5 |
| 1-20 | 5 | 5 | 5 | 5 | 5 | 5 |
| 1-21 | 5 | 5 | 5 | 5 | 5 | 5 |
| 1-22 | 5 | 5 | 5 | 5 | 5 | 5 |
| 1-24 | 5 | 5 | 5 | 5 | 5 | 5 |
| 1-25 | 5 | 5 | 5 | 5 | 5 | 5 |
| 1-26 | 5 | 5 | 5 | 5 | 5 | 5 |
| 1-27 | 5 | 5 | 5 | 5 | 5 | 5 |
| 1-29 | 5 | 5 | 5 | 5 | 5 | 5 |
| 1-30 | 5 | 5 | 5 | 5 | 5 | 5 |
| 1-32 | 5 | 5 | 5 | 5 | 5 | 5 |
| 1-33 | 5 | 4 | 4 | 5 | 5 | 5 |
| 1-38 | 5 | 5 | 5 | 5 | 5 | 5 |
| 1-41 | 5 | 5 | 5 | 5 | 5 | 5 |
| 1-43 | 5 | 5 | 5 | 5 | 5 | 5 |
| 1-44 | 5 | 5 | 5 | 5 | 5 | 5 |
| 1-45 | 5 | 5 | 5 | 5 | 5 | 5 |
| 1-46 | 5 | 5 | 5 | 5 | 5 | 5 |
| 1-48 | 5 | 5 | 5 | 5 | 5 | 5 |

TABLE 64

| Compound No. | Herbicidal effects | | | | | |
|---|---|---|---|---|---|---|
| | Ec | Di | Po | Am | Ch | Ci |
| 1-49 | 5 | 5 | 5 | 5 | 5 | 5 |
| 1-51 | 5 | 5 | 5 | 5 | 5 | 5 |
| 1-54 | 5 | 5 | 4 | 5 | 5 | 5 |
| 1-60 | 5 | 5 | 5 | 5 | 5 | 5 |
| 1-61 | 5 | 5 | 5 | 5 | 5 | 5 |
| 1-62 | 5 | 5 | 5 | 5 | 5 | 5 |
| 1-63 | 5 | 5 | 5 | 5 | 5 | 5 |
| 1-64 | 5 | 5 | 5 | 5 | 5 | 5 |
| 1-65 | 5 | 5 | 5 | 5 | 5 | 5 |
| 1-66 | 5 | 5 | 5 | 5 | 5 | 5 |
| 1-67 | 5 | 5 | 5 | 5 | 5 | 5 |
| 1-68 | 5 | 5 | 5 | 5 | 5 | 5 |
| 1-69 | 5 | 5 | 5 | 5 | 5 | 5 |
| 1-70 | 5 | 5 | 5 | 5 | 5 | 5 |
| 1-71 | 5 | 5 | 5 | 5 | 5 | 5 |
| 1-72 | 5 | 5 | 5 | 5 | 5 | 5 |
| 1-76 | 5 | 5 | 5 | 5 | 5 | 5 |
| 1-77 | 5 | 5 | 5 | 5 | 5 | 5 |
| 1-78 | 5 | 5 | 5 | 5 | 5 | 5 |
| 1-80 | 5 | 5 | 5 | 5 | 5 | 5 |
| 1-81 | 5 | 5 | 5 | 5 | 5 | 5 |
| 1-82 | 4 | 5 | 5 | 5 | 5 | 5 |
| 1-84 | 5 | 5 | 5 | 5 | 5 | 5 |
| 1-87 | 5 | 5 | 5 | 5 | 5 | 5 |
| 1-90 | 5 | 5 | 5 | 5 | 5 | 5 |
| 1-91 | 5 | 5 | 5 | 5 | 5 | 5 |
| 1-99 | 5 | 5 | 5 | 5 | 5 | 5 |
| 1-102 | 5 | 5 | 5 | 5 | 5 | 5 |
| 1-104 | 5 | 5 | 5 | 5 | 5 | 5 |

TABLE 65

| Compound No. | Herbicidal effects | | | | | |
|---|---|---|---|---|---|---|
| | Ec | Di | Po | Am | Ch | Ci |
| 1-105 | 5 | 5 | 5 | 5 | 5 | 5 |
| 1-106 | 5 | 5 | 5 | 5 | 5 | 5 |

TABLE 65-continued

| Compound No. | Herbicidal effects | | | | | |
|---|---|---|---|---|---|---|
| | Ec | Di | Po | Am | Ch | Ci |
| 1-108 | 5 | 5 | 5 | 5 | 5 | 5 |
| 1-116 | 4 | 4 | 5 | 5 | 5 | 5 |
| 1-119 | 5 | 5 | 5 | 5 | 5 | 5 |
| 1-121 | 5 | 5 | 5 | 5 | 5 | 5 |
| 1-122 | 5 | 5 | 5 | 5 | 5 | 5 |
| 1-123 | 4 | 5 | 5 | 5 | 5 | 5 |
| 1-124 | 5 | 5 | 5 | 5 | 5 | 5 |
| 1-125 | 5 | 5 | 5 | 5 | 5 | 5 |
| 1-126 | 5 | 5 | 5 | 5 | 5 | 5 |
| 1-127 | 4 | 5 | 5 | 5 | 5 | 5 |
| 1-129 | 5 | 5 | 5 | 5 | 5 | 5 |
| 1-133 | 5 | 5 | 5 | 5 | 5 | 5 |
| 1-134 | 5 | 5 | 5 | 5 | 5 | 5 |
| 1-135 | 5 | 5 | 5 | 5 | 5 | 5 |
| 1-136 | 5 | 5 | 5 | 5 | 5 | 5 |
| 1-138 | 5 | 5 | 5 | 5 | 5 | 5 |
| 1-139 | 5 | 5 | 5 | 5 | 5 | 5 |
| 1-140 | 4 | 5 | 5 | 5 | 5 | 5 |
| 1-141 | 5 | 5 | 5 | 5 | 5 | 5 |
| 1-142 | 5 | 5 | 5 | 5 | 5 | 5 |
| 1-143 | 5 | 5 | 5 | 5 | 5 | 5 |
| 1-144 | 5 | 5 | 5 | 5 | 5 | 5 |
| 1-145 | 5 | 5 | 5 | 5 | 5 | 5 |
| 1-148 | 5 | 5 | 5 | 5 | 5 | 5 |
| 1-149 | 5 | 5 | 5 | 5 | 5 | 5 |
| 1-150 | 5 | 5 | 5 | 5 | 5 | 5 |
| 1-151 | 5 | 5 | 5 | 5 | 5 | 5 |

TABLE 66

| Compound No. | Herbicidal effects | | | | | |
|---|---|---|---|---|---|---|
| | Ec | Di | Po | Am | Ch | Ci |
| 1-152 | 5 | 5 | 5 | 5 | 5 | 5 |
| 1-154 | 5 | 5 | 5 | 5 | 5 | 5 |
| 1-155 | 5 | 5 | 5 | 5 | 5 | 5 |
| 1-157 | 5 | 5 | 5 | 5 | 5 | 5 |
| 1-158 | 5 | 5 | 5 | 5 | 5 | 5 |
| 1-159 | 5 | 5 | 5 | 5 | 5 | 5 |
| 1-160 | 5 | 5 | 5 | 5 | 5 | 5 |
| 1-161 | 5 | 5 | 5 | 5 | 5 | 5 |
| 1-162 | 5 | 5 | 5 | 5 | 5 | 5 |
| 1-163 | 5 | 5 | 5 | 5 | 5 | 5 |
| 1-164 | 5 | 5 | 5 | 5 | 5 | 5 |
| 1-165 | 5 | 5 | 5 | 5 | 5 | 5 |
| 1-166 | 4 | 5 | 5 | 5 | 5 | 5 |
| 1-167 | 5 | 5 | 5 | 5 | 5 | 5 |
| 1-168 | 5 | 5 | 5 | 5 | 5 | 5 |
| 1-169 | 5 | 5 | 5 | 5 | 5 | 5 |
| 1-170 | 5 | 5 | 5 | 5 | 5 | 5 |
| 1-171 | 5 | 5 | 5 | 5 | 5 | 5 |
| 1-172 | 5 | 5 | 5 | 5 | 5 | 5 |
| 1-173 | 5 | 5 | 5 | 5 | 5 | 5 |
| 1-174 | 5 | 5 | 5 | 5 | 5 | 5 |
| 1-175 | 5 | 5 | 5 | 5 | 5 | 5 |
| 1-176 | 5 | 5 | 5 | 5 | 5 | 5 |
| 1-178 | 5 | 5 | 5 | 5 | 5 | 5 |
| 1-179 | 5 | 5 | 5 | 5 | 5 | 5 |
| 1-180 | 4 | 4 | 5 | 5 | 5 | 5 |
| 1-181 | 5 | 5 | 5 | 5 | 5 | 5 |
| 1-182 | 5 | 5 | 5 | 5 | 5 | 5 |
| 1-183 | 4 | 5 | 5 | 5 | 5 | 5 |

TABLE 67

| Compound No. | Herbicidal effects | | | | | |
|---|---|---|---|---|---|---|
| | Ec | Di | Po | Am | Ch | Ci |
| 1-184 | 5 | 5 | 5 | 5 | 5 | 5 |
| 1-187 | 5 | 5 | 5 | 5 | 5 | 5 |
| 1-188 | 5 | 5 | 5 | 5 | 5 | 5 |
| 1-189 | 5 | 5 | 5 | 5 | 5 | 5 |
| 1-190 | 5 | 5 | 5 | 5 | 5 | 5 |
| 1-191 | 5 | 5 | 5 | 5 | 5 | 5 |
| 1-192 | 5 | 5 | 5 | 5 | 5 | 5 |
| 1-193 | 5 | 5 | 5 | 5 | 5 | 5 |
| 1-194 | 5 | 5 | 5 | 5 | 5 | 5 |
| 1-195 | 5 | 5 | 5 | 5 | 5 | 5 |
| 1-196 | 5 | 5 | 5 | 5 | 5 | 5 |
| 1-197 | 5 | 5 | 5 | 5 | 5 | 5 |
| 1-198 | 5 | 5 | 5 | 5 | 5 | 5 |
| 1-199 | 4 | 5 | 5 | 5 | 5 | 5 |
| 1-200 | 5 | 5 | 5 | 5 | 5 | 5 |
| 1-201 | 4 | 5 | 5 | 5 | 5 | 5 |
| 1-202 | 5 | 5 | 5 | 5 | 5 | 5 |
| 1-203 | 5 | 5 | 5 | 5 | 5 | 5 |
| 1-204 | 5 | 5 | 5 | 5 | 5 | 5 |
| 1-205 | 5 | 5 | 5 | 5 | 5 | 5 |
| 1-206 | 5 | 5 | 5 | 5 | 5 | 5 |
| 1-207 | 5 | 5 | 5 | 5 | 5 | 5 |
| 1-208 | 5 | 5 | 5 | 5 | 5 | 5 |
| 1-210 | 4 | 5 | 5 | 5 | 5 | 5 |
| 1-211 | 4 | 5 | 5 | 5 | 5 | 5 |
| 1-256 | 5 | 5 | 5 | 5 | 5 | 5 |
| 1'-1 | 5 | 5 | 5 | 5 | 5 | 5 |
| 1'-3 | 5 | 5 | 5 | 5 | 5 | 5 |
| 1'-4 | 5 | 5 | 5 | 5 | 5 | 5 |

TABLE 68

| Compound No. | Herbicidal effects | | | | | |
|---|---|---|---|---|---|---|
| | Ec | Di | Po | Am | Ch | Ci |
| 1'-5 | 5 | 5 | 5 | 5 | 5 | 5 |
| 1'-6 | 5 | 5 | 5 | 5 | 5 | 5 |
| 2-1 | 5 | 5 | 5 | 5 | 5 | 5 |
| 2-2 | 5 | 5 | 5 | 5 | 5 | 5 |
| 2-4 | 5 | 5 | 5 | 5 | 5 | 5 |
| 2-7 | 5 | 5 | 5 | 5 | 5 | 5 |
| 2-10 | 5 | 5 | 5 | 5 | 5 | 5 |
| 2-11 | 5 | 5 | 5 | 5 | 5 | 5 |
| 2-12 | 5 | 5 | 5 | 5 | 5 | 5 |
| 2-13 | 5 | 5 | 5 | 5 | 5 | 5 |
| 2-14 | 5 | 5 | 5 | 5 | 5 | 5 |
| 2-15 | 5 | 5 | 5 | 5 | 5 | 5 |
| 2-16 | 5 | 5 | 5 | 5 | 5 | 5 |
| 2-17 | 5 | 5 | 5 | 5 | 5 | 5 |
| 2-19 | 5 | 5 | 5 | 5 | 5 | 5 |
| 2-25 | 5 | 5 | 5 | 5 | 5 | 5 |
| 2-26 | 5 | 5 | 5 | 5 | 5 | 5 |
| 2-29 | 5 | 5 | 5 | 5 | 5 | 5 |
| 2-31 | 5 | 5 | 5 | 5 | 5 | 5 |
| 2'-1 | 5 | 5 | 5 | 5 | 5 | 5 |
| 3-1 | 5 | 5 | 5 | 5 | 5 | 5 |
| 3-5 | 5 | 5 | 5 | 5 | 5 | 5 |
| 3-6 | 5 | 5 | 5 | 5 | 5 | 5 |
| 3-7 | 5 | 5 | 5 | 5 | 5 | 5 |
| 4-1 | 5 | 5 | 5 | 5 | 5 | 5 |
| 4-2 | 5 | 5 | 5 | 5 | 5 | 5 |
| 4-3 | 5 | 5 | 5 | 5 | 5 | 5 |
| 4-4 | 5 | 5 | 5 | 5 | 5 | 5 |
| 4-5 | 5 | 5 | 5 | 5 | 5 | 5 |

TABLE 69

| Compound No. | Herbicidal effects | | | | | |
|---|---|---|---|---|---|---|
| | Ec | Di | Po | Am | Ch | Ci |
| 4-6 | 5 | 4 | 5 | 5 | 5 | 5 |
| 4-7 | 5 | 5 | 5 | 5 | 5 | 5 |
| 4-10 | 5 | 5 | 5 | 5 | 5 | 5 |
| 4-16 | 5 | 5 | 5 | 5 | 5 | 5 |
| 4-24 | 4 | 5 | 5 | 5 | 5 | 5 |
| 4-27 | 4 | 5 | 5 | 5 | 5 | 5 |
| 4-28 | 4 | 5 | 5 | 5 | 5 | 5 |
| 4-29 | 5 | 5 | 5 | 5 | 5 | 5 |
| 4-31 | 5 | 5 | 5 | 5 | 5 | 5 |
| 4-32 | 5 | 5 | 5 | 5 | 5 | 5 |
| 4-33 | 5 | 5 | 5 | 5 | 5 | 5 |
| 4-34 | 5 | 5 | 5 | 5 | 5 | 5 |
| 4-35 | 5 | 5 | 5 | 5 | 5 | 5 |
| 4-36 | 5 | 5 | 5 | 5 | 5 | 5 |
| 4-37 | 5 | 5 | 5 | 5 | 5 | 5 |
| 5-1 | 5 | 5 | 5 | 5 | 5 | 5 |
| 5-2 | 5 | 5 | 5 | 5 | 5 | 5 |
| 5-3 | 5 | 5 | 5 | 5 | 5 | 5 |
| 6-2 | 4 | 5 | 5 | 5 | 5 | 5 |
| 6-7 | 5 | 5 | 5 | 5 | 5 | 5 |
| 6-8 | 5 | 5 | 5 | 5 | 5 | 5 |
| 6-9 | 5 | 5 | 5 | 5 | 5 | 5 |
| 6-10 | 5 | 5 | 5 | 5 | 5 | 5 |
| 6-14 | 5 | 5 | 5 | 5 | 5 | 5 |
| 6-19 | 5 | 5 | 5 | 5 | 5 | 5 |
| 7-1 | 5 | 5 | 5 | 5 | 5 | 5 |
| 9-1 | 5 | 5 | 5 | 5 | 5 | 5 |
| 9-2 | 5 | 5 | 5 | 5 | 5 | 5 |
| Comparative 1 | 0 | 0 | 0 | 5 | 1 | — |

TEST EXAMPLE 4 (Test on crop plant selectivity by upland field soil treatment)

In a plastic pot (surface area: 600 cm²) filled with sand, cotton (Go), *Digitaria ciliaris* (Di), green foxtail (Se), pale smartweed (Po), slender amaranth (Am), common lambsquarters (Ch) and China jute (Ab) were sown and covered with soil. Next day, a prescribed amount of the active ingredient ($g^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the application in accordance with the standards as identified in Table 47. The results are shown in Tables 70 to 73. Symbol—represents "not tested".

TABLE 70

| Compound No. | Dose a i, g /10 a | Herbicidal effects | | | | | | Phytotoxicity |
|---|---|---|---|---|---|---|---|---|
| | | Di | Se | Po | Am | Ch | Ab | Go |
| 1-14 | 6.3 | 5 | 5 | 5 | 5 | 5 | 5 | 0 |
| | 1.6 | 5 | — | 5 | 5 | 5 | 4 | 0 |
| 1-15 | 6.3 | — | 5 | 5 | 5 | 5 | 5 | 1 |
| | 1.6 | — | 5 | 5 | 5 | 5 | 5 | 0 |
| 1-16 | 6.3 | — | 5 | 5 | 5 | 5 | 5 | 0 |
| | 1.6 | — | 5 | 5 | 5 | 5 | 5 | 0 |
| 1-17 | 6.3 | — | 5 | 5 | 5 | 5 | 4 | 0 |
| | 1.6 | — | 5 | 5 | 5 | 5 | 5 | 0 |
| 1-18 | 6.3 | — | 5 | 5 | 5 | 5 | 5 | 1 |
| | 1.6 | — | 5 | 5 | 5 | 5 | 5 | 1 |
| 1-25 | 6.3 | — | 5 | 5 | 5 | 5 | 5 | 1 |
| 1-27 | 6.3 | — | 5 | 5 | 5 | 5 | 5 | 1 |
| | 1.6 | — | 5 | 5 | 5 | 5 | 5 | 1 |

TABLE 70-continued

| Compound No. | Dose a i, g /10 a | Herbicidal effects | | | | | | Phytotoxicity |
|---|---|---|---|---|---|---|---|---|
| | | Di | Se | Po | Am | Ch | Ab | Go |
| 1-30 | 6.3 | — | 5 | 5 | 5 | 5 | 5 | 1 |
| | 1.6 | — | 5 | 5 | 5 | 5 | 5 | 0 |
| 1-41 | 6.3 | — | 5 | 5 | 5 | 5 | 5 | 1 |
| 1-43 | 6.3 | — | 5 | 5 | 5 | 5 | 4 | 0 |
| 1-44 | 6.3 | — | 5 | 5 | 5 | 5 | 5 | 1 |
| 1-65 | 6.3 | — | 5 | 5 | 5 | 5 | 5 | 0 |
| | 1.6 | — | 5 | 5 | 5 | 5 | 5 | 0 |
| 1-71 | 6.3 | — | 5 | 5 | 5 | 5 | 5 | 1 |
| 1-72 | 6.3 | — | 5 | 5 | 5 | 5 | 5 | 0 |
| | 1.6 | — | 5 | 5 | 5 | 5 | 5 | 0 |
| 1-87 | 6.3 | — | 5 | 5 | 5 | 5 | 5 | 1 |
| 1-90 | 6.3 | — | 5 | 5 | 5 | 5 | 5 | 1 |
| 1-91 | 6.3 | — | 5 | 5 | 5 | 5 | 5 | 1 |
| | 1.6 | — | 5 | 5 | 5 | 5 | 5 | 0 |
| 1-119 | 6.3 | — | 5 | 5 | 5 | 5 | 5 | 0 |
| 1-122 | 6.3 | — | 5 | 5 | 5 | 5 | 5 | 0 |

TABLE 71

| Compound No. | Dose a i, g /10 a | Herbicidal effects | | | | | | Phytotoxicity |
|---|---|---|---|---|---|---|---|---|
| | | Di | Se | Po | Am | Ch | Ab | Go |
| 1-136 | 6.3 | — | 5 | 5 | 5 | 5 | 5 | 1 |
| 1-138 | 6.3 | — | 5 | 5 | 5 | 5 | 4 | 1 |
| 1-150 | 6.3 | — | 5 | 5 | 5 | 5 | 5 | 0 |
| 1-151 | 6.3 | — | 5 | 5 | 5 | 5 | 5 | 1 |
| 1-154 | 6.3 | — | 5 | 5 | 5 | 5 | 5 | 0 |
| 1-155 | 6.3 | — | 5 | 5 | 5 | 5 | 5 | 0 |
| | 1.6 | — | 5 | 5 | 5 | 5 | 5 | 0 |
| 1-160 | 6.3 | — | 5 | 5 | 5 | 5 | 5 | 1 |
| 1-167 | 6.3 | — | 5 | 5 | 5 | 5 | 5 | 1 |
| 1-170 | 6.3 | — | 5 | 5 | 5 | 5 | 5 | 1 |
| 1-171 | 6.3 | — | 5 | 5 | 5 | 5 | 5 | 0 |
| 1-172 | 6.3 | — | 5 | 5 | 5 | 5 | 5 | 1 |
| 1-173 | 6.3 | — | 5 | 5 | 5 | 5 | 5 | 1 |
| 1-178 | 6.3 | — | 5 | 5 | 5 | 5 | 5 | 1 |
| | 1.6 | — | 5 | 5 | 5 | 5 | 5 | 1 |
| 1-179 | 6.3 | — | 5 | 5 | 5 | 5 | 5 | 0 |
| 1-181 | 6.3 | — | 5 | 5 | 5 | 5 | 5 | 0 |
| 1-182 | 6.3 | — | 5 | 5 | 5 | 5 | 5 | 0 |
| 1-187 | 6.3 | — | 5 | 5 | 5 | 5 | 5 | 0 |
| 1-188 | 6.3 | — | 5 | 5 | 5 | 5 | 5 | 0 |
| 1-189 | 6.3 | — | 5 | 5 | 5 | 5 | 5 | 0 |
| 1-191 | 6.3 | — | 5 | 5 | 5 | 5 | 5 | 1 |
| 1-192 | 6.3 | — | 5 | 5 | 5 | 5 | 5 | 0 |
| 1-194 | 6.3 | — | 5 | 5 | 5 | 5 | 5 | 1 |
| 1-196 | 6.3 | — | 5 | 5 | 5 | 5 | 5 | 0 |
| 1-197 | 6.3 | — | 5 | 5 | 5 | 5 | 5 | 1 |
| 1-202 | 6.3 | — | 5 | 5 | 5 | 5 | 5 | 1 |
| | 1.6 | — | 5 | 5 | 5 | 5 | 5 | 1 |
| 1-205 | 6.3 | — | 5 | 5 | 5 | 5 | 4 | 1 |

TABLE 72

| Compound No. | Dose a i, g /10 a | Herbicidal effects | | | | | | Phytotoxicity |
|---|---|---|---|---|---|---|---|---|
| | | Di | Se | Po | Am | Ch | Ab | Go |
| 1-207 | 6.3 | — | 5 | 5 | 5 | 5 | 5 | 0 |
| 1-208 | 6.3 | — | 5 | 4 | 5 | 5 | 5 | 1 |
| 1'-1 | 6.3 | — | 5 | 5 | 5 | 5 | 5 | 0 |
| 1'-4 | 6.3 | — | 5 | 5 | 5 | 5 | 5 | 0 |
| 1'-5 | 6.3 | — | 5 | 5 | 5 | 5 | 5 | 0 |
| | 1.6 | — | 4 | 5 | 5 | 5 | 5 | 0 |
| 2-1 | 1.6 | 5 | 5 | 5 | 5 | 5 | 5 | 2 |

TABLE 72-continued

| Compound No. | Dose a i, g /10 a | Herbicidal effects Di | Se | Po | Am | Ch | Ab | Phytotoxicity Go |
|---|---|---|---|---|---|---|---|---|
| 2-7 | 6.3 | 5 | 5 | 5 | 5 | 5 | 5 | 1 |
|  | 1.6 | 5 | 4 | 5 | 5 | 4 | 5 | 0 |
| 2-15 | 6.3 | — | 5 | 5 | 5 | 5 | 5 | 0 |
| 2-25 | 6.3 | — | 5 | 5 | 5 | 5 | 5 | 0 |
|  | 1.6 | — | 5 | 5 | 5 | 5 | 5 | 0 |
| 2-26 | 6.3 | — | 5 | 5 | 5 | 5 | 5 | 1 |
| 2'-1 | 6.3 | — | 5 | 5 | 5 | 5 | 5 | 1 |
| 3-1 | 6.3 | — | 5 | 5 | 5 | 5 | 5 | 1 |
|  | 1.6 | — | 5 | 5 | 5 | 5 | 5 | 0 |
| 4-1 | 6.3 | — | 5 | 5 | 5 | 5 | 5 | 1 |
|  | 1.6 | — | 5 | 5 | 5 | 5 | 5 | 0 |
| 4-2 | 6.3 | — | 5 | 5 | 5 | 5 | 5 | 2 |
|  | 1.6 | — | 5 | 5 | 5 | 5 | 5 | 1 |
| 4-3 | 6.3 | — | 5 | 5 | 5 | 5 | 5 | 0 |
| 4-4 | 6.3 | — | 5 | 5 | 5 | 5 | 5 | 1 |
|  | 1.6 | — | 5 | 5 | 5 | 5 | 5 | 0 |
| 4-5 | 6.3 | — | 5 | 5 | 5 | 5 | 5 | 2 |
| 4-7 | 6.3 | — | 5 | 5 | 5 | 5 | 5 | 1 |
| 4-28 | 6.3 | — | 5 | 5 | 5 | 5 | 5 | 1 |
|  | 1.6 | — | 5 | 5 | 5 | 5 | 5 | 0 |
| 5-2 | 6.3 | — | 5 | 5 | 5 | 5 | 5 | 1 |
| 6-9 | 6.3 | 5 | — | 5 | 5 | 5 | 5 | 0 |

TABLE 73

| Compound No. | Dose a i, g /10 a | Herbicidal effects Di | Se | Po | Am | Ch | Ab | Phytotoxicity Go |
|---|---|---|---|---|---|---|---|---|
| 6-10 | 6.3 | 5 | 5 | 5 | 5 | 5 | 5 | 1 |
|  | 1.6 | 5 | 4 | 5 | 5 | 5 | 4 | 0 |
| 6-19 | 6.3 | 5 | 5 | 5 | 5 | 5 | 5 | 0 |
|  | 1.6 | 5 | 5 | 5 | 5 | 5 | 3 | 0 |
| 7-1 | 6.3 | — | 5 | 5 | 5 | — | 5 | 1 |
| 9-1 | 6.3 | 5 | 5 | 5 | 5 | 5 | 5 | 0 |
|  | 1.6 | 5 | 5 | 4 | 5 | 5 | 5 | 0 |
| 9-2 | 6.3 | 5 | 5 | 5 | 5 | 5 | 5 | 0 |
|  | 1.6 | 5 | 5 | 5 | 5 | 5 | 5 | 0 |

TEST EXAMPLE 5 (Test on crop plant selectivity by upland field soil treatment)

In a plastic pot (surface area: 600 cm$^2$) filled with sand, wheat (Tr), *Digitaria ciliaris* (Di), green foxtail (Se), pale smartweed (Po), slender amaranth (Am), common lambsquarters (Ch) and China jute (Ab) were sown and covered with soil. Next day, a prescribed amount of the active ingredient (g$^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the application in accordance with the standards as identified in Table 47. The results are shown in Tables 74–76. Symbol—represents "not tested".

TABLE 74

| Compound No. | Dose a i, g /10 a | Herbicidal effects Di | Se | Po | Am | Ch | Ab | Phytotoxicity Tr |
|---|---|---|---|---|---|---|---|---|
| 1-15 | 1.6 | — | 5 | 5 | 5 | 5 | 5 | 2 |
| 1-16 | 6.3 | — | 5 | 5 | 5 | 5 | 5 | 1 |
|  | 1.6 | — | 5 | 5 | 5 | 5 | 5 | 1 |
| 1-17 | 1.6 | — | 5 | 5 | 5 | 5 | 5 | 1 |
| 1-18 | 1.6 | — | 5 | 5 | 5 | 5 | 5 | 2 |
| 1-27 | 1.6 | — | 5 | 5 | 5 | 5 | 5 | 1 |
| 1-30 | 1.6 | — | 5 | 5 | 5 | 5 | 5 | 2 |
| 1-43 | 6.3 | — | 5 | 5 | 5 | 5 | 4 | 1 |
| 1-44 | 6.3 | — | 5 | 5 | 5 | 5 | 5 | 1 |
| 1-65 | 6.3 | — | 5 | 5 | 5 | 5 | 5 | 1 |
|  | 1.6 | — | 5 | 5 | 5 | 5 | 5 | 0 |
| 1-71 | 6.3 | — | 5 | 5 | 5 | 5 | 5 | 2 |
| 1-72 | 1.6 | — | 5 | 5 | 5 | 5 | 5 | 1 |
| 1-87 | 6.3 | — | 5 | 5 | 5 | 5 | 5 | 1 |
| 1-90 | 6.3 | — | 5 | 5 | 5 | 5 | 5 | 1 |
| 1-91 | 1.6 | — | 5 | 5 | 5 | 5 | 5 | 1 |
| 1-136 | 6.3 | — | 5 | 5 | 5 | 5 | 5 | 2 |
|  | 1.6 | — | 5 | 5 | 5 | 5 | 4 | 1 |
| 1-138 | 6.3 | — | 5 | 5 | 5 | 5 | 4 | 1 |
| 1-151 | 6.3 | — | 5 | 5 | 5 | 5 | 5 | 2 |
| 1-154 | 1.6 | — | 5 | 5 | 5 | 5 | — | 1 |
| 1-155 | 6.3 | — | 5 | 5 | 5 | 5 | 5 | 2 |
|  | 1.6 | — | 5 | 5 | 5 | 5 | 5 | 1 |
| 1-160 | 6.3 | — | 5 | 5 | 5 | 5 | 5 | 2 |
| 1-167 | 6.3 | — | 5 | 5 | 5 | 5 | 5 | 1 |
| 1-171 | 6.3 | — | 5 | 5 | 5 | 5 | 5 | 1 |
| 1-173 | 6.3 | — | 5 | 5 | 5 | 5 | 5 | 1 |
| 1-178 | 1.6 | — | 5 | 5 | 5 | 5 | 5 | 1 |
| 1-179 | 6.3 | — | 5 | 5 | 5 | 5 | 5 | 1 |

TABLE 75

| Compound No. | Dose a i, g /10 a | Herbicidal effects Di | Se | Po | Am | Ch | Ab | Phytotoxicity Tr |
|---|---|---|---|---|---|---|---|---|
| 1-181 | 6.3 | — | 5 | 5 | 5 | 5 | 5 | 1 |
| 1-182 | 6.3 | — | 5 | 5 | 5 | 5 | 5 | 1 |
| 1-187 | 6.3 | — | 5 | 5 | 5 | 5 | 5 | 1 |
| 1-188 | 6.3 | — | 5 | 5 | 5 | 5 | 5 | 1 |
| 1-189 | 6.3 | — | 5 | 5 | 5 | 5 | 5 | 1 |
| 1-191 | 6.3 | — | 5 | 5 | 5 | 5 | 5 | 1 |
| 1-192 | 6.3 | — | 5 | 5 | 5 | 5 | 5 | 2 |
| 1-194 | 6.3 | — | 5 | 5 | 5 | 5 | 5 | 1 |
| 1-197 | 6.3 | — | 5 | 5 | 5 | 5 | 5 | 1 |
| 1-202 | 1.6 | — | 5 | 5 | 5 | 5 | 5 | 1 |
| 1-205 | 6.3 | — | 5 | 5 | 5 | 5 | 4 | 1 |
| 1-207 | 6.3 | — | 5 | 5 | 5 | 5 | 5 | 1 |
| 1-208 | 6.3 | — | 5 | 4 | 5 | 5 | 5 | 1 |
| 1'-1 | 6.3 | — | 5 | 5 | 5 | 5 | 5 | 1 |
| 1'-4 | 6.3 | — | 5 | 5 | 5 | 5 | 5 | 1 |
| 1'-5 | 6.3 | — | 5 | 5 | 5 | 5 | 5 | 1 |
|  | 1.6 | — | 4 | 5 | 5 | 5 | 5 | 1 |
| 2-1 | 1.6 | 5 | 5 | 5 | 5 | 5 | 5 | 0 |
| 2-2 | 6.3 | — | 5 | 5 | 5 | 5 | 5 | 2 |
| 2-4 | 1.6 | 5 | 5 | 5 | 5 | 4 | 3 | 0 |
| 2-7 | 1.6 | 5 | 5 | 5 | 5 | 4 | 5 | 0 |
| 2-15 | 6.3 | — | 5 | 5 | 5 | 5 | 5 | 1 |
| 2-25 | 6.3 | — | 5 | 5 | 5 | 5 | 5 | 2 |
|  | 1.6 | — | 5 | 5 | 5 | 5 | 5 | 1 |
| 2-26 | 6.3 | — | 5 | 5 | 5 | 5 | 5 | 1 |
| 2'-1 | 6.3 | — | 5 | 5 | 5 | 5 | 5 | 2 |
| 3-1 | 6.3 | — | 5 | 5 | 5 | 5 | 5 | 1 |
| 4-1 | 6.3 | — | 5 | 5 | 5 | 5 | 5 | 2 |
|  | 1.6 | — | 5 | 5 | 5 | 5 | 5 | 1 |

TABLE 76

| Compound No. | Dose a i, g /10 a | Herbicidal effects Di | Se | Po | Am | Ch | Ab | Phytotoxicity Tr |
|---|---|---|---|---|---|---|---|---|
| 4-2 | 1.6 | — | 5 | 5 | 5 | 5 | 5 | 1 |
| 4-3 | 6.3 | — | 5 | 5 | 5 | 5 | 5 | 2 |
| 4-4 | 1.6 | — | 5 | 5 | 5 | 5 | 5 | 2 |
| 4-5 | 6.3 | — | 5 | 5 | 5 | 5 | 5 | 1 |
| 4-7 | 6.3 | — | 5 | 5 | 5 | 5 | 5 | 1 |
| 4-28 | 6.3 | — | 5 | 5 | 5 | 5 | 5 | 2 |
| 5-2 | 6.3 | — | 5 | 5 | 5 | 5 | 5 | 1 |
| 6-10 | 1.6 | 5 | 4 | 5 | 5 | 5 | 4 | 0 |
| 6-19 | 6.3 | 5 | 5 | 5 | 5 | 5 | 5 | 0 |
|  | 1.6 | 5 | 5 | 5 | 5 | 5 | 3 | 0 |
| 7-1 | 6.3 | — | 5 | 5 | 5 | — | 5 | 2 |
| 9-1 | 6.3 | 5 | 5 | 4 | 5 | 5 | 5 | 1 |
|  | 1.6 | 5 | 5 | 5 | 5 | 5 | 5 | 0 |

TEST EXAMPLE 6 (Test on crop plant selectivity by upland field soil treatment)

In a plastic pot (surface area: 600 cm$^2$) filled with sand, soybean (Gl), *Digitaria ciliaris* (Di), green foxtail (Se), Johnsongrass (So), pale smartweed (Po), slender amaranth (Am), common lambsquarters (Ch) and China jute (Ab) were sown and covered with soil. Next day, a prescribed amount of the active ingredient (g$^{ai}$/10a) of a wettable powder prepared in accordance with Formulation Example 1 was diluted with water and applied uniformly to the soil surface by a small-sized sprayer in an amount of 100 lit. per 10 ares. The plants were then cultured in a green house, and the evaluation of the herbicidal effects and phytotoxicity was conducted on the 21st day after the application in accordance with the standards as identified in Table 47. The results are shown in Tables 77 to 79. Symbol—represents "not tested".

TABLE 77

| Compound No. | Dose a i, g /10 a | Herbicidal effects Di | Se | So | Po | Am | Ch | Ab | Phytotoxicity Gl |
|---|---|---|---|---|---|---|---|---|---|
| 1-15 | 1.6 | — | 5 | — | 5 | 5 | 5 | 5 | 2 |
| 1-16 | 1.6 | — | 5 | — | 5 | 5 | 5 | 5 | 1 |
| 1-17 | 1.6 | — | 5 | — | 5 | 5 | 5 | 5 | 0 |
| 1-18 | 1.6 | — | 5 | — | 5 | 5 | 5 | 5 | 1 |
| 1-25 | 6.3 | — | 5 | — | 5 | 5 | 5 | 5 | 2 |
| 1-30 | 1.6 | — | 5 | — | 5 | 5 | 5 | 5 | 1 |
| 1-43 | 6.3 | — | 5 | — | 5 | 5 | 5 | 4 | 1 |
| 1-44 | 6.3 | — | 5 | — | 5 | 5 | 5 | 5 | 1 |
| 1-65 | 6.3 | — | 5 | — | 5 | 5 | 5 | 5 | 1 |
|  | 1.6 | — | 5 | — | 5 | 5 | 5 | 5 | 1 |
| 1-72 | 6.3 | — | 5 | — | 5 | 5 | 5 | 5 | 2 |
|  | 1.6 | — | 5 | — | 5 | 5 | 5 | 5 | 1 |
| 1-87 | 6.3 | — | 5 | — | 5 | 5 | 5 | 5 | 1 |
| 1-90 | 6.3 | — | 5 | — | 5 | 5 | 5 | 5 | 2 |
|  | 1.6 | — | 5 | — | 5 | 5 | 5 | 5 | 2 |
| 1-91 | 6.3 | — | 5 | — | 5 | 5 | 5 | 5 | 1 |
|  | 1.6 | — | 5 | — | 5 | 5 | 5 | 5 | 0 |
| 1-119 | 6.3 | — | 5 | — | 5 | 5 | 5 | 5 | 2 |
| 1-122 | 6.3 | — | 5 | — | 5 | 5 | 5 | 5 | 2 |
| 1-136 | 6.3 | — | 5 | — | 5 | 5 | 5 | 5 | 1 |
|  | 1.6 | — | 5 | — | 5 | 5 | 5 | 4 | 0 |
| 1-138 | 6.3 | — | 5 | — | 5 | 5 | 5 | 4 | 2 |
| 1-150 | 6.3 | — | 5 | — | 5 | 5 | 5 | 5 | 1 |
| 1-151 | 6.3 | — | 5 | — | 5 | 5 | 5 | 5 | 0 |
| 1-154 | 6.3 | — | 5 | — | 5 | 5 | 5 | 5 | 1 |
| 1-155 | 6.3 | — | 5 | — | 5 | 5 | 5 | 5 | 0 |
|  | 1.6 | — | 5 | — | 5 | 5 | 5 | 5 | 0 |

TABLE 77-continued

| Compound No. | Dose a i, g /10 a | Herbicidal effects Di | Se | So | Po | Am | Ch | Ab | Phytotoxicity Gl |
|---|---|---|---|---|---|---|---|---|---|
| 1-160 | 6.3 | — | 5 | — | 5 | 5 | 5 | 5 | 1 |
| 1-167 | 6.3 | — | 5 | — | 5 | 5 | 5 | 5 | 1 |

TABLE 78

| Compound No. | Dose a i, g /10 a | Herbicidal effects Di | Se | So | Po | Am | Ch | Ab | Phytotoxicity Gl |
|---|---|---|---|---|---|---|---|---|---|
| 1-170 | 6.3 | — | 5 | — | 5 | 5 | 5 | 5 | 2 |
| 1-171 | 6.3 | — | 5 | — | 5 | 5 | 5 | 5 | 1 |
| 1-173 | 6.3 | — | 5 | — | 5 | 5 | 5 | 5 | 1 |
| 1-181 | 6.3 | — | 5 | — | 5 | 5 | 5 | 5 | 1 |
| 1-182 | 6.3 | — | 5 | — | 5 | 5 | 5 | 5 | 1 |
| 1-187 | 6.3 | — | 5 | — | 5 | 5 | 5 | 5 | 1 |
| 1-188 | 6.3 | — | 5 | — | 5 | 5 | 5 | 5 | 1 |
| 1-189 | 6.3 | — | 5 | — | 5 | 5 | 5 | 5 | 1 |
| 1-191 | 6.3 | — | 5 | — | 5 | 5 | 5 | 5 | 2 |
| 1-192 | 6.3 | — | 5 | — | 5 | 5 | 5 | 5 | 1 |
| 1-194 | 6.3 | — | 5 | — | 5 | 5 | 5 | 5 | 1 |
| 1-197 | 6.3 | — | 5 | — | 5 | 5 | 5 | 5 | 1 |
| 1-202 | 1.6 | — | 5 | — | 5 | 5 | 5 | 5 | 2 |
| 1-205 | 6.3 | — | 5 | — | 5 | 5 | 5 | 4 | 1 |
| 1-207 | 6.3 | — | 5 | — | 5 | 5 | 5 | 5 | 1 |
| 1-208 | 6.3 | — | 5 | — | 4 | 5 | 5 | 5 | 2 |
| 1'-1 | 6.3 | — | 5 | — | 5 | 5 | 5 | 5 | 1 |
| 1'-4 | 6.3 | — | 5 | — | 5 | 5 | 5 | 5 | 1 |
| 1'-5 | 6.3 | — | 5 | — | 5 | 5 | 5 | 5 | 2 |
|  | 1.6 | — | 4 | — | 5 | 5 | 5 | 5 | 1 |
| 2-1 | 6.3 | 5 | 5 | 5 | 5 | 5 | 5 | 5 | 1 |
|  | 1.6 | 5 | 5 | 5 | 5 | 5 | 5 | 5 | 0 |
| 2-7 | 6.3 | 5 | 5 | 5 | 5 | 5 | 5 | 5 | 0 |
|  | 1.6 | 5 | 5 | 5 | 5 | 5 | 5 | 5 | 0 |
| 2-15 | 6.3 | — | 5 | — | 5 | 5 | 5 | 5 | 1 |
| 2-25 | 6.3 | — | 5 | — | 5 | 5 | 5 | 5 | 1 |
|  | 1.6 | — | 5 | — | 5 | 5 | 5 | 5 | 0 |
| 2-26 | 6.3 | — | 5 | — | 5 | 5 | 5 | 5 | 1 |
| 2'-1 | 6.3 | — | 5 | — | 5 | 5 | 5 | 5 | 1 |

TABLE 79

| Compound No. | Dose a i, g /10 a | Herbicidal effects Di | Se | So | Po | Am | Ch | Ab | Phytotoxicity Gl |
|---|---|---|---|---|---|---|---|---|---|
| 3-1 | 6.3 | — | 5 | — | 5 | 5 | 5 | 5 | 1 |
| 4-1 | 6.3 | — | 5 | — | 5 | 5 | 5 | 5 | 2 |
|  | 1.6 | — | 5 | — | 5 | 5 | 5 | 5 | 1 |
| 4-2 | 1.6 | — | 5 | — | 5 | 5 | 5 | 5 | 1 |
| 4-3 | 6.3 | — | 5 | — | 5 | 5 | 5 | 5 | 1 |
| 4-4 | 6.3 | — | 5 | — | 5 | 5 | 5 | 5 | 2 |
| 4-5 | 6.3 | — | 5 | — | 5 | 5 | 5 | 5 | 2 |
| 4-7 | 6.3 | — | 5 | — | 5 | 5 | 5 | 5 | 1 |
| 4-28 | 1.6 | — | 5 | — | 5 | 5 | 5 | 5 | 2 |
| 5-2 | 6.3 | — | 5 | — | 5 | 5 | 5 | 5 | 1 |
| 6-9 | 6.3 | 5 | — | 5 | 5 | 5 | 5 | 5 | 0 |
| 6-10 | 1.6 | 5 | 4 | 5 | 5 | 5 | 5 | 4 | 0 |
| 6-19 | 6.3 | 5 | 5 | 5 | 5 | 5 | 5 | 5 | 0 |
|  | 1.6 | 5 | 5 | 4 | 5 | 5 | 3 | 3 | 0 |
| 7-1 | 6.3 | — | 5 | — | 5 | — | 5 | 5 | 1 |
| 9-2 | 1.6 | 5 | 5 | 5 | 5 | 5 | 5 | 5 | 1 |

TEST EXAMPLE 7 (Test on crop plant selectivity by upland field soil treatment)

In a plastic pot (surface area: 600 cm$^2$) filled with sand, corn (Ze), green foxtail (Se), pale smartweed (Po), slender amaranth (Am), common lambsquarters (Ch) and China jute (Ab) were sown and covered with soil. Next day, a prescribed amount of the active ingredient ($g^{ai}/10a$) of a wettable powder prepared in accordance with Formulation Example 1 was diluted with water and applied uniformly to the soil surface by a small-sized sprayer in an amount of 100 lit per 10 ares. The plants were then cultured in a green house, and the evaluation of the herbicidal effects and phytotoxicity was conducted on the 21st day after the application in accordance with the standards as identified in Table 47. The results are shown in Tables 80 to 82.

TABLE 80

| Compound No. | Dose a i, g /10 a | Herbicidal effects | | | | | Phytotoxicity Ze |
|---|---|---|---|---|---|---|---|
| | | Se | Po | Am | Ch | Ab | |
| 1-15 | 1.6 | 5 | 5 | 5 | 5 | 5 | 1 |
| 1-16 | 6.3 | 5 | 5 | 5 | 5 | 5 | 1 |
| | 1.6 | 5 | 5 | 5 | 5 | 5 | 0 |
| 1-17 | 6.3 | 5 | 5 | 5 | 5 | 4 | 1 |
| | 1.6 | 5 | 5 | 5 | 5 | 5 | 1 |
| 1-18 | 6.3 | 5 | 5 | 5 | 5 | 5 | 2 |
| | 1.6 | 5 | 5 | 5 | 5 | 5 | 1 |
| 1-25 | 6.3 | 5 | 5 | 5 | 5 | 5 | 1 |
| 1-30 | 6.3 | 5 | 5 | 5 | 5 | 5 | 2 |
| | 1.6 | 5 | 5 | 5 | 5 | 5 | 1 |
| 1-41 | 6.3 | 5 | 5 | 5 | 5 | 5 | 1 |
| 1-43 | 6.3 | 5 | 5 | 5 | 5 | 4 | 1 |
| 1-44 | 6.3 | 5 | 5 | 5 | 5 | 5 | 1 |
| 1-65 | 6.3 | 5 | 5 | 5 | 5 | 5 | 2 |
| | 1.6 | 5 | 5 | 5 | 5 | 5 | 1 |
| 1-72 | 1.6 | 5 | 5 | 5 | 5 | 5 | 0 |
| 1-87 | 6.3 | 5 | 5 | 5 | 5 | 5 | 1 |
| 1-90 | 6.3 | 5 | 5 | 5 | 5 | 5 | 2 |
| | 1.6 | 5 | 5 | 5 | 5 | 5 | 1 |
| 1-91 | 6.3 | 5 | 5 | 5 | 5 | 5 | 2 |
| | 1.6 | 5 | 5 | 5 | 5 | 5 | 1 |
| 1-119 | 6.3 | 5 | 5 | 5 | 5 | 5 | 1 |
| 1-122 | 6.3 | 5 | 5 | 5 | 5 | 5 | 1 |
| 1-136 | 1.6 | 5 | 5 | 5 | 5 | 5 | 1 |
| 1-138 | 6.3 | 5 | 5 | 5 | 5 | 4 | 2 |
| 1-150 | 6.3 | 5 | 5 | 5 | 5 | 5 | 1 |
| 1-154 | 6.3 | 5 | 5 | 5 | 5 | 5 | 1 |
| 1-155 | 6.3 | 5 | 5 | 5 | 5 | 5 | 0 |
| | 1.6 | 5 | 5 | 5 | 5 | 5 | 0 |

TABLE 81

| Compound No. | Dose a i, g /10 a | Herbicidal effects | | | | | Phytotoxicity Ze |
|---|---|---|---|---|---|---|---|
| | | Se | Po | Am | Ch | Ab | |
| 1-160 | 6.3 | 5 | 5 | 5 | 5 | 5 | 1 |
| 1-167 | 6.3 | 5 | 5 | 5 | 5 | 5 | 0 |
| 1-171 | 6.3 | 5 | 5 | 5 | 5 | 5 | 0 |
| 1-172 | 6.3 | 5 | 5 | 5 | 5 | 5 | 2 |
| 1-173 | 6.3 | 5 | 5 | 5 | 5 | 5 | 1 |
| 1-178 | 1.6 | 5 | 5 | 5 | 5 | 5 | 2 |
| 1-179 | 6.3 | 5 | 5 | 5 | 5 | 5 | 1 |
| 1-182 | 6.3 | 5 | 5 | 5 | 5 | 5 | 1 |
| 1-187 | 6.3 | 5 | 5 | 5 | 5 | 5 | 1 |
| 1-188 | 6.3 | 5 | 5 | 5 | 5 | 5 | 0 |
| 1-189 | 6.3 | 5 | 5 | 5 | 5 | 5 | 1 |
| 1-191 | 6.3 | 5 | 5 | 5 | 5 | 5 | 1 |
| 1-192 | 6.3 | 5 | 5 | 5 | 5 | 5 | 2 |
| 1-194 | 6.3 | 5 | 5 | 5 | 5 | 5 | 0 |
| 1-196 | 6.3 | 5 | 5 | 5 | 5 | 5 | 1 |
| 1-197 | 6.3 | 5 | 5 | 5 | 5 | 5 | 1 |
| 1-202 | 1.6 | 5 | 5 | 5 | 5 | 5 | 1 |
| 1-205 | 6.3 | 5 | 5 | 5 | 5 | 4 | 2 |
| 1-207 | 6.3 | 5 | 5 | 5 | 5 | 5 | 1 |
| 1-208 | 6.3 | 5 | 4 | 5 | 5 | 5 | 1 |
| 1'-1 | 6.3 | 5 | 5 | 5 | 5 | 5 | 1 |
| 1'-4 | 6.3 | 5 | 5 | 5 | 5 | 5 | 1 |
| 1'-5 | 6.3 | 5 | 5 | 5 | 5 | 5 | 2 |
| | 1.6 | 4 | 5 | 5 | 5 | 5 | 1 |
| 2-25 | 1.6 | 5 | 5 | 5 | 5 | 5 | 1 |
| 2-26 | 6.3 | 5 | 5 | 5 | 5 | 5 | 1 |
| 3-1 | 6.3 | 5 | 5 | 5 | 5 | 5 | 2 |
| | 1.6 | 5 | 5 | 5 | 5 | 5 | 2 |

TABLE 82

| Compound No. | Dose a i, g /10 a | Herbicidal effects | | | | | Phytotoxicity Ze |
|---|---|---|---|---|---|---|---|
| | | Se | Po | Am | Ch | Ab | |
| 4-1 | 6.3 | 5 | 5 | 5 | 5 | 5 | 1 |
| | 1.6 | 5 | 5 | 5 | 5 | 5 | 0 |
| 4-2 | 6.3 | 5 | 5 | 5 | 5 | 5 | 1 |
| | 1.6 | 5 | 5 | 5 | 5 | 5 | 1 |
| 4-3 | 6.3 | 5 | 5 | 5 | 5 | 5 | 1 |
| 4-4 | 6.3 | 5 | 5 | 5 | 5 | 5 | 2 |
| | 1.6 | 5 | 5 | 5 | 5 | 5 | 1 |
| 4-5 | 6.3 | 5 | 5 | 5 | 5 | 5 | 0 |
| 4-7 | 6.3 | 5 | 5 | 5 | 5 | 5 | 2 |
| 4-28 | 1.6 | 5 | 5 | 5 | 5 | 5 | 1 |
| 5-2 | 6.3 | 5 | 5 | 5 | 5 | 5 | 0 |

TEST EXAMPLE 8 (Test on crop plant selectivity by upland field foliage treatment)

In a plastic pot (surface area: 600 cm$^2$) filled with sand, cotton (Go), pale smartweed (Po), slender amaranth (Am), common lambsquarters (Ch) and China jute (Ab) were sown and cultured in a green house for 2 weeks. Then, a prescribed amount of the active ingredient ($g^{ai}/10a$) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 47. The results are shown in Table 83.

TABLE 83

| Compound No. | Dose a i, g /10 a | Herbicidal effects | | | | Phytotoxicity Go |
|---|---|---|---|---|---|---|
| | | Po | Am | Ch | Ab | |
| 1-182 | 1.6 | 5 | 5 | 5 | 5 | 2 |
| 1-187 | 1.6 | 5 | 5 | 5 | 5 | 2 |
| 1-194 | 1.6 | 5 | 5 | 5 | 5 | 2 |

TEST EXAMPLE 9 (Test on crop plant selectivity by upland field foliage treatment)

In a plastic pot (surface area: 600 cm$^2$) filled with sand, wheat (Tr), pale smartweed (Po), slender amaranth (Am), common lambsquarters (Ch) and China jute (Ab) were sown and cultured in a green house for 2 weeks. Then, a prescribed amount of the active ingredient ($g^{ai}/10a$) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 47. The results are shown in Tables 84 to 86.

TABLE 84

| Compound No. | Dose a i, g /10 a | Herbicidal effects | | | | Phytotoxicity |
|---|---|---|---|---|---|---|
| | | Po | Am | Ch | Ab | Tr |
| 1-16 | 1.6 | 5 | 5 | 5 | 5 | 2 |
| 1-20 | 1.6 | 5 | 5 | 5 | 5 | 2 |
| 1-22 | 1.6 | 5 | 5 | 5 | 5 | 2 |
| 1-25 | 1.6 | 5 | 5 | 5 | 5 | 2 |
| 1-26 | 1.6 | 5 | 5 | 5 | 5 | 2 |
| 1-30 | 1.6 | 5 | 5 | 5 | 5 | 2 |
| 1-31 | 1.6 | 5 | 5 | 5 | 5 | 2 |
| 1-38 | 1.6 | 5 | 5 | 5 | 5 | 2 |
| 1-41 | 1.6 | 5 | 5 | 5 | 5 | 2 |
| 1-43 | 1.6 | 5 | 5 | 5 | 5 | 2 |
| 1-44 | 1.6 | 5 | 5 | 5 | 5 | 2 |
| 1-48 | 1.6 | 5 | 5 | 5 | 5 | 2 |
| 1-52 | 1.6 | 5 | 5 | 5 | 5 | 1 |
| 1-62 | 1.6 | 5 | 5 | 5 | 5 | 2 |
| 1-65 | 1.6 | 5 | 5 | 5 | 5 | 2 |
| 1-69 | 1.6 | 5 | 5 | 5 | 5 | 1 |
| 1-91 | 1.6 | 5 | 5 | 5 | 5 | 2 |
| 1-106 | 1.6 | 5 | 5 | 5 | 5 | 2 |
| 1-119 | 1.6 | 5 | 5 | 5 | 4 | 2 |
| 1-122 | 1.6 | 5 | 5 | 5 | 5 | 2 |
| 1-125 | 1.6 | 5 | 5 | 5 | 5 | 2 |
| 1-126 | 1.6 | 5 | 5 | 5 | 5 | 2 |
| 1-134 | 1.6 | 5 | 5 | 5 | 5 | 2 |
| 1-158 | 1.6 | 5 | 5 | 5 | 5 | 2 |
| 1-159 | 1.6 | 5 | 5 | 5 | 5 | 1 |
| 1-160 | 1.6 | 5 | 5 | 5 | 5 | 2 |
| 1-162 | 1.6 | 5 | 5 | 5 | 5 | 2 |
| 1-170 | 1.6 | 5 | 5 | 5 | 5 | 1 |
| 1-171 | 1.6 | 5 | 5 | 5 | 5 | 2 |

TABLE 85

| Compound No. | Dose a i, g /10 a | Herbicidal effects | | | | Phytotoxicity |
|---|---|---|---|---|---|---|
| | | Po | Am | Ch | Ab | Tr |
| 1-176 | 1.6 | 5 | 5 | 5 | 5 | 1 |
| 1-178 | 1.6 | 5 | 5 | 5 | 5 | 2 |
| 1-179 | 1.6 | 5 | 5 | 5 | 5 | 2 |
| 1-181 | 1.6 | 5 | 5 | 5 | 5 | 2 |
| 1-182 | 1.6 | 5 | 5 | 5 | 5 | 1 |
| 1-184 | 1.6 | 5 | 5 | 5 | 5 | 2 |
| 1-187 | 1.6 | 5 | 5 | 5 | 5 | 2 |
| 1-191 | 1.6 | 5 | 5 | 5 | 5 | 2 |
| 1-194 | 1.6 | 5 | 5 | 5 | 5 | 1 |
| 1-196 | 1.6 | 5 | 5 | 5 | 5 | 2 |
| 1-197 | 1.6 | 5 | 5 | 5 | 5 | 2 |
| 1-199 | 1.6 | 5 | 5 | 5 | 5 | 2 |
| 1-200 | 1.6 | 5 | 5 | 5 | 5 | 2 |
| 1-201 | 1.6 | 5 | 5 | 5 | 5 | 2 |
| 1-202 | 1.6 | 5 | 5 | 5 | 5 | 2 |
| 1-203 | 1.6 | 5 | 5 | 5 | 5 | 2 |
| 1-204 | 1.6 | 5 | 5 | 5 | 5 | 2 |
| 1-208 | 1.6 | 5 | 5 | 5 | 5 | 2 |
| 1'-5 | 1.6 | 5 | 5 | 5 | 5 | 1 |
| 2-15 | 1.6 | 5 | 5 | 5 | 5 | 2 |
| 2-18 | 1.6 | 5 | 5 | 5 | 5 | 2 |
| 2-19 | 1.6 | 5 | 5 | 5 | 5 | 1 |
| 2-25 | 1.6 | 5 | 5 | 5 | 5 | 2 |
| 2-26 | 1.6 | 5 | 5 | 5 | 5 | 2 |
| 2-31 | 1.6 | 5 | 5 | 5 | 5 | 2 |
| 3-5 | 1.6 | 5 | 5 | 5 | 5 | 1 |
| 3-6 | 1.6 | 5 | 5 | 5 | 5 | 2 |
| 3-7 | 1.6 | 5 | 5 | 5 | 5 | 2 |
| 4-1 | 1.6 | 5 | 5 | 5 | 5 | 2 |

TABLE 86

| Compound No. | Dose a i, g /10 a | Herbicidal effects | | | | Phytotoxicity |
|---|---|---|---|---|---|---|
| | | Po | Am | Ch | Ab | Tr |
| 4-2 | 1.6 | 5 | 5 | 5 | 5 | 2 |
| 4-3 | 1.6 | 5 | 5 | 5 | 5 | 2 |
| 4-5 | 1.6 | 5 | 5 | 5 | 5 | 2 |
| 4-27 | 1.6 | 5 | 5 | 5 | 5 | 2 |
| 4-28 | 1.6 | 5 | 5 | 5 | 5 | 2 |
| 4-32 | 1.6 | 5 | 5 | 5 | 5 | 2 |
| 4-33 | 1.6 | 5 | 5 | 5 | 5 | 2 |
| 4-34 | 1.6 | 5 | 5 | 5 | 5 | 2 |
| 4-35 | 1.6 | 5 | 5 | 5 | 5 | 2 |
| 4-36 | 1.6 | 5 | 5 | 5 | 5 | 2 |
| 4-38 | 1.6 | 5 | 5 | 5 | 5 | 2 |
| 4-39 | 1.6 | 5 | 5 | 5 | 5 | 2 |
| 5-2 | 1.6 | 5 | 5 | 5 | 5 | 2 |
| 5-3 | 1.6 | 5 | 5 | 5 | 5 | 1 |
| 7-1 | 1.6 | 5 | 5 | 5 | 5 | 2 |

TEST EXAMPLE 10 (Test on crop plant selectivity by upland field foliage treatment)

In a plastic pot (surface area: 600 cm$^2$) filled with sand, soybean (Gl), pale smartweed (Po), slender amaranth (Am), common lambsquarters (Ch) and China jute (Ab) were sown and cultured in a green house for 2 weeks. Then, a prescribed amount of the active ingredient ($g^{ai}$/10a) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 47. The results are shown in Table 87.

TABLE 87

| Compound No. | Dose a i, g /10 a | Herbicidal effects | | | | Phytotoxicity |
|---|---|---|---|---|---|---|
| | | Po | Am | Ch | Ab | Gl |
| 1-22 | 1.6 | 5 | 5 | 5 | 5 | 2 |
| 1-26 | 1.6 | 5 | 5 | 5 | 5 | 2 |
| 1-52 | 1.6 | 5 | 5 | 5 | 5 | 2 |
| 1-69 | 1.6 | 5 | 5 | 5 | 5 | 2 |
| 1-119 | 1.6 | 5 | 5 | 5 | 4 | 2 |
| 1-126 | 1.6 | 5 | 5 | 5 | 5 | 2 |
| 1-159 | 1.6 | 5 | 5 | 5 | 5 | 2 |
| 1-171 | 1.6 | 5 | 5 | 5 | 5 | 2 |
| 1-184 | 1.6 | 5 | 5 | 5 | 5 | 2 |
| 1-187 | 1.6 | 5 | 5 | 5 | 5 | 2 |
| 1-199 | 1.6 | 5 | 5 | 5 | 5 | 2 |
| 1-208 | 1.6 | 5 | 5 | 5 | 5 | 2 |
| 4-3 | 1.6 | 5 | 5 | 5 | 5 | 2 |
| 4-32 | 1.6 | 5 | 5 | 5 | 5 | 2 |
| 5-2 | 1.6 | 5 | 5 | 5 | 5 | 2 |

TEST EXAMPLE 11 (Test on crop plant selectivity by upland field foliage treatment)

In a plastic pot (surface area: 600 cm$^2$) filled with sand, corn (Ze), pale smartweed (Po), slender amaranth (Am), common lambsquarters (Ch) and China jute (Ab) were sown and cultured in a green house for 2 weeks. Then, a prescribed amount of the active ingredient (g$^{ai}$/10a) of a wettable powder prepared in accordance with Formulation Example 1 was diluted with water and applied onto the entire foliages of the plants from above by a small-sized sprayer in an amount of 100 lit. per 10 ares. The plants were then cultured in a green house, and the evaluation of the herbicidal effects and phytotoxicity was conducted on the 14th day after the treatment in accordance with the standards as identified in Table 47. The results are shown in Tables 88 to 90.

TABLE 88

| Compound No. | Dose a i, g /10 a | Herbicidal effects Po | Am | Ch | Ab | Phytotoxicity Ze |
|---|---|---|---|---|---|---|
| 1-16 | 1.6 | 5 | 5 | 5 | 5 | 2 |
| 1-18 | 1.6 | 5 | 5 | 5 | 5 | 2 |
| 1-22 | 1.6 | 5 | 5 | 5 | 5 | 2 |
| 1-25 | 1.6 | 5 | 5 | 5 | 5 | 2 |
| 1-26 | 1.6 | 5 | 5 | 5 | 5 | 2 |
| 1-30 | 1.6 | 5 | 5 | 5 | 5 | 2 |
| 1-31 | 1.6 | 5 | 5 | 5 | 5 | 2 |
| 1-38 | 1.6 | 5 | 5 | 5 | 5 | 2 |
| 1-41 | 1.6 | 5 | 5 | 5 | 5 | 2 |
| 1-52 | 1.6 | 5 | 5 | 5 | 5 | 2 |
| 1-62 | 1.6 | 5 | 5 | 5 | 5 | 2 |
| 1-65 | 1.6 | 5 | 5 | 5 | 5 | 2 |
| 1-66 | 1.6 | 5 | 5 | 5 | 5 | 2 |
| 1-69 | 1.6 | 5 | 5 | 5 | 5 | 2 |
| 1-72 | 1.6 | 5 | 5 | 5 | 5 | 2 |
| 1-106 | 1.6 | 5 | 5 | 5 | 5 | 2 |
| 1-119 | 1.6 | 5 | 5 | 5 | 4 | 2 |
| 1-125 | 1.6 | 5 | 5 | 5 | 5 | 2 |
| 1-126 | 1.6 | 5 | 5 | 5 | 5 | 2 |
| 1-134 | 1.6 | 5 | 5 | 5 | 5 | 2 |
| 1-159 | 1.6 | 5 | 5 | 5 | 5 | 2 |
| 1-162 | 1.6 | 5 | 5 | 5 | 5 | 2 |
| 1-170 | 1.6 | 5 | 5 | 5 | 5 | 0 |
| 1-171 | 1.6 | 5 | 5 | 5 | 5 | 1 |
| 1-176 | 1.6 | 5 | 5 | 5 | 5 | 1 |
| 1-178 | 1.6 | 5 | 5 | 5 | 5 | 2 |
| 1-179 | 1.6 | 5 | 5 | 5 | 5 | 1 |
| 1-181 | 1.6 | 5 | 5 | 5 | 5 | 2 |
| 1-182 | 1.6 | 5 | 5 | 5 | 5 | 1 |

TABLE 89

| Compound No. | Dose a i, g /10 a | Herbicidal effects Po | Am | Ch | Ab | Phytotoxicity Ze |
|---|---|---|---|---|---|---|
| 1-184 | 1.6 | 5 | 5 | 5 | 5 | 1 |
| 1-187 | 1.6 | 5 | 5 | 5 | 5 | 2 |
| 1-191 | 1.6 | 5 | 5 | 5 | 5 | 2 |
| 1-194 | 1.6 | 5 | 5 | 5 | 5 | 1 |
| 1-196 | 1.6 | 5 | 5 | 5 | 5 | 2 |
| 1-197 | 1.6 | 5 | 5 | 5 | 5 | 2 |
| 1-199 | 1.6 | 5 | 5 | 5 | 5 | 2 |
| 1-200 | 1.6 | 5 | 5 | 5 | 5 | 2 |
| 1-201 | 1.6 | 5 | 5 | 5 | 5 | 2 |
| 1-203 | 1.6 | 5 | 5 | 5 | 5 | 2 |
| 1-204 | 1.6 | 5 | 5 | 5 | 5 | 2 |
| 1-208 | 1.6 | 5 | 5 | 5 | 5 | 2 |
| 1'-5 | 1.6 | 5 | 5 | 5 | 5 | 1 |
| 2-1 | 0.1 | 5 | 5 | 5 | 5 | 0 |
| 2-17 | 1.6 | 5 | 5 | 5 | 5 | 2 |

TABLE 89-continued

| Compound No. | Dose a i, g /10 a | Herbicidal effects Po | Am | Ch | Ab | Phytotoxicity Ze |
|---|---|---|---|---|---|---|
| 2-18 | 1.6 | 5 | 5 | 5 | 5 | 2 |
| 2-19 | 1.6 | 5 | 5 | 5 | 5 | 1 |
| 2-25 | 1.6 | 5 | 5 | 5 | 5 | 2 |
| 2-26 | 1.6 | 5 | 5 | 5 | 5 | 2 |
| 2-31 | 1.6 | 5 | 5 | 5 | 5 | 2 |
| 3-5 | 1.6 | 5 | 5 | 5 | 5 | 2 |
| 3-6 | 1.6 | 5 | 5 | 5 | 5 | 2 |
| 4-3 | 1.6 | 5 | 5 | 5 | 5 | 2 |
| 4-4 | 1.6 | 5 | 5 | 5 | 5 | 2 |
| 4-5 | 1.6 | 5 | 5 | 5 | 5 | 1 |
| 4-26 | 1.6 | 5 | 5 | 5 | 5 | 1 |
| 4-27 | 1.6 | 5 | 5 | 5 | 5 | 2 |
| 4-28 | 1.6 | 5 | 5 | 5 | 5 | 2 |
| 4-32 | 1.6 | 5 | 5 | 5 | 5 | 2 |

TABLE 90

| Compound No. | Dose a i, g /10 a | Herbicidal effects Po | Am | Ch | Ab | Phytotoxicity Ze |
|---|---|---|---|---|---|---|
| 4-33 | 1.6 | 5 | 5 | 5 | 5 | 2 |
| 4-38 | 1.6 | 5 | 5 | 5 | 5 | 2 |
| 5-2 | 1.6 | 5 | 5 | 5 | 5 | 2 |
| 5-3 | 1.6 | 5 | 5 | 5 | 5 | 2 |
| 6-9 | 1.6 | 5 | 5 | 5 | 5 | 1 |
| 6-10 | 1.6 | 4 | 5 | 5 | 5 | 1 |
| 7-1 | 1.6 | 5 | 5 | 5 | 5 | 2 |

What is claimed is:

1. A pyridone derivative represented by the general formula:

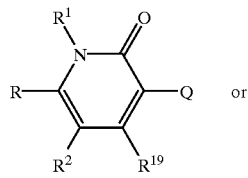

(I-1)

or

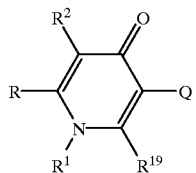

(I-2)

{wherein R is a $C_1$–$C_6$ alkyl group or a $C_1$–$C_6$ haloalkyl group, $R^1$ is a hydrogen atom, a $C_1$–$C_6$ alkyl group, a $C_1$–$C_6$ haloalkyl group, an acetyl group, a group of —N=CR$^{13}$R$^{14}$ or a group of —NR$^{23}$R$^{24}$, each of $R^{13}$ and $R^{14}$ which are independent of each other, is a hydrogen atom, a $C_1$–$C_6$ alkyl group, a group of —NR$^{23}$R$^{24}$ or a phenyl group (said group may be substituted by a halogen atom, a nitro group, a $C_1$–$C_6$ alkyl group, a $C_1$–$C_6$ haloalkyl group or a $C_1$–$C_6$ alkoxy group), each of $R^{23}$ and $R^{24}$ which are independent of each other, is a hydrogen atom, a $C_1$–$C_6$ alkyl group, a $C_1$–$C_6$ haloalkyl group, a $C_1$–$C_6$ alkylcarbonyl group, a $C_1$–$C_6$ alkoxycarbonyl group, a benzoyl group (said group may be substituted by a halogen atom, a nitro group, a $C_1$–$C_6$ alkyl group, a $C_1$–$C_6$ haloalkyl group or a $C_1$–$C_6$ alkoxy group), a phenoxycarbonyl group (said group may be substituted by a halogen atom, a nitro group, a $C_1$–$C_6$ alkyl group, a $C_1$–$C_6$ haloalkyl group or a $C_1$–$C_6$ alkoxy group), a formyl group or a $C_1$–$C_6$ alkylsulfonyl group, $R^2$ is a hydrogen atom, a $C_1$–$C_6$ alkyl group, a carboxyl group or a $C_1$–$C_6$ alkoxycarbonyl group, $R^{19}$ is a hydrogen atom, a halogen atom, a $C_1$–$C_6$ alkoxy group, a cyano group or a $C_1$–$C_6$ alkyl group, and Q represents a formula of

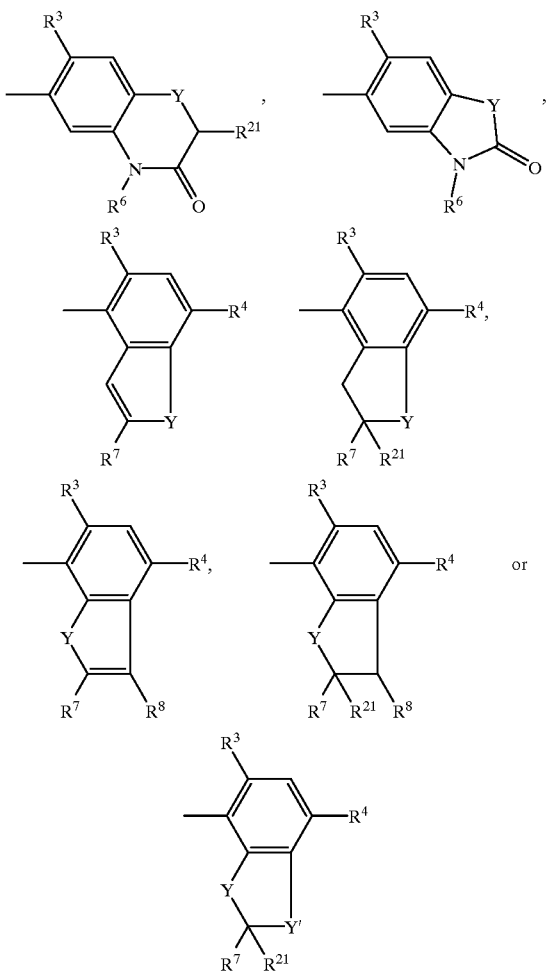

wherein $R^3$ is a hydrogen atom or a halogen atom, $R^4$ is a hydrogen atom, a halogen atom, a nitro group, a $C_1$–$C_6$ alkoxycarbonyl $C_1$–$C_6$ alkoxy group, a $C_1$–$C_6$ alkoxycarbonyl $C_1$–$C_6$ alkylthio group, a $C_1$–$C_6$ alkoxycarbonyl $C_1$–$C_6$ alkylamino group, a benzyloxy group (said group may be substituted by a halogen atom, a nitro group, a $C_1$–$C_6$ alkyl group or a $C_1$–$C_6$ alkoxy group), a hydroxyl group, a thiol group, a amino group or a cyano group, Y is an oxygen atom, a sulfur atom or a group of —$NR^{21}$—, $R^{21}$ is a hydrogen atom, a $C_1$–$C_6$ alkyl group, a $C_3$–$C_6$ alkenyl group or a $C_3$–$C_6$ alkynyl group, $R^6$ is a hydrogen atom, a Cl-$C_6$ alkyl group, a $C_3$–$C_6$ alkenyl group, a $C_3$–$C_6$ alkynyl group, a $C_1$–$C_6$ haloalkyl group, a $C_3$–$C_6$ haloalkenyl group, a $C_1$–$C_6$ alkoxy $C_1$–$C_6$ alkyl group, a $C_1$–$C_6$ alkoxycarbonyl group, a $C_1$–$C_6$ alkoxycarbonyl $C_1$–$C_6$ alkyl group, a cyano $C_1$–$C_6$ alkyl group, a benzyl group (said group may be substituted by a halogen atom, a nitro group, a $C_1$–$C_6$ alkyl group or a $C_1$–$C_6$ alkoxy group) or a group of —$CH_2$ (3–6 membered hetero ring), $R^7$ is a hydrogen atom, a halogen atom, a $C_1$–$C_6$ alkyl group, a $C_3$–$C_6$ cycloalkyl group, a $C_2$–$C_6$ alkenyl group, a $C_3$–$C_6$ alkynyl group, a $C_1$–$C_6$ haloalkyl group, a $C_1$–$C_6$ alkoxy $C_1$–$C_6$ alkyl group, a cyano group, a $C_1$–$C_6$ hydroxyalkyl group, a group of —$CO_2R^{10}$, a formyl group, an acyl group, a $C_1$–$C_6$ alkylthio $C_1$–$C_6$ alkyl group, a $C_1$–$C_6$ alkylsulfinyl $C_1$–$C_6$ alkyl group, a $C_1$–$C_6$ alkylsulfonyl $C_1$–$C_6$ alkyl group, a $C_1$–$C_6$ haloalkylthio $C_1$–$C_6$ alkyl group, a $C_1$–$C_6$ haloalkylsulfinyl $C_1$–$C_6$ alkyl group, a $C_1$–$C_6$ haloalkylsulfonyl $C_1$–$C_6$ alkyl group or a carboxyl group, $R^{10}$ is a hydrogen atom, a sodium atom, a $C_1$–$C_6$ alkyl group, a $C_3$–$C_6$ alkenyl group, a $C_3$–$C_6$ alkynyl group, a $C_3$–$C_8$ cycloalkyl group, a $C_1$–$C_6$ haloalkyl group, a $C_3$–$C_6$ haloalkenyl group, a $C_3$–$C_8$ cycloalkyl $C_1$–$C_6$ alkyl group, a $C_1$–$C_6$ alkoxy $C_1$–$C_6$ alkyl group, a $C_1$–$C_6$ alkylthio $C_1$–$C_6$ alkyl group, a $C_1$–$C_6$ alkylsulfinyl $C_1$–$C_6$ alkyl group, a $C_1$–$C_6$ alkylsulfonyl $C_1$–$C_6$ alkyl group, a $C_1$–$C_6$ alkoxycarbonyl $C_1$–$C_6$ alkyl group, a $C_3$–$C_6$ alkenyloxycarbonyl $C_1$–$C_6$ alkyl group, a $C_3$–$C_6$ alkynyloxycarbonyl $C_1$–$C_6$ alkyl group, a $C_3$–$C_8$ cycloalkyloxycarbonyl $C_1$–$C_6$ alkyl group, a $C_1$–$C_6$ alkoxy $C_1$–$C_6$ alkoxycarbonyl $C_1$–$C_6$ alkyl group, a halo $C_1$–$C_6$ alkoxycarbonyl $C_1$–$C_6$ alkyl group, a halo $C_3$–$C_6$ alkenyloxycarbonyl $C_1$–$C_6$ alkyl group, a benzyloxycarbonyl $C_1$–$C_6$ alkyl group (the benzyl group of said group may be substituted by a halogen atom, a nitro group, a $C_1$–$C_6$ alkyl group, a $C_1$–$C_6$ haloalkyl group or a $C_1$–$C_6$ alkoxy group), a $C_1$–$C_6$ alkylthiocarbonyl $C_1$–$C_6$ alkyl group, a $C_1$–$C_6$ alkylsulfinyl $C_1$–$C_6$ alkoxycarbonyl $C_1$–$C_6$ alkyl group, a $C_1$–$C_6$ alkylsulfonyl $C_1$–$C_6$ alkoxycarbonyl $C_1$–$C_6$ alkyl group, a $C_1$–$C_6$ monoalkylcarbamoyl $C_1$–$C_6$ alkyl group, a $C_1$–$C_6$ dialkylcarbamoyl $C_1$–$C_6$ alkyl group, a $C_1$–$C_6$ alkylthio $C_1$–$C_6$ alkoxycarbonyl $C_1$–$C_6$ alkyl group, a phenoxycarbonyl $C_1$–$C_6$ alkyl group (the phenyl group of said group may be substituted by a halogen atom, a nitro group, a $C_1$–$C_6$ alkyl group, a $C_1$–$C_6$ haloalkyl group or a $C_1$–$C_6$ alkoxy group), a $C_1$–$C_6$ alkoxycarbonyl $C_1$–$C_6$ alkoxycarbonyl $C_1$–$C_6$ alkyl group, a benzyl group (said group may be substituted by a halogen atom, a nitro group, a $C_1$–$C_6$ alkyl group, a $C_1$–$C_6$ haloalkyl group or a $C_1$–$C_6$ alkoxy group) or a phenyl group (said group may be substituted by a halogen atom, a nitro group, a $C_1$–$C_6$ alkyl group, a $C_1$–$C_6$ haloalkyl group or a $C_1$–$C_6$ alkoxy group), $R^8$ is a hydrogen atom, a $C_1$–$C_6$ alkyl group, a $C_1$–$C_6$ haloalkyl group, an acyl group, a halogen atom or a nitro group, and Y' is an oxygen atom, a sulfur atom, a group of —$NR^{21}$— or a group of —CO—}.

2. A pyridone derivative represented by the general formula:

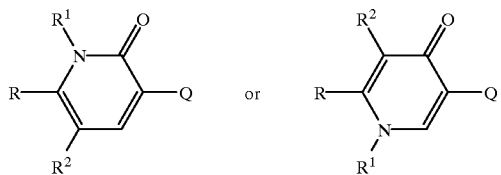

{wherein R is a $C_1$–$C_6$ alkyl group or a $C_1$–$C_6$ haloalkyl group, $R^1$ is a hydrogen atom, a $C_1$–$C_6$ alkyl group, a $C_1$–$C_6$ haloalkyl group, an acetyl group, an amino group, a $C_1$–$C_6$ alkoxycarbonylamino group or a $C_1$–$C_6$ alkylcarbonylamino group (provided that when $R^1$ is a hydrogen atom, R is a $C_1$–$C_6$ haloalkyl group), $R^2$ is a hydrogen atom, a $C_1$–$C_6$ alkyl group, a carboxyl group or a $C_1$–$C_6$ alkoxycarbonyl group, and Q represents a formula of

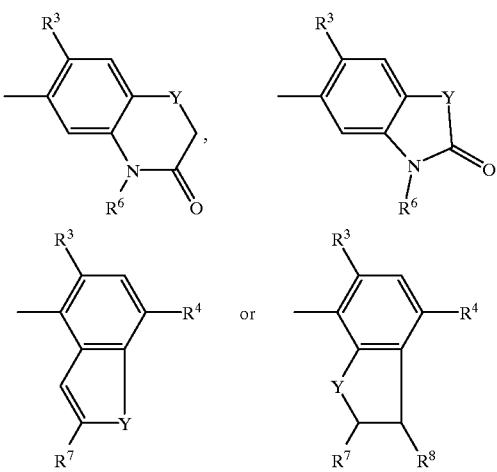

wherein $R^3$ is a hydrogen atom or a halogen atom, $R^4$ is a hydrogen atom, a halogen atom, a nitro group, a $C_1$–$C_6$ alkoxycarbonyl $C_1$–$C_6$ alkoxy group, a $C_1$–$C_6$ alkoxycarbonyl $C_1$–$C_6$ alkylthio group, a $C_1$–$C_6$ alkoxycarbonyl $C_1$–$C_6$ alkylamino group, a benzyloxy group (said group may be substituted by a halogen atom, a nitro group, a $C_1$–$C_6$ alkyl group or a $C_1$–$C_6$ alkoxy group), a hydroxyl group, a thiol group, an amino group or a cyano group, $R^6$ is a hydrogen atom, a $C_1$–$C_6$ alkyl group, a $C_3$–$C_6$ alkenyl group, a $C_3$–$C_6$ alkynyl group, a $C_1$–$C_6$ haloalkyl group, a $C_3$–$C_6$ haloalkenyl group, a $C_1$–$C_6$ alkoxy $C_1$–$C_6$ alkyl group, a $C_1$–$C_6$ alkoxycarbonyl group, a cyano $C_1$–$C_6$ alkyl group or an oxiranemethyl group, $R^7$ is a hydrogen atom, a halogen atom, a $C_1$–$C_6$ alkyl group, a $C_3$–$C_6$ cycloalkyl group, a $C_3$–$C_6$ alkenyl group, a $C_3$–$C_6$ alkynyl group, a $C_1$–$C_6$ haloalkyl group, a $C_1$–$C_6$ alkoxy $C_1$–$C_6$ alkyl group, a cyano group, a $C_1$–$C_6$ hydroxyalkyl group, a group of —$CO_2R^{10}$; an acyl group, a $C_1$–$C_6$ alkylsulfonyl $C_1$–$C_6$ alkyl group, a $C_1$–$C_6$ alkylthio $C_1$–$C_6$ alkyl group, a $C_1$–$C_6$ alkylsulfinyl $C_1$–$C_6$ alkyl group or a carboxyl group, $R^8$ is a hydrogen atom, a $C_1$–$C_6$ alkyl group, a $C_1$–$C_6$ haloalkyl group, an acyl group, a halogen atom or a nitro group, Y is an oxygen atom, a sulfur atom or a group of —NH—, $R^{10}$ is a hydrogen atom, a $C_1$–$C_6$ alkyl group, a $C_3$–$C_6$ alkenyl group, a $C_3$–$C_6$ alkynyl group, a $C_3$–$C_8$ cycloallyl group, a $C_1$–$C_6$ haloalkyl group, a $C_3$–$C_6$ haloalkenyl group, a $C_3$–$C_8$ cycloalkyl $C_1$–$C_6$ alkyl group, a $C_1$–$C_6$ alkoxy $C_1$–$C_6$ alkyl group, a $C_1$–$C_6$ alkylthio $C_1$–$C_6$ alkyl group, a $C_1$–$C_6$ alkylsulfinyl $C_1$–$C_6$ alkyl group, a $C_1$–$C_6$ alkylsulfonyl $C_1$–$C_6$ alkyl group, a $C_1$–$C_6$ alkoxycarbonyl $C_1$–$C_6$ alkyl group, a $C_3$–$C_6$ alkenyloxycarbonyl $C_1$–$C_6$ alkyl group, a $C_3$–$C_6$ alkynyloxycarbonyl $C_1$–$C_6$ alkyl group, a $C_3$–$C_8$ cycloalkyloxycarbonyl $C_1$–$C_6$ alkyl group, a $C_1$–$C_6$ alkoxy $C_1$–$C_6$ alkoxycarbonyl $C_1$–$C_6$ alkyl group, a halo $C_1$–$C_6$ alkoxycarbonyl $C_1$–$C_6$ alkyl group, a halo $C_3$–$C_6$ alkenyloxycarbonyl $C_1$–$C_6$ alkyl group, a benzyloxycarbonyl $C_1$–$C_6$ alkyl group (the benzyl group of said group may be substituted by a halogen atom, a nitro group, a $C_1$–$C_6$ alkyl group, a $C_1$–$C_6$ haloalkyl group or a $C_1$–$C_6$ alkoxy group), a $C_1$–$C_6$ alkylthiocarbonyl $C_1$–$C_6$ alkyl group, a $C_1$–$C_6$ alkylsulfinyl $C_1$–$C_6$ alkoxycarbonyl $C_1$–$C_6$ alkyl group, a $C_1$–$C_6$ alkylsulfonyl $C_1$–$C_6$ alkoxycarbonyl $C_1$–$C_6$ alkyl group, a $C_1$–$C_6$ monoalkylaminocarbonyl $C_1$–$C_6$ alkyl group, a $C_1$–$C_6$ dialkylaminocarbonyl $C_1$–$C_6$ alkyl group, a $C_1$–$C_6$ alkylthio $C_1$–$C_6$ alkoxycarbonyl $C_1$–$C_6$ alkyl group, a phenyloxycarbonyl $C_1$–$C_6$ alkyl group (the phenyl group of said group may be substituted by a halogen atom, a nitro group, a $C_1$–$C_6$ alkyl group, a $C_1$–$C_6$ haloalkyl group or a $C_1$–$C_6$ alkoxy group), a $C_1$–$C_6$ alkoxycarbonyl $C_1$–$C_6$ alkoxycarbonyl $C_1$–$C_6$ alkyl group, a benzyl group (said group may be substituted by a halogen atom, a nitro group, a $C_1$–$C_6$ alkyl group, a $C_1$–$C_6$ haloalkyl group or a $C_1$–$C_6$ alkoxy group) or a phenyl group (said group may be substituted by a halogen atom, a nitro group, a $C_1$–$C_6$ alkyl group, a $C_1$–$C_6$ haloalkyl group or a $C_1$–$C_6$ alkoxy group)}.

3. The pyridone derivative of claims 1, wherein the general formula is:

[I-1]

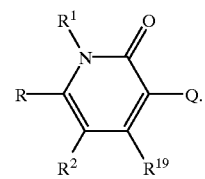

4. The pyridone derivative of claims 1, wherein the general formula is:

[I-2]

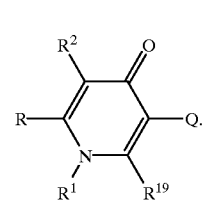

5. The pyridone derivative of claims 1, wherein the general formula is:

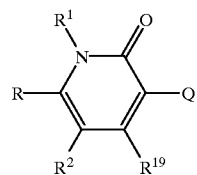

(wherein R is a $C_1$–$C_6$ haloalkyl group).

6. The pyridone derivative of claims 1, wherein the general formula is:

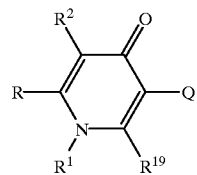

(wherein R is a $C_1$–$C_6$ haloalkyl group).

7. A herbicidal composition comprising the pyridone derivative as defined in claim 1, as an active ingredient, and a carrier.

* * * * *